(12) United States Patent
Larson et al.

(10) Patent No.: US 11,253,608 B2
(45) Date of Patent: Feb. 22, 2022

(54) RECOMBINANT ADENOVIRUSES CARRYING TRANSGENES

(71) Applicant: EpicentRx, Inc., La Jolla, CA (US)

(72) Inventors: Christopher Larson, San Diego, CA (US); Bryan Oronsky, Los Altos Hills, CA (US); Tony R. Reid, San Diego, CA (US)

(73) Assignee: EPICENTRX, INC., La Jolla, CA (US)

( * ) Notice: Subject to any disclaimer, the term of this patent is extended or adjusted under 35 U.S.C. 154(b) by 318 days.

(21) Appl. No.: 15/991,745

(22) Filed: May 29, 2018

(65) Prior Publication Data
US 2018/0369404 A1 Dec. 27, 2018

Related U.S. Application Data

(60) Provisional application No. 62/511,822, filed on May 26, 2017.

(51) Int. Cl.
| | | |
|---|---|---|
| *C12N 15/85* | (2006.01) | |
| *A61K 47/68* | (2017.01) | |
| *A61P 35/00* | (2006.01) | |
| *A61K 47/69* | (2017.01) | |
| *C12N 7/04* | (2006.01) | |
| *A61K 48/00* | (2006.01) | |
| *C12N 15/62* | (2006.01) | |
| *C12N 7/02* | (2006.01) | |
| *C12N 15/86* | (2006.01) | |

(52) U.S. Cl.
CPC ...... *A61K 47/6829* (2017.08); *A61K 47/6851* (2017.08); *A61K 47/6901* (2017.08); *A61K 48/0025* (2013.01); *A61K 48/0066* (2013.01); *A61K 48/0083* (2013.01); *A61P 35/00* (2018.01); *C12N 7/025* (2013.01); *C12N 7/045* (2013.01); *C12N 15/62* (2013.01); *C12N 15/85* (2013.01); *C12N 15/86* (2013.01); *C12N 2710/10343* (2013.01)

(58) Field of Classification Search
CPC ............ A61K 47/6829; A61K 47/6851; A61K 47/6901; A61K 48/0025; A61K 48/0066; A61K 48/0083; A61P 35/00; C12N 7/025; C12N 7/045; C12N 15/62; C12N 15/85; C12N 15/86; C12N 2710/10343
See application file for complete search history.

(56) References Cited

U.S. PATENT DOCUMENTS

| | | | | |
|---|---|---|---|---|
| 2003/0133912 A1* | 7/2003 | Davidson | ............. | C07K 14/005 424/93.2 |
| 2004/0091456 A1* | 5/2004 | Nakai | ................... | A61K 48/00 424/93.2 |
| 2005/0158278 A1 | 7/2005 | Vogels et al. | | |
| 2006/0292682 A1* | 12/2006 | Hawkins | ................ | C12N 15/86 435/235.1 |
| 2016/0017294 A1 | 1/2016 | Reid et al. | | |
| 2016/0319304 A1* | 11/2016 | Brown | ..................... | A61P 35/00 |
| 2020/0123571 A1* | 4/2020 | Burny | ...................... | C12N 7/00 |

FOREIGN PATENT DOCUMENTS

| | | |
|---|---|---|
| WO | WO-2000003029 A2 | 1/2000 |
| WO | WO-2000031285 A1 | 6/2000 |
| WO | WO-2000052186 A1 | 9/2000 |
| WO | WO-2010101921 A2 | 9/2010 |
| WO | WO-2016174200 A2 | 11/2016 |
| WO | WO 2018/218240 A1 | 11/2018 |

OTHER PUBLICATIONS

Genbank Accession No. AY601635.1, Human adenovirus type 5 strain NHRC Ad5FS 7151, complete genome, Apr. 12, 2006 [online]. [Retrieved on Aug. 14, 2018]. Retrieved from the internet: <URL: https://www.ncbi.nlm.nih.gov/nuccore/AY601635.1?& feature=CDS> Entire document (Year: 2006).*
Genbank Accession No. AY601635.1, Human adenovirus type 5 strain NHRC Ad5FS 7151, complete genome, Apr. 12, 2006 [online]. [Retrieved on Aug. 14, 2018). Retrieved from the internet: <URL: https://www.ncbi.nlm.nih.gov/nuccore/AY601635.1?&feature=CDS> Entire document, 18 pages.
International Search Report and Written Opinion dated Oct. 16, 2018, for International Application No. PCT/2018/034888, 11 pages.
Larson et al., (2015). "Going Viral: A Review of Replication-Selective Oncolytic Adenoviruses," Oncotarget, 6(24):19976-89.
Leppard et al., (1997). "E4 Gene Function in Adenovirus, Adenovirus Vector and Adeno-Associated Associated Virus Infections," J. Gen. Virol., 78:2131-8.
Mizuguchi et al., (2000). "IRES-Dependent Second Gene Expression Is Significantly Lower Than Cap-Dependent First Gene Expression in a Bicistronic Vector," Mol. Ther., 1(4):376-82.
NCBI Reference Sequence AC_000008.1, "Human Adenovirus 5, Complete Genome," Aug. 13, 2018, Retrieved on May 8, 2020, Retrieved from the internet: <https://www.ncbi.nlm.nih.gov/nuccore/AC_000008>, 14 pages.
Seila et al., (2008). "Divergent Transcription From Active Promoters," Science, 322(5909):1849-51.
Choi et al., (2013). "Oncolytic Adenovirus Expressing IL-23 and p35 Elicits IFN-[gamma]-and TNF-[alpha]-Co-Producing T Cell-Mediated Antitumor Immunity," PLOS One, 8(7):1-15.

(Continued)

*Primary Examiner* — Mindy G Brown

(74) *Attorney, Agent, or Firm* — Morrison & Foerster LLP

(57) ABSTRACT

Disclosed herein are recombinant adenoviruses with one or more nucleotide sequences inserted between two viral transcription units, formulations comprising the recombinant adenoviruses, and methods of treatment using the recombinant adenoviruses. In some embodiments, the one or more nucleotide sequences are inserted in an IX-E2 insertion site and/or an L5-E4 insertion site.

24 Claims, 14 Drawing Sheets

Specification includes a Sequence Listing.

(56) References Cited

OTHER PUBLICATIONS

Extended European Search Report and Written Opinion dated Feb. 22, 2021, for European Patent Application No. 18806954.6, 11 pages.

* cited by examiner

Initial IX-E2 design

Transgene insertion site

Revised IX-E2 design

Transgene insertion site

A549 Cells

HT29 Cells

ADS12 Cells

F244 Cells

RECOMBINANT ADENOVIRUSES CARRYING TRANSGENES

CROSS-REFERENCE TO RELATED APPLICATION

The present application claims priority to, and the benefits of U.S. Provisional Patent Application No. 62/511,822 filed May 26, 2017, which is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is EPRX_002_01WO_SeqList_ST25.txt. The text file is about 128 KB, was created on May 29, 2018 and is being submitted electronically via EFS-Web.

FIELD OF THE INVENTION

The invention described herein generally relates to the fields of virology, virotherapy, and molecular biology.

BACKGROUND

The uses of virotherapy to treat diseases such as cancer encompass employing replication-selective viruses armed with therapeutic genes or transgenes. Of the variety of infectious viral species developed as virotherapy agents, adenoviruses have emerged as one of the most promising because not only are they minimally toxic to normal non-transformed cells but their genomes, comprised of multiple endogenous genes, are amenable to manipulation, which generally takes the form of deletion of endogenous genes and insertion of exogenous ones. The downside to this manipulation is that most endogenous gene deletions or exogenous gene additions slow down or attenuate the replicative and infectivity potential of the virus. (Larson et al., Oncotarget, 6(24):19976-89 (2015))

The reduced replication efficiency of viruses carrying transgenes in these regions is undesirable because, such as in the case of an oncolytic virus for the treatment of cancer, it impairs the ability of the virus to multiply within tumors and infect neighboring cancerous cells, decreases the number of viral genome copies within infected cells and therefore likely reduces transcription of the therapeutic transgene, and increases the size of production cultures required to manufacture the virus. Therefore, a need exists for a new method to improve the ability of recombinant adenoviruses to replicate to high levels in targeted cells or tissues such as in tumors, thereby rapidly turning the targeted cells or tissues into a "factory" for the production of particular exogenous gene products.

Typically, to have oncolytic viruses express two or more separate protein or polypeptide chains requires the use of more than one virus vector or the use of linker, such as an internal ribosome entry site (IRES), between two transgenes. Both methods have significant drawbacks. Two or more virus vectors may not all express well within a single cell or tissue. As known in the art, the sequence downstream of the IRES is expressed at much lower levels than the sequence upstream. (Mizuguchi et al., Mol. Ther. 1(4):376-82 (2000)) In addition, the linker, being non-endogenous, has the potential for immunogenicity. Therefore, a need exists for more efficient viral vectors to express more than one peptide chain within a single virus.

SUMMARY OF THE INVENTION

The invention is based, in part, upon the discovery that recombinant adenoviruses with one or more nucleotide sequences inserted between two viral transcription units in the viral genome can efficiently replicate and express the nucleotide sequences in targeted cells or tissues, do not significantly impact the oncolytic activity of the virus. The vectors of this invention can be advantageously used where equal levels of two or more transgenes are desired or to express completely native chains from dual chain proteins.

In one aspect, the invention provides a recombinant adenovirus comprising a nucleotide sequence inserted in an insertion site, wherein the insertion site is located between the stop codon of a first viral transcription unit and the stop codon of a second viral transcription unit, wherein the stop codon of the first viral transcription unit is nearer to the stop codon of the second viral transcription unit than the start site of the first viral transcription unit is to the stop codon of the second viral transcription unit, wherein the stop codon of the second viral transcription is nearer to the stop codon of the first viral transcription unit than the start site of the second viral transcription unit is to the stop codon of the first viral transcription unit, and wherein there is no viral transcription unit between the first viral transcription unit and the second viral transcription unit before the nucleotide sequence is inserted.

In certain embodiments, the first viral transcription unit is adenovirus IX gene and the second viral transcription unit is adenovirus IVa2 gene. In certain embodiments, the first viral transcription unit is adenovirus fiber gene and the second viral transcription unit is ORF6 or ORF6/7 of adenovirus E4 gene. In certain embodiments, the recombinant adenovirus is a type 5 adenovirus (Ad5). In certain embodiments, the recombinant adenovirus is a type 35 adenovirus (Ad35).

In certain embodiments, a nucleotide sequence in inserted in the IX-E2 insertion site. In certain embodiments, the IX-E2 insertion site is located between the stop codon of adenovirus IX gene and the stop codon of adenovirus IVa2 gene. In certain embodiments, the nucleotide sequence is inserted between nucleotides corresponding to about 4029 and 4093 of the Ad5 genome (SEQ ID NO: 1). In certain embodiments, the nucleotide sequence is inserted between nucleotides corresponding to 4029 and 4050, nucleotides corresponding to 4050 and 4070, or nucleotides corresponding to 4070 and 4093 of the Ad5 genome (SEQ ID NO: 1). In certain embodiments, the nucleotide sequence is inserted between nucleotides corresponding to about 3899 and 3970 of the Ad35 genome (SEQ ID NO: 41). In certain embodiments, the nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In certain embodiments, a nucleotide sequence is inserted in an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the nucleotide sequence is inserted between nucleotides corresponding to 32785 to 32916 of the Ad5 genome (SEQ ID NO: 1). In certain embodiments, the nucleotide sequence is inserted between nucleotides corresponding to 32785 and 32800, nucleotides corresponding to 32800 and 32820, nucleotides corresponding to 32820 and 32840, nucleotides corresponding to 32840 and 32860, nucleotides corresponding to 32860 and 32880, nucleotides corresponding to 32880 and 32900, or nucleotides corresponding to about 32901 and 32916 of the Ad5 genome (SEQ ID NO: 1). In certain embodiments, the nucleotide sequence is inserted between nucleotides corresponding to about 31799 and 31821 of the Ad35 genome (SEQ ID NO: 41). In certain embodiments, the nucleotide sequence is inserted between nucleotides corresponding to 31799 and 32810, or nucleotides corresponding to 32810 and 31821 of the Ad35 genome (SEQ ID NO: 41).

In certain embodiments, the foregoing recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E1b-19k insertion site is located between the start site of E1b-19K and the stop codon of E1b-19K. In certain embodiments, the E3 insertion site is located between the stop codon of adenovirus pVIII gene and the start site of adenovirus Fiber gene.

In certain embodiments, the invention provides a recombinant adenovirus comprising a first nucleotide sequence inserted in an IX-E2 insertion site and a second nucleotide sequence inserted in an L5-E4 insertion site.

In certain embodiments, the first nucleotide sequence is inserted between nucleotides corresponding to about 4029 and 4093 of the Ad5 genome (SEQ ID NO: 1). In certain embodiments, the first nucleotide sequence is inserted between nucleotides corresponding to 4029 and 4050, nucleotides corresponding to 4050 and 4070, or nucleotides corresponding to 4070 and 4093 of the Ad5 genome (SEQ ID NO: 1). In certain embodiments, the first nucleotide sequence is inserted between nucleotides corresponding to about 3899 and 3970 of the Ad35 genome (SEQ ID NO: 41). In certain embodiments, the first nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In certain embodiments, the second nucleotide sequence is inserted between nucleotides corresponding to 32785 to 32916 of the Ad5 genome (SEQ ID NO: 1). In certain embodiments, the second nucleotide sequence is inserted between nucleotides corresponding to 32785 and 32800, nucleotides corresponding to 32800 and 32820, nucleotides corresponding to 32820 and 32840, nucleotides corresponding to 32840 and 32860, nucleotides corresponding to 32860 and 32880, nucleotides corresponding to 32880 and 32900, or nucleotides corresponding to about 32901 and 32916 of the Ad5 genome (SEQ ID NO: 1). In certain embodiments, the second nucleotide sequence is inserted between nucleotides corresponding to about 31799 and 31821 of the Ad35 genome (SEQ ID NO: 41). In certain embodiments, the second nucleotide sequence is inserted between nucleotides corresponding to 31799 and 32810, or nucleotides corresponding to 32810 and 31821 of the Ad35 genome (SEQ ID NO: 41).

In certain embodiments, the nucleotide sequence, the first nucleotide sequence, and/or the second nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence (comprising one or more transgenes) is inserted between the first polyadenylation signal and the third polyadenylation signal. In some embodiments, the one or more transgenes is inserted between the first polyadenylation signal and the third polyadenylation signal. In certain embodiments, wherein the second polyadenylation signal is in the opposite transcriptional direction of the third polyadenylation signal.

In certain embodiments, the nucleotide sequence is inserted in the L5-E4 insertion site, and the first polyadenylation signal is the polyadenylation signal of the fiber (L5) gene, the second polyadenylation signal is the polyadenylation signal of the transgene, and the third polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence (comprising one or more transgenes) is inserted between the first polyadenylation signal and the fourth polyadenylation signal. In some embodiments, the one or more transgenes is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the nucleotide sequence is inserted in the L5-E4 insertion site, and the first polyadenylation signal is the polyadenylation signal of the fiber (L5) gene, the third polyadenylation signal is the polyadenylation signal of the transgene, and the fourth polyadenylation signal is the polyadenylation signal of the ORF6 or ORF6/7 of the adenovirus E4 gene. In certain embodiments, the nucleotide sequence is inserted in the IX-E2 insertion site, the first polyadenylation signal is the polyadenylation signal of the IX gene, the third polyadenylation signal is the polyadenylation signal of the transgene, and the fourth polyadenylation signal is the polyadenylation signal of the adenovirus IVa2 gene.

In certain embodiments, the promoter is a ubiquitous promoter, a tissue-specific promoter, or tumor-specific promoter.

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

In certain embodiments, the nucleotide sequence further comprises a consensus Kozak sequence. In certain embodiments, the recombinant adenovirus comprises a partial or complete deletion of the nucleotide sequence encoding the adenoviral death protein (ADP).

In certain embodiments, the foregoing recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E1b-19k insertion site is located between the start site of E1b-19K and the stop codon of E1b-19K. In certain embodiments, the E3 insertion site is located between the stop codon of adenovirus pVIII gene and the start site of adenovirus Fiber gene.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 nucleotides adjacent the start site of E1b-19K. In certain embodiments, the E1b-19K insertion site comprises a deletion corresponding to nucleotides 1714-1917 of the Ad5 genome (SEQ ID NO: 1), or the first therapeutic transgene is inserted between nucleotides corresponding to 1714 and 1917 of the Ad5 genome (SEQ ID NO: 1). In certain embodiments, the first therapeutic transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), the first therapeutic transgene, and TCACCAGG (SEQ ID NO: 2).

In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In certain embodiments, the E3 insertion site is located between the stop codon of E3-10.5K and the stop codon of E3-14.7K. In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In certain embodiments, the E3 insertion site comprises a deletion of about 1050 nucleotides adjacent the stop codon of E3-10.5K, e.g., the E3 insertion site comprises a deletion of 1063 nucleotides adjacent the stop codon of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or the second therapeutic transgene is inserted between nucleotides corresponding to 29773 and 30836 of the Ad5 genome (SEQ ID NO: 1). In certain embodiments, the E3 insertion site comprises a deletion corresponding to nucleotides 29119-30622 of the Ad35 genome (SEQ ID NO: 41).

In certain embodiments, the recombinant adenovirus comprises an E1a promoter having a deletion of a functional Pea3 binding site. For example, the virus may comprise a deletion of nucleotides corresponding to about −300 to about −250 upstream of the initiation site of E1a or a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 4).

In certain embodiments, the recombinant adenovirus comprises a modified TATA box-based promoter operably linked to a gene, wherein the modified TATA box-based promoter lacks a functional TATA box and permits selective expression of the gene in a hyperproliferative cell and/or a modified CAAT box-based promoter operably linked to a gene, wherein the modified CAAT box-based promoter lacks a functional CAAT box and permits selective expression of the gene in a hyperproliferative cell.

In certain embodiments, wherein the modified TATA box-based promoter is an early gene promoter. In certain embodiments, the modified TATA box-based promoter is an E1a promoter, E1b promoter, or E4 promoter. In certain embodiments, the modified TATA box-based promoter is an E1a promoter.

In certain embodiments, the modification included in the modified TATA box-based promoter comprises a deletion of the entire TATA box. In certain embodiments, the recombinant adenovirus comprises a deletion of nucleotides corresponding to −27 to −24, −31 to −24, −44 to +54, or −146 to +54 of the E1a promoter. In certain embodiments, the deletion comprises a deletion of nucleotides corresponding to 472 to 475, 468 to 475, 455 to 552, or 353 to 552 of the Ad5 genome (SEQ ID NO: 1).

In certain embodiments, the recombinant adenovirus comprises a polynucleotide deletion that results in a virus comprising the sequence CTAGGACTG (SEQ ID NO: 5), AGTGCCCG (SEQ ID NO: 44) and/or TATTCCCG (SEQ ID NO: 45).

In certain embodiments, the modified CAAT box-based promoter is an early gene promoter. In certain embodiments, the modified CAAT box-based promoter is an E1a promoter, E1b promoter, or E4 promoter. In certain embodiments, the modified CAAT box-based promoter is an E1a promoter.

In certain embodiments, the modification included in the modified CAAT box-based promoter comprises a deletion of the entire CAAT box. In certain embodiments, the recombinant adenovirus comprises a deletion of nucleotides corresponding to −76 to −68 of the E1a promoter.

In certain embodiments, the recombinant adenovirus comprises a deletion of nucleotides corresponding to 423 to 431 of the Ad5 genome (SEQ ID NO: 1). In certain embodiments, the recombinant adenovirus comprises a polynucleotide deletion that results in a virus comprising the sequence TTCCGTGGCG (SEQ ID NO: 46). In certain embodiments, the recombinant adenovirus comprises a deletion of nucleotides corresponding to 477 to 484 of the Ad35 genome (SEQ ID NO: 41).

In certain embodiments, the inserted nucleotide sequence comprises a first nucleotide sequence comprising a first transgene, and a second nucleotide sequence comprising a second transgene, wherein the first nucleotide sequence and the second nucleotide sequence are separated by a linker. In certain embodiments, the linker encodes a peptide cleavable by a protease or proteases. In certain embodiments, the linker encodes an internal ribosome entry site (IRES) or a self-cleaving 2A peptide. The IRES may, e.g., be selected from the group consisting of the encephalomyocarditis virus IRES, the foot-and-mouth disease virus IRES, and the poliovirus IRES. In certain embodiments, wherein the nucleotide sequence is inserted in the IX-E2 insertion or the L5-E4 insertion site, wherein the recombinant adenovirus further comprise a third nucleotide sequence comprising a third transgene inserted in an E1b-19K insertion site, an E3 insertion site, or an E4 insertion site.

In certain embodiments, one or more of the nucleotide sequence, the first nucleotide sequence, the second nucleotide sequence, and the third nucleotide sequence comprises one or more transgenes.

In certain embodiments, one or more of the transgene, the first transgene, and the second transgene encodes a monomeric, dimeric, trimeric, tetrameric, or multimeric protein, or a part thereof. In certain embodiments, one or more of the transgene, the first transgene, and/or the second transgene encodes a RNA that has a therapeutic activity. In certain embodiments, one or more of the transgene, the first transgene, and/or the second transgene encodes a fusion protein comprising at least one binding domain.

In certain embodiments, one or more of the transgene, the first transgene, and the second transgene encodes an immunomodulatory molecule. In certain embodiments, the immunomodulatory molecule is a costimulatory ligand, a cytokine, or a cytokine receptor. In certain embodiments, the immunomodulatory molecule is selected from the group consisting of IL-1, IL-2, IL-3, IL-4, IL-5, IL-6, IL-7, IL-8, IL-9, IL-7, IL-10, IL-10 trap, IL-10R, IL-12A/p35, IL-12B/p40, IL-15, IL-15 receptor fusion protein, IL-23A/p19, IL24, IL-27, IL-33, IL-35, IL-15, an IL-15 receptor fusion protein, TGF-β, a TGF-β trap, an IL-10 trap, VEGF, indoleamin-2,3-dioxygenase (IDO), inducible T-cell co-stimulator ligand (ICOS-L), CD80, CD137L, TNF-α, IFN-α, IFN-β, IFN-γ, or GM-CSF, GITR ligand (GITRL), OX40 ligand (OX40L), CD40 ligand (CD40L), drug-inducible CD40 (iCD40), CD154, CD70, CD86, CD137, CD137L, BORIS/CTCFL, TNFSF9, FGF, ICAM, Podocalyxin, functional fragments thereof, and derivatives thereof.

In certain embodiments, one or more of the transgenes, the first transgene, and the second transgene encodes an antigen-binding molecule. In certain embodiments, the antigen-binding molecule is an anti-PD-1 antibody, an anti-TGF-β antibody, an anti-PD-L1 antibody, and an anti-CTLA-4 antibody, or functional fragments thereof.

In certain embodiments, one or more of the transgenes, the first transgene, and the second transgene encodes an antigen or a ligand to the antigen. In certain embodiments, the antigen is selected from the group consisting of CAIX, CEA, CD5, CD7, CD10, CD19, CD20, CD22, CD30, CD33, CD34, CD38, CD41, CD44, CD49f, CD56, CD74, CD80, CD133, CD138, a cytomegalovirus (CMV) infected cell antigen, 4-1BB, EGP-2, EGP-40, EpCAM, erbB2, erbB3, erbB4, FBP, Fetal acetylcholine receptor, KRAS, HPV E6, E7, BING-4, EphA3, calcium activated chloride channel-2, cyclin B1, 9D7, Ep-CAM, PRAME, SSX-2, immature laminin receptor, folate receptor-a, telomerase, tyrosinase, melan-A, NY-ESO-1, GD2, GD3, hTERT, IL13R-a2, x-light chain, KDR, LeY, LI cell adhesion molecule, MAGE-A1, MAGE-A3, MART1, MART2, MUC1, Mesothelin, HER-2/neu, EGFRvIII, NKG2D ligands, NY-ES0-1, gp100, TRP-1/-2, TRP-1/-2, P polypeptide, MC1R, prostate specific antigen, BRAF, androgen-receptor, β-catenin, BRCA1/2, CDK4, CML66, fibronectin, p53, TGF-βRII, T cell receptor, oncofetal antigen, 5T4, PSCA, PSMA, ROR1, TAG-72, VEGF-R2, WT-1, functional fragments thereof, and derivatives thereof.

In certain embodiments, one or more of the transgenes, the first transgene, and the second transgene encodes a toxin. In certain embodiments, the toxin is *pseudomonas* exotoxin, ricin toxin, or diphtheria toxin.

In certain embodiments, one or more of the transgenes, the first transgene, and the second transgene encodes an enzyme. In certain embodiments, the enzyme is selected from the group consisting of beta-glucuronidase, beta-galactosidase, beta-glucosidase, carboxypeptidase, beta-lactamase, esterase, metalloproteinase, relaxin, collagenase, streptokinase, arginase, NOS-2, fragments thereof, and derivatives thereof.

In certain embodiments, one or more of the transgenes, the first transgene, and the second transgene encodes a cell cycle control agent, a growth factor, an anticoagulant, a pro-drug activating gene, a tumor suppressor gene, an apoptotic gene, an anti-platelet agent, a clotting factor, a cystic fibrosis transmembrane conductance regulator (CFTR) protein, fragments thereof, or derivatives thereof.

In certain embodiments, one or more of the transgenes, the first transgene, and the second transgene encodes angiostatin, endostatin, acetylcholine, DKK1/Wnt, Ox40L, GITRL, secreted flagellin, thymidine kinase, functional fragments thereof, or derivatives thereof.

In certain embodiments, the recombinant adenovirus is oncolytic. In certain embodiments, the recombinant adenovirus selectively replicates in a hyperproliferative cell. In certain embodiments, the recombinant adenovirus selectively expresses a transgene in a hyperproliferative cell. In certain embodiments, the hyperproliferative cell is a tumor cell.

In another aspect, the invention provides an isolated nucleotide sequence comprising any of the foregoing recombinant adenovirus sequence, optionally wherein the nucleotide sequence is cDNA. In another aspect, the invention provides an isolated vector comprising the adenovirus nucleotide sequence. In another aspect, the invention provides an isolated cell comprising the adenovirus nucleotide sequence or the vector.

In another aspect, the invention provides a method of inhibiting proliferation of a tumor cell comprising exposing the tumor cell to an effective amount of any of the foregoing recombinant adenoviruses to inhibit proliferation of the tumor cell.

In another aspect, the invention provides a method of treating a condition in a subject. In some embodiments, the condition is cancer. The method comprises administering to the subject an effective amount of a recombinant adenoviruses described herein to treat the cancer disease in the subject.

In another aspect, the invention provides a method of inhibiting tumor growth in a subject in need thereof, wherein the method comprising administering to the subject to an effective amount of any of the foregoing recombinant adenoviruses to inhibit tumor growth. In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

In another aspect, the invention provides a method of treating a disease or condition in a subject in need thereof, wherein the method comprising administering to the subject an effective amount of any of the foregoing recombinant adenoviruses. In certain embodiments, the disease or condition is selected from the group consisting of an infection, diabetic retinopathy, psoriasis, rheumatoid arthritis, endometriosis, macular degenerative disorders and benign growth disorders such as prostate enlargement and lipomas, a vascular disorder, a cardiovascular disease, cirrhosis of the liver, a connective tissue disorder, a tumor, a vascular lesion, an ulcerative lesion, an inflammation, thrombosis, and neointima formation.

In certain embodiments, the subject is a mammal. In certain embodiments, the subject is a human. In certain embodiments, the subject is a pediatric human. In certain embodiments, the subject is an adult human.

In certain embodiments, the recombinant adenovirus is administered by intramuscular, intravenous, intraarterial, intratumoral, intradermal, inhalation, transdermal, topical, eye drops, intranasal, transmucosal, and/or rectal administration.

In certain embodiments, the foregoing methods further comprising administering to the subject one or more therapies selected from the group consisting of surgery, radiation, chemotherapy, immunotherapy, hormone therapy, and virotherapy.

In certain embodiments, the foregoing methods further comprise administering to the subject one or more immune checkpoint modulators. In certain embodiments, the immune checkpoint modulator is an inhibitor, an antagonist, or an agonist of one or more molecules selected from the group consisting of PD-1, PD-L1, PD-L2, 2B4, TIGIT, LAG3, Tim3, BTLA, CD160, GITR, KIR, 4-1BB, and CTLA4.

In another aspect, the invention provides a pharmaceutical composition comprising any of the foregoing recombinant adenoviruses and at least one pharmaceutically acceptable carrier or diluent.

In another aspect, the invention provides a formulation for adenoviruses comprising:

a) one or more of any of the foregoing recombinant adenoviruses;

b) at least one buffer;

c) at least one tonicity modifier;

d) at least one sugar or at least one stabilizing agent, or both; and wherein the formulation has a pH ranging between about 7.0 and about 9.0.

In certain embodiments, any of the foregoing formulations has an osmolarity of about 200 mOs/L to about 800 mOs/L. In certain embodiments, the recombinant adenovirus in any of the foregoing formulations is at concentration from about $1 \times 10^7$ vp/mL to $1 \times 10^{13}$ vp/mL.

These and other aspects and advantages of the invention are illustrated by the following figures, detailed description and claims.

DESCRIPTION OF THE DRAWINGS

The invention can be more completely understood with reference to the following drawings.

mCD80-(IX)mCD137L-(L5)mICAM1, labeled as 19K-IX-5], or the control virus [TAV-(19k)Empty-(IX)Empty-(L5) Empty, labeled as Empty].

Figure 13:
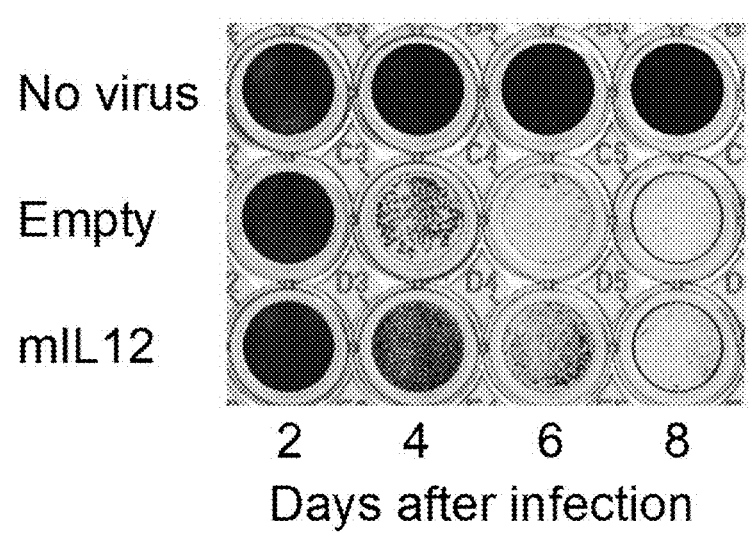

FIG. 13 depicts oncolytic activity of the viruses TAV-IX5-Empty (labeled "Empty") and TAV-IX5-mIL12 (labeled "mIL12") in A549 cells after infection at an MOI of 5. Wells were stained with crystal violet on the indicated days after infection.

Figure 14:
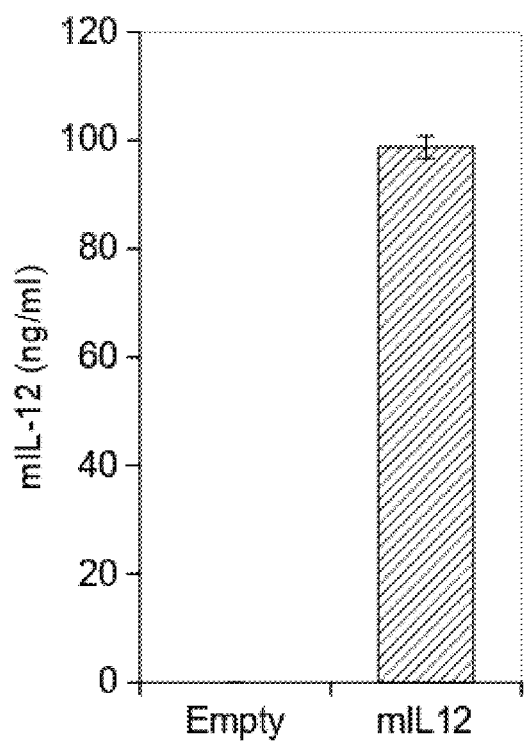

FIG. 14 transgene expression of the virus TAV-IX5-mIL12. A549 cells were infected with TAV-IX5-Empty (labeled "Empty") or TAV-IX5-mIL12 (labeled "mIL12") at an MOI of 5, and conditioned media was collected five days after infection and used in an ELISA to measure heterodimeric mouse IL-12. High levels of mouse IL-12 were expressed with the TAV-IX5-mIL12 virus and not the control TAV-IX5-Empty virus. Bars depict the mean IL-12 level of triplicate samples and error bars depict standard deviation.

DETAILED DESCRIPTION

The invention is based, in part, upon the discovery that recombinant adenoviruses with one or more nucleotide sequences inserted between two viral transcription units in the viral genome can efficiently replicate and express the nucleotide sequences in targeted cells or tissues.

I. Recombinant Adenovirus

Adenoviruses are non-enveloped and icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes, but is not limited to, bovine adenovirus types 1, 2, 3, 4, 7, and 10. The term canine adenoviruses includes, but is not limited to, canine types 1 (strains CLL, Glaxo, RI261, Utrect, Toronto 26-61) and 2. The term equine adenoviruses includes, but is not limited to, equine types 1 and 2. The term porcine adenoviruses includes, but is not limited to, porcine types 3 and 4.

In some embodiments, provided are recombinant viruses derived from human adenovirus types 5 and 35. The terms "viral vector" and "virus" are used interchangeably herein to refer to any of the obligate intracellular parasites having no protein-synthesizing or energy-generating mechanism.

The adenovirus replication cycle has two phases: an early phase, during which transcription units E1A, E1B, E2A, E2B, E3, and E4 are expressed. The proteins coded for by genes within these transcription units are mostly involved in regulation of viral transcription, in replication of viral DNA, and in suppression of the host response to infection. The L1-L5 transcription units are transcribed later in the viral reproductive cycle, and code mostly for proteins that make up components of the viral capsid or are involved in assembly of the capsid. The L1-L5 transcription units are expressed primarily from the major late promoter (MLP).

The general structure of the mature Adenovirion is conserved among different Adenoviral species. The Adenoviral capsid is composed of three major proteins (II, III, and IV) and five minor proteins, VI, VIII, IX, IIIa, and IVa2. "IVa2 gene" used herein refers to the gene encoding the IVa2 protein, modified versions, and/or fragment thereof. "IX gene" used herein refers to the gene encoding the IX protein, modified versions, and/or fragment thereof.

Figure 1:
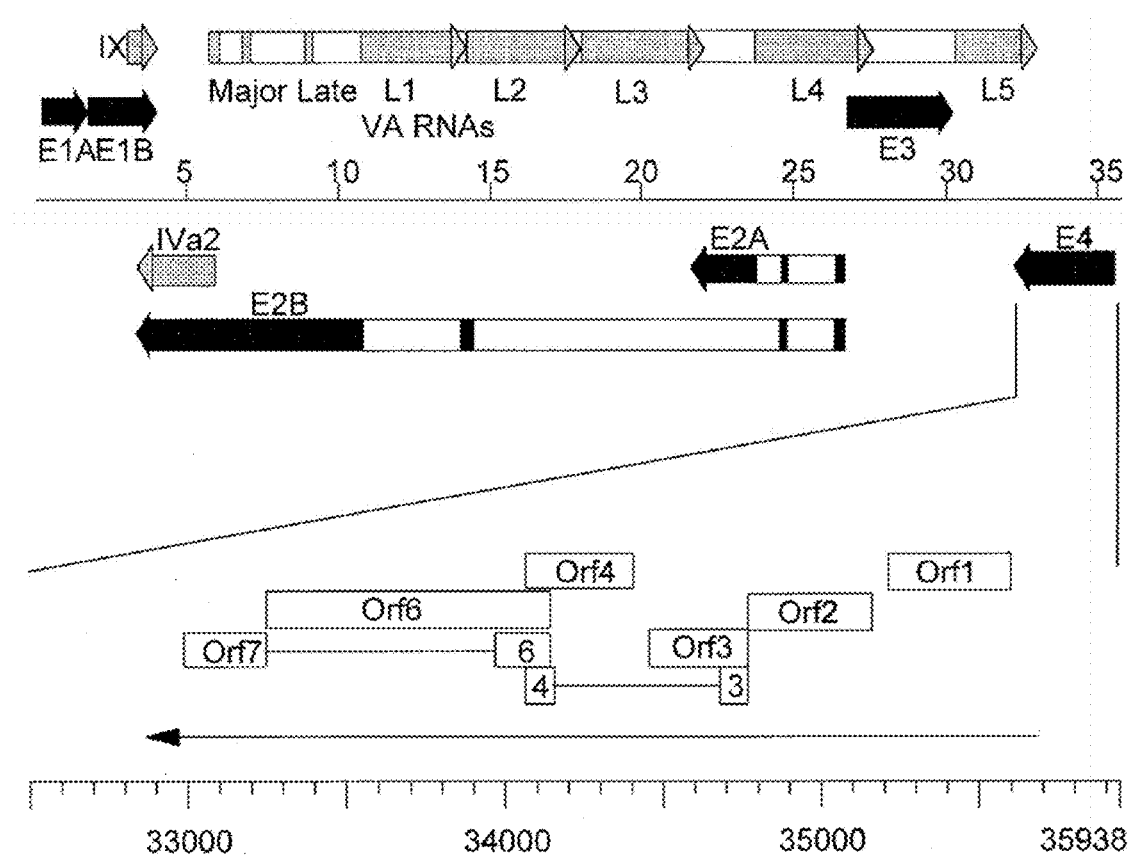
FIG. 1 is a graph depicting the genome organization of human Ad5. At the top of the figure the genome is represented as a line with lengths marked in kbp from the conventional left end. Thick arrows represent early and late transcription units (black and grey, respectively). Open boxes represent the major introns. The E4 gene is enlarged as a line scale with lengths in bp. The primary transcript is shown as a black arrow in a 5' to 3' direction and each of the potential encoded proteins is shown as an open box; proteins whose coding regions are split by intron sequences are shown as boxes linked by a line.

A schematic representation of the Ad5 genome and a detail of the E4 gene are shown in FIG. 1. Primary transcripts from E4 are subject to alternative splicing events and are predicted to encode seven different polypeptides: ORF1, ORF2, ORF3, ORF3/4, ORF4, ORF5, ORF6, and ORF6/7. (Leppard et al., Journal of General Virology, 78:2131-8 (1997)) "ORF" is used herein to refer to either the polypeptide or the nucleotide sequence encoding the polypeptide, modified versions, and/or fragment thereof.

In addition, the fiber protein (also known as protein IV or SPIKE) forms spikes that protrude from each vertex of the icosahedral capsid. "Fiber gene" used herein refers to the gene encoding the fiber protein, also known as L5 gene, modified versions, and/or fragment thereof.

A. Insertion Sites

In one aspect, the invention provides a recombinant adenovirus comprising a nucleotide sequence inserted in an insertion site, wherein the insertion site is located between the stop codon of a first viral transcription unit and the stop codon of a second viral transcription unit, wherein the stop codon of the first viral transcription unit is nearer to the stop codon of the second viral transcription unit than the start site of the first viral transcription unit is to the stop codon of the second viral transcription unit, wherein the stop codon of the second viral transcription is nearer to the stop codon of the first viral transcription unit than the start site of the second viral transcription unit is to the stop codon of the first viral transcription unit. In some embodiments, the first viral transcription unit and the second viral transcription unit are adjacent to each other in the adenoviral genome, e.g., there is no viral transcription unit between the first viral transcription unit and the second viral transcription unit before the nucleotide sequence is inserted.

The term "viral transcription unit" used herein refers a linear sequence of nucleotide sequence that extends from a transcription start site to a transcription stop site in the viral genome. The viral transcription unit may be naturally occurring, modified, or fragment thereof. The terms "viral transcription unit" and "virus gene" are used interchangeably herein.

In certain embodiments, the recombinant adenovirus is a human adenovirus. In some embodiments, the recombinant adenovirus is a human adenovirus type 1, 2, 3, 4, 4a, 5, 6, 7, 8, 9, 10, 11, 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, or 91. In some embodiment, the recombinant adenovirus is a type 5 adenovirus (Ad5) or a type 35 adenovirus (Ad35).

In certain embodiments, the first viral transcription unit is adenovirus IX gene and the second viral transcription unit is adenovirus IVa2 gene. In certain embodiments, the first viral transcription unit is adenovirus fiber gene and the second viral transcription unit is ORF6 or ORF6/7 of adenovirus E4 gene.

In certain embodiments, the insertion site is the IX-E2 insertion site. In certain embodiments, the IX-E2 insertion site is located between the stop codon of adenovirus IX gene and the stop codon of adenovirus IVa2 gene. In certain embodiments, the nucleotide sequence is inserted between nucleotides corresponding to 4029 and 4093 of the Ad5 genome (SEQ ID NO: 1). In certain embodiments, the nucleotide sequence is inserted between nucleotides corresponding to 4029 and 4050, nucleotides corresponding to 4051 and 4070, or nucleotides corresponding to 4071 and 4093 of the Ad5 genome (SEQ ID NO: 1). In certain embodiments, the nucleotide sequence is inserted between nucleotides corresponding to 3899 and 3970 of the Ad35 genome (SEQ ID NO: 41). In certain embodiments, the nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In some embodiments, the IX-E2 insertion site has at least 60%, at least 70%, at least 80%, at least 90%, at least 95%, or at least 99% identity to nucleotides corresponding to 4029 and 4093 of the Ad5 genome (SEQ ID NO: 1). In some embodiments, the IX-E2 insertion site has at least 60%, at least 70%, at least 80%, at least 90%, at least 95%, or at least 99% identity to nucleotides corresponding to 3899 and 3970 of the Ad35 genome (SEQ ID NO: 41).

In certain embodiments, the insertion site is an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the nucleotide sequence is inserted between nucleotides corresponding to 32785 to 32916 of the Ad5 genome (SEQ ID NO: 1). In certain embodiments, the nucleotide sequence is inserted between nucleotides corresponding to 32785 and 32800, nucleotides corresponding to 32801 and 32820, nucleotides corresponding to 32821 and 32840, nucleotides corresponding to 32841 and 32860, nucleotides corresponding to 32861 and 32880, nucleotides corresponding to 32881 and 32900, or nucleotides corresponding to 32901 and 32916 of the Ad5 genome (SEQ ID NO: 1). In certain embodiments, the nucleotide sequence is inserted between nucleotides corresponding to 31799 and 31821 of the Ad35 genome (SEQ ID NO: 41). In certain embodiments, the nucleotide sequence is inserted between nucleotides corresponding to 31799 and 32810, or nucleotides corresponding to 32810 and 31821 of the Ad35 genome (SEQ ID NO: 41).

In some embodiments, the L5-E4 insertion site has at least 60%, at least 70%, at least 80%, at least 90%, at least 95%, or at least 99% identity to nucleotides corresponding to 32785 to 32916 of the Ad5 genome (SEQ ID NO: 1). In some embodiments, the L5-E4 insertion site has at least 60%, at least 70%, at least 80%, at least 90%, at least 95%, or at least 99% identity to nucleotides corresponding to 31799 and 31821 of the Ad35 genome (SEQ ID NO: 41).

Recombinant adenoviruses with insertions of exogenous nucleotide sequence in the IX-E2 insertion site and/or the L5-E4 insertion site have not been previously described. Such recombinant adenoviruses unexpectedly show very good tumor selective expression in tumor cells compared with in normal cells. In one aspect, the invention provides a method of expressing native proteins. In another aspect, the invention provides a method of expressing native structure, such as dimeric or multimeric proteins.

In another aspect, the invention provides a method of expressing two or more therapeutic transgenes in a target cell. The method comprises exposing the cell to an effective amount of the recombinant virus described herein to express the target transgenes.

In certain embodiments, the nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence is inserted between the first polyadenylation signal and the third polyadenylation signal. In certain embodiments, wherein the second polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the fiber (L5) gene, the second polyadenylation signal is the polyadenylation signal of the transgene, and the third polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the fiber (L5) gene, the third polyadenylation signal is the polyadenylation signal of the transgene, and the fourth polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the third polyadenylation signal is the polyadenylation signal of the transgene, and the fourth polyadenylation signal is the polyadenylation signal of the adenovirus IVa2 gene.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of affecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In certain embodiments, the promoter is a ubiquitous promoter, a tissue-specific promoter, or tumor-specific promoter.

In some embodiments, the transgene is operably linked to a ubiquitous promoter, such as βAct promoter, EF1 promoter, EGR1 promoter, eIF4A1 promoter, FerH promoter, FerL promoter, GAPDH promoter, GRP78 promoter, GRP94 promoter, HSP70 promoter, β-Kin promoter, PGK-1 promoter, ROSA promoter, Ubiquitin B promoter, SV40 promoter, or CMV promoter. In one embodiment, high-level constitutive expression will be desired. Examples of useful constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g. Boshart et al, Cell, 41:521-530 (1985)), the SV40 promoter, the dihydrofolate reductase promoter, the β-actin promoter, the phosphoglycerol kinase (PGK) promoter, and the EF1α promoter (Invitrogen). Inducible promoters, regulated by exogenously supplied compounds, are also useful and include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al. Proc. Natl. Acad. Sci. USA, 93:3346-3351 (1996)), the tetracycline-repressible system (Gossen et al, Proc. Natl. Acad Sci. USA, 89:5547-5551 (1992)), the tetracycline-inducible system (Gossen et al, Science. 268: 1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Other types of inducible promoters which may be useful in this context are those which are regulated by a specific physiological state, e.g., temperature, acute phase, a particular differentiation state of the cell, or in replicating cells only.

In another embodiment, a native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter, such as B29 promoter (B cells), CD14 promoter (Monocytic cells), CD43 promoter (Leukocytes & platelets), CD45 promoter (Haematopoietic cells), CD68 promoter (Macrophages), Desmin promoter (Muscle), Elastase-1 promoter (Pancreatic acinar cells), Endoglin promoter (Endothelial cells), Endoglin promoter (Endothelial cells), Flt-1 promoter (Endothelial cells) GFAP promoter (Astrocytes), GPIIb promoter (Megakaryocytes), ICAM-2 promoter (Endothelial cells), mouse INF-β promoter (Hematopoietic cells), Mb promoter (Muscle), NphsI promoter (Podocytes), OG-2 promoter (Osteoblasts, Odonblasts), SP-B promoter (Lung), SYN1 promoter (Neurons), WASP promoter (Hematopoietic cells), SV40/bAlb promoter (Liver), or SV40/hAlb promoter (Liver). Tissue-specific promoters are active in a specific type of cells or tissues. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters (see Li et al., Nat. Biotech., 17:241-245 (1999)). Examples of promoters that are tissue-specific are known for liver (albumin, Miyatake et al. J. Virol. 71:5124-32 (1997); hepatitis B virus core promoter, Sandig et al., Gene Ther., 3:1002-9 (1996); alpha-fetoprotein (AFP). Arbuthnot et al., Hum. Gene Ther., 7:1503-14 (1996)), bone osteocalcin (Stein et al., Mol. Biol. Rep., 24:185-96 (1997)), bone sialoprotein (Chen et al., J. Bone Miner. Rep., 11:654-64 (1996)),0 lymphocytes (CD2, Hansal et al., J. Immumnol., 161:1063-8 (1998); immunoglobulin heavy chain; T cell receptor a chain), neuronal such as neuron-specific enolase (NSE) promoter (Andersen et al., Cell. Mol. Neurobiol., 13:503-15 (1993)), neurofilament light-chain gene (Piccioli et al., Proc. Natl. Acad. Sci. USA, 88:5611-5 (1991)), and the neuron-specific vgf gene (Piccioli et al., Neuron. 15:373-84 (1995)), among others.

Another embodiment of the transgene includes a transgene operably linked to a tumor-specific promoter, such as AFP promoter (Hepatocellular carcinoma), CCKAR promoter (Pancreatic cancer), CEA promoter (Epithelial cancers), c-erbB2 promoter (Breast & pancreas cancer), COX-2 promoter (Tumor), E2F-1 promoter (Tumor), HE4 promoter (Tumor), LP promoter (Tumor), MUC1 promoter (Carcinoma cells), PSA promoter (Prostate and prostate cancers), Survivin promoter (Tumor), TRP1 promoter (Melanocytes & melanoma), Tyr promoter (Melanocytes & melanoma), CXCR4 promoter (Tumor), or AFP/hAFP promoter (Hepatocellular carcinoma). Tumor-specific promoter are active specifically in tumor cells.

In certain embodiments, the nucleotide sequence further comprises a consensus Kozak sequence. In certain embodiments, the recombinant adenovirus comprises a partial or complete deletion of the nucleotide sequence encoding the adenoviral death protein (ADP).

In certain embodiments, the invention provides a recombinant adenovirus comprising a first nucleotide sequence inserted in an IX-E2 insertion site and a second nucleotide sequence inserted in an L5-E4 insertion site. These embodiments enable the adenoviruses to express two or more separate exogenous transgenes. This approach has certain advantages over adenoviruses expressing a fusion protein comprising two transgenes with a self-cleavable linker joining them because the cleaved linker may be potentially immunogenic.

In certain embodiments, the recombinant adenovirus comprises, in a 5' to 3' orientation: (i) a first polyadenylation signal; (ii) a promoter; (iii) a first nucleotide sequence comprising a first transgene; (iv) a linker; (v) a second nucleotide sequence comprising a second transgene; (vi) a second polyadenylation signal; and (vii) a third polyadenylation signal; wherein the transgene is operably linked to the promoter. In certain embodiments, wherein the second polyadenylation signal is in the opposite transcriptional direction of the third polyadenylation signal. In certain embodiments, the recombinant adenovirus comprises, in a 5' to 3' orientation: (i) a first polyadenylation signal; (ii) a second polyadenylation signal; (iii) a promoter; (iv) a first nucleotide sequence comprising a first transgene; (v) a linker; (vi) a second nucleotide sequence comprising a second transgene; (vii) a third polyadenylation signal; and (viii) a fourth polyadenylation signal; wherein the transgene is operably linked to the promoter. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

In certain embodiments, the recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E3 insertion site is located between the stop codon of adenovirus pVIII gene and the start site of adenovirus Fiber gene (L5). In certain embodiments, an E4 insertion site is located between the start codon of ORF1 to the stop codon of ORF6/7 of the adenovirus E4 gene.

In certain embodiments, the recombinant adenovirus further comprises a first nucleotide sequence inserted in the IX-E2 insertion site and a second nucleotide sequence inserted in the E1b-19K insertion site. In certain embodiments, the recombinant adenovirus further comprises a first nucleotide sequence inserted in the IX-E2 insertion site and a second nucleotide sequence inserted in the E3 insertion site. In certain embodiments, the recombinant adenovirus further comprises a first nucleotide sequence inserted in the IX-E2 insertion site and a second nucleotide sequence inserted in the E4 insertion site.

In certain embodiments, the recombinant adenovirus further comprises a first nucleotide sequence inserted in the L5-E4 insertion site and a second nucleotide sequence inserted in the E1b-19K insertion site. In certain embodiments, the recombinant adenovirus further comprises a first nucleotide sequence inserted in the L5-E4 insertion site and a second nucleotide sequence inserted in the E3 insertion site. In certain embodiments, the recombinant adenovirus further comprises a first nucleotide sequence inserted in the L5-E4 insertion site and a second nucleotide sequence inserted in the E4 insertion site.

In certain embodiments, the recombinant adenovirus further comprises a first nucleotide sequence inserted in the IX-E2 insertion site and a second nucleotide sequence inserted in the L5-E4 insertion site, and a third nucleotide sequence inserted in the E1b-19K insertion site, the E3 insertion site, or the E4 insertion site.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant virus is provided that includes an E1b-19K insertion site, e.g., the adenovirus has an exogenous nucleotide sequence inserted into an E1b-19K insertion site. In certain embodiments, the insertion site is located between the start site of E1b-19K and the stop codon of E1b-19K.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent to the start site of E1b-19K. In certain embodiments, the E1b-19K insertion site comprises a deletion of about 200 nucleotides, e.g., 202 nucleotides adjacent to the start site of E1b-19K. In certain embodiments, the E1b-19K insertion site comprises a deletion corresponding to nucleotides 1714-1917 of the Ad5 genome (SEQ ID NO: 1), or, an exogenous nucleotide sequence encoding a transgene is inserted between nucleotides corresponding to 1714 and 1917 of the Ad5 genome (SEQ ID NO: 1). In certain embodiments, an exogenous nucleotide sequence encoding a transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), an exogenous nucleotide sequence encoding a transgene, and TCACCAGG (SEQ ID NO: 2). In certain embodiments, the E1b-19K insertion site comprises a deletion corresponding to nucleotides 1611-2153 or 1611-1915 of the Ad35 genome (SEQ ID NO: 41).

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 nucleotides adjacent the start site of E1b-19K. In certain embodiments, the E1b-19K insertion site comprises a deletion corresponding to nucleotides 1714-1917 of the Ad5 genome (SEQ ID NO: 1), or the first therapeutic transgene is inserted between nucleotides corresponding to 1714 and 1917 of the Ad5 genome (SEQ ID NO: 1). In certain embodiments, the first therapeutic transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), the first therapeutic transgene, and TCACCAGG (SEQ ID NO: 2).

In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In certain embodiments, the E3 insertion site is located between the stop codon of E3-10.5K and the stop codon of E3-14.7K. In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In certain embodiments, the E3 insertion site comprises a deletion of about 1050 nucleotides adjacent the stop codon of E3-10.5K, e.g., the E3 insertion site comprises a deletion of 1063 nucleotides adjacent the stop codon of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or the second therapeutic transgene is inserted between nucleotides corresponding to 29773 and 30836 of the Ad5 genome (SEQ ID NO: 1). In certain embodiments, the E3 insertion site comprises a deletion corresponding to nucleotides 27199-30622 of the Ad35 genome (SEQ ID NO: 41).

In certain embodiments, an E4 insertion site comprises any one of the ORF of the E4 gene, i.e., between the start codon of ORF1 to the stop codon of ORF6/7. For example, a nucleotide sequence can be inserted in E4 ORF1, and/or E4 ORF2. In certain embodiments, portions of or the entire E4 region may be deleted. In certain embodiments, in any of the foregoing viruses, the recombinant adenovirus further comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 or 34083-35541 of the Ad5 genome (SEQ ID NO: 1). In certain embodiments, the E4 deletion comprises a deletion corresponding to nucleotides 33004-34422 or 31827-34415 of the Ad35 genome (SEQ ID NO: 41).

B. Modified Transcriptional Control Region

Previously developed oncolytic viruses include the oncolytic serotype 5 adenovirus (Ad5) referred to as TAV-255 in PCT Publication No. WO2010/101921 which is transcriptionally attenuated in normal cells but transcriptionally active in cancer cells. It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences. These three Pea3 and E2F deletions attenuate replication in growth-arrested, normal cells but not in malignant ones, indicating that these DNA sequences are only dispensable for transcriptional regulation and growth in cancer cells.

In certain embodiments, any of the foregoing recombinant adenoviruses comprises a modified E1a regulatory sequence. In certain embodiments, the recombinant adenovirus comprises an E1a promoter having a deletion of a functional Pea3 binding site. For example, the virus may comprise a deletion of nucleotides corresponding to about −300 to about −250 upstream of the initiation site of E1a or a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 4).

In certain embodiments, the recombinant adenovirus comprises a modified TATA box-based promoter operably linked to a gene, wherein the modified TATA box-based promoter lacks a functional TATA box and permits selective expression of the gene in a hyperproliferative cell and/or a modified CAAT box-based promoter operably linked to a gene, wherein the modified CAAT box-based promoter lacks a functional CAAT box and permits selective expression of the gene in a hyperproliferative cell.

In certain embodiments, wherein the modified TATA box-based promoter is an early gene promoter. In certain embodiments, the modified TATA box-based promoter is an E1a promoter, E1b promoter, or E4 promoter. In certain embodiments, the modified TATA box-based promoter is an E1a promoter.

In certain embodiments, the modification included in the modified TATA box-based promoter comprises a deletion of the entire TATA box. In certain embodiments, the recombinant adenovirus comprises a deletion of nucleotides corresponding to −27 to −24, −31 to −24, −44 to +54, or −146 to +54 of the E1a promoter. In certain embodiments, the deletion comprises a deletion of nucleotides corresponding to 472 to 475, 468 to 475, 455 to 552, or 353 to 552 of the Ad5 genome (SEQ ID NO: 1). In certain embodiments, the deletion comprises a deletion of nucleotides corresponding 477 to 484 of the Ad35 genome (SEQ ID NO: 41).

In certain embodiments, the recombinant adenovirus comprises a polynucleotide deletion that results in a virus comprising the sequence CTAGGACTG (SEQ ID NO: 5), AGTGCCCG (SEQ ID NO: 44) and/or TATTCCCG (SEQ ID NO: 45).

In certain embodiments, the modified CAAT box-based promoter is an early gene promoter. In certain embodiments, the modified CAAT box-based promoter is an E1a promoter, E1b promoter, or E4 promoter. In certain embodiments, the modified CAAT box-based promoter is an E1a promoter.

In certain embodiments, the modification included in the modified CAAT box-based promoter comprises a deletion of the entire CAAT box. In certain embodiments, the recombinant adenovirus comprises a deletion of nucleotides corresponding to −76 to −68 of the E1a promoter.

In certain embodiments, the recombinant adenovirus comprises a deletion of nucleotides corresponding to 423 to 431 of the Ad5 genome (SEQ ID NO: 1). In certain embodiments, the recombinant adenovirus comprises a polynucleotide deletion that results in a virus comprising the sequence TTCCGTGGCG (SEQ ID NO: 46). In certain embodiments, the recombinant adenovirus comprises a deletion of nucleotides corresponding to 477 to 484 of the Ad35 genome (SEQ ID NO: 41).

In certain embodiments, the invention provides a method of expressing two therapeutic transgenes, when expressed, produce a single polypeptide chain, which may be cleaved posttranslationally into two polypeptide chains. In certain embodiments, the recombinant adenovirus further comprises the nucleotide sequence comprises a first nucleotide sequence comprising a first transgene and a second nucleotide sequence comprising a second transgene, wherein the first nucleotide sequence and the second nucleotide sequence are separated by a linker. In certain embodiments, the linker encodes a peptide cleavable by a protease or proteases. In certain embodiments, the linker encodes an internal ribosome entry site (IRES). The IRES may, e.g., be selected from the group consisting of the encephalomyocarditis virus IRES, the foot-and-mouth disease virus IRES, and the poliovirus IRES. In certain embodiments, the nucleotide sequence is inserted in the IX-E2 insertion or the L5-E4 insertion site, wherein the recombinant adenovirus further comprise a third nucleotide sequence inserted in an E1b-19K insertion site, an E3 insertion site, or an E4 insertion site.

In certain embodiments, the virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In one embodiment, the modification of a regulatory sequence or promoter comprises a modification of sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells but attenuates expression in normal cells.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In one embodiment, at least one of these seven binding sites, or a functional binding site, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, the recombinant adenovirus comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In one embodiment, at least one Pea3 binding site, or a functional Pea3 binding site, is deleted. The deleted Pea3 binding site can be Pea3 I, Pea3 II, Pea3 III, Pea3 IV, and/or Pea3 V. In one embodiment, the deleted Pea3 binding site is Pea3 II, Pea3 III, Pea3 IV, and/or Pea3 V. In another embodiment, the deleted Pea3 binding site is Pea3 IV and/or Pea3 V. In another embodiment, the deleted Pea3 binding site is Pea3 II and/or Pea3 III. In another embodiment, the deleted Pea3 binding site is both Pea3 II and Pea3 III. In another embodiment, the Pea3 I binding site, or a functional Pea3 I binding site, is retained.

In one embodiment, at least one E2F binding site, or a functional E2F binding site, is deleted. In another embodiment, at least one E2F binding site, or a functional E2F binding site, is retained. In one embodiment, the retained E2F binding site is E2F I and/or E2F II. In another embodiment, the retained E2F binding site is E2F II. In another embodiment, the total deletion consists essentially of one or more of Pea3 II, Pea3 III, Pea3 IV, and/or Pea3 V. In one embodiment, the virus has a deletion of a 50 base pair region located from −305 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 4).

In one embodiment, the recombinant adenovirus has the same or similar E1a modification as in the oncolytic serotype 5 adenovirus (Ad5) called TAV-255 described in PCT Publication No. WO2010101921 and US Publication No. 20160017294A1, each of which is incorporated by reference herein in its entirety. It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences. These three Pea3 and E2F deletions attenuate replication in growth-arrested, normal cells but not in malignant ones, indicating that these DNA sequences are only dispensable for transcriptional regulation and growth in cancer cells.

In certain embodiments, the recombinant adenovirus comprises an E1a promoter having one or more deletions of a functional Pea3 binding site. In certain embodiments, the deletion comprises a deletion of nucleotides corresponding to about −300 to about −250 upstream of the initiation site of E1a. In certain embodiments, wherein the deletion comprises a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1). In certain embodiments, the E1a promoter comprises the sequence GGTGTTTTGG (SEQ ID NO: 4).

In one embodiment, the recombinant adenovirus comprises one or more Pea3 transcription binding site deletions without one or more E2F transcription binding site deletions in the E1A region. In other embodiment, the recombinant adenovirus comprises one or more E2F transcription binding site deletions without one or more Pea3 transcription binding site deletions in the E1A region.

In certain embodiments, the recombinant oncolytic adenovirus comprises a modified TATA box-based promoter operably linked to a gene, wherein the modified TATA box-based promoter lacks a functional TATA box and permits selective expression of the gene in a hyperproliferative and/or non-growth arrested cell. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

As used herein, a "modified TATA box" refers to a TATA box that has a deletion, substitution, or addition of one or more nucleotides relative to a wild-type TATA box sequence.

For example, the virus may comprise a deletion of nucleotides corresponding to −29 to −26, −33 to −26, −44 to +52, or −148 to +52 upstream of the initiation site of E1a. In certain embodiments, the deletion comprises a deletion of nucleotides corresponding to 353-552 of the Ad5 genome (SEQ ID NO: 1). In certain embodiments, the TATA box deletion results in an E1a promoter that comprises the sequence CTAGGACTG (SEQ ID NO: 5), AGTGCCCG (SEQ ID NO: 44) and/or TATTCCCG (SEQ ID NO: 45).

In certain embodiments, the recombinant oncolytic adenovirus comprises a modified CAAT box-based promoter operably linked to a gene, wherein the modified CAAT box-based promoter lacks a functional CAAT box and permits selective expression of the gene in a hyperproliferative cell and/or non-growth arrested. The TATA box-based promoter and the CAAT box-based promoter may be the same promoter (e.g., the Ad5 E1a promoter), or may be different promoters.

As used herein, "CAAT box" refers to a nucleotide sequence that is capable of binding to a C/EBP or NF-Y protein. A CAAT box typically comprises a consensus sequence of GG(T/C)CAATCT.

As used herein, a "modified CAAT box" refers to a CAAT box that has a deletion, substitution, or addition of one or more nucleotides relative to a wild-type CAAT box sequence.

As used herein, a "functional CAAT box" refers to a CAAT box that is capable of binding to a C/EBP or NF-Y protein, e.g., a CAAT box that has at least 100%, at least 90%, at least 80%, at least 70%, at least 60%, at least 50%, or at least 40%, of the a C/EBP or NF-Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF-Y binding activity of a corresponding wild-type CAAT box sequence. Assays for determining whether a C/EBP or NF-Y protein binds to a CAAT box are known in the art. Exemplary binding assays include electrophoretic mobility shift assays, chromatin immunoprecipitation assays, and DNAse footprinting assays.

As used herein, "CAAT box-based promoter" refers to any gene promoter that contains a CAAT box.

As used herein, a "modified CAAT box-based promoter" refers to a CAAT box-based promoter that has been modified by a deletion, substitution, or addition of one or more nucleotides relative to a wild-type CAAT box-based promoter. In certain embodiments, the modification included in the modified CAAT box-based promoter comprises a deletion of one or more nucleotides of the wild-type CAAT box-based promoter sequence. In certain embodiments, the modification included in the modified CAAT box-based promoter consists of a deletion of one or more nucleotides of the wild-type CAAT box-based promoter sequence. In certain embodiments, the modification included in the modified CAAT box-based promoter comprises a deletion of the entire CAAT box of the wild-type CAAT box-based promoter sequence. In certain embodiments, the modification included in the modified CAAT box-based promoter consists of a deletion of the entire CAAT box of the wild-type CAAT box-based promoter sequence. In certain embodiments, the modification included in the modified CAAT box-based promoter comprises a deletion of the entire CAAT box-based promoter. In certain embodiments, the modification included in the modified CAAT box-based promoter consists of a deletion of the entire CAAT box-based promoter. In certain embodiments, the modification included in the modified CAAT box-based promoter does not comprise an addition of or a substitution with a separate, functional promoter sequence.

Nucleic acids encoding viral genes can be incorporated into plasmids and introduced into host cells through conventional transfection or transformation techniques. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome). Alternative technologies for the generation of adenovirus include utilization of the bacterial artificial chromosome (BAC) system, in vivo bacterial recombination in a recA+ bacterial strain utilizing two plasmids containing complementary adenoviral sequences, and the yeast artificial chromosome (YAC) system.

In certain embodiments, a recombinant adenovirus of the invention is an oncolytic virus, e.g., a virus that exhibits tumor-selective replication and/or viral mediated lysis. In certain embodiments, a recombinant adenovirus of the invention exhibits selective expression of a therapeutic transgene in a hyperproliferative cell, e.g., a cancer cell, a tumor cell, relative to a non-hyperproliferative cell. In certain embodiments, the expression of a therapeutic transgene in a non-hyperproliferative cell is about 90%, about 80%, about 70%, about 60%, about 50%, about 40%, about 30%, about 20%, about 10%, or about 5% of the expression of the gene in the hyperproliferative cell. In certain embodiments, the virus exhibits no detectable expression of a therapeutic transgene in a non-hyperproliferative cell. Therapeutic transgene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

C. Transgenes

The recombinant adenovirus disclosed herein comprise one or more exogenous nucleotide sequences inserted in any of the foregoing insertion sites, e.g., an IX-E2 insertion site, an L5-E4 insertion site, an E1b-19K insertion site, an E3 insertion site, or an E4 insertion site.

In certain embodiments, the nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence is inserted between the first polyadenylation signal and the third polyadenylation signal. In certain embodiments, wherein the second polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the L5 transcription unit, the second polyadenylation signal is the polyadenylation signal of the transgene, and the third polyadenylation signal is the polyadenylation signal of the E4 transcription unit. In certain embodiments, the nucleotide sequence is inserted in the IX-E2 insertion site, and the first polyadenylation signal is the polyadenylation signal of the IX transcription unit, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the L5 transcription unit, the third polyadenylation signal is the polyadenylation signal of the transgene, and the fourth polyadenylation signal is the polyadenylation signal of the E4 transcription unit. In certain embodiments, the nucleotide sequence is inserted in the IX-E2 insertion site, and the first polyadenylation signal is the polyadenylation signal of the IX transcription unit, the third polyadenylation signal is the polyadenylation signal of the transgene, and the fourth polyadenylation signal is the polyadenylation signal of the adenovirus IVa2 gene.

In certain embodiments, the recombinant adenovirus further comprises the nucleotide sequence comprises a first nucleotide sequence comprising a first transgene and a second nucleotide sequence comprising a second transgene, wherein the first nucleotide sequence and the second nucleotide sequence are separated by a linker.

In certain embodiments, the nucleotide sequence comprises, in a 5' to 3' orientation: (i) a first polyadenylation signal; (ii) a promoter; (iii) a first nucleotide sequence comprising a first transgene; (iv) a linker; (v) a second nucleotide sequence comprising a second transgene; (vi) a second polyadenylation signal; and (vii) a third polyadenylation signal; wherein the transgene is operably linked to the promoter. In certain embodiments, wherein the second polyadenylation signal is in the opposite transcriptional direction of the third polyadenylation signal. In certain embodiments, the nucleotide sequence comprises, in a 5' to 3' orientation: (i) a first polyadenylation signal; (ii) a second polyadenylation signal; (iii) a promoter; (iv) a first nucleotide sequence comprising a first transgene; (v) a linker; (vi) a second nucleotide sequence comprising a second transgene; (vii) a third polyadenylation signal; and (viii) a fourth polyadenylation signal; wherein the transgene is operably linked to the promoter. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the linker encodes a peptide cleavable by a protease or proteases. In certain embodiments, the linker encodes internal ribosome entry site (IRES) or a self-cleaving 2A peptide. The IRES may, e.g., be selected from the group consisting of the encephalomyocarditis virus IRES, the foot-and-mouth disease virus IRES, and the poliovirus IRES. In certain embodiments, wherein the nucleotide sequence is inserted in the IX-E2 insertion or the L5-E4 insertion site, wherein the recombinant adenovirus further comprise a third nucleotide sequence inserted in an E1b-19K insertion site, an E3 insertion site, or an E4 insertion site.

In certain embodiments, one or more of the nucleotide sequence, the first nucleotide sequence, the second nucleotide sequence, and the third nucleotide sequence comprises one or more transgenes.

In certain embodiments, one or more of the nucleotide sequence, the first nucleotide sequence, the second nucleotide sequence, and the third nucleotide sequence comprises:
  a) a transcriptional initiation region;
  b) a nucleotide sequence comprising a transgene, wherein the transgene is under transcriptional control of the transcriptional initiation region; and
  c) a transcriptional termination region.

In some embodiments, the transcriptional initiation region comprises a promoter.

In certain embodiments, one or more of the transgenes, the first transgene, and the second transgene encodes a monomeric, dimeric, trimeric, tetrameric, or multimeric protein, or a part thereof. In certain embodiments, one or more of the transgene, the first transgene, and the second transgene encodes a RNA that has a therapeutic activity. In certain embodiments, one or more of the transgene, the first transgene, and the second transgene encodes a fusion protein comprising at least one binding domain.

In certain embodiments, one or more of the transgene, the first transgene, and the second transgene encodes an immunomodulatory molecule. In certain embodiments, the immunomodulatory molecule is a costimulatory ligand, a cytokine, or a cytokine receptor. In certain embodiments, the immunomodulatory molecule is selected from the group consisting of IL-1, IL-2, IL-3, IL-4, IL-5, IL-6, IL-7, IL-8, IL-9, IL-7, IL-10, IL-10 trap, IL-10R, IL-12A/p35, IL-12B/p40, IL-15, IL-23A/p19, IL-24, IL-27, IL-33, IL-35, IL-15, an IL-15 receptor fusion protein, TGF-β, a TGF-β trap, an IL-10 trap, VEGF, VEGF trap, indoleamin-2,3-dioxygenase (IDO), inducible T-cell co-stimulator ligand (ICOS-L), CD80, CD137L, TNF-α, IFN-α, IFN-β, IFN-γ, GM-CSF, GITR ligand (GITRL), OX40 ligand (OX40L), CD40 ligand (CD40L)/CD154, CD70, CD86, CD137, CD137L, BORIS/CTCFL, bone morphogenetic protein (BMP), TNFSF9, FGF, ICAM, Podocalyxin, functional fragments thereof, and derivatives thereof.

In certain embodiments, the transgene encodes a fusion protein that comprise, in an N- to C-terminal orientation: a soluble portion of an extracellular domain of a cytokine receptor; an amino acid linker; an immunoglobulin (Ig) hinge region; and an immunoglobulin (Ig) Fc domain. In some embodiments, the cytokine receptor is TGFβ type II (TβRII) receptor.

In certain embodiments, a nucleotide sequence encoding CD80 or a functional fragment thereof is inserted in the IX-E2 insertion site, and a nucleotide sequence encoding CD137L or a functional fragment thereof is inserted in the L5-E4 insertion site. In certain embodiments, a nucleotide sequence encoding CD137L or a functional fragment thereof is inserted in the IX-E2 insertion site, and a nucleotide sequence encoding CD80 or a functional fragment thereof is inserted in the L5-E4 insertion site.

In certain embodiments, the recombinant adenovirus comprises a nucleotide sequence encoding IL-12A/p35 or a functional fragment thereof, a nucleotide sequence encoding IL-12B/p40 or a functional fragment thereof, and a nucleotide sequence encoding IFN-α or a functional fragment thereof. These nucleotide sequences may be inserted in the IX-E2 insertion site, the L5-E4 insertion site, the E1b-19K insertion site, the E3 insertion site, and/or the E4 insertion site.

In certain embodiments, one or more of the transgenes, the first transgene, and/or the second transgene encodes an antigen-binding molecule. In certain embodiments, the antigen-binding molecule is an anti-PD-1 antibody, an anti-TGF-β antibody, an anti-PD-L1 antibody, and an anti-CTLA-4 antibody, or functional fragments thereof. Exemplary anti-PD-1 antibodies include nivolumab (Bristol-Myers Squibb Co.), pembrolizumab (KEYTRUDA®, Merck & Co.) and Atezolizumab (formerly MPDL3280A), MEDI4736, Avelumab, and PDR001.

In certain embodiments, one or more of the transgenes, the first transgene, and the second transgene encodes an antigen or a ligand to the antigen. In certain embodiments, the antigen is selected from the group consisting of CAIX, CEA, CD5, CD7, CD10, CD19, CD20, CD22, CD30, CD33, CD34, CD38, CD41, CD44, CD49f, CD56, CD74, CD80, CD133, CD135 (Flt3), Flt3I, CD138, a cytomegalovirus (CMV) infected cell antigen, 4-1BB, EGP-2, EGP-40, EpCAM, erbB2, erbB3, erbB4, FBP, Fetal acetylcholine receptor, KRAS, HPV E6, E7, BING-4, EphA3, calcium activated chloride channel-2, cyclin B1, 9D7, SAP-1, PRAME, SSX-2, immature laminin receptor, folate receptor-a, telomerase, tyrosinase, melan-A, NY-ESO-1, GD2, GD3, hTERT, IL13R-a2, x-light chain, KDR, LeY, LI cell adhesion molecule, MAGE-A1, MAGE-A3, MART1, MART2, MUC1, Mesothelin, HER-2/neu, EGFRvIII, NKG2D ligands, NY-ES0-1, gp100, TRP-1/-2, TRP-1/-2, P polypeptide, MC1R, prostate specific antigen, BRAF, androgen-receptor, β-catenin, BRCA1/2, CDK4, CML66, fibronectin, p53, TGF-βRII, T cell receptor, oncofetal antigen, 5T4, PSCA, PSMA, ROR1, TAG-72, VEGF-R2, WT-1, functional fragments thereof, and derivatives thereof.

In certain embodiments, one or more of the transgene, the first transgene, and the second transgene encodes a toxin. In certain embodiments, the toxin is *pseudomonas* exotoxin, ricin toxin, or diphtheria toxin.

In certain embodiments, one or more of the transgene, the first transgene, and the second transgene encodes an enzyme. In certain embodiments, the enzyme is selected from the group consisting of beta-glucuronidase, beta-galactosidase, beta-glucosidase, carboxypeptidase, beta-lactamase, esterase, metalloproteinase, relaxin, collagenase, streptokinase, arginase, NOS-2, fragments thereof, and derivatives thereof.

In certain embodiments, one or more of the transgene, the first transgene, and the second transgene encodes a cell cycle control agent, a growth factor, an anticoagulant, a pro-drug activating gene, a tumor suppressor gene, an apoptotic gene, an anti-platelet agent, a clotting factor, a cystic fibrosis transmembrane conductance regulator (CFTR) protein, fragments thereof, or derivatives thereof.

In certain embodiments, one or more of the transgene, the first transgene, and the second transgene encodes angiostatin, endostatin, acetylcholine, DKK1/Wnt, Ox40L, GITRL, secreted flagellin, thymidine kinase, functional fragments thereof, or derivatives thereof.

II. Methods of Treatment

In another aspect, the invention provides a method of inhibiting proliferation of a tumor cell comprising exposing the tumor cell to an effective amount of any of the foregoing recombinant adenoviruses to inhibit proliferation of the tumor cell.

In another aspect, the invention provides a method of inhibiting tumor growth in a subject in need thereof, wherein the method comprising administering to the subject to an effective amount of any of the foregoing recombinant adenoviruses to inhibit tumor growth. In some embodiments, the tumor is a HER2/neu positive tumor, and wherein the recombinant adenovirus comprises an E1a promoter having no more than one deletion of a functional Pea3 binding site. In some embodiments, the HER2/neu positive tumor is from breast cancer, gastric cancer, ovarian cancer, bladder cancer, salivary gland cancer, endometrial cancer, pancreatic cancer, or non-small-cell lung cancer (NSCLC).

In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

The recombinant adenoviruses disclosed herein can be can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

In one aspect, the invention provides a method of treating a hyperproliferative disease, in a subject. The method comprises administering to the subject an effective amount of a recombinant virus described herein to treat the hyperproliferative disease in the subject. In certain embodiments, the hyperproliferative disease is selected from the group consisting of cancer, atherosclerosis, rheumatoid arthritis, psoriasis, lupus, idiopathic pulmonary fibrosis, scleroderma and cirrhosis. In certain embodiments, the hyperproliferative disease is cancer.

In some embodiments, the invention provides a method of treating cancer in a subject. The method comprises administering to the subject an effective amount of a recombinant adenoviruses described herein to treat the cancer disease in the subject.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, and pancreatic cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In some aspects, the invention provides a method of inhibiting proliferation of a tumor cell comprising exposing the tumor cell to an effective amount of any of the foregoing recombinant adenoviruses.

In another aspect, the invention provides a method of inhibiting tumor growth in a subject in need thereof, wherein the method comprising administering to the subject to an effective amount of any of the foregoing recombinant adenoviruses. In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

In another aspect, the invention provides a method of treating a disease or condition in a subject in need thereof, wherein the method comprising administering to the subject to an effective amount of any of the foregoing recombinant adenoviruses. In certain embodiments, the disease or condition is selected from the group consisting of an infection, diabetic retinopathy, psoriasis, rheumatoid arthritis, endometriosis, macular degenerative disorders and benign growth disorders such as prostate enlargement and lipomas, a vascular disorder, a cardiovascular disease, an infection, cirrhosis of the liver, a connective tissue disorder, a tumor, a vascular lesion, an ulcerative lesion, an inflammation, thrombosis, and neointima formation.

In certain embodiments, the subject is a mammal. In certain embodiments, the subject is a human. In certain embodiments, the subject is a pediatric human. In certain embodiments, the subject is an adult human.

In certain embodiments, the recombinant adenovirus is administered by intramuscular, intravenous, intraarterial, or intratumoral injection. In certain embodiments, the recombinant adenovirus is administered by intradermal, inhalation, transdermal, topical, eye drops, intranasal, transmucosal, and rectal administration.

In certain embodiments, the foregoing recombinant adenoviruses are administered to the subject in combination with one or more therapies selected from the group consisting of surgery, radiation, chemotherapy, immunotherapy, hormone therapy, and virotherapy.

In certain embodiments, the recombinant adenoviruses of the invention are administered in combination with a tyrosine kinase inhibitor, e.g., erlotinib.

In certain embodiments, the recombinant adenoviruses of the invention are administered in combination with one or more immune checkpoint modulators. In certain embodiments, the immune checkpoint modulator is an inhibitor, an antagonist, or an agonist of one or more molecules selected from the group consisting of PD-1, PD-L1, PD-L2, 2B4, TIGIT, LAG3, Tim3, BTLA, CD160, GITR, KIR, 4-1BB, and CTLA4. In some embodiments the immune checkpoint modulators are antibodies to PD-1, PD-L1, PD-L2, 2B4, TIGIT, LAG3, Tim3, BTLA, CD160, GITR, KIR, 4-1BB, and/or CTLA4. Exemplary anti-PD-1 antibodies include nivolumab (Bristol-Myers Squibb Co.), pembrolizumab (KEYTRUDA®, Merck & Co.) and Atezolizumab (formerly MPDL3280A), MEDI4736, Avelumab, and PDR001.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant virus of the present invention) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of a recombinant virus is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the virus, and the disease being treated. Exemplary dosing frequencies are once per day, once per week and once every two weeks. One route of administration is parenteral, e.g., intravenous infusion. Formulation of virus-based drugs is within ordinary skill in the art. In certain embodiments, a recombinant virus is lyophilized, and then reconstituted in buffered saline, at the time of administration.

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

III. Pharmaceutical Composition/Formulation

The present disclosure also provides a pharmaceutical composition comprising any of the foregoing recombinant adenoviruses and at least one pharmaceutically acceptable carrier or diluent. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration.

Pharmaceutical compositions and formulations containing the recombinant adenoviruses disclosed herein can be formulated to be compatible with its intended route of administration. Examples of routes of administration are intramuscular, intravenous, intraarterial, or intratumoral intradermal, inhalation, transdermal, topical, transmucosal, and rectal administration.

In one aspect, the present disclosure provides an adenovirus formulation for the stabilization and storage of recombinant adenoviruses. In some embodiments, the invention provides a formulation for adenoviruses comprising:

e) one or more of any of the foregoing recombinant adenoviruses;

f) at least one buffer;

g) at least one tonicity modifier;

h) at least one sugar or at least one stabilizing agent, or both; and wherein the formulation has a pH ranging between about 7.0 and about 9.0.

In certain embodiments, the stabilizing agent is glycerol. In certain embodiments, the stabilizing agent is at about 2% to about 5% (v/v).

In certain embodiments, the buffer is Tris (includes Tris-HCl and/or mono-Tris), TES, HEPES, brucine tetrahydrate, EPPS, tricine, or histidine. In certain embodiments, the buffer is at concentration of about 1 mM to about 30 mM.

In some embodiments, the tonicity modifier is $MgCl_2$, $MnCl_2$, $CaCl_2$, $ZnCl_2$, NaCl, or KCl. In one embodiment, the tonicity modifier is NaCl. In one embodiment, the tonicity modifier is at concentration of about 0.1 mM to about 5 mM. In one embodiment, the tonicity modifier is at concentration of about 10 mM to about 250 mM. In one embodiment, the tonicity modifier is at concentration of about 25 mM to about 100 mM. In one embodiment, the tonicity modifier is at concentration of about 25 mM.

In certain embodiments, the formulation comprises a first tonicity modifier and a second tonicity modifier, wherein the first tonicity modifier is a monovalent cation, and wherein the second tonicity modifier is a divalent cation. In certain embodiments, the monovalent cation is NaCl or KCl. In certain embodiments, the divalent cation is $MgCl_2$, $MnCl_2$, $CaCl_2$, or $ZnCl_2$. In certain embodiments, the tonicity modifier or the divalent cation is at a concentration of about 0.1 mM to about 5 mM.

In some embodiments, the sugar is sucrose or trehalose. In one embodiment, the sugar is sucrose. In one embodiment, the sugar is at weight to volume percentage from about 2% to about 8%. In one embodiment, the sugar is at weight to volume percentage from about 3% to about 5%. In one embodiment, the sugar is at weight to volume percentage of about 5%.

In certain embodiments, any of the foregoing formulations further comprise at least one non-ionic surfactant. In certain embodiments, the non-ionic surfactant is polysorbate-80 or polysorbate-40. In one embodiment, the non-ionic surfactant is at a concentration of about 0.001% to about 1%. In one embodiment, the non-ionic surfactant is at a concentration of about 0.02%.

In certain embodiments, any of the foregoing formulations further comprise at least one inhibitor of free radical oxidation. In certain embodiments, the inhibitor of free radical oxidation is EDTA. In one embodiment, the inhibitor of free radical oxidation is at a concentration of about 0.01 mM to about 5 mM. In one embodiment, the inhibitor of free radical oxidation is at a concentration of about 0.05 mM to about 2 mM. In one embodiment, the inhibitor of free radical oxidation is at a concentration of about 0.1 mM.

In certain embodiments, any of the foregoing formulations further comprise at least one cryoprotectant. In certain embodiments, the cryoprotectant is EtOH. In some embodiments, the cryoprotectant is a concentration of about 0.01% to 5%. In some embodiments, the cryoprotectant is a concentration of about 0.1% to 2%. In one embodiment, the cryoprotectant is at a concentration of about 0.5%.

In some embodiments, the formulation has an osmolarity of about 200 mOs/L to about 800 mOs/L. In some embodiments, the formulation has an osmolarity of about 300 mOs/L to about 600 mOs/L. In some embodiments, the formulation has an osmolarity of about 400 mOs/L to about 500 mOs/L.

In certain embodiments, the recombinant oncolytic adenovirus in any of the foregoing formulations is at concentration from about $1 \times 10^7$ vp/mL to $1 \times 10^{13}$ vp/mL.

In certain embodiments, the formulation comprises about 20 mM Tris, about 25 mM NaCl, about 2.5% glycerol, and wherein the formulation has a pH of about 8.0. In certain embodiments, the formulation comprises about 20 mM Tris, about 25 mM NaCl, about 3-5% sucrose, and wherein the formulation has a pH of about 8.0. In certain embodiments, the formulation comprises about 10 mM Tris, about 75 mM NaCl, about 5% sucrose, about 0.02% polysorbate-80, about 1 mM MgCl2, about 0.1 mM EDTA, about 0.5% EtOH, and wherein the formulation has a pH of about 8.0.

In certain embodiments, any of the foregoing formulations further comprise at least one immunoadjuvant. In certain embodiments, the immunoadjuvant is selected from 1) Alum, 2) Saponins, 3) non-ionic polymer surfactants, 4) monophosphoryl lipid A, 5) muramyl dipeptides, and 6) cytokines.

In certain embodiments, any of the foregoing formulations further comprise at least one dye. In certain embodiments, any of the foregoing formulations further comprise at least one reversible protease inhibitor. In certain embodiments, the reversible protease inhibitor is an inhibitor of an L3/p23 cysteine protease. In certain embodiments, any of the foregoing formulations further comprise an antioxidant. In certain embodiments, the antioxidant is vitamin A, vitamin C, vitamin E, vitamin B6, vitamin B12, folic acid, or folate.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following working examples are illustrative and are not intended to be limiting and it will be readily understood by one of skill in the art that other embodiments may be utilized.

Example 1

The nucleotide sequence of an exemplary IX-E2 insertion site (nucleotide 4029 to 4093 numbering according to NCBI Reference Sequence AC_000008.1 (SEQ ID NO: 1)) is as follows. The stop codon of adenovirus IX gene ("TAA" on left; SEQ ID NO: 8) and the stop codon of adenovirus IVa2 gene ("TTA" on the right; SEQ ID NO: 9) are underlined.

```
                                         (SEQ ID NO: 6)
TAAAACATAAATAAAAAACCAGACTCTGTTTGGATTTGGATCAAGCAAGT

GTCTTGCTGTCTTTA
```

Example 2

The nucleotide sequence of an exemplary L5-E4 insertion site (nucleotide 32785 to 32916 numbering according to NCBI Reference Sequence AC_000008.1 (SEQ ID NO: 1)) is as follows. The stop codon of adenovirus fiber gene ("TAA" on left; SEQ ID NO: 8) and the stop codon of ORF6/7 of adenovirus E4 gene ("TCA" on the right; SEQ ID NO: 10) are underlined.

```
                                         (SEQ ID NO: 7)
TAAAGAATCGTTTGTGTTATGTTTCAACGTGTTTATTTTTCAATTGCAGA

AAATTTCAAGTCATTTTTCATTCAGTAGTATAGCCCCACCACCACATAGC

TTATACAGATCACCGTACCTTAATCAAACTCA
```

Example 3

To generate viruses with transgenes cloned into an expression cassette in the L5-E4 site, a plasmid with adenoviral nucleotide sequence (which contained deletions of the RIDα, RIDβ, and 14.7k genes in the E3 region and the ORF1-ORF4 genes in the E4 region) was modified by inserting into the L5-E4 site an expression cassette with the SV40 promoter and terminator with an intervening SwaI restriction site ("ATTTAAAT" SEQ ID NO: 11). The nucleotide sequence of this modification, from the polyadenylation signal of the L5 transcription unit ("AATAAA" SEQ ID NO: 12) to the polyadenylation signal of the E4 transcription unit ("TTTATT" SEQ ID NO: 13) is:

SEQ ID NO: 14
[L5 initial Empty]
AATAAAGAATCGTTTGTGTTATGTTTCAACCTGTGGAATGTGTGTCAGTT

AGGGTGTGGAAAGTCCCCAGGCTCCCCAGCAGGCAGAAGTATGCAAAGCA

TGCATCTCAATTAGTCAGCAACCAGGTGTGGAAAGTCCCCAGGCTCCCCA

GCAGGCAGAAGTATGCAAAGCATGCATCTCAATTAGTCAGCAACCATAGT

CCCGCCCCTAACTCCGCCCATCCCGCCCCTAACTCCGCCCAGTTCCGCCC

ATTCTCCGCCCCATGGCTGACTAATTTTTTTATTTATGCAGAGGCCGAG

GCCGCCTCTGCCTCTGAGCTATTCCAGAAGTAGTGAGGAGGCTTTTTTGG

AGGCCTAGGCTTTTGCAAAAAGCTTTGCAAAGATTTAAATAACTTGTTTA

TTGCAGCTTATAATGGTTACAAATAAAGCAATAGCATCACAAATTTCACA

AATAAAGCATTTTTTTCACTGCATTCTAGTTGTGGTTTGTCCAAACTCAT

CAATGTATCTTATCATGTCTGGTGTTTATT

In SEQ ID NO: 14, the polyadenylation signals of the L5 and E4 transcription units, and the nucleotides of the SwaI restriction site, are underlined.

A transgene encoding the mouse GMCSF was then cloned into the SwaI site, generating the sequence:

SEQ ID NO: 15
[L5 initial mGMCSF]
AATAAAGAATCGTTTGTGTTATGTTTCAACCTGTGGAATGTGTGTCAGTT

AGGGTGTGGAAAGTCCCCAGGCTCCCCAGCAGGCAGAAGTATGCAAAGCA

TGCATCTCAATTAGTCAGCAACCAGGTGTGGAAAGTCCCCAGGCTCCCCA

GCAGGCAGAAGTATGCAAAGCATGCATCTCAATTAGTCAGCAACCATAGT

CCCGCCCCTAACTCCGCCCATCCCGCCCCTAACTCCGCCCAGTTCCGCCC

ATTCTCCGCCCCATGGCTGACTAATTTTTTTATTTATGCAGAGGCCGAG

GCCGCCTCTGCCTCTGAGCTATTCCAGAAGTAGTGAGGAGGCTTTTTTGG

AGGCCTAGGCTTTTGCAAAAAGCTTTGCAAAGATTTATGTGGCTGCAGAA

CCTGCTGTTCCTGGGCATCGTGGTGTACAGCCTGAGCGCCCCCACCAGAT

CCCCCATCACCGTGACCAGACCCTGGAAGCACGTGGAAGCCATCAAAGAG

GCCCTGAACCTGCTGGACGACATGCCCGTGACCCTGAACGAAGAGGTGGA

AGTGGTGTCCAACGAGTTCAGCTTCAAGAAACTGACCTGCGTGCAGACCA

GACTGAAGATCTTCGAGCAGGGCCTGAGAGGCAACTTCACCAAGCTGAAG

GGCGCTCTGAACATGACCGCCAGCTACTACCAGACCTACTGCCCTCCCAC

ACCCGAGACAGACTGCGAGACACAGGTCACAACCTACGCCGACTTCATCG

ACAGCCTGAAAACCTTCCTGACCGACATCCCCTTCGAGTGCAAGAAACCC

GGCCAGAAGTGAAAATAACTTGTTTATTGCAGCTTATAATGGTTACAAAT

AAAGCAATAGCATCACAAATTTCACAAATAAAGCATTTTTTTCACTGCAT

TCTAGTTGTGGTTTGTCCAAACTCATCAATGTATCTTATCATGTCTGGTG

TTTATT

In SEQ ID NO: 15, the polyadenylation signals of the L5 and E4 transcription units, and the residual nucleotides of the SwaI restriction site are underlined, and the transgene encoding the mouse GMCSF are bolded.

The virus TAV-(L5-E4)mGMCSF was generated to carry the following modifications (compared to the dl309 strain of adenovirus type 5): the TAV-255 deletion in the E1A promoter to confer selective replication in cancerous cells, a deletion of the 5' end of the viral E1B-19K gene which does not extend into the viral E1B-55K gene, a deletion of the E3 RIDα, RIDβ, and 14.7k genes, the sequence of SEQ ID NO: 15, and a deletion of the E4 ORF1-ORF4 genes.

Figure 2:
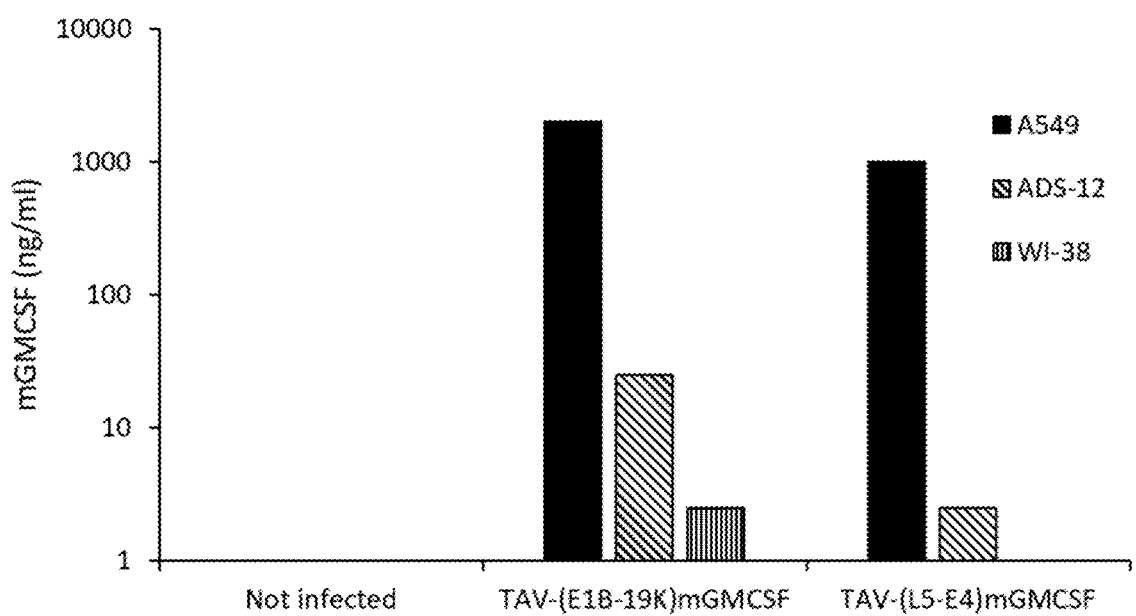
FIG. 2 depicts the mouse GMCSF expression level from A549, ADS-12, and WI-38 cells infected with the virus TAV-(E1B-19K)mGMCSF or TAV-(L5-E4)mGMCSF or kept as non-infected controls. Mouse GMCSF expression was measured in their conditioned media.

To test for mGMCSF expression: A549 cells (human cancer cell line), ADS-12 cells (mouse cancer cell line), and WI38 cells (human normal cell line) were infected with TAV-(L5-E4)mGMCSF at an MOI (multiplicity of infection) of 5. As a control, additional cells were cultured without infection or were infected with the virus TAV-(E1B-19K)mGMCSF which carries the following modifications compared to the dl309 strain of adenovirus type 5: the TAV-255 deletion in the E1A promoter, and the mGMCSF gene replacing the 5' end of the E1B-19K gene without disrupting the E1B-55K gene. Four days after infection, the conditioned media was used in an ELISA to measure mouse GMCSF expression. Results are shown in FIG. 2: both viruses gave high levels of expression in A549 cells, moderate expression in ADS-12 cells, and low levels of expression in WI38 cells.

Example 4

To investigate an expression cassette insertion at the IX-E2 site, initially, we inserted an expression cassette with the cytomegalovirus immediate early promoter (CMV promoter) and the transcription terminator of bovine growth hormone (BGH terminator) including a NotI restriction site ("GCGGCCGC" SEQ ID NO: 16) between the promoter and terminator to facilitate insertion of a transgene. Its nucleotide sequence from the polyadenylation signal of IX ("AATAAA" SEQ ID NO: 12) to the polyadenylation signal of the E2 transcription unit ("TTTATT" SEQ ID NO: 13) is:

SEQ ID NO: 17
[IX initial Empty]
AATAAAAAACCAGACTCTGTTTGGATTTGGATCAAGCAAGTGTCTTGCTG

TCTTACGGTAAATGGCCCGCCTGGCTGACCGCCCAACGACCCCCGCCCAT

TGACGTCAATAATGACGTATGTTCCCATAGTAACGCCAATAGGGACTTTC

CATTGACGTCAATGGGTGGAGTATTTACGGTAAACTGCCCACTTGGCAGT

ACATCAAGTGTATCATATGCCAAGTACGCCCCCTATTGACGTCAATGACG

GTAAATGGCCCGCCTGGCATTATGCCCAGTACATGACCTTATGGGACTTT

CCTACTTGGCAGTACATCTACGTATTAGTCATCGCTATTACCATGGTGAT

```
GCGGTTTTGGCAGTACATCAATGGGCGTGGATAGCGGTTTGACTCACGGG

GATTTCCAAGTCTCCACCCCATTGACGTCAATGGGAGTTTGTTTTGGCAC

CAAAATCAACGGGACTTTCCAAAATGTCGTAACAACTCCGCCCCATTGAC

GCAAATGGGCGGTAGGCGTGTACGGTGGGAGGTCTATATAAGCAGAGCTC

TCTGGCTAACTAGAGAACCCACTGCTTACTGGCTTATCGAAATTAATACG

ACTCACTATAGGGAGACCCGCGGCCGCCTGTGCCTTCTAGTTGCCAGCCA

TCTGTTGTTTGCCCCTCCCCCGTGCCTTCCTTGACCCTGGAAGGTGCCAC

TCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGG

GAGGATTGGGAAGACAATAGCAGGCATGCTGGGGATGCGGTGGGCTCTAT

GGTTTATT
```

The polyadenylation signals of the IX and E2 transcripts, and the NotI restriction site, are underlined.

The virus TAV IX-WT L5-Empty carried the TAV-255 deletion in the E1A promoter, wild-type viral sequence in the IX-E2 site, and the sequence SEQ ID NO: 14 (the empty expression cassette in the L5-E4 site). The virus TAV IX-WT L5-IL7 carried the TAV-255 deletion in the E1A promoter, wild-type viral sequence in the IX-E2 site, and the sequence SEQ ID NO: 18 (see below with capital letters indicating the mouse IL-7 gene and lower case letters representing flanking nucleotides from the L5-E4 expression cassette including underlined residual nucleotides from the SwaI restriction site) cloned into the L5-E4 cassette of SEQ ID NO: 14.

SEQ ID NO: 18
[L5 mIL7]
```
gctttgcaaagatttATGTTCCATGTTTCTTTTAGATATATCTTTGGAAT

TCCTCCACTGATCCTTGTTCTGCTGCCTGTCACATCATCTGAGTGCCACA

TTAAAGACAAAGAAGGTAAAGCATATGAGAGTGTACTGATGATCAGCATC

GATGAATTGGACAAAATGACAGGAACTGATAGTAATTGCCCGAATAATGA

ACCAAACTTTTTTAGAAAACATGTATGTGATGATACAAAGGAAGCTGCTT

TTCTAAATCGTGCTGCTCGCAAGTTGAAGCAATTTCTTAAAATGAATATC

AGTGAAGAATTCAATGTCCACTTACTAACAGTATCACAAGGCACACAAAC

ACTGGTGAACTGCACAAGTAAGGAAGAAAAAAACGTAAAGGAACAGAAAA

AGAATGATGCATGTTTCCTAAAGAGACTACTGAGAGAAATAAAAACTTGT

TGGAATAAAATTTTGAAGGGCAGTATATAAaaataacttgtttattgcag
```

The virus TAV IX-WT L5-GMCSF carried the TAV-255 deletion in the E1A promoter, wild-type viral sequence in the IX-E2 site, and the sequence SEQ ID NO: 19 (with capital letters indicating the mouse GMCSF gene and lower case letters representing flanking nucleotides from the L5-E4 expression cassette including underlined residual nucleotides from the SwaI restriction site) cloned into the L5-E4 cassette of SEQ ID NO: 14. This virus carries wild-type mouse GMCSF and not the codon-optimized form of mouse GMCSF used in the virus TAV-(L5-E4)mGMCSF shown in SEQ ID NO: 15.

SEQ ID NO: 19
[L5 wt mGMCSF]
```
gctttgcaaagatttATGTGGCTGCAGAATTTACTTTTCCTGGGCATTGT

GGTCTACAGCCTCTCAGCACCCACCCGCTCACCCATCACTGTCACCCGGC

CTTGGAAGCATGTAGAGGCCATCAAAGAAGCCCTGAACCTCCTGGATGAC

ATGCCTGTCACGTTGAATGAAGAGGTAGAAGTCGTCTCTAACGAGTTCTC

CTTCAAGAAGCTAACATGTGTGCAGACCCGCCTGAAGATATTCGAGCAGG

GTCTACGGGCAATTTCACCAAACTCAAGGGCGCCTTGAACATGACAGCC

AGCTACTACCAGACATACTGCCCCCCAACTCCGGAAACGGACTGTGAAAC

ACAAGTTACCACCTATGCGGATTTCATAGACAGCCTTAAAACCTTTCTGA

CTGATATCCCCTTTGAATGCAAAAAACCAGGCCAAAAATGAaaataactt gtttattgcag
```

The virus TAV IX-GMCSF L5-IL7 carried the TAV-255 deletion in the E1A promoter, the sequence SEQ ID NO: 20 (with capital letters indicating the mouse GMCSF gene and lower case letters representing the flanking nucleotides of the IX-E2 expression cassette including underlined residual nucleotides from the NotI restriction site) cloned into the IX-E2 cassette of SEQ ID NO: 17, and mouse IL-7 cloned into the L5-E4 cassette as depicted in SEQ ID NO: 18 and SEQ ID NO: 14. The sequence of mouse GMCSF was identical in the viruses TAV IX-WT L5-GMCSF and TAV IX-GMCSF L5-IL7 but was inserted in the IX-E2 expression cassette of one virus and the L5-E4 expression cassette in the other virus.

SEQ ID NO: 20
[IX wt mGMCSF]
```
atagggagacccgcggccATGTGGCTGCAGAATTTACTTTTCCTGGGCATTGTGGTCTACAG

CCTCTCAGCACCCACCCGCTCACCCATCACTGTCACCCGGCCTTGGAAGCATGTAGAGGCCA

TCAAAGAAGCCCTGAACCTCCTGGATGACATGCCTGTCACGTTGAATGAAGAGGTAGAAGTC

GTCTCTAACGAGTTCTCCTTCAAGAAGCTAACATGTGTGCAGACCCGCCTGAAGATATTCGA

GCAGGGTCTACGGGCAATTTCACCAAACTCAAGGGCGCCTTGAACATGACAGCCAGCTACT
```

```
ACCAGACATACTGCCCCCCAACTCCGGAAACGGACTGTGAAACACAAGTTACCACCTATGCG

GATTTCATAGACAGCCTTAAAACCTTTCTGACTGATATCCCCTTTGAATGCAAAAAACCAGG

CCAAAAATGAggccgctgtgccttctagt
```

Figure 3:
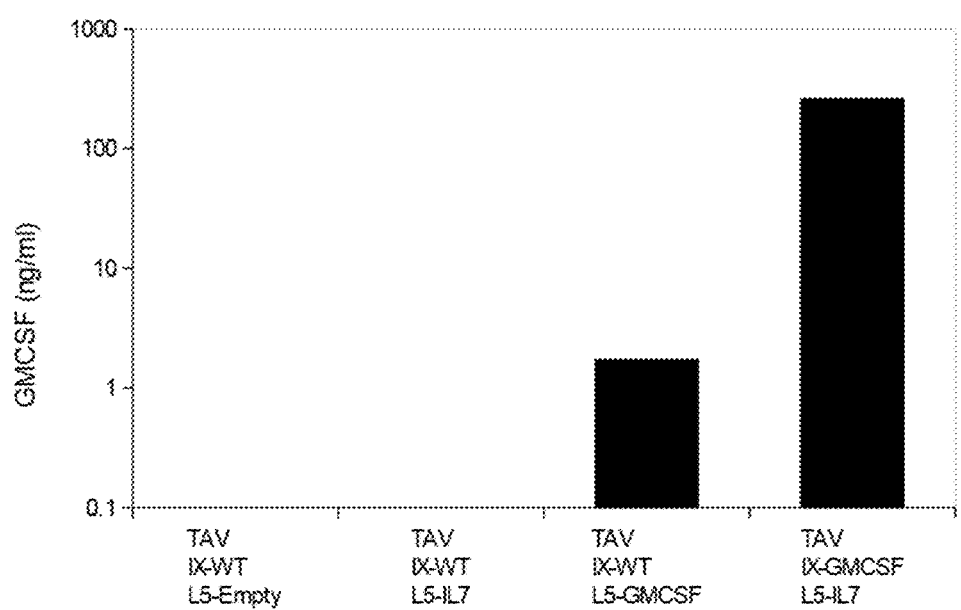
FIG. 3 depicts GMCSF expression level from A549 cells infected with virus TAV IX-WT L5-Empty, TAV IX-WT L5-IL7, TAV IX-WT L5-GMCSF, or TAV IX-GMCSF L5-IL7. GMCSF expression was measured in the conditioned media. Higher expression was seen when GMCSF was expressed from the IX-E2 expression cassette than from the L5-E4 expression cassette.

To test for transgene expression from these viruses, A549 cells were infected with the viruses at an MOI of 5 and four days later the conditioned media was collected and used in ELISAs for IL-7 and GMCSF. The ELISA for GMCSF showed substantially higher expression from the cassette in the IX-E2 site driven by the CMV promoter than from the cassette in the L5-E4 site driven by the SV40 promoter, as depicted in FIG. 3.

Example 5

Figure 4:
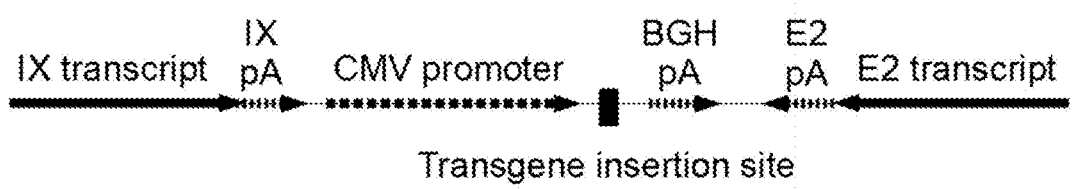
FIG. 4 depicts the initial design and revised design of the IX-E2 insertion site.
Figure 4:
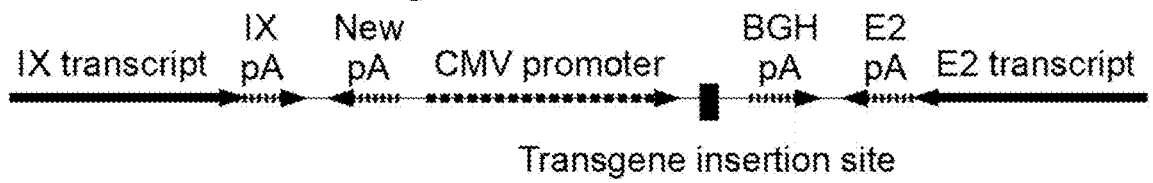

In viruses of the initial IX-E2 design (FIG. 4), we suspected that viral growth could be further optimized by blocking any potential for the CMV promoter driving transcription in the opposite direction from what was intended (Seila et al., Science. (2008) 322(5909):1849-51). We therefore revised the insert in this site so both the 5' and 3' ends of the insert contain polyadenylation signals oriented to polyadenylate transcripts going both into the insert from the normal viral genes and out of the insert toward the normal viral genes. See the revised IX-E2 design in FIG. 4.

The nucleotide sequence of the revised insert, from the polyadenylation signal of the IX transcript to the polyadenylation signal of the E2 transcript, is:

Each forward polyadenylation signal ("AATAAA" SEQ ID NO: 12) and reverse polyadenylation signal ("TTTATT" SEQ ID NO: 13), and the NotI site ("GCGGCCGC" SEQ ID NO: 16), are underlined. Viruses carrying the expression cassette with the revised IX-E2 design grew more efficiently than the viruses with the initial IX-E2 design.

Example 6

The virus TAV-IXrL5-Empty carried the TAV-255 deletion in the viral E1A promoter, SEQ ID NO: 21 (the empty expression cassette of the revised IX-E2 design) and SEQ ID NO: 14 (the empty expression cassette in the L5-E4 site). The virus TAV-IXrL5-hIL12 carries the TAV-255 deletion in the viral E1A promoter, a gene encoding the human IL12A chain in the revised IX-E2 expression cassette (depicted in SEQ ID NO: 22), and a gene encoding the human IL12B chain in the L5-E4 expression cassette (depicted in SEQ ID NO: 23). In SEQ ID NO: 22, each forward polyadenylation signal ("AATAAA" SEQ ID NO: 12) and reverse polyadenylation signal ("TTTATT" SEQ ID NO: 13), and the residual nucleotides from the NotI site are underlined, and the gene encoding the human IL12A chain are bolded. In SEQ ID NO: 23, the polyadenylation signals of the L5 and

SEQ ID NO: 21

[IX revised Empty]

```
AATAAAATACACCTTTTTTCGATTGTACGTATTTTTATTTACGGTAAATGGCCCGCCTGGCT

GACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAGT

ACATCAAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTACGTA

TTAGTCATCGCTATTACCATGGTGATGCGGTTTTGGCAGTACATCAATGGGCGTGGATAGCG

GTTTGACTCACGGGGATTTCCAAGTCTCCACCCCATTGACGTCAATGGGAGTTTGTTTTGGC

ACCAAAATCAACGGGACTTTCCAAAATGTCGTAACAACTCCGCCCCATTGACGCAAATGGGC

GGTAGGCGTGTACGGTGGGAGGTCTATATAAGCAGAGCTCTCTGGCTAACTAGAGAACCCAC

TGCTTACTGGCTTATCGAAATTAATACGACTCACTATAGGGAGACCCGCGGCCGCTGTGCCT

TCTAGTTGCCAGCCATCTGTTGTTTGCCCCTCCCCCGTGCCTTCCTTGACCCTGGAAGGTGC

CACTCCCACTGTCCTTTCCTAATAAAAAACCAGACTCTGTTTGGATTTGGATCAAGCAAGTG

TCTTGCTGTCTTTATT
```

E4 transcription units, and the residual nucleotides of the SwaI restriction site are underlined, and the gene encoding the human IL12B chain are bolded.

SEQ ID NO: 22
[IX revised hIL12A]
<u>AATAAA</u>ATACACCTTTTTTCGATTGTACGTATT<u>TTTATT</u>TACGGTAAATGGCCCGCCTGGCT

GACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAGT

ACATCAAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTACGTA

TTAGTCATCGCTATTACCATGGTGATGCGGTTTTGGCAGTACATCAATGGGCGTGGATAGCG

GTTTGACTCACGGGGATTTCCAAGTCTCCACCCCATTGACGTCAATGGGAGTTTGTTTTGGC

ACCAAAATCAACGGGACTTTCCAAAATGTCGTAACAACTCCGCCCCATTGACGCAAATGGGC

GGTAGGCGTGTACGGTGGGAGGTCTATATAAGCAGAGCTCTCTGGCTAACTAGAGAACCCAC

TGCTTACTGGCTTATCGAAATTAATACGACTCACTATAGGGAGACCC<u>GCGGCC</u>ATGTGGCCC

CCTGGGTCAGCCTCCCAGCCACCGCCCTCACCTGCCGCGGCCACAGGTCTGCATCCAGCGGC

TCGCCCTGTGTCCCTGCAGTGCCGGCTCAGCATGTGTCCAGCGCGCAGCCTCCTCCTTGTGG

CTACCCTGGTCCTCCTGGACCACCTCAGTTTGGCCAGAAACCTCCCCGTGGCCACTCCAGAC

CCAGGAATGTTCCCATGCCTTCACCACTCCCAAAACCTGCTGAGGGCCGTCAGCAACATGCT

CCAGAAGGCCAGACAAACTCTAGAATTTTACCCTTGCACTTCTGAAGAGATTGATCATGAAG

ATATCACAAAAGATAAAACCAGCACAGTGGAGGCCTGTTTACCATTGGAATTAACCAAGAAT

GAGAGTTGCCTAAATTCCAGAGAGACCTCTTTCATAACTAATGGGAGTTGCCTGGCCTCCAG

AAAGACCTCTTTTATGATGGCCCTGTGCCTTAGTAGTATTTATGAAGACTTGAAGATGTACC

AGGTGGAGTTCAAGACCATGAATGCAAAGCTTCTGATGGATCCTAAGAGGCAGATCTTTCTA

GATCAAAACATGCTGGCAGTTATTGATGAGCTGATGCAGGCCCTGAATTTCAACAGTGAGAC

TGTGCCACAAAAATCCTCCCTTGAAGAACCGGATTTTTATAAAACTAAAATCAAGCTCTGCA

TACTTCTTCATGCTTTCAGAATTCGGGCAGTGACTATTGATAGAGTGATGAGCTATCTGAAT

GCTTCCTAA<u>GGCCGC</u>TGTGCCTTCTAGTTGCCAGCCATCTGTTGTTTGCCCCTCCCCCGTGC

CTTCCTTGACCCTGGAAGGTGCCACTCCCACTGTCCTTTCCT<u>AATAAA</u>AAACCAGACTCTGT

TTGGATTTGGATCAAGCAAGTGTCTTGCTGTC<u>TTTATT</u>

SEQ ID NO: 23
[L5 initial hIL12B]
<u>AATAAA</u>GAATCGTTTGTGTTATGTTTCAACCTGTGGAATGTGTGTCAGTTAGGGTGTGGAAA

GTCCCCAGGCTCCCCAGCAGGCAGAAGTATGCAAAGCATGCATCTCAATTAGTCAGCAACCA

GGTGTGGAAAGTCCCCAGGCTCCCCAGCAGGCAGAAGTATGCAAAGCATGCATCTCAATTAG

TCAGCAACCATAGTCCCGCCCCTAACTCCGCCCATCCCGCCCCTAACTCCGCCCAGTTCCGC

CCATTCTCCGCCCCATGGCTGACTAATTTTTTTTATTTATGCAGAGGCCGAGGCCGCCTCTG

CCTCTGAGCTATTCCAGAAGTAGTGAGGAGGCTTTTTTGGAGGCCTAGGCTTTTGCAAAAAG

CTTTGCAAAG<u>ATTT</u>ATGTGTCACCAGCAGTTGGTCATCTCTTGGTTTTCCCTGGTTTTCTG

GCATCTCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTA

TCACCTGGACCTTGGACCAGAGCAGTGAGGTCTTAGGCTCTGGCAAAACCCTGACCATCCAA

GTCAAAGAGTTTGGAGATGCTGGCCAGTACACCTGTCACAAAGGAGGCGAGGTTCTAAGCCA

-continued
```
TTCGCTCCTGCTGCTTCACAAAAAGGAAGATGGAATTTGGTCCACTGATATTTTAAAGGACC

AGAAAGAACCCAAAAATAAGACCTTTCTAAGATGCGAGGCCAAGAATTATTCTGGACGTTTC

ACCTGCTGGTGGCTGACGACAATCAGTACTGATTTGACATTCAGTGTCAAAAGCAGCAGAGG

CTCTTCTGACCCCCAAGGGGTGACGTGCGGAGCTGCTACACTCTCTGCAGAGAGAGTCAGAG

GGGACAACAAGGAGTATGAGTACTCAGTGGAGTGCCAGGAGGACAGTGCCTGCCCAGCTGCT

GAGGAGAGTCTGCCCATTGAGGTCATGGTGGATGCCGTTCACAAGCTCAAGTATGAAAACTA

CACCAGCAGCTTCTTCATCAGGGACATCATCAAACCTGACCCACCCAAGAACTTGCAGCTGA

AGCCATTAAAGAATTCTCGGCAGGTGGAGGTCAGCTGGGAGTACCCTGACACCTGGAGTACT

CCACATTCCTACTTCTCCCTGACATTCTGCGTTCAGGTCCAGGGCAAGAGCAAGAGAGAAAA

GAAAGATAGAGTCTTCACGGACAAGACCTCAGCCACGGTCATCTGCCGCAAAAATGCCAGCA

TTAGCGTGCGGGCCCAGGACCGCTACTATAGCTCATCTTGGAGCGAATGGGCATCTGTGCCC

TGCAGTTAGAAATAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACTCATC

AATGTATCTTATCATGTCTGGTGTTTATT
```

The virus WT-IXrL5-hIL12 was created with an identical genomic structure as TAV-IXrL5-hIL12 except that it carries a wild-type E1A promoter instead of carrying the TAV-255 deletion in the E1A promoter. Each of these viruses also has a deletion of the E3 RIDα, RIDβ, and 14.7k genes and a deletion of the E4 ORF1-ORF4 genes.

To compare this design approach with another strategy to incorporate IL12 into an oncolytic adenovirus, we tested an adenovirus carrying a gene encoding the human IL12A and IL12B chains linked by a furin cleavage site (amino acids RAKR; SEQ ID NO: 24) carried in the E1B-19K site. When the fusion protein was synthesized by the cell, the furin site was cleaved between the final R of the RAKR sequence and the next amino acid (the first amino acid of mature IL12A) by the enzyme furin in the Golgi. We previously found that using a furin cleavage site as a linker led to high level expression of the heterodimeric IL12 protein. The nucleic acid sequence of that fusion gene (capitalized), the flanking SalI and XhoI restriction sites used for cloning (underlined), and the adenoviral nucleotides indicating the site where it was inserted in the adenoviral genome (lower case) is:

SEQ ID NO: 25
[hIL12 furin]
```
atctgacctcgtcgacATGTGTCACCAGCAGTTGGTCATCTCTTGGTTTTCCCTGGTTTTC

TGGCATCTCCCCTCGTGGCCATATGGGAACTGAAGAAAGATGTTTATGTCGTAGAATTGGAT

TGGTATCCGGATGCCCCTGGAGAAATGGTGGTCCTCACCTGTGACACCCCTGAAGAAGATGG

TATCACCTGGACCTTGGACCAGAGCAGTGAGGTCTTAGGCTCTGGCAAAACCCTGACCATCC

AAGTCAAAGAGTTTGGAGATGCTGGCCAGTACACCTGTCACAAAGGAGGCGAGGTTCTAAGC

CATTCGCTCCTGCTGCTTCACAAAAAGGAAGATGGAATTTGGTCCACTGATATTTTAAAGGA

CCAGAAAGAACCCAAAAATAAGACCTTTCTAAGATGCGAGGCCAAGAATTATTCTGGACGTT

TCACCTGCTGGTGGCTGACGACAATCAGTACTGATTTGACATTCAGTGTCAAAAGCAGCAGA

GGCTCTTCTGACCCCCAAGGGGTGACGTGCGGAGCTGCTACACTCTCTGCAGAGAGAGTCAG

AGGGGACAACAAGGAGTATGAGTACTCAGTGGAGTGCCAGGAGGACAGTGCCTGCCCAGCTG

CTGAGGAGAGTCTGCCCATTGAGGTCATGGTGGATGCCGTTCACAAGCTCAAGTATGAAAAC

TACACCAGCAGCTTCTTCATCAGGGACATCATCAAACCTGACCCACCCAAGAACTTGCAGCT

GAAGCCATTAAAGAATTCTCGGCAGGTGGAGGTCAGCTGGGAGTACCCTGACACCTGGAGTA

CTCCACATTCCTACTTCTCCCTGACATTCTGCGTTCAGGTCCAGGGCAAGAGCAAGAGAGAA

AAGAAAGATAGAGTCTTCACGGACAAGACCTCAGCCACGGTCATCTGCCGCAAAAATGCCAG

CATTAGCGTGCGGGCCCAGGACCGCTACTATAGCTCATCTTGGAGCGAATGGGCATCTGTGC

CCTGCAGTCGTGCTAAGCGAAGAAACCTCCCCGTGGCCACTCCAGACCCAGGAATGTTCCCA
```

-continued
```
TGCCTTCACCACTCCCAAAACCTGCTGAGGGCCGTCAGCAACATGCTCCAGAAGGCCAGACA

AACTCTAGAATTTTACCCTTGCACTTCTGAAGAGATTGATCATGAAGATATCACAAAAGATA

AAACCAGCACAGTGGAGGCCTGTTTACCATTGGAATTAACCAAGAATGAGAGTTGCCTAAAT

TCCAGAGAGACCTCTTTCATAACTAATGGGAGTTGCCTGGCCTCCAGAAAGACCTCTTTTAT

GATGGCCCTGTGCCTTAGTAGTATTTATGAAGACTTGAAGATGTACCAGGTGGAGTTCAAGA

CCATGAATGCAAAGCTTCTGATGGATCCTAAGAGGCAGATCTTTCTAGATCAAACATGCTG

GCAGTTATTGATGAGCTGATGCAGGCCCTGAATTTCAACAGTGAGACTGTGCCACAAAAATC

CTCCCTTGAAGAACCGGATTTTTATAAAACTAAAATCAAGCTCTGCATACTTCTTCATGCTT

TCAGAATTCGGGCAGTGACTATTGATAGAGTGATGAGCTATCTGAATGCTTCCTAATA
```
ctcgagtcaccaggcg

The virus TAV-hIL12-furin carries the TAV-255 deletion in the E1A promoter and SEQ ID NO: 25 in the E1B-19K region. The control virus TAV-Δ19k carries the TAV-255 deletion in the E1A promoter and a deletion of the E1B-19K region.

Figure 5:
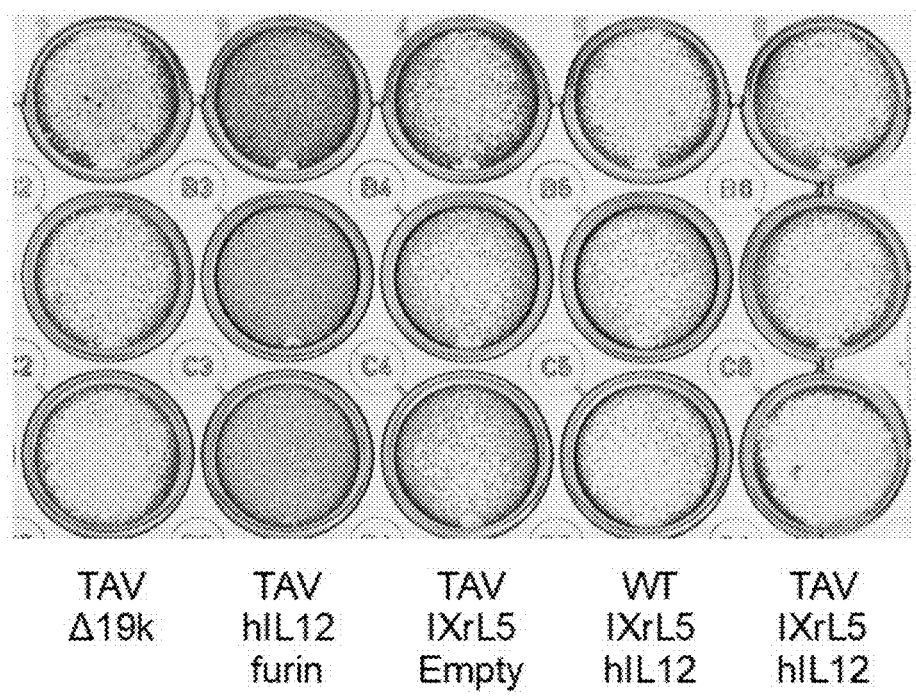
FIG. 5 depicts A549 cells infected virus (TAV-Δ19k, TAV-hIL12-furin, TAV-TAV-IXrL5-Empty, WT-IXrL5-hIL12, or TAV-IXrL5-hIL12) in triplicate and stained with crystal violet (staining live cells purple) four days after infection.

To test for oncolytic activity and IL12 expression, A549 cells were infected with TAV-Δ19k, TAV-hIL12-furin, TAV-TAV-IXrL5-Empty, and TAV-IXrL5-hIL12 at an MOI of 5 in triplicate. Four days after infection, the conditioned media was collected and IL12 was measured in an ELISA that detects only the assembled IL12A-IL12B heterodimer, and the remaining cells were stained with crystal violet. As shown in FIG. 5, TAV-hIL12-furin was slightly less lytic than the corresponding control virus TAV-Δ19k which is in agreement with our general experience when transgenes are inserted in the E1B-19K region, while TAV-IXrL5-hIL12 was as lytic as TAV-IXrL5-Empty and TAV-Δ19k. This demonstrated that insertion of expression cassettes in the IX-E2 and L5-E4 regions has minimal impact on viral fitness and may be superior to insertion of transgenes in the E1B-19K region in this regard.

Figure 6:
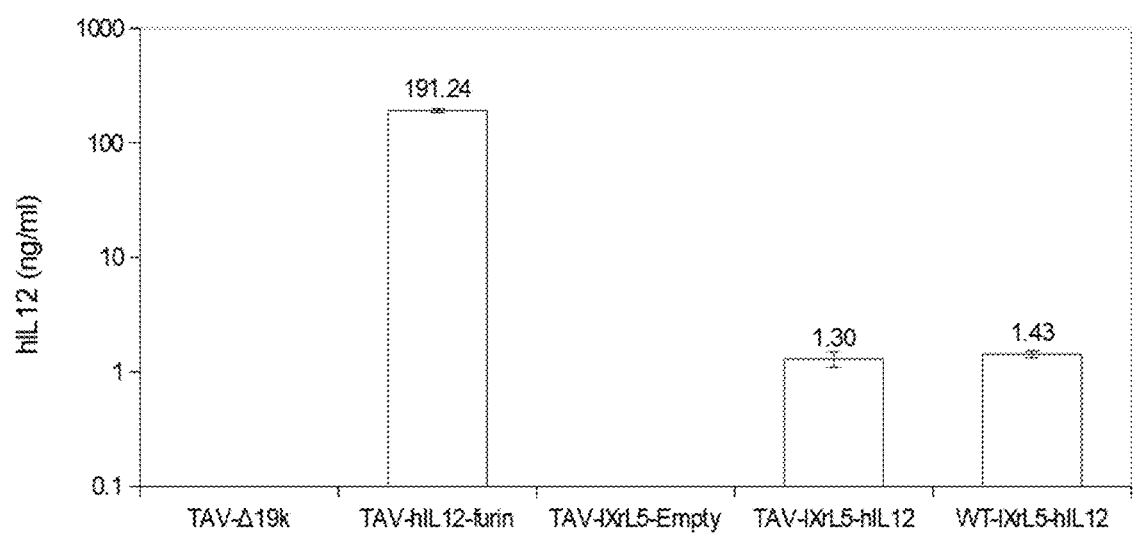
FIG. 6 depicts IL-12 expression level from A549 cells infected with virus (TAV-Δ19k, TAV-hIL12-furin, TAV-TAV-IXrL5-Empty, WT-IXrL5-hIL12, or TAV-IXrL5-hIL12). The A549 cells were infected with the indicated virus in triplicate, and IL12 in the conditioned media was measured with an ELISA four days after infection.

As shown in FIG. 6, TAV-hIL12-furin expressed higher levels of IL12 than the viruses using IX-E2 and L5-E4 cassettes. This suggested that at least one of the two expression cassettes may be suboptimal and prompted further investigation into improving the design. However, the IL12 protein generated from TAV-hIL12-furin contains a non-native RAKR sequence (the remaining furin recognition site) at the C-terminus of the IL12B chain which might lead to undesirable in vivo effects such as immunogenicity against the transgene or against native IL12, whereas the IL12 generated by TAV-IXrL5-hIL12 has the advantage that it is completely native.

Example 7

Based on the relatively low expression from the L5-E4 cassette compared to the IX-E2 cassette observed, we hypothesized that the L5-E4 cassette was the cause of the low expression of the IL-12 heterodimer. We revised the L5-E4 region to include bidirectional polydenylation signals at both ends, similar to the approach that was used for the IX-E2 region.

The nucleotide sequence SEQ ID NO: 26 was cloned into the L5-E4 region, showing the polyadenylation signals of the L5 and E4 transcripts at the 5' and 3' ends and all polyadenylation signals and the SwaI restriction site underlined.

SEQ ID NO: 26
[L5 revised SV40]
```
AATAAAAGGTTTATTCTGTGGAATGTGTGTCAGTTAGGGTGTGGAAAGTCCCCAGGCTCCCC

AGCAGGCAGAAGTATGCAAAGCATGCATCTCAATTAGTCAGCAACCAGGTGTGGAAAGTCCC

CAGGCTCCCCAGCAGGCAGAAGTATGCAAAGCATGCATCTCAATTAGTCAGCAACCATAGTC

CCGCCCCTAACTCCGCCCATCCCGCCCCTAACTCCGCCCAGTTCCGCCCATTCTCCGCCCCA

TGGCTGACTAATTTTTTTTATTTATGCAGAGGCCGAGGCCGCCTCTGCCTCTGAGCTATTCC

AGAAGTAGTGAGGAGGCTTTTTGGAGGCCTAGGCTTTTGCAAAAAGCTTTGCAAAGATTTA

AATAACTTGTTTATTGCAGCTTATAATGGTTACAAATAAAGAATCGTTTGTGTTATGTTTCA

ACGTGTTTATT
```

The virus TAV-(IXr)Empty-(L5r)Empty was made with the TAV-255 deletion in the E1A promoter, the revised IX-E2 cassette without a transgene in the IX-E2 region shown in SEQ ID NO: 21, and the revised L5-E4 cassette without a transgene in the L5-E4 region shown in SEQ ID NO: 26.

The virus TAV-(IXr)mIL7-(L5r)mGMCSF contained the TAV-255 deletion in the E1A promoter, the revised IX-E2 cassette shown in SEQ ID NO: 21 with the mouse GMCSF gene cloned into the NotI site as shown in SEQ ID NO: 20, and the revised L5-E4 cassette shown in SEQ ID NO: 26 with the mouse IL-7 gene cloned into the SwaI site as shown in SEQ ID NO: 18.

The virus TAV-(IXr)mGMCSF-(L5r)mIL7 contained the TAV-255 deletion in the E1A promoter, the revised IX-E2 cassette shown in SEQ ID NO: 21 with the mouse IL-7 gene cloned into the NotI site as shown in SEQ ID NO: 27, and the revised L5-E4 cassette shown in SEQ ID NO: 26 with the mouse GMCSF gene cloned into the SwaI site as shown in SEQ ID NO: 19. Thus, the viruses TAV-(IXr)mGMCSF-(L5r)mIL7 and TAV-(IXr)mIL7-(L5r)mGMCSF differed only in which gene of IL-7 and GMCSF was inserted into which site: the revised IX-E2 or the revised L5-E4 site.

SEQ ID NO: 27
[IX mIL7]
atagggagacccgcggccATGTTCCATGTTTCTTTTAGATATATCTTTGGAATTCCTCCACT

GATCCTTGTTCTGCTGCCTGTCACATCATCTGAGTGCCACATTAAAGACAAAGAAGGTAAAG

CATATGAGAGTGTACTGATGATCAGCATCGATGAATTGGACAAAATGACAGGAACTGATAGT

AATTGCCCGAATAATGAACCAAACTTTTTTAGAAAACATGTATGTGATGATACAAAGGAAGC

TGCTTTTCTAAATCGTGCTGCTCGCAAGTTGAAGCAATTTCTTAAAATGAATATCAGTGAAG

AATTCAATGTCCACTTACTAACAGTATCACAAGGCACACAAACACTGGTGAACTGCACAAGT

AAGGAAGAAAAAAACGTAAAGGAACAGAAAAAGAATGATGCATGTTTCCTAAAGAGACTACT

GAGAGAAATAAAAACTTGTTGGAATAAAATTTTGAAGGGCAGTATATAAggccgctgtgcct tctagt

To test transgene expression from these viruses, A549 cells were infected with each virus at an MOI of 5 in triplicate. Conditioned media was collected four days later and GMCSF and IL-7 were measured in ELISAs. For both IL-7 and GMCSF, expression was higher from the virus carrying the gene in the revised IX-E2 site than the revised L5-E4 site. This confirmed the previous finding that the expression cassette at IX-E2 using the CMV promoter expressed at higher levels than the cassette at L5-E4 using the SV40 promoter and this was not affected by revising the L5-E4 site to include bidirectional polyadenylation signals.

Example 8

We next investigated further improving the promoter in the L5-E4 site. The SV40 promoter that was initially used had a point mutation of G (in the wild-type SV40 sequence) to T (in the L5-E4 insert) at the major transcription start site, so we generated an L5-E4 insert with that nucleotide changed back to the wild-type G as shown in SEQ ID NO: 28 with the previously mutated nucleotide, the polyadenylation signals, and the SwaI restriction site underlined. We also investigated using a different promoter, and generated an L5-E4 insert that used the human EF1A promoter instead of the SV40 promoter. SEQ ID NO: 29 shows the L5-E4 insert using the human EF1A promoter, shown from the polyadenylation signal from the L5 transcript to the polyadenylation signal of the E4 transcript, with the polyadenylation signals and the SwaI restriction site underlined.

SEQ ID NO: 28
[L5 revised SV40 wt Empty]
AATAAAAGGTTTATTCTGTGGAATGTGTGTCAGTTAGGGTGTGGAAAGTCCCCAGGCTCCCC

AGCAGGCAGAAGTATGCAAAGCATGCATCTCAATTAGTCAGCAACCAGGTGTGGAAAGTCCC

CAGGCTCCCCAGCAGGCAGAAGTATGCAAAGCATGCATCTCAATTAGTCAGCAACCATAGTC

CCGCCCCTAACTCCGCCCATCCCGCCCCTAACTCCGCCCAGTTCCGCCCATTCTCCGCCCCA

TGGCTGACTAATTTTTTTTATTTATGCAGAGGCCGAGGCCGCCTCGGCCTCTGAGCTATTCC

AGAAGTAGTGAGGAGGCTTTTTGGAGGCCTAGGCTTTTGCAAAAAGCTTTGCAAAGATTTA

AATAACTTGTTTATTGCAGCTTATAATGGTTACAAATAAAGAATCGTTTGTGTTATGTTTCA

ACGTGTTTATT

SEQ ID NO: 29
[L5 revised EF1A Empty]
AATAAAAGGTTTATTAGGCGGCCTCCCCGTCACCACCCCCCCAACCCGCCCCGACCGGAGC

TGAGAGTAATTCATACAAAAGGACTCGCCCCTGCCTTGGGGAATCCCAGGGACCGTCGTTAA

ACTCCCACTAACGTAGAACCCAGAGATCGCTGCGTTCCCGCCCCCTCACCCGCCCGCTCTCG

TCATCACTGAGGTGGAGAAGAGCATGCGTGAGGCTCCGGTGCCCGTCAGTGGGCAGAGCGCA

CATCGCCCACAGTCCCCGAGAAGTTGGGGGGAGGGGTCGGCAATTGAACCGGTGCCTAGAGA

```
AGGTGGCGCGGGGTAAACTGGGAAAGTGATGTCGTGTACTGGCTCCGCCTTTTTCCCGAGGG

TGGGGGAGAACCGTATATAAGTGCAGTAGTCGCCGTGAACGTTCTTTTTCGCAACGGGTTTG

CCGCCAGAACACAATTTAAATAACTTGTTTATTGCAGCTTATAATGGTTACAAATAAAGAAT

CGTTTGTGTTATGTTTCAACGTGTTTATT
```

To test these revised expression cassettes in L5-E4, we generated viruses carrying the mouse IL-7 gene in the IX-E2 site and the mouse GMCSF gene in the new L5-E4 sites. The mouse IL-7 gene used in the IX-E2 site was modified by introducing a silent mutations in two regions near the 3' end of the gene with sequence AATAAA that might by processed as a polyadenylation signal to lead to reduced expression, substituting synonymous sequences that would not change the encoded protein sequence but would eliminate the internal AATAAA sequences; SEQ ID NO: 30 shows that nucleotide sequence with the IL-7 coding nucleotides capitalized and the mutations underlined, and the flanking nucleotides of the IX-E2 cassette in lower case with the residual nucleotides from the NotI site underlined. To attempt to improve expression of the mouse GMCSF gene in the L5-E4 sites, a consensus Kozak sequence (nucleotides GCCACC) was included between the residual nucleotides of the SwaI site and the start codon of the GMCSF gene; SEQ ID NO: 31 shows the nucleotide sequence with the mouse GMCSF gene and the Kozak sequence capitalized with the Kozak sequence underlined, and with the flanking nucleotides of the L5-E4 cassette in lower case with the residual nucleotides from the SwaI site underlined.

SEQ ID NO: 30

[mIL7 no poly-A]

atagggagacccgcggccATGTTCCATGTTTCTTTTAGATATATCTTTGGAATTCCTCCACT

GATCCTTGTTCTGCTGCCTGTCACATCATCTGAGTGCCACATTAAAGACAAAGAAGGTAAAG

CATATGAGAGTGTACTGATGATCAGCATCGATGAATTGGACAAAATGACAGGAACTGATAGT

AATTGCCCGAATAATGAACCAAACTTTTTTAGAAAACATGTATGTGATGATACAAAGGAAGC

TGCTTTTCTAAATCGTGCTGCTCGCAAGTTGAAGCAATTTCTTAAAATGAATATCAGTGAAG

AATTCAATGTCCACTTACTAACAGTATCACAAGGCACACAAACACTGGTGAACTGCACAAGT

AAGGAAGAAAAAAACGTAAAGGAACAGAAAAAGAATGATGCATGTTTCCTAAAGAGACTACT

GAGAGAAATCAAAACTTGTTGGAACAAAATTTTGAAGGGCAGTATATAAggccgctgtgcct tctagt

SEQ ID NO: 31

[mGMCSF Kozak]

atttGCCACCATGTGGCTGCAGAATTTACTTTTCCTGGGCATTGTGGTCTACAGCCTCTCAG

CACCCACCCGCTCACCCATCACTGTCACCCGGCCTTGGAAGCATGTAGAGGCCATCAAAGAA

GCCCTGAACCTCCTGGATGACATGCCTGTCACGTTGAATGAAGAGGTAGAAGTCGTCTCTAA

CGAGTTCTCCTTCAAGAAGCTAACATGTGTGCAGACCCGCCTGAAGATATTCGAGCAGGGTC

TACGGGGCAATTTCACCAAACTCAAGGGCGCCTTGAACATGACAGCCAGCTACTACCAGACA

TACTGCCCCCCAACTCCGGAAACGGACTGTGAAACACAAGTTACCACCTATGCGGATTTCAT

AGACAGCCTTAAAACCTTTCTGACTGATATCCCCTTTGAATGCAAAAAACCAGGCCAAAAAT

GAaaataacttgtttattgcag

The virus TAV-(IXr)mIL7noPA-(L5SV40 wt)KozakmGMCSF contained the TAV-255 deletion in the E1A promoter, the revised IX-E2 insert shown in SEQ ID NO: 21 with the mouse IL-7 gene with synonymous mutations at the potential internal polyadenylation sites cloned into the NotI site as shown in SEQ ID NO: 30, and the L5-E4 insert with the wild-type SV40 promoter shown in SEQ ID NO: 28 with the mouse GMCSF gene including a consensus Kozak sequence cloned into the SwaI site as shown in SEQ ID NO: 31. The virus TAV-(IXr)mIL7noPA-(L5EF1A)KozakmGMCSF contains the TAV-255 deletion in the E1A promoter, the revised IX-E2 insert shown in SEQ ID NO: 21 with the mouse IL-7 gene with synonymous mutations at the potential internal polyadenylation sites cloned into the NotI site as shown in SEQ ID NO: 30, and the L5-E4 insert with the human EF1A promoter shown in SEQ ID NO: 29 with the mouse GMCSF gene including a consensus Kozak sequence cloned into the SwaI site as shown in SEQ ID NO: 31.

Figure 7:
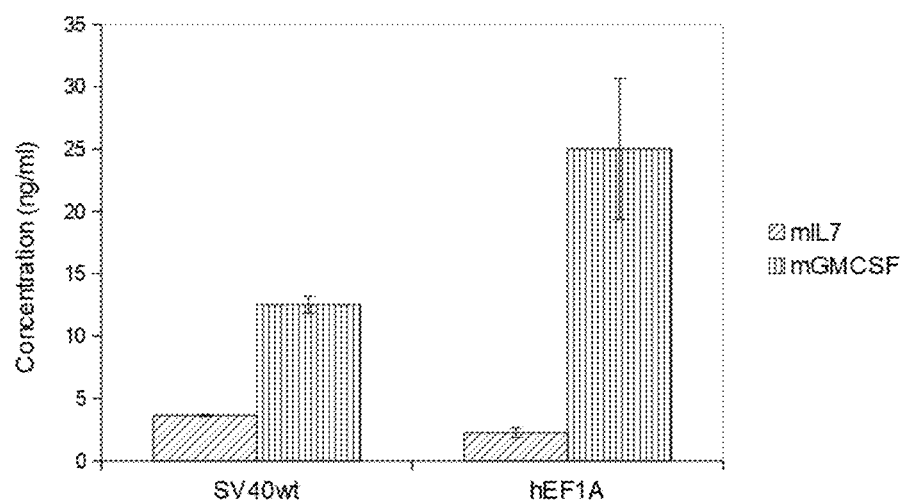
FIG. 7 depicts IL-17 and GMCSF expression level from A549 cells infected with either TAV-(IXr)mIL7noPA-(L5 SV40 wt)KozakmGMCSF (labeled SV40 wt) or TAV-(IXr)mIL7noPA-(L5EF1A)KozakmGMC SF (labeled hEF1A).

To test these viruses for transgene expression, A549 cells were infected with the two viruses in triplicate at an MOI of 5. Four days later, conditioned media was collected and used in ELISAs to measure IL-7 and GMCSF expression. Results are shown in FIG. 7. The human EF1A promoter had moderately higher expression and was chosen for further development. The virus TAV-(IXr)mIL7noPA-(L5EF1A)KozakmGMCSF was prepared as a pharmaceutical agent for mouse experiments by amplifying the virus in serum-free suspension culture of SF-BMAdR 281 cells (derived from A549 cells), lysing the cells, purifying the virus with chromatography, and dialyzing into a buffer with 25 mM NaCl, 20 mM Tris, 2.5% glycerol at pH 8. The virus thus prepared had a viral particle concentration of $5.8 \times 10^{11}$ vp/ml and an infectious titer of $3.0 \times 10^{10}$ IU/ml.

Example 9

We further investigated whether deletion of the adenoviral death protein (ADP) could improve expression of the transgenes. ADP is expressed late during viral replication and lyses the host cell to release progeny virions, so its removal might allow cells to live and express the transgenes longer before they are killed. The nucleotide sequence of the ADP gene in the context of the E3 RIDα, RIDβ, and 14.7K deletion used in the TAV-(IXr)mIL7noPA-(L5EF1A)KozakmGMCSF virus is shown in SEQ ID NO: 32 with the nucleotides encoding ADP capitalized, the site of the E3 RIDα, RIDβ, and 14.7K deletion as a hyphen, and the flanking adenoviral nucleotides in lowercase. To create the ΔADP deletion, the underlined nucleotides within SEQ ID NO: 32 were deleted.

SEQ ID NO: 32

[ADP]
Gaaaatgccttaatttactaagttacaaagctaatgtcaccactaactgctttactcgctgc ttgcaaaacaaattcaaaaagttagcattataattagaataggatttaaaccccccggtcat ttcctgctcaataccattccctgaacaattgactctatgtgggatatgctccagcgctaca accttgaagtcaggcttcctggatgtcagcatctgactttggccagcacctgtcccgcggat ttgttccagtccaactacagcgacccaccctaacagagATGACCAACACAACCAACGCGGCC

GCCGCTACCGGACTTACATCTACCACAAATACACCCCAAGTTTCTGCCTTTGTCAATAACTG

GGATAACTTGGGCATGTGGTGGTTCTCCATAGCGCTTATGTTTGTATGCCTTATTATTATGT

GGCTCATCTGCTGCCTAAAGCGCAAACGCGCCCGACCACCCATCTATAGTCCCATCATTGTG

CTACACCCAAACAATGATGGAATCCATAGATTGGACGGACTGAAACACATGTTCTTTTCTCT

TACAGTATGAtaataaaaaaaaataataaagca

The virus TAV-(IXr)mIL7noPA-(L5EF1A)KozakmGMCSF-ΔADP was created with an identical genome to TAV-(IXr)mIL7noPA-(L5EF1A)KozakmGMCSF except that it also contains a deletion of the nucleotides of the ADP gene as underlined of SEQ ID NO: 32.

Figure 8:
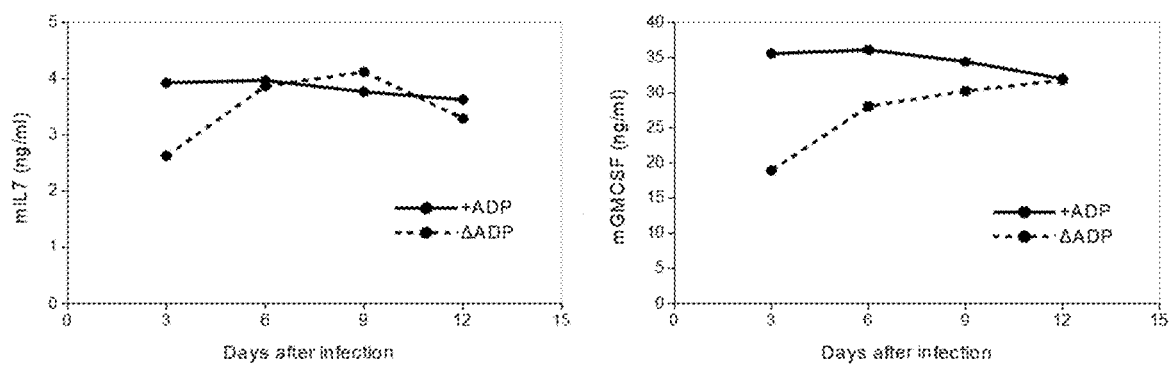
FIG. 8 depicts IL-17 and GMCSF expression level from A549 cells infected with the ADP gene intact [TAV-(IXr)mIL7noPA-(L5EF1A)KozakmGMCSF, labeled as +ADP] or deleted [TAV-(IXr)mIL7noPA-(L5EF1A)KozakmGMCSF-ΔADP, labeled as ΔADP]. Conditioned media was collected at the indicated times after infection and IL-7 and GMCSF were measured in ELISAs.
Figure 9:
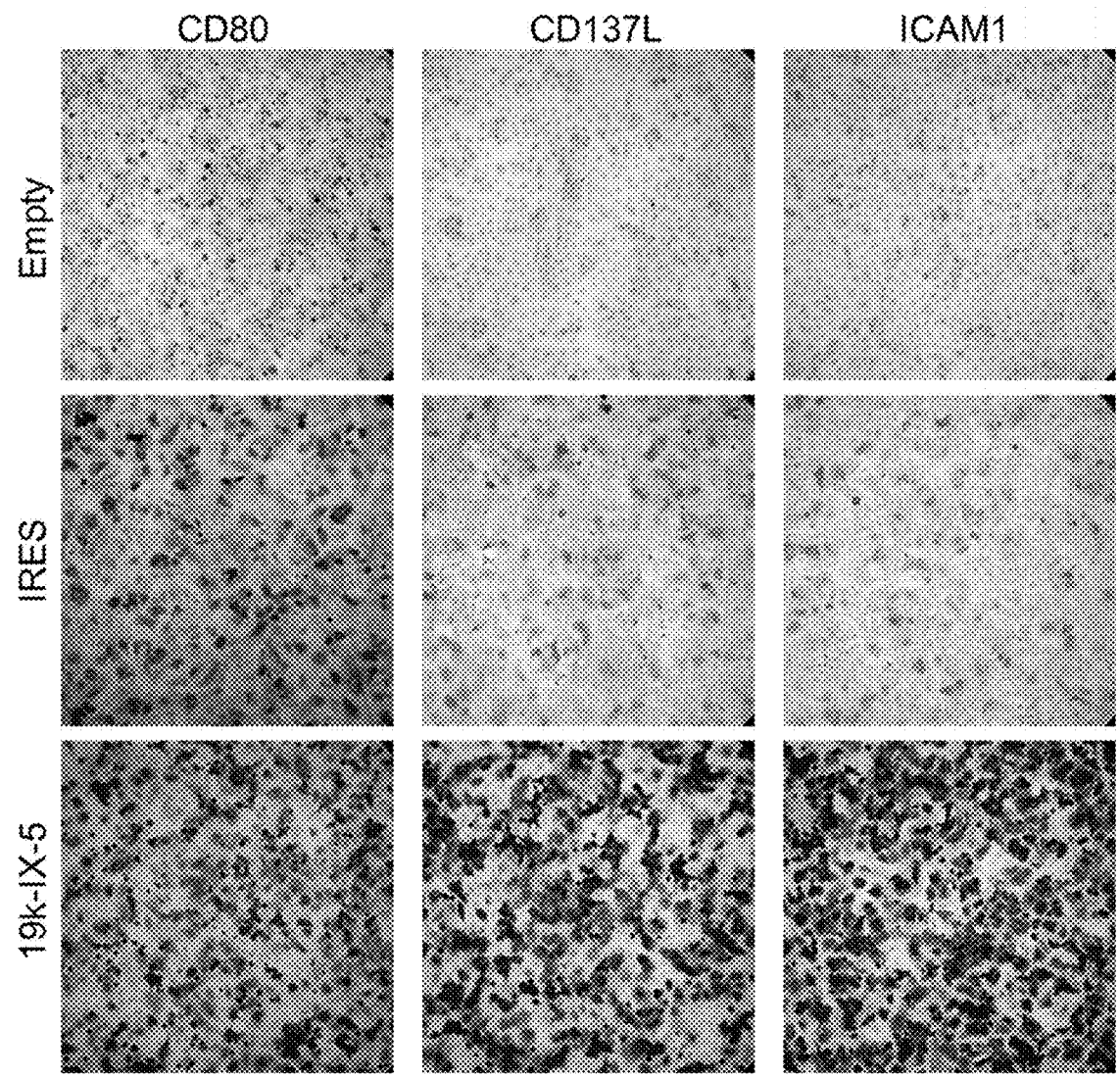
FIG. 9 depicts CD80, CD137L, and ICAM1 staining in A549 cells infected with virus [TAV-mCD80(IRES)mCD137L(IRES)mICAM1, labeled as IRES], [TAV-(19k)mCD80-(IX)mCD137L-(L5)mICAM1, labeled as 19K-IX-5], or the control virus [TAV-(19k)Empty-(IX)Empty-(L5) Empty, labeled as Empty].
Figure 10:
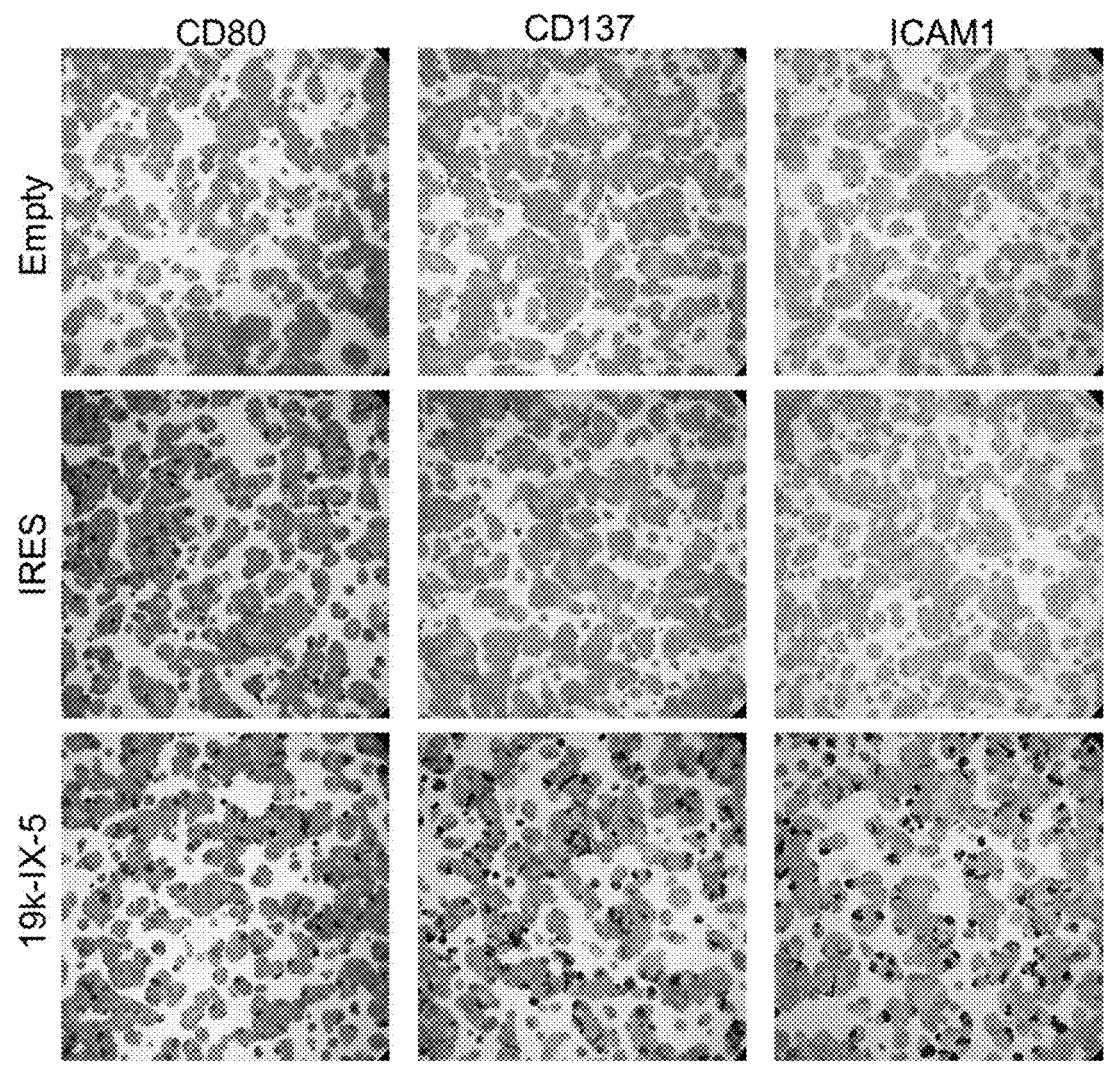
FIG. 10 depicts CD80, CD137L, and ICAM1 staining in HT29 cells infected with virus [TAV-mCD80(IRES)mCD137L(IRES)mICAM1, labeled as IRES], [TAV-(19k)mCD80-(IX)mCD137L-(L5)mICAM1, labeled as 19K-IX-5], or the control virus [TAV-(19k)Empty-(IX)Empty-(L5) Empty, labeled as Empty].
Figure 11:
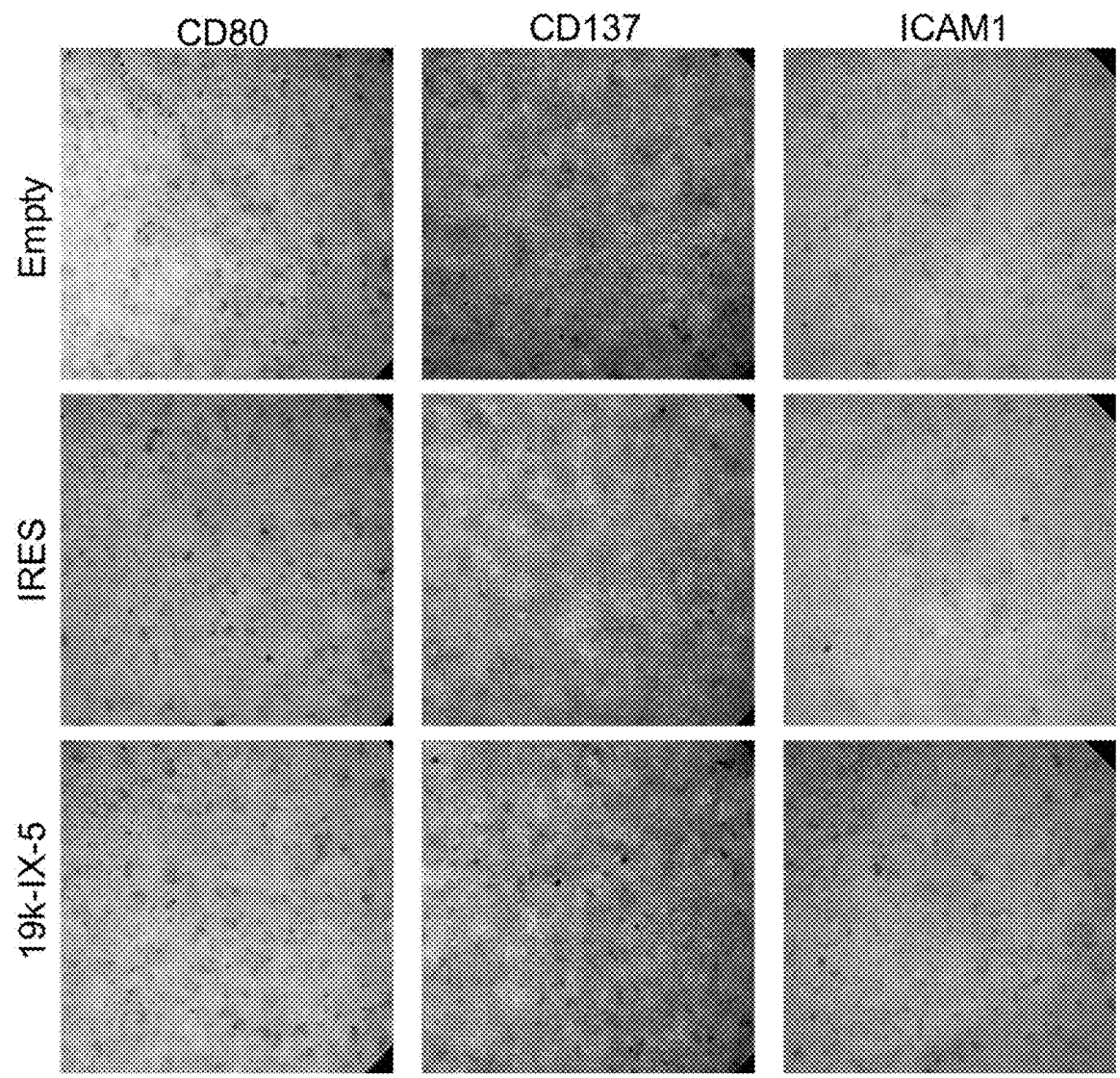
FIG. 11 depicts CD80, CD137L, and ICAM1 staining in ADS12 cells infected with virus [TAV-mCD80(IRES)mCD137L(IRES)mICAM1, labeled as IRES], [TAV-(19k)mCD80-(IX)mCD137L-(L5)mICAM1, labeled as 19K-IX-5], or the control virus [TAV-(19k)Empty-(IX)Empty-(L5) Empty, labeled as Empty].
Figure 12:
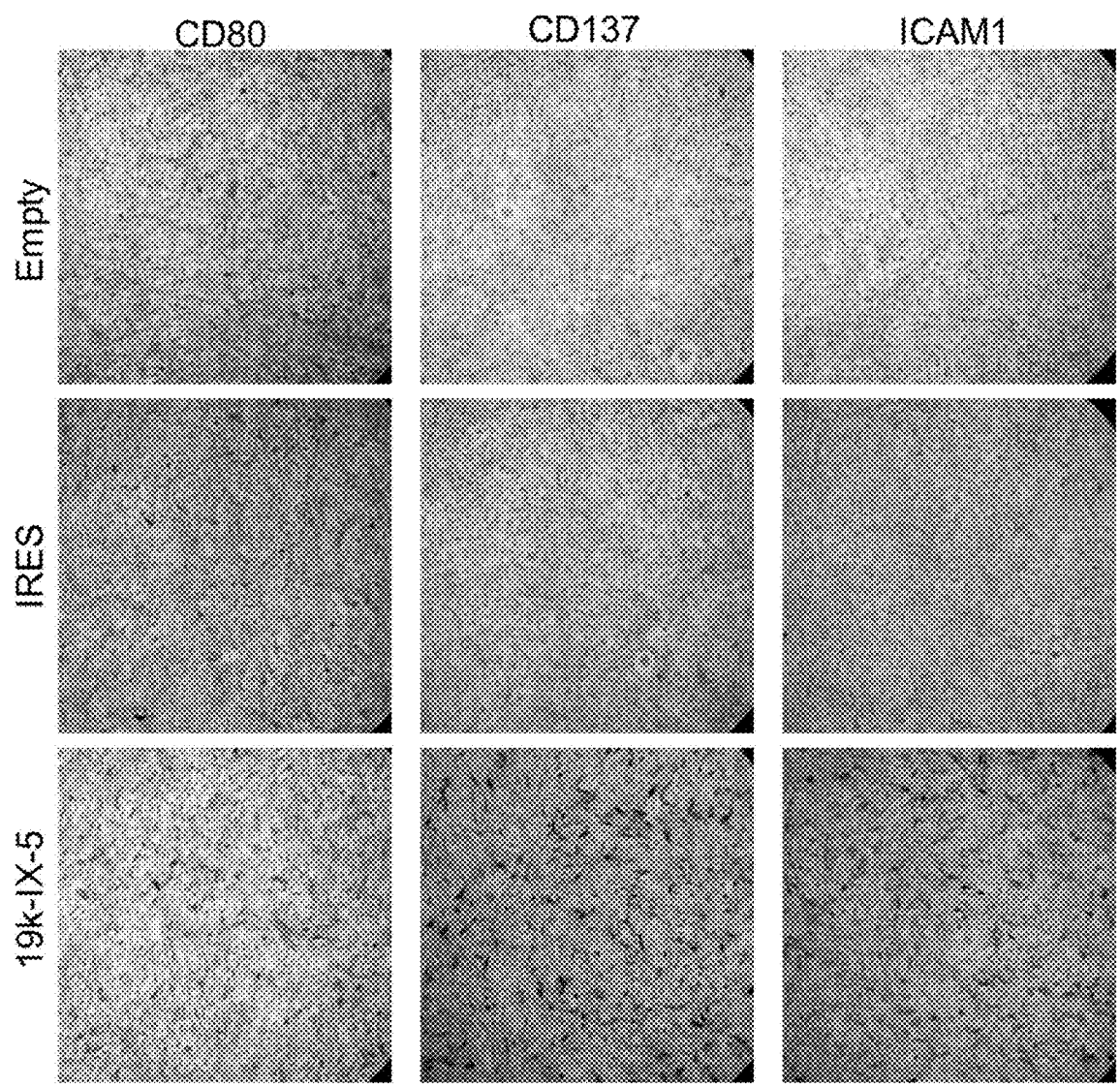
FIG. 12 depicts CD80, CD137L, and ICAM1 staining in F244 cells infected with virus [TAV-mCD80(IRES)mCD137L(IRES)mICAM1, labeled as IRES], [TAV-(19k)

To test whether ADP deletion leads to longer term and higher transgene expression, A549 cells were infected with TAV-(IXr)mIL7noPA-(L5EF1A)KozakmGMCSF and TAV-(IXr)mIL7noPA-(L5EF1A)KozakmGMCSF-ΔADP at an MOI of 5, and every three days after infection the conditioned media was collected to measure IL-7 and GMCSF in an ELISA. Results are shown in FIG. 8. There was no convincing difference in transgene expression levels between the two viruses, although the cells were observed during the course of the experiment and cell death was delayed from about 3 days after infection with TAV-(IXr)mIL7noPA-(L5EF1A)KozakmGMCSF to about 9 days after infection with TAV-(IXr)mIL7noPA-(L5EF1A)KozakmGMCSF-ΔADP. So although expression of the soluble cytokines as in this experiment was not enhanced, for some applications such as expression of costimulatory molecules on the infected cell's surface, it might be advantageous to delete ADP so the cell survives longer and the costimulatory molecule on its surface can activate target cells over a longer period of time.

Example 10

We then used the IX-E2 and L5-E4 sites as part of the design of a virus expressing three transgenes: the costimulatory molecules CD80 and CD137L and the adhesion molecule ICAM1. We previously created a virus carrying all three of these transgenes in place of the 5' end of the viral E1B-19K gene with an IRES between each of the three transgenes. The nucleotide sequence of that virus in the E1B-19K region is shown in SEQ ID NO: 33, with 5' flanking adenoviral nucleotide sequence and a SalI restriction site used for cloning (lower case), mouse CD80 (capitalized), the IRES from encephalomyocarditis virus (lower case), mouse CD137L (capitalized), the IRES from foot and mouth disease virus (lower case), mouse ICAM1 (capitalized), and 3' flanking adenoviral nucleotide sequence including an XhoI restriction site used for cloning. That virus, TAV-mCD80(IRES)mCD137L(IRES)mICAM1, contains the TAV-255 deletion in the E1A promoter, SEQ ID NO: 33 in the E1B-19K site, and deletions of the E3 region ADP, RIDα, RIDβ, and 14.7K genes and the E4 region ORF1-4 genes.

SEQ ID NO: 33

[Costim IRES]

atctgacctcgtcgacATGGCTTGCAATTGTCAGTTGATGCAGGATACACCACTCCTCAAGT

TTCCATGTCCAAGGCTCATTCTTCTCTTTGTGCTGCTGATTCGTCTTTCACAAGTGTCTTCA

GATGTTGATGAACAACTGTCCAAGTCAGTGAAAGATAAGGTATTGCTGCCTTGCCGTTACAA

CTCTCCTCATGAAGATGAGTCTGAAGACCGAATCTACTGGCAAAAACATGACAAAGTGGTGC

TGTCTGTCATTGCTGGGAAACTAAAAGTGTGGCCCGAGTATAAGAACCGGACTTTATATGAC

AACACTACCTACTCTCTTATCATCCTGGGCCTGGTCCTTTCAGACCGGGGCACATACAGCTG

TGTCGTTCAAAAGAAGGAAAGAGGAACGTATGAAGTTAAACACTTGGCTTTAGTAAAGTTGT

CCATCAAAGCTGACTTCTCTACCCCCAACATAACTGAGTCTGGAAACCCATCTGCAGACACT

AAAAGGATTACCTGCTTTGCTTCCGGGGGTTTCCCAAAGCCTCGCTTCTCTTGGTTGGAAAA

TGGAAGAGAATTACCTGGCATCAATACGACAATTTCCCAGGATCCTGAATCTGAATTGTACA

CCATTAGTAGCCAACTAGATTTCAATACGACTCGCAACCACACCATTAAGTGTCTCATTAAA

TATGGAGATGCTCACGTGTCAGAGGACTTCACCTGGGAAAAACCCCCAGAAGACCCTCCTGA

TAGCAAGAACACACTTGTGCTCTTTGGGGCAGGATTCGGCGCAGTAATAACAGTCGTCGTCA

TCGTTGTCATCATCAAATGCTTCTGTAAGCACAGAAGCTGTTTCAGAAGAAATGAGGCAAGC

AGAGAAACAAACAACAGCCTTACCTTCGGGCCTGAAGAAGCATTAGCTGAACAGACCGTCTT

CCTTTAGtaacgttactggccgaagccgcttggaataaggccggtgtgcgtttgtctatatg ttattttccaccatattgccgtcttttggcaatgtgagggcccggaaacctggccctgtctt cttgacgagcattcctaggggtctttcccctctcgccaaaggaatgcaaggtctgttgaatg tcgtgaaggaagcagttcctctggaagcttcttgaagacaaacaacgtctgtagcgaccctt tgcaggcagcggaaccccccacctggcgacaggtgcctctgcggccaaaagccacgtgtata agatacacctgcaaaggcggcacaaccccagtgccacgttgtgagttggatagttgtggaaa gagtcaaatggctctcctcaagcgtattcaacaaggggctgaaggatgcccagaaggtaccc cattgtatgggatctgatctggggcctcggtgcacatgctttacatgtgtttagtcgaggtt aaaaaacgtctaggccccccgaaccacggggacgtggttttcctttgaaaaacacgatgata atATGGACCAGCACACACTTGATGTGGAGGATACCGCGGATGCCAGACATCCAGCAGGTACT

TCGTGCCCCTCGGATGCGGCGCTCCTCAGAGATACCGGGCTCCTCGCGGACGCTGCGCTCCT

CTCAGATACTGTGCGCCCCACAAATGCCGCGCTCCCCACGGATGCTGCCTACCCTGCGGTTA

ATGTTCGGGATCGCGAGGCCGCGTGGCCGCCTGCACTGAACTTCTGTTCCCGCCACCCAAAG

CTCTATGGCCTAGTCGCTTTGGTTTTGCTGCTTCTGATCGCCGCCTGTGTTCCTATCTTCAC

CCGCACCGAGCCTCGGCCAGCGCTCACAATCACCACCTCGCCCAACCTGGGTACCCGAGAGA

ATAATGCAGACCAGGTCACCCCTGTTTCCCACATTGGCTGCCCCAACACTACACAACAGGGC

TCTCCTGTGTTCGCCAAGCTACTGGCTAAAAACCAAGCATCGTTGTGCAATACAACTCTGAA

CTGGCACAGCCAAGATGGAGCTGGGAGCTCATACCTATCTCAAGGTCTGAGGTACGAAGAAG

ACAAAAAGGAGTTGGTGGTAGACAGTCCCGGGCTCTACTACGTATTTTTGGAACTGAAGCTC

AGTCCAACATTCACAAACACAGGCCACAAGGTGCAGGGCTGGGTCTCTCTTGTTTTGCAAGC

AAAGCCTCAGGTAGATGACTTTGACAACTTGGCCCTGACAGTGGAACTGTTCCCTTGCTCCA

TGGAGAACAAGTTAGTGGACCGTTCCTGGAGTCAACTGTTGCTCCTGAAGGCTGGCCACCGC

```
CTCAGTGTGGGTCTGAGGGCTTATCTGCATGGAGCCCAGGATGCATACAGAGACTGGGAGCT
GTCTTATCCCAACACCACCAGCTTTGGACTCTTTCTTGTGAAACCCGACAACCCATGGGAAT
GAggtttccacaactgataaaactcgtgcaacttgaaactccgcctggtctttccaggtcta
gaggggttacactttgtactgtgctcgactccacgcccggtccactggcgggtgttagtagc
agcactgttgtttcgtagcggagcatggtggccgtgggaactcctccttggtgacaagggcc
cacggggccgaaagccacgtccagacggacccaccatgtgtgcaaccccagcacggcaactt
ttactgcgaacaccaccttaaggtgacactggtactggtactcggtcactggtgacaggcta
aggatgcccttcaggtaccccgaggtaacacgggacactcgggatctgagaaggggattggg
acttcttaaaagtgcccagtttaaaaagcttctacgcctgaataggcgaccggaggccggc
gcctttccattacccactactaaatccATGGCTTCAACCCGTGCCAAGCCCACGCTACCTCT
GCTCCTGGCCCTGGTCACCGTTGTGATCCCTGGGCCTGGTGATGCTCAGGTATCCATCCATC
CCAGAGAAGCCTTCCTGCCCCAGGGTGGGTCCGTGCAGGTGAACTGTTCTTCCTCATGCAAG
GAGGACCTCAGCCTGGGCTTGGAGACTCAGTGGCTGAAAGATGAGCTCGAGAGTGGACCCAA
CTGGAAGCTGTTTGAGCTGAGCGAGATCGGGGAGGACAGCAGTCCGCTGTGCTTTGAGAACT
GTGGCACCGTGCAGTCGTCCGCTTCCGCTACCATCACCGTGTATTCGTTTCCGGAGAGTGTG
GAGCTGAGACCTCTGCCAGCCTGGCAGCAAGTAGGCAAGGACCTCACCCTGCGCTGCCACGT
GGATGGTGGAGCACCGCGGACCCAGCTCTCAGCAGTGCTGCTCCGTGGGGAGGAGATACTGA
GCCGCCAGCCAGTGGGTGGGCACCCCAAGGACCCCAAGGAGATCACATTCACGGTGCTGGCT
AGCAGAGGGGACCACGGAGCCAATTTCTCATGCCGCACAGAACTGGATCTCAGGCCGCAAGG
GCTGGCATTGTTCTCTAATGTCTCCGAGGCCAGGAGCCTCCGGACTTTCGATCTTCCAGCTA
CCATCCCAAAGCTCGACACCCCTGACCTCCTGGAGGTGGGCACCCAGCAGAAGTTGTTTTGC
TCCCTGGAAGGCCTGTTTCCTGCCTCTGAAGCTCGGATATACCTGGAGCTGGGAGGCCAGAT
GCCGACCCAGGAGAGCACAAACAGCAGTGACTCTGTGTCAGCCACTGCCTTGGTAGAGGTGA
CTGAGGAGTTCGACAGAACCCTGCCGCTGCGCTGCGTTTTGGAGCTAGCGGACCAGATCCTG
GAGACGCAGAGGACCTTAACAGTCTACAACTTTTCAGCTCCGGTCCTGACCCTGAGCCAGCT
GGAGGTCTCGGAAGGGAGCCAAGTAACTGTGAAGTGTGAAGCCCACAGTGGGTCGAAGGTGG
TTCTTCTGAGCGGCGTCGAGCCTAGGCCACCCACCCCGCAGGTCCAATTCACACTGAATGCC
AGCTCGGAGGATCACAAACGAAGCTTCTTTTGCTCTGCCGCTCTGGAGGTGGCGGGAAAGTT
CCTGTTTAAAAACCAGACCCTGGAACTGCACGTGCTGTATGGTCCTCGGCTGGACGAGACGG
ACTGCTTGGGGAACTGGACCTGGCAAGAGGGGTCTCAGCAGACTCTGAAATGCCAGGCCTGG
GGGAACCCATCTCCTAAGATGACCTGCAGACGGAAGGCAGATGGTGCCCTGCTGCCCATCGG
GGTGGTGAAGTCTGTCAAACAGGAGATGAATGGTACATACGTGTGCCATGCCTTTAGCTCCC
ATGGGAATGTCACCAGGAATGTGTACCTGACAGTACTGTACCACTCTCAAAATAACTGGACT
ATAATCATTCTGGTGCCAGTACTGCTGGTCATTGTGGGCCTCGTGATGGCAGCCTCTTATGT
TTATAACCGCCAGAGAAAGATCAGGATATACAAGTTACAGAAGGCTCAGGAGGAGGCCATAA
AACTCAAGGGACAAGCCCCACCTCCCTGActcgagtcaccaggcg
```

We found that expression of genes after an IRES has generally been poor compared to genes where translation is not initiated by an IRES, so we investigated using the IX-E2 and L5-E4 sites as an alternative strategy. We generated the virus TAV-(19k)mCD80-(IX)mCD137L-(L5)mICAM1 carrying mouse CD80 in the E1B-19K site as shown in SEQ ID NO: 34 the CD80 gene capitalized and the flanking adenoviral sequence and restriction sites lower case (this used a Bsu36I restriction site instead of the SalI and XhoI restriction sites used in the other viruses), the mouse CD137L gene in the IX-E2 site of SEQ ID NO: 21 with the CD137L gene inserted in the NotI site as shown in SEQ ID NO: 35 with the CD137L gene capitalized and the flanking expression cassette sequence and residual NotI restriction site in lowercase, and the mouse ICAM1 gene in the L5-E4 site of SEQ ID NO: 29 with the ICAM1 gene inserted in the SwaI site as shown in SEQ ID NO: 36 with the ICAM1 gene capitalized and the flanking expression cassette sequence and residual SwaI site in lowercase. This virus also contains the TAV-255 deletion in the E1A promoter, deletion of the E3 region ADP, RIDα, RIDβ, and 14.7K genes, and deletion of the E4 region ORF1-4 genes.

SEQ ID NO: 34
[19k mCD80]
atctgacctcATGGCTTGCAATTGTCAGTTGATGCAGGATACACCACTCCTCAAGTTTCCAT

GTCCAAGGCTCATTCTTCTCTTTGTGCTGCTGATTCGTCTTTCACAAGTGTCTTCAGATGTT

GATGAACAACTGTCCAAGTCAGTGAAAGATAAGGTATTGCTGCCTTGCCGTTACAACTCTCC

TCATGAAGATGAGTCTGAAGACCGAATCTACTGGCAAAAACATGACAAAGTGGTGCTGTCTG

TCATTGCTGGGAAACTAAAAGTGTGGCCCGAGTATAAGAACCGGACTTTATATGACAACACT

ACCTACTCTCTTATCATCCTGGGCCTGGTCCTTTCAGACCGGGGCACATACAGCTGTGTCGT

TCAAAAGAAGGAAAGAGGAACGTATGAAGTTAAACACTTGGCTTTAGTAAAGTTGTCCATCA

AAGCTGACTTCTCTACCCCCAACATAACTGAGTCTGGAAACCCATCTGCAGACACTAAAAGG

ATTACCTGCTTTGCTTCCGGGGGTTTCCCAAAGCCTCGCTTCTCTTGGTTGGAAAATGGAAG

AGAATTACCTGGCATCAATACGACAATTTCCCAGGATCCTGAATCTGAATTGTACACCATTA

GTAGCCAACTAGATTTCAATACGACTCGCAACCACACCATTAAGTGTCTCATTAAATATGGA

GATGCTCACGTGTCAGAGGACTTCACCTGGGAAAAACCCCCAGAAGACCCTCCTGATAGCAA

GAACACACTTGTGCTCTTTGGGGCAGGATTCGGCGCAGTAATAACAGTCGTCGTCATCGTTG

TCATCATCAAATGCTTCTGTAAGCACAGAAGCTGTTTCAGAAGAAATGAGGCAAGCAGAGAA

ACAAACAACAGCCTTACCTTCGGGCCTGAAGAAGCATTAGCTGAACAGACCGTCTTCCTTTA

Gtcaggtgaatctgggtcacc

SEQ ID NO: 35
[IX mCD137L]
atagggagacccgcggccATGGACCAGCACACACTTGATGTGGAGGATACCGCGGATGCCAG

ACATCCAGCAGGTACTTCGTGCCCCTCGGATGCGGCGCTCCTCAGAGATACCGGGCTCCTCG

CGGACGCTGCGCTCCTCTCAGATACTGTGCGCCCCACAAATGCCGCGCTCCCCACGGATGCT

GCCTACCCTGCGGTTAATGTTCGGGATCGCGAGGCCGCGTGGCCGCCTGCACTGAACTTCTG

TTCCCGCCACCCAAAGCTCTATGGCCTAGTCGCTTTGGTTTTGCTGCTTCTGATCGCCGCCT

GTGTTCCTATCTTCACCCGCACCGAGCCTCGGCCAGCGCTCACAATCACCACCTCGCCCAAC

CTGGGTACCCGAGAGAATAATGCAGACCAGGTCACCCCTGTTTCCCACATTGGCTGCCCCAA

CACTACACAACAGGGCTCTCCTGTGTTCGCCAAGCTACTGGCTAAAAACCAAGCATCGTTGT

GCAATACAACTCTGAACTGGCACAGCCAAGATGGAGCTGGGAGCTCATACCTATCTCAAGGT

CTGAGGTACGAAGAAGACAAAAAGGAGTTGGTGGTAGACAGTCCCGGGCTCTACTACGTATT

TTTGGAACTGAAGCTCAGTCCAACATTCACAAACACAGGCCACAAGGTGCAGGGCTGGGTCT

CTCTTGTTTTGCAAGCAAAGCCTCAGGTAGATGACTTTGACAACTTGGCCCTGACAGTGGAA

CTGTTCCCTTGCTCCATGGAGAACAAGTTAGTGGACCGTTCCTGGAGTCAACTGTTGCTCCT

GAAGGCTGGCCACCGCCTCAGTGTGGGTCTGAGGGCTTATCTGCATGGAGCCCAGGATGCAT

-continued

```
ACAGAGACTGGGAGCTGTCTTATCCCAACACCACCAGCTTTGGACTCTTTCTTGTGAAACCC

GACAACCCATGGGAATGAggccgctgtgccttctagt
```

SEQ ID NO: 36

[L5 mICAM1]
```
cgccagaacacatttATGGCTTCAACCCGTGCCAAGCCCACGCTACCTCTGCTCCTGGCCCT

GGTCACCGTTGTGATCCCTGGGCCTGGTGATGCTCAGGTATCCATCCATCCCAGAGAAGCCT

TCCTGCCCCAGGGTGGGTCCGTGCAGGTGAACTGTTCTTCCTCATGCAAGGAGGACCTCAGC

CTGGGCTTGGAGACTCAGTGGCTGAAAGATGAGCTCGAGAGTGGACCCAACTGGAAGCTGTT

TGAGCTGAGCGAGATCGGGGAGGACAGCAGTCCGCTGTGCTTTGAGAACTGTGGCACCGTGC

AGTCGTCCGCTTCCGCTACCATCACCGTGTATTCGTTTCCGGAGAGTGTGGAGCTGAGACCT

CTGCCAGCCTGGCAGCAAGTAGGCAAGGACCTCACCCTGCGCTGCCACGTGGATGGTGGAGC

ACCGCGGACCCAGCTCTCAGCAGTGCTGCTCCGTGGGGAGGAGATACTGAGCCGCCAGCCAG

TGGGTGGGCACCCCAAGGACCCCAAGGAGATCACATTCACGGTGCTGGCTAGCAGAGGGGAC

CACGGAGCCAATTTCTCATGCCGCACAGAACTGGATCTCAGGCCGCAAGGGCTGGCATTGTT

CTCTAATGTCTCCGAGGCCAGGAGCCTCCGGACTTTCGATCTTCCAGCTACCATCCCAAAGC

TCGACACCCCTGACCTCCTGGAGGTGGGCACCCAGCAGAAGTTGTTTTGCTCCCTGGAAGGC

CTGTTTCCTGCCTCTGAAGCTCGGATATACCTGGAGCTGGGAGGCCAGATGCCGACCCAGGA

GAGCACAAACAGCAGTGACTCTGTGTCAGCCACTGCCTTGGTAGAGGTGACTGAGGAGTTCG

ACAGAACCCTGCCGCTGCGCTGCGTTTTGGAGCTAGCGGACCAGATCCTGGAGACGCAGAGG

ACCTTAACAGTCTACAACTTTTCAGCTCCGGTCCTGACCCTGAGCCAGCTGGAGGTCTCGGA

AGGGAGCCAAGTAACTGTGAAGTGTGAAGCCCACAGTGGGTCGAAGGTGGTTCTTCTGAGCG

GCGTCGAGCCTAGGCCACCCACCCCGCAGGTCCAATTCACACTGAATGCCAGCTCGGAGGAT

CACAAACGAAGCTTCTTTTGCTCTGCCGCTCTGGAGGTGGCGGGAAAGTTCCTGTTTAAAAA

CCAGACCCTGGAACTGCACGTGCTGTATGGTCCTCGGCTGGACGAGACGGACTGCTTGGGGA

ACTGGACCTGGCAAGAGGGGTCTCAGCAGACTCTGAAATGCCAGGCCTGGGGGAACCCATCT

CCTAAGATGACCTGCAGACGGAAGGCAGATGGTGCCCTGCTGCCCATCGGGGTGGTGAAGTC

TGTCAAACAGGAGATGAATGGTACATACGTGTGCCATGCCTTTAGCTCCCATGGGAATGTCA

CCAGGAATGTGTACCTGACAGTACTGTACCACTCTCAAAATAACTGGACTATAATCATTCTG

GTGCCAGTACTGCTGGTCATTGTGGGCCTCGTGATGGCAGCCTCTTATGTTTATAACCGCCA

GAGAAAGATCAGGATATACAAGTTACAGAAGGCTCAGGAGGAGGCCATAAAACTCAAGGGAC

AAGCCCCACCTCCCTGAaaataacttgtttattgcag
```

To test for expression from these two viruses: A549 cells, HT29 cells, ADS12 cells, and F244 cells were infected at an MOI of 3 with TAV-mCD80(IRES)mCD137L(IRES)mICAM1, TAV-(19k)mCD80-(IX)mCD137L-(L5)mICAM1, or the control virus TAV-(19k)Empty-(IX)Empty-(L5) Empty which has the same structure as TAV-(19k)mCD80-(IX)mCD137L-(L5)mICAM1 but without the transgenes. Two days later, the cells were stained for CD80, CD137L, and ICAM1 and results are shown in FIG. 9-FIG. 12. While there was poor expression of the CD137L and ICAM1 genes when expressed after the IRESes in TAV-mCD80(IRES)mCD137L(IRES)mICAM1, there was robust expression of those genes from the IX-E2 and L5-E4 sites with TAV-(19k)mCD80-(IX)mCD137L-(L5)mICAM1.

Example 11

While the experiments described above used an adenovirus based on human adenovirus type 5, other adenoviruses have a very similar structure and have clearly identifiable sites homologous to the IX-E2 and L5-E4 sites described above. For example, human adenovirus type 35 has the sequence in the IX-E2 site shown in SEQ ID NO: 37 and has the sequence in the L5-E4 site shown in SEQ ID NO: 38 where the polyadenylation signals are underlined in each sequence.

SEQ ID NO: 37

[Ad35 wt IX-E2]
AATAAAAAAAATTCCAGAATCAATGAATAAATAAACGAGCTTGTTGTTGA

TTTAAAATCAAGTGTTTTTATT

SEQ ID NO: 38

[Ad35 wt L5-E4]
AATAAAGTTTAAGTGTTTTTATT

To determine whether expression cassettes could be inserted into these sites, the IX-E2 site was modified with the same sequence used in the adenovirus type 5 revised IX-E2 site as shown in SEQ ID NO: 39 (the expression cassette was inserted in the opposite orientation as with adenovirus type 5, so the flanking viral sequence in lowercase is the reverse complement of conventional annotation which is shown in SEQ ID NO: 37, and the L5-E4 site was modified with the same sequence used in the adenovirus type 5 site with the EF1A promoter as shown in SEQ ID NO: 40. An adenovirus type 35 carrying both of those expression cassettes in site IX-E2 and L5-E4 as well as deletions in the E3 RIDα, RIDβ, and 14.7K genes and the E4 ORF1-4 genes was rescued, demonstrating that these sites can be used for insertion of expression cassettes in other serotypes of adenovirus. The strategy of inserting an expression cassette between two adjacent transcription units with polyadenylation sites facing each other is not in principle restricted to adenoviruses and could potentially be applied to other viruses as well.

SEQ ID NO: 39

[Ad35 IX-E2 cassette]
tcgagatcggtggtccagggcataccgtgcgcgaaaaatgaaataaaATACACCTTTTTTCG

ATTGTACGTATTTTTATTTACGGTAAATGGCCCGCCTGGCTGACCGCCCAACGACCCCCGCC

CATTGACGTCAATAATGACGTATGTTCCCATAGTAACGCCAATAGGGACTTTCCATTGACGT

CAATGGGTGGAGTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACA

TGACCTTATGGGACTTTCCTACTTGGCAGTACATCTACGTATTAGTCATCGCTATTACCATG

GTGATGCGGTTTTGGCAGTACATCAATGGGCGTGGATAGCGGTTTGACTCACGGGGATTTCC

AAGTCTCCACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTACGGTGGGAG

GTCTATATAAGCAGAGCTCTCTGGCTAACTAGAGAACCCACTGCTTACTGGCTTATCGAAAT

TAATACGACTCACTATAGGGAGACCCGCGGCCGCTGTGCCTTCTAGTTGCCAGCCATCTGTT

GTTTGCCCCTCCCCCGTGCCTTCCTTGACCCTGGAAGGTGCCACTCCCACTGTCCTTTCCTA

ATAAAaacacttgatttttaaatcaacaacaagctcgtttatttat

SEQ ID NO: 40

[Ad35 L5-E4 cassette]
tttcttttcttacattacagaagacgacaactaaaataaaAGGTTTATTAGGCGGCCTCCCC

GTCACCACCCCCCCAACCCGCCCCGACCGGAGCTGAGAGTAATTCATACAAAAGGACTCGC

CCCTGCCTTGGGGAATCCCAGGGACCGTCGTTAAACTCCCACTAACGTAGAACCCAGAGATC

GCTGCGTTCCCGCCCCCTCACCCGCCCGCTCTCGTCATCACTGAGGTGGAGAAGAGCATGCG

TGAGGCTCCGGTGCCCGTCAGTGGGCAGAGCGCACATCGCCCACAGTCCCCGAGAAGTTGGG

GGGAGGGGTCGGCAATTGAACCGGTGCCTAGAGAAGGTGGCGCGGGGTAAACTGGGAAAGTG

ATGTCGTGTACTGGCTCCGCCTTTTTCCCGAGGGTGGGGGAGAACCGTATATAAGTGCAGTA

GTCGCCGTGAACGTTCTTTTTCGCAACGGGTTTGCCGCCAGAACACAATTTAAATAACTTGT

TTATTGCAGCTTATAATGGTTACAaataaagtttaagtgttttatttaaaatcacaaaatt cg

Example 12

We used the revised IX-E2 and L5-E4 sites to generate a virus carrying the mouse IL12A and IL12B genes for use as a model in preclinical experiments. The gene for mouse IL12A was cloned into the NotI restriction site of the revised IX-E2 site with an expression cassette shown in SEQ ID NO: 21 to generate the sequence of SEQ ID NO: 42, with the residual nucleotides of the NotI restriction site underlined. The gene for mouse IL12B was cloned into the SwaI restriction site of the L5-E4 site with an expression cassette using the EF1A promoter shown in SEQ ID NO: 29 to generate the sequence of SEQ ID NO: 43, with the residual nucleotides of the SwaI restriction site underlined.

SEQ ID NO: 42

CTATAGGGAGACCC<u>GCGGCC</u>ATGTGTCAATCACGCTACCTCCTCTTTTTGGCCACCCTTGCC

CTCCTAAACCACCTCAGTTTGGCCAGGGTCATTCCAGTCTCTGGACCTGCCAGGTGTCTTAG

CCAGTCCCGAAACCTGCTGAAGACCACAGATGACATGGTGAAGACGGCCAGAGAAAAACTGA

AACATTATTCCTGCACTGCTGAAGACATCGATCATGAAGACATCACACGGGACCAAACCAGC

ACATTGAAGACCTGTTTACCACTGGAACTACACAAGAACGAGAGTTGCCTGGCTACTAGAGA

GACTTCTTCCACAACAAGAGGGAGCTGCCTGCCCCCACAGAAGACGTCTTTGATGATGACCC

TGTGCCTTGGTAGCATCTATGAGGACTTGAAGATGTACCAGACAGAGTTCCAGGCCATCAAC

GCAGCACTTCAGAATCACAACCATCAGCAGATCATTCTAGACAAGGGCATGCTGGTGGCCAT

CGATGAGCTGATGCAGTCTCTGAATCATAATGGCGAGACTCTGCGCCAGAAACCTCCTGTGG

GAGAAGCAGACCCTTACAGAGTGAAAATGAAGCTCTGCATCCTGCTTCACGCCTTCAGCACC

CGCGTCGTGACCATCAACAGGGTGATGGGCTATCTGAGCTCCGCCTGA<u>GGCCGC</u>TGTGCCTT

CTAGTT

SEQ ID NO: 43

TTGCCGCCAGAACACA<u>ATTT</u>ATGTGTCCTCAGAAGCTAACCATCTCCTGGTTTGCCATCGTT

TTGCTGGTGTCTCCACTCATGGCCATGTGGGAGCTGGAGAAAGACGTTTATGTTGTAGAGGT

GGACTGGACTCCCGATGCCCCTGGAGAAACAGTGAACCTCACCTGTGACACGCCTGAAGAAG

ATGACATCACCTGGACCTCAGACCAGAGACATGGAGTCATAGGCTCTGGAAAGACCCTGACC

ATCACTGTCAAAGAGTTTCTAGATGCTGGCCAGTACACCTGCCACAAAGGAGGCGAGACTCT

GAGCCACTCACATCTGCTGCTCCACAAGAAGGAAAATGGAATTTGGTCCACTGAAATTTTAA

AAAATTTCAAAAACAAGACTTTCCTGAAGTGTGAAGCACCAAATTACTCCGGACGGTTCACG

TGCTCATGGCTGGTGCAAAGAAACATGGACTTGAAGTTCAACATCAAGAGCAGTAGCAGTTC

CCCTGACTCTCGGGCAGTGACATGTGGAATGGCGTCTCTGTCTGCAGAGAAGGTCACACTGG

ACCAAAGGGACTATGAGAAGTATTCAGTGTCCTGCCAGGAGGATGTCACCTGCCCAACTGCC

GAGGAGACCCTGCCCATTGAACTGGCGTTGGAAGCACGGCAGCAGAATAAATATGAGAACTA

CAGCACCAGCTTCTTCATCAGGGACATCATCAAACCAGACCCGCCCAAGAACTTGCAGATGA

AGCCTTTGAAGAACTCACAGGTGGAGGTCAGCTGGGAGTACCCTGACTCCTGGAGCACTCCC

CATTCCTACTTCTCCCTCAAGTTCTTTGTTCGAATCCAGCGCAAGAAAGAAAAGATGAAGGA

GACAGAGGAGGGGTGTAACCAGAAAGGTGCGTTCCTCGTAGAGAAGACATCTACCGAAGTCC

AATGCAAAGGCGGGAATGTCTGCGTGCAAGCTCAGGATCGCTATTACAATTCCTCATGCAGC

AAGTGGGCATGTGTTCCCTGCAGGGTCCGATCCTAG<u>AAAT</u>AACTTGTTTATTGCAG

The virus TAV-IX5-Empty was generated carrying the TAV-255 deletion in the E1A promoter, the IX-E2 expression cassette without a transgene shown in SEQ ID NO: 21, and the L5-E4 expression cassette without a transgene shown in SEQ ID NO: 29. The virus TAV-IX5-mIL12 was generated carrying the TAV-255 deletion in the E1A promoter, the IX-E2 expression cassette including the mouse IL12A gene of SEQ ID NO: 42, and the L5-E4 expression cassette including the mouse IL12B gene of SEQ ID NO: 43.

To test these viruses for oncolysis, A549 cells were infected with the TAV-IX5-Empty or TAV-IX5-mIL12 viruses at an MOI of 5 or kept as non-infected controls, and wells were stained with crystal violet every two days after infection. As shown in FIG. 13, both the empty control virus and the virus carrying mouse IL-12 were lytic within 4-6 days.

To test for transgene expression, A549 cells were infected with the TAV-IX5-Empty or TAV-IX5-mIL12 viruses at an MOI of 5 in triplicate and conditioned media was collected five days after infection to measure mouse IL-12 with an ELISA detecting only the heterodimer with both the mouse IL12A and mouse IL12B chains. As shown in FIG. 14, TAV-IX5-mIL12 induced expression of high levels of the IL-12 heterodimer.

Human Adenovirus 5, Complete Genome

NCBI Reference Sequence. AC_000008.1

(SEQ ID NO: 1)

>AC_000008.1 Human adenovirus 5, complete genome
CATCATCAATAATATACCTTATTTTGGATTGAAGCCAATATGATAATGAGGGGGTGGAGTTTGTGACGTG

GCGCGGGGCGTGGGAACGGGGCGGGTGACGTAGTAGTGTGGCGGAAGTGTGATGTTGCAAGTGTGGCGGA

ACACATGTAAGCGACGGATGTGGCAAAAGTGACGTTTTTGGTGTGCGCCGGTGTACACAGGAAGTGACAA

TTTTCGCGCGGTTTTAGGCGGATGTTGTAGTAAATTTGGGCGTAACCGAGTAAGATTTGGCCATTTTCGC

GGGAAAACTGAATAAGAGGAAGTGAAATCTGAATAATTTTGTGTTACTCATAGCGCGTAATATTTGTCTA

GGGCCGCGGGGACTTTGACCGTTTACGTGGAGACTCGCCCAGGTGTTTTTCTCAGGTGTTTTCCGCGTTC

CGGGTCAAAGTTGGCGTTTTATTATTATAGTCAGCTGACGTGTAGTGTATTTATACCCGGTGAGTTCCTC

AAGAGGCCACTCTTGAGTGCCAGCGAGTAGAGTTTTCTCCTCCGAGCCGCTCCGACACCGGGACTGAAAA

TGAGACATATTATCTGCCACGGAGGTGTTATTACCGAAGAAATGGCCGCCAGTCTTTTGGACCAGCTGAT

CGAAGAGGTACTGGCTGATAATCTTCCACCTCCTAGCCATTTTGAACCACCTACCCTTCACGAACTGTAT

GATTTAGACGTGACGGCCCCCGAAGATCCCAACGAGGAGGCGGTTTCGCAGATTTTTCCCGACTCTGTAA

TGTTGGCGGTGCAGGAAGGGATTGACTTACTCACTTTTCCGCCGGCGCCCGGTTCTCCGGAGCCGCCTCA

CCTTTCCCGGCAGCCCGAGCAGCCGGAGCAGAGAGCCTTGGGTCCGGTTTCTATGCCAAACCTTGTACCG

GAGGTGATCGATCTTACCTGCCACGAGGCTGGCTTTCCACCCAGTGACGACGAGGATGAAGAGGGTGAGG

AGTTTGTGTTAGATTATGTGGAGCACCCCGGGCACGGTTGCAGGTCTTGTCATTATCACCGGAGGAATAC

GGGGGACCCAGATATTATGTGTTCGCTTTGCTATATGAGGACCTGTGGCATGTTTGTCTACAGTAAGTGA

AAATTATGGGCAGTGGGTGATAGAGTGGTGGGTTTGGTGTGGTAATTTTTTTTTAATTTTTACAGTTTT

GTGGTTTAAAGAATTTTGTATTGTGATTTTTTTAAAAGGTCCTGTGTCTGAACCTGAGCCTGAGCCCGAG

CCAGAACCGGAGCCTGCAAGACCTACCCGCCGTCCTAAAATGGCGCCTGCTATCCTGAGACGCCCGACAT

CACCTGTGTCTAGAGAATGCAATAGTAGTACGGATAGCTGTGACTCCGGTCCTTCTAACACACCTCCTGA

GATACACCCGGTGGTCCCGCTGTGCCCCATTAAACCAGTTGCCGTGAGAGTTGGTGGGCGTCGCCAGGCT

GTGGAATGTATCGAGGACTTGCTTAACGAGCCTGGGCAACCTTTGGACTTGAGCTGTAAACGCCCCAGGC

CATAAGGTGTAAACCTGTGATTGCGTGTGTGGTTAACGCCTTTGTTTGCTGAATGAGTTGATGTAAGTTT

AATAAAGGGTGAGATAATGTTTAACTTGCATGGCGTGTTAAATGGGGCGGGGCTTAAAGGGTATATAATG

CGCCGTGGGCTAATCTTGGTTACATCTGACCTCATGGAGGCTTGGGAGTGTTTGGAAGATTTTTCTGCTG

TGCGTAACTTGCTGGAACAGAGCTCTAACAGTACCTCTTGGTTTTGGAGGTTTCTGTGGGGCTCATCCCA

GGCAAAGTTAGTCTGCAGAATTAAGGAGGATTACAAGTGGGAATTTGAAGAGCTTTTGAAATCCTGTGGT

GAGCTGTTTGATTCTTTGAATCTGGGTCACCAGGCGCTTTTCCAAGAGAAGGTCATCAAGACTTTGGATT

TTTCCACACCGGGGCGCGCTGCGGCTGCTGTTGCTTTTTTGAGTTTTATAAAGGATAAATGGAGCGAAGA

AACCCATCTGAGCGGGGGGTACCTGCTGGATTTTCTGGCCATGCATCTGTGGAGAGCGGTTGTGAGACAC

AAGAATCGCCTGCTACTGTTGTCTTCCGTCCGCCCGGCGATAATACCGACGGAGGAGCAGCAGCAGCAGC

AGGAGGAAGCCAGGCGGCGGCGGCAGGAGCAGAGCCCATGGAACCCGAGAGCCGGCCTGGACCCTCGGGA

ATGAATGTTGTACAGGTGGCTGAACTGTATCCAGAACTGAGACGCATTTTGACAATTACAGAGGATGGGC

AGGGGCTAAAGGGGGTAAAGAGGGAGCGGGGGGCTTGTGAGGCTACAGAGGAGGCTAGGAATCTAGCTTT

TAGCTTAATGACCAGACACCGTCCTGAGTGTATTACTTTTCAACAGATCAAGGATAATTGCGCTAATGAG

CTTGATCTGCTGGCGCAGAAGTATTCCATAGAGCAGCTGACCACTTACTGGCTGCAGCCAGGGGATGATT

TTGAGGAGGCTATTAGGGTATATGCAAAGGTGGCACTTAGGCCAGATTGCAAGTACAAGATCAGCAAACT

TGTAAATATCAGGAATTGTTGCTACATTTCTGGGAACGGGGCCGAGGTGGAGATAGATACGGAGGATAGG

-continued

```
GTGGCCTTTAGATGTAGCATGATAAATATGTGGCCGGGGGTGCTTGGCATGGACGGGGTGGTTATTATGA
ATGTAAGGTTTACTGGCCCCAATTTTAGCGGTACGGTTTTCCTGGCCAATACCAACCTTATCCTACACGG
TGTAAGCTTCTATGGGTTTAACAATACCTGTGTGGAAGCCTGGACCGATGTAAGGGTTCGGGGCTGTGCC
TTTTACTGCTGCTGGAAGGGGGTGGTGTGTCGCCCCAAAAGCAGGGCTTCAATTAAGAAATGCCTCTTTG
AAAGGTGTACCTTGGGTATCCTGTCTGAGGGTAACTCCAGGGTGCGCCACAATGTGGCCTCCGACTGTGG
TTGCTTCATGCTAGTGAAAAGCGTGGCTGTGATTAAGCATAACATGGTATGTGGCAACTGCGAGGACAGG
GCCTCTCAGATGCTGACCTGCTCGGACGGCAACTGTCACCTGCTGAAGACCATTCACGTAGCCAGCCACT
CTCGCAAGGCCTGGCCAGTGTTTGAGCATAACATACTGACCCGCTGTTCCTTGCATTTGGGTAACAGGAG
GGGGGTGTTCCTACCTTACCAATGCAATTTGAGTCACACTAAGATATTGCTTGAGCCCGAGAGCATGTCC
AAGGTGAACCTGAACGGGGTGTTTGACATGACCATGAAGATCTGGAAGGTGCTGAGGTACGATGAGACCC
GCACCAGGTGCAGACCCTGCGAGTGTGGCGGTAAACATATTAGGAACCAGCCTGTGATGCTGGATGTGAC
CGAGGAGCTGAGGCCCGATCACTTGGTGCTGGCCTGCACCCGCGCTGAGTTTGGCTCTAGCGATGAAGAT
ACAGATTGAGGTACTGAAATGTGTGGGCGTGGCTTAAGGGTGGGAAAGAATATATAAGGTGGGGTCTTA
TGTAGTTTTGTATCTGTTTTGCAGCAGCCGCCGCCGCCATGAGCACCAACTCGTTTGATGGAAGCATTGT
GAGCTCATATTTGACAACGCGCATGCCCCCATGGGCCGGGGTGCGTCAGAATGTGATGGGCTCCAGCATT
GATGGTCGCCCCGTCCTGCCCGCAAACTCTACTACCTTGACCTACGAGACCGTGTCTGGAACGCCGTTGG
AGACTGCAGCCTCCGCCGCGCTTCAGCCGCTGCAGCCACCGCCCGCGGGATTGTGACTGACTTTGCTTT
CCTGAGCCCGCTTGCAAGCAGTGCAGCTTCCCGTTCATCCGCCCGCGATGACAAGTTGACGGCTCTTTTG
GCACAATTGGATTCTTTGACCCGGGAACTTAATGTCGTTTCTCAGCAGCTGTTGGATCTGCGCCAGCAGG
TTTCTGCCCTGAAGGCTTCCTCCCCTCCCAATGCGGTTTAAAACATAAATAAAAAACCAGACTCTGTTTG
GATTTGGATCAAGCAAGTGTCTTGCTGTCTTTATTTAGGGGTTTTGCGCGCGCGGTAGGCCCGGGACCAG
CGGTCTCGGTCGTTGAGGGTCCTGTGTATTTTTTCCAGGACGTGGTAAAGGTGACTCTGGATGTTCAGAT
ACATGGGCATAAGCCCGTCTCTGGGGTGGAGGTAGCACCACTGCAGAGCTTCATGCTGCGGGTGGTGTT
GTAGATGATCCAGTCGTAGCAGGAGCGCTGGGCGTGGTGCCTAAAAATGTCTTTCAGTAGCAAGCTGATT
GCCAGGGGCAGGCCCTTGGTGTAAGTGTTTACAAAGCGGTTAAGCTGGGATGGGTGCATACGTGGGGATA
TGAGATGCATCTTGGACTGTATTTTTAGGTTGGCTATGTTCCCAGCCATATCCCTCCGGGGATTCATGTT
GTGCAGAACCACCAGCACAGTGTATCCGGTGCACTTGGGAAATTTGTCATGTAGCTTAGAAGGAAATGCG
TGGAAGAACTTGGAGACGCCCTTGTGACCTCCAAGATTTTCCATGCATTCGTCCATAATGATGGCAATGG
GCCCACGGGCGGCGGCCTGGGCGAAGATATTTCTGGGATCACTAACGTCATAGTTGTGTTCCAGGATGAG
ATCGTCATAGGCCATTTTTACAAAGCGCGGGCGGAGGGTGCCAGACTGCGGTATAATGGTTCCATCCGGC
CCAGGGGCGTAGTTACCCTCACAGATTTGCATTTCCCACGCTTTGAGTTCAGATGGGGGGATCATGTCTA
CCTGCGGGGCGATGAAGAAAACGGTTTCCGGGGTAGGGGAGATCAGCTGGGAAGAAAGCAGGTTCCTGAG
CAGCTGCGACTTACCGCAGCCGGTGGGCCCGTAAATCACACCTATTACCGGGTGCAACTGGTAGTTAAGA
GAGCTGCAGCTGCCGTCATCCCTGAGCAGGGGGCCACTTCGTTAAGCATGTCCCTGACTCGCATGTTTT
CCCTGACCAAATCCGCCAGAAGGCGCTCGCCGCCCAGCGATAGCAGTTCTTGCAAGGAAGCAAAGTTTTT
CAACGGTTTGAGACCGTCCGCCGTAGGCATGCTTTTGAGCGTTTGACCAAGCAGTTCCAGGCGGTCCCAC
AGCTCGGTCACCTGCTCTACGGCATCTCGATCCAGCATATCTCCTCGTTTCGCGGGTTGGGGCGGCTTTC
GCTGTACGGCAGTAGTCGGTGCTCGTCCAGACGGGCCAGGGTCATGTCTTTCCACGGGCGCAGGGTCCTC
GTCAGCGTAGTCTGGGTCACGGTGAAGGGGTGCGCTCCGGGCTGCGCGCTGGCCAGGGTGCGCTTGAGGC
TGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAG
```

-continued

```
GGGCAGTGCAGACTTTTGAGGGCGTAGAGCTTGGGCGCGAGAAATACCGATTCCGGGGAGTAGGCATCCG

CGCCGCAGGCCCCGCAGACGGTCTCGCATTCCACGAGCCAGGTGAGCTCTGGCCGTTCGGGGTCAAAAAC

CAGGTTTCCCCCATGCTTTTTGATGCGTTTCTTACCTCTGGTTTCCATGAGCCGGTGTCCACGCTCGGTG

ACGAAAAGGCTGTCCGTGTCCCCGTATACAGACTTGAGAGGCCTGTCCTCGAGCGGTGTTCCGCGGTCCT

CCTCGTATAGAAACTCGGACCACTCTGAGACAAAGGCTCGCGTCCAGGCCAGCACGAAGGAGGCTAAGTG

GGAGGGGTAGCGGTCGTTGTCCACTAGGGGGTCCACTCGCTCCAGGGTGTGAAGACACATGTCGCCCTCT

TCGGCATCAAGGAAGGTGATTGGTTTGTAGGTGTAGGCCACGTGACCGGGTGTTCCTGAAGGGGGCTAT

AAAAGGGGGTGGGGGCGCGTTCGTCCTCACTCTCTTCCGCATCGCTGTCTGCGAGGGCCAGCTGTTGGGG

TGAGTACTCCCTCTGAAAAGCGGGCATGACTTCTGCGCTAAGATTGTCAGTTTCCAAAAACGAGGAGGAT

TTGATATTCACCTGGCCCGCGGTGATGCCTTTGAGGGTGGCCGCATCCATCTGGTCAGAAAAGACAATCT

TTTTGTTGTCAAGCTTGGTGGCAAACGACCCGTAGAGGGCGTTGGACAGCAACTTGGCGATGGAGCGCAG

GGTTTGGTTTTTGTCGCGATCGGCGCGCTCCTTGGCCGCGATGTTTAGCTGCACGTATTCGCGCGCAACG

CACCGCCATTCGGGAAAGACGGTGGTGCGCTCGTCGGGCACCAGGTGCACGCGCCAACCGCGGTTGTGCA

GGGTGACAAGGTCAACGCTGGTGGCTACCTCTCCGCGTAGGCGCTCGTTGGTCCAGCAGAGGCGGCCGCC

CTTGCGCGAGCAGAATGGCGGTAGGGGGTCTAGCTGCGTCTCGTCCGGGGGGTCTGCGTCCACGGTAAAG

ACCCCGGGCAGCAGGCGCGCGTCGAAGTAGTCTATCTTGCATCCTTGCAAGTCTAGCGCCTGCTGCCATG

CGCGGGCGGCAAGCGCGCGCTCGTATGGGTTGAGTGGGGGACCCCATGGCATGGGGTGGGTGAGCGCGGA

GGCGTACATGCCGCAAATGTCGTAAACGTAGAGGGGCTCTCTGAGTATTCCAAGATATGTAGGGTAGCAT

CTTCCACCGCGGATGCTGGCGCGCACGTAATCGTATAGTTCGTGCGAGGGAGCGAGGAGGTCGGGACCGA

GGTTGCTACGGGCGGGCTGCTCTGCTCGGAAGACTATCTGCCTGAAGATGGCATGTGAGTTGGATGATAT

GGTTGGACGCTGGAAGACGTTGAAGCTGGCGTCTGTGAGACCTACCGCGTCACGCACGAAGGAGGCGTAG

GAGTCGCGCAGCTTGTTGACCAGCTCGGCGGTGACCTGCACGTCAGGGCGCAGTAGTCCAGGGTTTCCT

TGATGATGTCATACTTATCCTGTCCCTTTTTTTCCACAGCTCGCGGTTGAGGACAAACTCTTCGCGGTC

TTTCCAGTACTCTTGGATCGGAAACCCGTCGGCCTCCGAACGGTAAGAGCCTAGCATGTAGAACTGGTTG

ACGGCCTGGTAGGCGCAGCATCCCTTTTCTACGGGTAGCGCGTATGCCTGCGCGGCCTTCCGGAGCGAGG

TGTGGGTGAGCGCAAAGGTGTCCCTGACCATGACTTTGAGGTACTGGTATTTGAAGTCAGTGTCGTCGCA

TCCGCCCTGCTCCCAGAGCAAAAAGTCCGTGCGCTTTTTGGAACGCGGATTTGGCAGGGCGAAGGTGACA

TCGTTGAAGAGTATCTTTCCCGCGCGAGGCATAAAGTTGCGTGTGATGCGGAAGGGTCCCGGCACCTCGG

AACGGTTGTTAATTACCTGGGCGGCGAGCACGATCTCGTCAAAGCCGTTGATGTTGTGGCCCACAATGTA

AAGTTCCAAGAAGCGCGGGATGCCCTTGATGGAAGGCAATTTTTTAAGTTCCTCGTAGGTGAGCTCTTCA

GGGGAGCTGAGCCCGTGCTCTGAAAGGGCCCAGTCTGCAAGATGAGGGTTGGAAGCGACGAATGAGCTCC

ACAGGTCACGGGCCATTAGCATTTGCAGGTGGTCGCGAAAGGTCCTAAACTGGCGACCTATGGCCATTTT

TTCTGGGGTGATGCAGTAGAAGGTAAGCGGGTCTTGTTCCCAGCGGTCCCATCCAAGGTTCGCGGCTAGG

TCTCGCGCGGCAGTCACTAGAGGCTCATCTCCGCCGAACTTCATGACCAGCATGAAGGGCACGAGCTGCT

TCCCAAAGGCCCCCATCCAAGTATAGGTCTCTACATCGTAGGTGACAAAGAGACGCTCGGTGCGAGGATG

CGAGCCGATCGGGAAGAACTGGATCTCCCGCCACCAATTGGAGGAGTGGCTATTGATGTGGTGAAAGTAG

AAGTCCCTGCGACGGGCCGAACACTCGTGCTGGCTTTTGTAAAAACGTGCGCAGTACTGGCAGCGGTGCA

CGGGCTGTACATCCTGCACGAGGTTGACCTGACGACCGCGCACAAGGAAGCAGAGTGGGAATTTGAGCCC

CTCGCCTGGCGGGTTTGGCTGGTGGTCTTCTACTTCGGCTGCTTGTCCTTGACCGTCTGGCTGCTCGAGG

GGAGTTACGGTGGATCGGACCACCACGCCGCGCGAGCCCAAAGTCCAGATGTCCGCGCGCGGCGGTCGGA
```

-continued

```
GCTTGATGACAACATCGCGCAGATGGGAGCTGTCCATGGTCTGGAGCTCCCGCGGCGTCAGGTCAGGCGG
GAGCTCCTGCAGGTTTACCTCGCATAGACGGGTCAGGGCGCGGGCTAGATCCAGGTGATACCTAATTTCC
AGGGGCTGGTTGGTGGCGGCGTCGATGGCTTGCAAGAGGCCGCATCCCCGCGGCGCGACTACGGTACCGC
GCGGCGGGCGGTGGGCGCGGGGGTGTCCTTGGATGATGCATCTAAAAGCGGTGACGCGGGCGAGCCCCC
GGAGGTAGGGGGGGCTCCGGACCCGCCGGGAGAGGGGGCAGGGGCACGTCGGCGCCGCGCGCGGGCAGGA
GCTGGTGCTGCGCGCGTAGGTTGCTGGCAACGCGACGACGCGGCGGTTGATCTCCTGAATCTGGCGCCT
CTGCGTGAAGACGACGGGCCCGGTGAGCTTGAGCCTGAAAGAGAGTTCGACAGAATCAATTTCGGTGTCG
TTGACGGCGGCCTGGCGCAAAATCTCCTGCACGTCTCCTGAGTTGTCTTGATAGGCGATCTCGGCCATGA
ACTGCTCGATCTCTTCCTCCTGGAGATCTCCGCGTCCGGCTCGCTCCACGGTGGCGGCGAGGTCGTTGGA
AATGCGGGCCATGAGCTGCGAGAAGGCGTTGAGGCCTCCCTCGTTCCAGACGCGGCTGTAGACCACGCCC
CCTTCGGCATCGCGGGCGCGCATGACCACCTGCGCGAGATTGAGCTCCACGTGCCGGGCGAAGACGGCGT
AGTTTCGCAGGCGCTGAAAGAGGTAGTTGAGGGTGGTGGCGGTGTGTTCTGCCACGAAGAAGTACATAAC
CCAGCGTCGCAACGTGGATTCGTTGATATCCCCCAAGGCCTCAAGGCGCTCCATGGCCTCGTAGAAGTCC
ACGGCGAAGTTGAAAAACTGGGAGTTGCGCGCCGACACGGTTAACTCCTCCTCCAGAAGACGGATGAGCT
CGGCGACAGTGTCGCGCACCTCGCGCTCAAAGGCTACAGGGGCCTCTTCTTCTTCTTCAATCTCCTCTTC
CATAAGGGCCTCCCCTTCTTCTTCTTCTGGCGGCGGTGGGGAGGGGGACACGGCGGCGACGACGGCGC
ACCGGGAGGCGGTCGACAAAGCGCTCGATCATCTCCCCGCGGCGACGGCGCATGGTCTCGGTGACGGCGC
GGCCGTTCTCGCGGGGGCGCAGTTGGAAGACGCCGCCCGTCATGTCCCGGTTATGGGTTGGCGGGGGCT
GCCATGCGGCAGGGATACGGCGCTAACGATGCATCTCAACAATTGTTGTGTAGGTACTCCGCCGCCGAGG
GACCTGAGCGAGTCCGCATCGACCGGATCGGAAAACCTCTCGAGAAAGGCGTCTAACCAGTCACAGTCGC
AAGGTAGGCTGAGCACCGTGGCGGGCGGCAGCGGGCGGCGGTCGGGGTTGTTTCTGGCGGAGGTGCTGCT
GATGATGTAATTAAAGTAGGCGGTCTTGAGACGGCGGATGGTCGACAGAAGCACCATGTCCTTGGGTCCG
GCCTGCTGAATGCGCAGGCGGTCGGCCATGCCCCAGGCTTCGTTTTGACATCGGCGCAGGTCTTTGTAGT
AGTCTTGCATGAGCCTTTCTACCGGCACTTCTTCTTCTCCTTCCTCTTGTCCTGCATCTCTTGCATCTAT
CGCTGCGGCGGCGGAGTTTGGCCGTAGGTGGCGCCCTCTTCCTCCCATGCGTGTGACCCCGAAGCCC
CTCATCGGCTGAAGCAGGGCTAGGTCGGCGACAACGCGCTCGGCTAATATGGCCTGCTGCACCTGCGTGA
GGGTAGACTGGAAGTCATCCATGTCCACAAAGCGGTGGTATGCGCCCGTGTTGATGGTGTAAGTGCAGTT
GGCCATAACGGACCAGTTAACGGTCTGGTGACCCGGCTGCGAGAGCTCGGTGTACCTGAGACGCGAGTAA
GCCCTCGAGTCAAATACGTAGTCGTTGCAAGTCCGCACCAGGTACTGGTATCCCACCAAAAGTGCGGCG
GCGGCTGGCGGTAGAGGGGCCAGCGTAGGGTGGCCGGGGCTCCGGGGCGAGATCTTCCAACATAAGGCG
ATGATATCCGTAGATGTACCTGGACATCCAGGTGATGCCGGCGGCGGTGGTGGAGGCGCGCGGAAAGTCG
CGGACGCGGTTCCAGATGTTGCGCAGCGGCAAAAAGTGCTCCATGGTCGGGACGCTCTGGCCGGTCAGGC
GCGCGCAATCGTTGACGCTCTAGACCGTGCAAAAGGAGAGCCTGTAAGCGGGCACTCTTCCGTGGTCTGG
TGGATAAATTCGCAAGGGTATCATGGCGGACGACCGGGGTTCGAGCCCCGTATCCGGCCGTCCGCCGTGA
TCCATGCGGTTACCGCCCGCGTGTCGAACCCAGGTGTGCGACGTCAGACAACGGGGAGTGCTCCTTTTG
GCTTCCTTCCAGGCGCGGCGGCTGCTGCGCTAGCTTTTTTGGCCACTGGCCGCGCGCAGCGTAAGCGGTT
AGGCTGGAAAGCGAAAGCATTAAGTGGCTCGCTCCCTGTAGCCGGAGGGTTATTTTCCAAGGGTTGAGTC
GCGGGACCCCCGGTTCGAGTCTCGGACCGGCCGGACTGCGGCGAACGGGGGTTTGCCTCCCCGTCATGCA
AGACCCCGCTTGCAAATTCCTCCGGAAACAGGGACGAGCCCCTTTTTTGCTTTTCCCAGATGCATCCGGT
GCTGCGGCAGATGCGCCCCCCTCCTCAGCAGCGGCAAGAGCAAGAGCAGCGGCAGACATGCAGGGCACCC
TCCCCTCCTCCTACCGCGTCAGGAGGGGCGACATCCGCGGTTGACGCGGCAGCAGATGGTGATTACGAAC
```

-continued

```
CCCCGCGGCGCCGGGCCCGGCACTACCTGGACTTGGAGGAGGGCGAGGGCCTGGCGCGGCTAGGAGCGCC
CTCTCCTGAGCGGTACCCAAGGGTGCAGCTGAAGCGTGATACGCGTGAGGCGTACGTGCCGCGGCAGAAC
CTGTTTCGCGACCGCGAGGGAGAGGAGCCCGAGGAGATGCGGGATCGAAAGTTCCACGCAGGGCGCGAGC
TGCGGCATGGCCTGAATCGCGAGCGGTTGCTGCGCGAGGAGGACTTTGAGCCCGACGCGCGAACCGGGAT
TAGTCCCGCGCGCACACGTGGCGGCCGCCGACCTGGTAACCGCATACGAGCAGACGGTGAACCAGGAG
ATTAACTTTCAAAAAAGCTTTAACAACCACGTGCGTACGCTTGTGGCGCGCGAGGAGGTGGCTATAGGAC
TGATGCATCTGTGGGACTTTGTAAGCGCGCTGGAGCAAAACCCAAATAGCAAGCCGCTCATGGCGCAGCT
GTTCCTTATAGTGCAGCACAGCAGGGACAACGAGGCATTCAGGGATGCGCTGCTAAACATAGTAGAGCCC
GAGGGCCGCTGGCTGCTCGATTTGATAAACATCCTGCAGAGCATAGTGGTGCAGGAGCGCAGCTTGAGCC
TGGCTGACAAGGTGGCCGCCATCAACTATTCCATGCTTAGCCTGGGCAAGTTTTACGCCCGCAAGATATA
CCATACCCCTTACGTTCCCATAGACAAGGAGGTAAAGATCGAGGGGTTCTACATGCGCATGGCGCTGAAG
GTGCTTACCTTGAGCGACGACCTGGGCGTTTATCGCAACGAGCGCATCCACAAGGCCGTGAGCGTGAGCC
GGCGGCGCGAGCTCAGCGACCGCGAGCTGATGCACAGCCTGCAAAGGGCCCTGGCTGGCACGGGCAGCGG
CGATAGAGAGGCCGAGTCCTACTTTGACGCGGGCGCTGACCTGCGCTGGGCCCCAAGCCGACGCGCCCTG
GAGGCAGCTGGGGCCGGACCTGGGCTGGCGGTGGCACCCGCGCGCGCTGGCAACGTCGGCGGCGTGGAGG
AATATGACGAGGACGATGAGTACGAGCCAGAGGACGGCGAGTACTAAGCGGTGATGTTTCTGATCAGATG
ATGCAAGACGCAACGGACCCGGCGGTGCGGGCGGCGCTGCAGAGCCAGCCGTCCGGCCTTAACTCCACGG
ACGACTGGCGCCAGGTCATGGACCGCATCATGTCGCTGACTGCGCGCAATCCTGACGCGTTCCGGCAGCA
GCCGCAGGCCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAGGCCGGCCTGGTCT
ACGACGCGCTGCTTCAGCGCGTGGCTCGTTACAACAGCGGCAACGTGCAGACCAACCTGGACCGGCTGGT
GGGGGATGTGCGCGAGGCCGTGGCGCAGCGTGAGCGCGCGCAGCAGCAGGGCAACCTGGGCTCCATGGTT
GCACTAAACGCCTTCCTGAGTACACAGCCCGCCAACGTGCCGCGGGGACAGGAGGACTACACCAACTTTG
TGAGCGCACTGCGGCTAATGGTGACTGAGACACCGCAAAGTGAGGTGTACCAGTCTGGGCCAGACTATTT
TTTCCAGACCAGTAGACAAGGCCTGCAGACCGTAAACCTGAGCCAGGCTTTCAAAAACTTGCAGGGGCTG
TGGGGGGTGCGGGCTCCCACAGGCGACCGCGCGACCGTGTCTAGCTTGCTGACGCCCAACTCGCGCCTGT
TGCTGCTGCTAATAGCGCCCTTCACGGACAGTGGCAGCGTGTCCCGGACACATACCTAGGTCACTTGCT
GACACTGTACCGCGAGGCCATAGGTCAGGCGCATGTGGACGAGCATACTTTCCAGGAGATTACAAGTGTC
AGCCGCGCGCTGGGCAGGAGGACACGGGCAGCCTGGAGGCAACCCTAAACTACCTGCTGACCAACCGGC
GGCAGAAGATCCCCTCGTTGCACAGTTTAAACAGCGAGGAGGAGCGCATTTTGCGCTACGTGCAGCAGAG
CGTGAGCCTTAACCTGATGCGCGACGGGTAACGCCCAGCGTGGCGCTGGACATGACCGCGCGCAACATG
GAACCGGGCATGTATGCCTCAAACCGGCCGTTTATCAACCGCCTAATGGACTACTTGCATCGCGCGGCCG
CCGTGAACCCCGAGTATTTCACCAATGCCATCTTGAACCCGCACTGGCTACCGCCCCTGGTTTCTACAC
CGGGGGATTCGAGGTGCCCGAGGGTAACGATGGATTCCTCTGGGACGACATAGACGACAGCGTGTTTTCC
CCGCAACCGCAGACCCTGCTAGAGTTGCAACAGCGCGAGCAGGCAGAGGCGGCGCTGCGAAAGGAAAGCT
TCCGCAGGCCAAGCAGCTTGTCCGATCTAGGCGCTGCGGCCCCGCGGTCAGATGCTAGTAGCCCATTTCC
AAGCTTGATAGGGTCTCTTACCAGCACTCGCACCACCCGCCCGCGCCTGCTGGGCGAGGAGGAGTACCTA
AACAACTCGCTGCTGCAGCCGCAGCGCGAAAAAAAACCTGCCTCCGGCATTTCCCAACAACGGGATAGAGA
GCCTAGTGGACAAGATGAGTAGATGGAAGACGTACGCGCAGGAGCACAGGGACGTGCCAGGCCCGCGCCC
GCCCACCCGTCGTCAAAGGCACGACCGTCAGCGGGGTCTGGTGTGGGAGGACGATGACTCGGCAGACGAC
```

-continued

```
AGCAGCGTCCTGGATTTGGGAGGGAGTGGCAACCCGTTTGCGCACCTTCGCCCCAGGCTGGGGAGAATGT
TTTAAAAAAAAAAAAGCATGATGCAAAATAAAAAACTCACCAAGGCCATGGCACCGAGCGTTGGTTTTCT
TGTATTCCCCTTAGTATGCGGCGCGCGGCGATGTATGAGGAAGGTCCTCCTCCCTCCTACGAGAGTGTGG
TGAGCGCGGCGCCAGTGGCGGCGGCGCTGGGTTCTCCCTTCGATGCTCCCCTGGACCCGCCGTTTGTGCC
TCCGCGGTACCTGCGGCCTACCGGGGGGAGAAACAGCATCCGTTACTCTGAGTTGGCACCCCTATTCGAC
ACCACCCGTGTGTACCTGGTGGACAACAAGTCAACGGATGTGGCATCCCTGAACTACCAGAACGACCACA
GCAACTTTCTGACCACGGTCATTCAAAACAATGACTACAGCCCGGGGGAGGCAAGCACACAGACCATCAA
TCTTGACGACCGGTCGCACTGGGGCGGCGACCTGAAAACCATCCTGCATACCAACATGCCAAATGTGAAC
GAGTTCATGTTTACCAATAAGTTTAAGGCGCGGGTGATGGTGTCGCGCTTGCCTACTAAGGACAATCAGG
TGGAGCTGAAATACGAGTGGGTGGAGTTCACGCTGCCCGAGGGCAACTACTCCGAGACCATGACCATAGA
CCTTATGAACAACGCGATCGTGGAGCACTACTTGAAAGTGGGCAGACAGAACGGGGTTCTGGAAAGCGAC
ATCGGGGTAAAGTTTGACACCCGCAACTTCAGACTGGGGTTTGACCCCGTCACTGGTCTTGTCATGCCTG
GGGTATATACAAACGAAGCCTTCCATCCAGACATCATTTTGCTGCCAGGATGCGGGGTGGACTTCACCCA
CAGCCGCCTGAGCAACTTGTTGGGCATCCGCAAGCGGCAACCCTTCCAGGAGGGCTTTAGGATCACCTAC
GATGATCTGGAGGGTGGTAACATTCCCGCACTGTTGGATGTGGACGCCTACCAGGCGAGCTTGAAAGATG
ACACCGAACAGGGCGGGGTGGCGCAGGCGGCAGCAACAGCAGTGGCAGCGGCGCGGAAGAGAACTCCAA
CGCGGCAGCCGCGGCAATGCAGCCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCCGCTGCGCAACCCG
AGGTCGAGAAGCCTCAGAAGAAACCGGTGATCAAACCCCTGACAGAGGACAGCAAGAAACGCAGTTACAA
CCTAATAAGCAATGACAGCACCTTCACCCAGTACCGCAGCTGGTACCTTGCATACAACTACGGCGACCCT
CAGACCGGAATCCGCTCATGGACCCTGCTTTGCACTCCTGACGTAACCTGCGGCTCGGAGCAGGTCTACT
GGTCGTTGCCAGACATGATGCAAGACCCCGTGACCTTCCGCTCCACGCGCCAGATCAGCAACTTTCCGGT
GGTGGGCGCCGAGCTGTTGCCCGTGCACTCCAAGAGCTTCTACAACGACCAGGCCGTCTACTCCCAACTC
ATCCGCCAGTTTACCTCTCTGACCCACGTGTTCAATCGCTTTCCCGAGAACCAGATTTTGGCGCGCCCGC
CAGCCCCCACCATCACCACCGTCAGTGAAAACGTTCCTGCTCTCACAGATCACGGGACGCTACCGCTGCG
CAACAGCATCGGAGGAGTCCAGCGAGTGACCATTACTGACGCCAGACGCCGCACCTGCCCCTACGTTTAC
AAGGCCCTGGGCATAGTCTCGCCGCGCGTCCTATCGAGCCGCACTTTTTGAGCAAGCATGTCCATCCTTA
TATCGCCCAGCAATAACACAGGCTGGGGCCTGCGCTTCCCAAGCAAGATGTTTGGCGGGGCCAAGAAGCG
CTCCGACCAACACCCAGTGCGCGTGCGCGGGCACTACCGCGCGCCCTGGGGCGCGCACAAACGCGGCCGC
ACTGGGCGCACCACCGTCGATGACGCCATCGACGCGGTGGTGGAGGAGGCGCGCAACTACACGCCCACGC
CGCCACCAGTGTCCACAGTGGACGCGGCCATTCAGACCGTGGTGCGCGGAGCCCGGCGCTATGCTAAAAT
GAAGAGACGGCGGAGGCGCGTAGCACGTCGCCACCGCCGCCGACCCGGCACTGCCGCCCAACGCGCGGCG
GCGGCCCTGCTTAACCGCGCACGTCGCACCGGCCGACGGGCGGCCATGCGGGCCGCTCGAAGGCTGGCCG
CGGGTATTGTCACTGTGCCCCCCAGGTCCAGGCGACGAGCGGCCGCCGCAGCAGCCGCGGCCATTAGTGC
TATGACTCAGGGTCGCAGGGGCAACGTGTATTGGGTGCGCGACTCGGTTAGCGGCCTGCGCGTGCCCGTG
CGCACCCGCCCCCCGCGCAACTAGATTGCAAGAAAAAACTACTTAGACTCGTACTGTTGTATGTATCCAG
CGGCGGCGGCGCGCAACGAAGCTATGTCCAAGCGCAAAATCAAAGAAGAGATGCTCCAGGTCATCGCGCC
GGAGATCTATGGCCCCCCGAAGAAGGAAGAGCAGGATTACAAGCCCCGAAAGCTAAAGCGGGTCAAAAAG
AAAAAGAAAGATGATGATGATGAACTTGACGACGAGGTGGAACTGCTGCACGCTACCGCGCCCAGGCGAC
GGGTACAGTGGAAAGGTCGACGCGTAAAACGTGTTTTGCGACCCGGCACCACCGTAGTCTTTACGCCCGG
TGAGCGCTCCACCCGCACCTACAAGCGCGTGTATGATGAGGTGTACGGCGACGAGGACCTGCTTGAGCAG
```

-continued

```
GCCAACGAGCGCCTCGGGGAGTTTGCCTACGGAAAGCGGCATAAGGACATGCTGGCGTTGCCGCTGGACG

AGGGCAACCCAACACCTAGCCTAAAGCCCGTAACACTGCAGCAGGTGCTGCCCGCGCTTGCACCGTCCGA

AGAAAAGCGCGGCCTAAAGCGCGAGTCTGGTGACTTGGCACCCACCGTGCAGCTGATGGTACCCAAGCGC

CAGCGACTGGAAGATGTCTTGGAAAAAATGACCGTGGAACCTGGGCTGGAGCCCGAGGTCCGCGTGCGGC

CAATCAAGCAGGTGGCGCCGGGACTGGGCGTGCAGACCGTGGACGTTCAGATACCCACTACCAGTAGCAC

CAGTATTGCCACCGCCACAGAGGGCATGGAGACACAAACGTCCCCGGTTGCCTCAGCGGTGGCGGATGCC

GCGGTGCAGGCGGTCGCTGCGGCCGCGTCCAAGACCTCTACGGAGGTGCAAACGGACCCGTGGATGTTTC

GCGTTTCAGCCCCCGGCGCCCGCGCGGTTCGAGGAAGTACGGCGCCGCCAGCGCGCTACTGCCCGAATA

TGCCCTACATCCTTCCATTGCGCCTACCCCCGGCTATCGTGGCTACACCTACCGCCCCAGAAGACGAGCA

ACTACCCGACGCCGAACCACCACTGGAACCCGCCGCCGCCGTCGCCGTCGCCAGCCCGTGCTGGCCCCGA

TTTCCGTGCGCAGGGTGGCTCGCGAAGGAGGCAGGACCCTGGTGCTGCCAACAGCGCGCTACCACCCCAG

CATCGTTTAAAAGCCGGTCTTTGTGGTTCTTGCAGATATGGCCCTCACCTGCCGCCTCCGTTTCCCGGTG

CCGGGATTCCGAGGAAGAATGCACCGTAGGAGGGGCATGGCCGGCCACGGCCTGACGGGCGGCATGCGTC

GTGCGCACCACCGGCGGCGGCGCGCGTCGCACCGTCGCATGCGCGGCGGTATCCTGCCCCTCCTTATTCC

ACTGATCGCCGCGGCGATTGGCGCCGTGCCCGGAATTGCATCCGTGGCCTTGCAGGCGCAGAGACACTGA

TTAAAAACAAGTTGCATGTGGAAAAATCAAAATAAAAAGTCTGGACTCTCACGCTCGCTTGGTCCTGTAA

CTATTTTGTAGAATGGAAGACATCAACTTTGCGTCTCTGGCCCCGCGACACGGCTCGCGCCCGTTCATGG

GAAACTGGCAAGATATCGGCACCAGCAATATGAGCGGTGGCGCCTTCAGCTGGGGCTCGCTGTGGAGCGG

CATTAAAAATTTCGGTTCCACCGTTAAGAACTATGGCAGCAAGGCCTGGAACAGCAGCACAGGCCAGATG

CTGAGGGATAAGTTGAAAGAGCAAAATTTCCAACAAAAGGTGGTAGATGGCCTGGCCTCTGGCATTAGCG

GGGTGGTGGACCTGGCCAACCAGGCAGTGCAAAATAAGATTAACAGTAAGCTTGATCCCCGCCCTCCCGT

AGAGGAGCCTCCACCGGCCGTGGAGACAGTGTCTCCAGAGGGGCGTGGCGAAAAGCGTCCGCGCCCCGAC

AGGGAAGAAACTCTGGTGACGCAAATAGACGAGCCTCCCTCGTACGAGGAGGCACTAAAGCAAGGCCTGC

CCACCACCCGTCCCATCGCGCCCATGGCTACCGGAGTGCTGGGCCAGCACACACCCGTAACGCTGGACCT

GCCTCCCCCCGCCGACACCCAGCAGAAACCTGTGCTGCCAGGCCCGACCGCCGTTGTTGTAACCCGTCCT

AGCCGCGCGTCCCTGCGCCGCGCCGCCAGCGGTCCGCGATCGTTGCGGCCCGTAGCCAGTGGCAACTGGC

AAAGCACACTGAACAGCATCGTGGGTCTGGGGGTGCAATCCCTGAAGCGCCGACGATGCTTCTGAATAGC

TAACGTGTCGTATGTGTGTCATGTATGCGTCCATGTCGCCGCCAGAGGAGCTGCTGAGCCGCCGCGCGCC

CGCTTTCCAAGATGGCTACCCCTTCGATGATGCCGCAGTGGTCTTACATGCACATCTCGGGCCAGGACGC

CTCGGAGTACCTGAGCCCCGGGCTGGTGCAGTTTGCCCGCGCCACCGAGACGTACTTCAGCCTGAATAAC

AAGTTTAGAAACCCCACGGTGGCGCCTACGCACGACGTGACCACAGACCGGTCCCAGCGTTTGACGCTGC

GGTTCATCCCTGTGGACCGTGAGGATACTGCGTACTCGTACAAGGCGCGGTTCACCCTAGCTGTGGGTGA

TAACCGTGTGCTGGACATGGCTTCCACGTACTTTGACATCCGCGGCGTGCTGGACAGGGGCCCTACTTTT

AAGCCCTACTCTGGCACTGCCTACAACGCCCTGGCTCCCAAGGGTGCCCCAAATCCTTGCGAATGGGATG

AAGCTGCTACTGCTCTTGAAATAAACCTAGAAGAAGAGGACGATGACAACGAAGACGAAGTAGACGAGCA

AGCTGAGCAGCAAAAAACTCACGTATTTGGGCAGGCGCCTTATTCTGGTATAAATATTACAAAGGAGGGT

ATTCAAATAGGTGTCGAAGGTCAAACACCTAAATATGCCGATAAAACATTTCAACCTGAACCTCAAATAG

GAGAATCTCAGTGGTACGAAACTGAAATTAATCATGCAGCTGGGAGAGTCCTTAAAAAGACTACCCCAAT

GAAACCATGTTACGGTTCATATGCAAAACCCACAAATGAAAATGGAGGGCAAGGCATTCTTGTAAAGCAA

CAAAATGGAAAGCTAGAAAGTCAAGTGGAAATGCAATTTTTCTCAACTACTGAGGCGACCGCAGGCAATG
```

-continued

```
GTGATAACTTGACTCCTAAAGTGGTATTGTACAGTGAAGATGTAGATATAGAAACCCCAGACACTCATAT
TTCTTACATGCCCACTATTAAGGAAGGTAACTCACGAGAACTAATGGGCCAACAATCTATGCCCAACAGG
CCTAATTACATTGCTTTTAGGGACAATTTTATTGGTCTAATGTATTACAACAGCACGGGTAATATGGGTG
TTCTGGCGGGCCAAGCATCGCAGTTGAATGCTGTTGTAGATTTGCAAGACAGAAACACAGAGCTTTCATA
CCAGCTTTTGCTTGATTCCATTGGTGATAGAACCAGGTACTTTTCTATGTGGAATCAGGCTGTTGACAGC
TATGATCCAGATGTTAGAATTATTGAAAATCATGGAACTGAAGATGAACTTCCAAATTACTGCTTTCCAC
TGGGAGGTGTGATTAATACAGAGACTCTTACCAAGGTAAAACCTAAAACAGGTCAGGAAATGGATGGGA
AAAAGATGCTACAGAATTTTCAGATAAAAATGAAATAAGAGTTGGAAATAATTTTGCCATGGAAATCAAT
CTAAATGCCAACCTGTGGAGAAATTTCCTGTACTCCAACATAGCGCTGTATTTGCCCGACAAGCTAAAGT
ACAGTCCTTCCAACGTAAAAATTTCTGATAACCCAAACACCTACGACTACATGAACAAGCGAGTGGTGGC
TCCCGGGTTAGTGGACTGCTACATTAACCTTGGAGCACGCTGGTCCCTTGACTATATGGACAACGTCAAC
CCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACAC
CTACGAGTGGAACTTCAGGAAGGATGTTAACATGGTTCTGCAGAGCTCCCTAGGAAATGACCTAAGGGTT
GACGGAGCCAGCATTAAGTTTGATAGCATTTGCCTTTACGCCACCTTCTTCCCCATGGCCCACAACACCG
CCTCCACGCTTGAGGCCATGCTTAGAAACGACACCAACGACCAGTCCTTTAACGACTATCTCTCCGCCGC
CAACATGCTCTACCCTATACCCGCCAACGCTACCAACGTGCCCATATCCATCCCCTCCCGCAACTGGGCG
GCTTTCCGCGGCTGGGCCTTCACGCGCCTTAAGACTAAGGAAACCCCATCACTGGGCTCGGGCTACGACC
CTTATTACACCTACTCTGGCTCTATACCCTACCTAGATGGAACCTTTTACCTCAACCACACCTTTAAGAA
GGTGGCCATTACCTTTGACTCTTCTGTCAGCTGGCCTGGCAATGACCGCCTGCTTACCCCCAACGAGTTT
GAAATTAAGCGCTCAGTTGACGGGGAGGGTTACAACGTTGCCCAGTGTAACATGACCAAAGACTGGTTCC
TGGTACAAATGCTAGCTAACTACAACATTGGCTACCAGGGCTTCTATATCCCAGAGAGCTACAAGGACCG
CATGTACTCCTTCTTTAGAAACTTCCAGCCCATGAGCCGTCAGGTGGTGGATGATACTAAATACAAGGAC
TACCAACAGGTGGGCATCCTACACCAACACAACAACTCTGGATTTGTTGGCTACCTTGCCCCCACCATGC
GCGAAGGACAGGCCTACCCTGCTAACTTCCCCTATCCGCTTATAGGCAAGACCGCAGTTGACAGCATTAC
CCAGAAAAGTTTCTTTGCGATCGCACCCTTTGGCGCATCCCATTCTCCAGTAACTTTATGTCCATGGGC
GCACTCACAGACCTGGGCCAAAACCTTCTCTACGCCAACTCCGCCCACGCGCTAGACATGACTTTTGAGG
TGGATCCCATGGACGAGCCCACCCTTCTTTATGTTTTGTTTGAAGTCTTTGACGTGGTCCGTGTGCACCG
GCCGCACCGCGCGTCATCGAAACCGTGTACCTGCGCACGCCCTTCTCGGCCGGCAACGCCACAACATAA
AGAAGCAAGCAACATCAACAACAGCTGCCGCCATGGGCTCCAGTGAGCAGGAACTGAAAGCCATTGTCAA
AGATCTTGGTTGTGGGCCATATTTTTTGGGCACCTATGACAAGCGCTTTCCAGGCTTTGTTTCTCCACAC
AAGCTCGCCTGCGCCATAGTCAATACGGCCGGTCGCGAGACTGGGGCGTACACTGGATGGCCTTTGCCT
GGAACCCGCACTCAAAAACATGCTACCTCTTTGAGCCCTTTGGCTTTTCTGACCAGCGACTCAAGCAGGT
TTACCAGTTTGAGTACGAGTCACTCCTGCGCCGTAGCGCCATTGCTTCTTCCCCCGACCGCTGTATAACG
CTGGAAAAGTCCACCCAAAGCGTACAGGGGCCCAACTCGGCCGCCTGTGGACTATTCTGCTGCATGTTTC
TCCACGCCTTTGCCAACTGGCCCCAAACTCCCATGGATCACAACCCCACCATGAACCTTATTACCGGGGT
ACCCAACTCCATGCTCAACAGTCCCCAGGTACAGCCCACCCTGCGTCGCAACCAGGAACAGCTCTACAGC
TTCCTGGAGCGCCACTCGCCCTACTTCCGCAGCCACAGTGCGCAGATTAGGAGCGCCACTTCTTTTTGTC
ACTTGAAAAACATGTAAAAATAATGTACTAGAGACACTTTCAATAAAGGCAAATGCTTTTATTTGTACAC
TCTCGGGTGATTATTTACCCCCACCCTTGCCGTCTGCGCCGTTTAAAAATCAAAGGGGTTCTGCCGCGCA
TCGCTATGCGCCACTGGCAGGGACACGTTGCGATACTGGTGTTTAGTGCTCCACTTAAACTCAGGCACAA
```

-continued

```
CCATCCGCGGCAGCTCGGTGAAGTTTTCACTCCACAGGCTGCGCACCATCACCAACGCGTTTAGCAGGTC

GGGCGCCGATATCTTGAAGTCGCAGTTGGGGCCTCCGCCCTGCGCGCGCGAGTTGCGATACACAGGGTTG

CAGCACTGGAACACTATCAGCGCCGGGTGGTGCACGCTGGCCAGCACGCTCTTGTCGGAGATCAGATCCG

CGTCCAGGTCCTCCGCGTTGCTCAGGGCGAACGGAGTCAACTTTGGTAGCTGCCTTCCCAAAAAGGGCGC

GTGCCCAGGCTTTGAGTTGCACTCGCACCGTAGTGGCATCAAAAGGTGACCGTGCCCGGTCTGGGCGTTA

GGATACAGCGCCTGCATAAAAGCCTTGATCTGCTTAAAAGCCACCTGAGCCTTTGCGCCTTCAGAGAAGA

ACATGCCGCAAGACTTGCCGGAAAACTGATTGGCCGGACAGGCCGCGTCGTGCACGCAGCACCTTGCGTC

GGTGTTGGAGATCTGCACCACATTTCGGCCCCACCGGTTCTTCACGATCTTGGCCTTGCTAGACTGCTCC

TTCAGCGCGCGCTGCCCGTTTTCGCTCGTCACATCCATTTCAATCACGTGCTCCTTATTTATCATAATGC

TTCCGTGTAGACACTTAAGCTCGCCTTCGATCTCAGCGCAGCGGTGCAGCCACAACGCGCAGCCCGTGGG

CTCGTGATGCTTGTAGGTCACCTCTGCAAACGACTGCAGGTACGCCTGCAGGAATCGCCCCATCATCGTC

ACAAAGGTCTTGTTGCTGGTGAAGGTCAGCTGCAACCCGCGGTGCTCCTCGTTCAGCCAGGTCTTGCATA

CGGCCGCCAGAGCTTCCACTTGGTCAGGCAGTAGTTTGAAGTTCGCCTTTAGATCGTTATCCACGTGGTA

CTTGTCCATCAGCGCGCGCAGCCTCCATGCCCTTCTCCCACGCAGACACGATCGGCACACTCAGCGGG

TTCATCACCGTAATTTCACTTTCCGCTTCGCTGGGCTCTTCCTCTTCCTCTTGCGTCCGCATACCACGCG

CCACTGGGTCGTCTTCATTCAGCCGCCGCACTGTGCGCTTACCTCCTTTGCCATGCTTGATTAGCACCGG

TGGGTTGCTGAAACCCACCATTTGTAGCGCCACATCTTCTCTTTCTTCCTCGCTGTCCACGATTACCTCT

GGTGATGGCGGGCGCTCGGGCTTGGGAGAAGGGCGCTTCTTTTTCTTCTTGGGCGCAATGGCCAAATCCG

CCGCCGAGGTCGATGGCCGCGGGCTGGGTGTGCGCGGCACCAGCGCGTCTTGTGATGAGTCTTCCTCGTC

CTCGGACTCGATACGCCGCCTCATCCGCTTTTTTGGGGGCGCCCGGGGAGGCGGCGGCGACGGGGACGGG

GACGACACGTCCTCCATGGTTGGGGACGTCGCGCCGCACCGCGTCCGCGCTCGGGGGTGGTTTCGCGCT

GCTCCTCTTCCCGACTGGCCATTTCCTTCTCCTATAGGCAGAAAAAGATCATGGAGTCAGTCGAGAAGAA

GGACAGCCTAACCGCCCCCTCTGAGTTCGCCACCACCGCCTCCACCGATGCCGCCAACGCGCCTACCACC

TTCCCCGTCGAGGCACCCCCGCTTGAGGAGGAGGAAGTGATTATCGAGCAGGACCCAGGTTTTGTAAGCG

AAGACGACGAGGACCGCTCAGTACCAACAGAGGATAAAAAGCAAGACCAGGACAACGCAGAGGCAAACGA

GGAACAAGTCGGGCGGGGGACGAAAGGCATGGCGACTACCTAGATGTGGGAGACGACGTGCTGTTGAAG

CATCTGCAGCGCCAGTGCGCCATTATCTGCGACGCGTTGCAAGAGCGCAGCGATGTGCCCCTCGCCATAG

CGGATGTCAGCCTTGCCTACGAACGCCACCTATTCTCACCGCGCGTACCCCCCAAACGCCAAGAAAACGG

CACATGCGAGCCCAACCCGCGCCTCAACTTCTACCCCGTATTTGCCGTGCCAGAGGTGCTTGCCACCTAT

CACATCTTTTTCCAAAACTGCAAGATACCCCTATCCTGCCGTGCCAACCGCAGCCGAGCGGACAAGCAGC

TGGCCTTGCGGCAGGGCGCTGTCATACCTGATATCGCCTCGCTCAACGAAGTGCCAAAAATCTTTGAGGG

TCTTGGACGCGACGAGAAGCGCGCGGCAAACGCTCTGCAACAGGAAAACAGCGAAAATGAAAGTCACTCT

GGAGTGTTGGTGGAACTCGAGGGTGACAACGCGCGCCTAGCCGTACTAAAACGCAGCATCGAGGTCACCC

ACTTTGCCTACCCGGCACTTAACCTACCCCCCAAGGTCATGAGCACAGTCATGAGTGAGCTGATCGTGCG

CCGTGCGCAGCCCCTGGAGAGGGATGCAAATTTGCAAGAACAAACAGAGGAGGGCCTACCCGCAGTTGGC

GACGAGCAGCTAGCGCGCTGGCTTCAAACGCGCGAGCCTGCCGACTTGGAGGAGCGACGCAAACTAATGA

TGGCCGCAGTGCTCGTTACCGTGGAGCTTGAGTGCATGCAGCGGTTCTTTGCTGACCCGGAGATGCAGCG

CAAGCTAGAGGAAACATTGCACTACACCTTTCGACAGGGCTACGTACGCCAGGCCTGCAAGATCTCCAAC

GTGGAGCTCTGCAACCTGGTCTCCTACCTTGGAATTTTGCACGAAAACCGCTTGGGCAAAACGTGCTTC

ATTCCACGCTCAAGGGCGAGGCGCGCCGCGACTACGTCCGCGACTGCGTTTACTTATTTCTATGCTACAC
```

-continued

```
CTGGCAGACGGCCATGGGCGTTTGGCAGCAGTGCTTGGAGGAGTGCAACCTCAAGGAGCTGCAGAAACTG
CTAAAGCAAAACTTGAAGGACCTATGGACGGCCTTCAACGAGCGCTCCGTGGCCGCGCACCTGGCGGACA
TCATTTTCCCCGAACGCCTGCTTAAAACCCTGCAACAGGGTCTGCCAGACTTCACCAGTCAAAGCATGTT
GCAGAACTTTAGGAACTTTATCCTAGAGCGCTCAGGAATCTTGCCCGCCACCTGCTGTGCACTTCCTAGC
GACTTTGTGCCCATTAAGTACCGCGAATGCCCTCCGCCGCTTTGGGGCCACTGCTACCTTCTGCAGCTAG
CCAACTACCTTGCCTACCACTCTGACATAATGGAAGACGTGAGCGGTGACGGTCTACTGGAGTGTCACTG
TCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTC
CGGGGCTGTGGACGTCGGCTTACCTTCGCAAATTTGTACCTGAGGACTACCACGCCCACGAGATTAGGTT
CTACGAAGACCAATCCCGCCCGCCAAATGCGGAGCTTACCGCCTGCGTCATTACCCAGGGCCACATTCTT
GGCCAATTGCAAGCCATCAACAAAGCCCGCCAAGAGTTTCTGCTACGAAAGGGACGGGGGGTTTACTTGG
ACCCCCAGTCCGGCGAGGAGCTCAACCCAATCCCCCGCCGCCGCAGCCCTATCAGCAGCAGCCGCGGGC
CCTTGCTTCCCAGGATGGCACCCAAAAAGAAGCTGCAGCTGCCGCCGCCACCCACGGACGAGGAGGAATA
CTGGGACAGTCAGGCAGAGGAGGTTTTGGACGAGGAGGAGGAGGACATGATGGAAGACTGGGAGAGCCTA
GACGAGGAAGCTTCCGAGGTCGAAGAGGTGTCAGACGAAACACCGTCACCCTCGGTCGCATTCCCCTCGC
CGGCGCCCCAGAAATCGGCAACCGGTTCCAGCATGGCTACAACCTCCGCTCCTCAGGCGCCGCCGGCACT
GCCCGTTCGCCGACCCAACCGTAGATGGGACACCACTGGAACCAGGGCCGGTAAGTCCAAGCAGCCGCCG
CCGTTAGCCCAAGAGCAACAACAGCGCCAAGGCTACCGCTCATGGCGCGGGCACAAGAACGCCATAGTTG
CTTGCTTGCAAGACTGTGGGGGCAACATCTCCTTCGCCCGCCGCTTTCTTCTCTACCATCACGGCGTGGC
CTTCCCCCGTAACATCCTGCATTACTACCGTCATCTCTACAGCCCATACTGCACCGGCGGCAGCGGCAGC
GGCAGCAACAGCAGCGGCCACACAGAAGCAAAGGCGACCGGATAGCAAGACTCTGACAAAGCCCAAGAAA
TCCACAGCGGCGGCAGCAGCAGGAGGAGGAGCGCTGCGTCTGGCGCCCAACGAACCCGTATCGACCCGCG
AGCTTAGAAACAGGATTTTTCCCACTCTGTATGCTATATTTCAACAGAGCAGGGGCCAAGAACAAGAGCT
GAAAATAAAAAACAGGTCTCTGCGATCCCTCACCCGCAGCTGCCTGTATCACAAAAGCGAAGATCAGCTT
CGGCGCACGCTGGAAGACGCGGAGGCTCTCTTCAGTAAATACTGCGCGCTGACTCTTAAGGACTAGTTTC
GCGCCCTTTCTCAAATTTAAGCGCGAAAACTACGTCATCTCCAGCGGCCACACCCGGCGCCAGCACCTGT
CGTCAGCGCCATTATGAGCAAGGAAATTCCCACGCCCTACATGTGGAGTTACCAGCCACAAATGGGACTT
GCGGCTGGAGCTGCCCAAGACTACTCAACCCGAATAAACTACATGAGCGCGGGACCCCACATGATATCCC
GGGTCAACGGAATCCGCGCCCACCGAAACCGAATTCTCTTGGAACAGGCGGCTATTACCACCACACCTCG
TAATAACCTTAATCCCCGTAGTTGGCCCGCTGCCCTGGTGTACCAGGAAAGTCCCGCTCCCACCACTGTG
GTACTTCCCAGAGACGCCCAGGCCGAAGTTCAGATGACTAACTCAGGGGCGCAGCTTGCGGGCGGCTTTC
GTCACAGGGTGCGGTCGCCCGGGCAGGGTATAACTCACCTGACAATCAGAGGGCGAGGTATTCAGCTCAA
CGACGAGTCGGTGAGCTCCTCGCTTGGTCTCCGTCCGGACGGGACATTTCAGATCGGCGGCGCCGGCCGT
CCTTCATTCACGCCTCGTCAGGCAATCCTAACTCTGCAGACCTCGTCCTCTGAGCCGCGCTCTGGAGGCA
TTGGAACTCTGCAATTTATTGAGGAGTTTGTGCCATCGGTCTACTTTAACCCCTTCTCGGGACCTCCCGG
CCACTATCCGGATCAATTTATTCCTAACTTTGACGCGGTAAAGGACTCGGCGGACAGGCTACGACTGAATG
TTAAGTGGAGAGGCAGAGCAACTGCGCCTGAAACACCTGGTCCACTGTCGCCGCCACAAGTGCTTTGCCC
GCGACTCCGGTGAGTTTTGCTACTTTGAATTGCCCGAGGATCATATCGAGGGCCCGGCGCACGGCGTCCG
GCTTACCGCCCAGGGAGAGCTTGCCCGTAGCCTGATTCGGGAGTTTACCCAGCGCCCCCTGCTAGTTGAG
CGGGACAGGGGACCCTGTGTTCTCACTGTGATTTGCAACTGTCCTAACCTTGGATTACATCAAGATCTTT
GTTGCCATCTCTGTGCTGAGTATAATAAATACAGAAATTAAAATATACTGGGGCTCCTATCGCCATCCTG
```

-continued

```
TAAACGCCACCGTCTTCACCCGCCCAAGCAAACCAAGGCGAACCTTACCTGGTACTTTTAACATCTCTCC

CTCTGTGATTTACAACAGTTTCAACCCAGACGGAGTGAGTCTACGAGAGAACCTCTCCGAGCTCAGCTAC

TCCATCAGAAAAAACACCACCCTCCTTACCTGCCGGGAACGTACGAGTGCGTCACCGGCCGCTGCACCAC

ACCTACCGCCTGACCGTAAACCAGACTTTTTCCGGACAGACCTCAATAACTCTGTTTACCAGAACAGGAG

GTGAGCTTAGAAAACCCTTAGGGTATTAGGCCAAAGGCGCAGCTACTGTGGGGTTTATGAACAATTCAAG

CAACTCTACGGGCTATTCTAATTCAGGTTTCTCTAGAATCGGGGTTGGGGTTATTCTCTGTCTTGTGATT

CTCTTTATTCTTATACTAACGCTTCTCTGCCTAAGGCTCGCCGCCTGCTGTGTGCACATTTGCATTTATT

GTCAGCTTTTTAAACGCTGGGGTCGCCACCCAAGATGATTAGGTACATAATCCTAGGTTTACTCACCCTT

GCGTCAGCCCACGGTACCACCCAAAAGGTGGATTTTAAGGAGCCAGCCTGTAATGTTACATTCGCAGCTG

AAGCTAATGAGTGCACCACTCTTATAAAATGCACCACAGAACATGAAAAGCTGCTTATTCGCCACAAAAA

CAAAATTGGCAAGTATGCTGTTTATGCTATTTGGCAGCCAGGTGACACTACAGAGTATAATGTTACAGTT

TTCCAGGGTAAAAGTCATAAAACTTTTATGTATACTTTTCCATTTTATGAAATGTGCGACATTACCATGT

ACATGAGCAAACAGTATAAGTTGTGGCCCCCACAAAATTGTGTGGAAAACACTGGCACTTTCTGCTGCAC

TGCTATGCTAATTACAGTGCTCGCTTTGGTCTGTACCCTACTCTATATTAAATACAAAAGCAGACGCAGC

TTTATTGAGGAAAGAAAATGCCTTAATTTACTAAGTTACAAAGCTAATGTCACCACTAACTGCTTTACT

CGCTGCTTGCAAAACAAATTCAAAAAGTTAGCATTATAATTAGAATAGGATTTAAACCCCCCGGTCATTT

CCTGCTCAATACCATTCCCCTGAACAATTGACTCTATGTGGGATATGCTCCAGCGCTACAACCTTGAAGT

CAGGCTTCCTGGATGTCAGCATCTGACTTTGGCCAGCACCTGTCCCGCGGATTTGTTCCAGTCCAACTAC

AGCGACCCACCCTAACAGAGATGACCAACACAACCAACGCGGCCGCCGCTACCGGACTTACATCTACCAC

AAATACACCCCAAGTTTCTGCCTTTGTCAATAACTGGGATAACTTGGGCATGTGGTGGTTCTCCATAGCG

CTTATGTTTGTATGCCTTATTATTATGTGGCTCATCTGCTGCCTAAAGCGCAAACGCGCCCGACCACCCA

TCTATAGTCCCATCATTGTGCTACACCCAAACAATGATGGAATCCATAGATTGGACGGACTGAAACACAT

GTTCTTTTCTCTTACAGTATGATTAAATGAGACATGATTCCTCGAGTTTTTATATTACTGACCCTTGTTG

CGCTTTTTTGTGCGTGCTCCACATTGGCTGCGGTTTCTCACATCGAAGTAGACTGCATTCCAGCCTTCAC

AGTCTATTTGCTTTACGGATTTGTCACCCTCACGCTCATCTGCAGCCTCATCACTGTGGTCATCGCCTTT

ATCCAGTGCATTGACTGGGTCTGTGTGCGCTTTGCATATCTCAGACACCATCCCAGTACAGGGACAGGA

CTATAGCTGAGCTTCTTAGAATTCTTTAATTATGAAATTTACTGTGACTTTTCTGCTGATTATTTGCACC

CTATCTGCGTTTTGTTCCCCGACCTCCAAGCCTCAAAGACATATATCATGCAGATTCACTCGTATATGGA

ATATTCCAAGTTGCTACAATGAAAAAAGCGATCTTTCCGAAGCCTGGTTATATGCAATCATCTCTGTTAT

GGTGTTCTGCAGTACCATCTTAGCCCTAGCTATATATCCCTACCTTGACATTGGCTGGAAACGAATAGAT

GCCATGAACCACCCAACTTTCCCCGCGCCCGCTATGCTTCCACTGCAACAAGTTGTTGCCGGCGGCTTTG

TCCCAGCCAATCAGCCTCGCCCCACTTCTCCCACCCCCACTGAAATCAGCTACTTTAATCTAACAGGAGG

AGATGACTGACACCCTAGATCTAGAAATGGACGGAATTATTACAGAGCAGCGCCTGCTAGAAAGACGCAG

GGCAGCGGCCGAGCAACAGCGCATGAATCAAGAGCTCCAAGACATGGTTAACTTGCACCAGTGCAAAAGG

GGTATCTTTTGTCTGGTAAAGCAGGCCAAAGTCACCTACGACAGTAATACCACCGGACACCGCCTTAGCT

ACAAGTTGCCAACCAAGCGTCAGAAATTGGTGGTCATGGTGGGAGAAAAGCCCATTACCATAACTCAGCA

CTCGGTAGAAACCGAAGGCTGCATTCACTCACCTTGTCAAGGACCTGAGGATCTCTGCACCCTTATTAAG

ACCCTGTGCGGTCTCAAAGATCTTATTCCCTTTAACTAATAAAAAAAAATAATAAAGCATCACTTACTTA

AAATCAGTTAGCAAATTTCTGTCCAGTTTATTCAGCAGCACCTCCTTGCCCTCCTCCCAGCTCTGGTATT

GCAGCTTCCTCCTGGCTGCAAACTTTCTCCACAATCTAAATGGAATGTCAGTTTCCTCCTGTTCCTGTCC
```

-continued

```
ATCCGCACCCACTATCTTCATGTTGTTGCAGATGAAGCGCGCAAGACCGTCTGAAGATACCTTCAACCCC
GTGTATCCATATGACACGGAAACCGGTCCTCCAACTGTGCCTTTTCTTACTCCTCCCTTTGTATCCCCCA
ATGGGTTTCAAGAGAGTCCCCCTGGGGTACTCTCTTTGCGCCTATCCGAACCTCTAGTTACCTCCAATGG
CATGCTTGCGCTCAAAATGGGCAACGGCCTCTCTCTGGACGAGGCCGGCAACCTTACCTCCCAAAATGTA
ACCACTGTGAGCCCACCTCTCAAAAAAACCAAGTCAAACATAAACCTGGAAATATCTGCACCCCTCACAG
TTACCTCAGAAGCCCTAACTGTGGCTGCCGCCGCACCTCTAATGGTCGCGGGCAACACACTCACCATGCA
ATCACAGGCCCCGCTAACCGTGCACGACTCCAAACTTAGCATTGCCACCCAAGGACCCCTCACAGTGTCA
GAAGGAAAGCTAGCCCTGCAAACATCAGGCCCCCTCACCACCACCGATAGCAGTACCCTTACTATCACTG
CCTCACCCCCTCTAACTACTGCCACTGGTAGCTTGGGCATTGACTTGAAAGAGCCCATTTATACACAAA
TGGAAAACTAGGACTAAAGTACGGGGCTCCTTTGCATGTAACAGACGACCTAAACACTTTGACCGTAGCA
ACTGGTCCAGGTGTGACTATTAATAATACTTCCTTGCAAACTAAAGTTACTGGAGCCTTGGGTTTTGATT
CACAAGGCAATATGCAACTTAATGTAGCAGGAGGACTAAGGATTGATTCTCAAAACAGACGCCTTATACT
TGATGTTAGTTATCCGTTTGATGCTCAAAACCAACTAAATCTAAGACTAGGACAGGGCCCTCTTTTTATA
AACTCAGCCCACAACTTGGATATTAACTACAACAAAGGCCTTTACTTGTTTACAGCTTCAAACAATTCCA
AAAAGCTTGAGGTTAACCTAAGCACTGCCAAGGGGTTGATGTTTGACGCTACAGCCATAGCCATTAATGC
AGGAGATGGGCTTGAATTTGGTTCACCTAATGCACCAAACACAAATCCCCTCAAAACAAAAATTGGCCAT
GGCCTAGAATTTGATTCAAACAAGGCTATGGTTCCTAAACTAGGAACTGGCCTTAGTTTTGACAGCACAG
GTGCCATTACAGTAGGAAACAAAAATAATGATAAGCTAACTTTGTGGACCACACCAGCTCCATCTCCTAA
CTGTAGACTAAATGCAGAGAAAGATGCTAAACTCACTTTGGTCTTAACAAAATGTGGCAGTCAAATACTT
GCTACAGTTTCAGTTTTGGCTGTTAAAGGCAGTTTGGCTCCAATATCTGGAACAGTTCAAAGTGCTCATC
TTATTATAAGATTTGACGAAAATGGAGTGCTACTAAACAATTCCTTCCTGGACCCAGAATATTGGAACTT
TAGAAATGGAGATCTTACTGAAGGCACAGCCTATACAAACGCTGTTGGATTTATGCCTAACCTATCAGCT
TATCCAAAATCTCACGGTAAAACTGCCAAAAGTAACATTGTCAGTCAAGTTTACTTAAACGGAGACAAAA
CTAAACCTGTAACACTAACCATTACACTAAACGGTACACAGGAAACAGGAGACACAACTCCAAGTGCATA
CTCTATGTCATTTTCATGGGACTGGTCTGGCCACAACTACATTAATGAAATATTTGCCACATCCTCTTAC
ACTTTTTCATACATTGCCCAAGAATAAAGAATCGTTTGTGTTATGTTTCAACGTGTTTATTTTTCAATTG
CAGAAAATTTCAAGTCATTTTTCATTCAGTAGTATAGCCCCACCACCACATAGCTTATACAGATCACCGT
ACCTTAATCAAACTCACAGAACCCTAGTATTCAACCTGCCACCTCCCTCCCAACACACAGAGTACACAGT
CCTTTCTCCCCGGCTGGCCTTAAAAAGCATCATATCATGGGTAACAGACATATTCTTAGGTGTTATATTC
CACACGGTTTCCTGTCGAGCCAAACGCTCATCAGTGATATTAATAAACTCCCCGGGCAGCTCACTTAAGT
TCATGTCGCTGTCCAGCTGCTGAGCCACAGGCTGCTGTCCAACTTGCGGTTGCTTAACGGGCGGCGAAGG
AGAAGTCCACGCCTACATGGGGGTAGAGTCATAATCGTGCATCAGGATAGGGCGGTGGTGCTGCAGCAGC
GCGCGAATAAACTGCTGCCGCCGCCGCTCCGTCCTGCAGGAATACAACATGGCAGTGGTCTCCTCAGCGA
TGATTCGCACCGCCCGCAGCATAAGGCGCCTTGTCCTCCGGGCACAGCAGCGCACCCTGATCTCACTTAA
ATCAGCACAGTAACTGCAGCACAGCACCACAATATTGTTCAAAATCCCACAGTGCAAGGCGCTGTATCCA
AAGCTCATGGCGGGACCACAGAACCCACGTGGCCATCATACCACAAGCGCAGGTAGATTAAGTGGCGAC
CCCTCATAAACACGCTGGACATAAACATTACCTCTTTTGGCATGTTGTAATTCACCACCTCCCGGTACCA
TATAAACCTCTGATTAAACATGGCGCCATCCACCACCATCCTAAACCAGCTGGCCAAAACCTGCCCGCCG
GCTATACACTGCAGGGAACCGGGACTGGAACAATGACAGTGGAGAGCCCAGGACTCGTAACCATGGATCA
TCATGCTCGTCATGATATCAATGTTGGCACAACACAGGCACACGTGCATACACTTCCTCAGGATTACAAG
CTCCTCCCGCGTTAGAACCATATCCCAGGGAACAACCCATTCCTGAATCAGCGTAAATCCCACACTGCAG
```

-continued

```
GGAAGACCTCGCACGTAACTCACGTTGTGCATTGTCAAAGTGTTACATTCGGGCAGCAGCGGATGATCCT

CCAGTATGGTAGCGCGGGTTTCTGTCTCAAAAGGAGGTAGACGATCCCTACTGTACGGAGTGCGCCGAGA

CAACCGAGATCGTGTTGGTCGTAGTGTCATGCCAAATGGAACGCCGGACGTAGTCATATTTCCTGAAGCA

AAACCAGGTGCGGGCGTGACAAACAGATCGCGTCTCCGGTCTCGCCGCTTAGATCGCTCTGTGTAGTAG

TTGTAGTATATCCACTCTCTCAAAGCATCCAGGCGCCCCTGGCTTCGGGTTCTATGTAAACTCCTTCAT

GCGCCGCTGCCCTGATAACATCCACCACCGCAGAATAAGCCACACCCAGCCAACCTACACATTCGTTCTG

CGAGTCACACACGGGAGGAGCGGGAAGAGCTGGAAGAACCATGTTTTTTTTTTATTCCAAAAGATTATC

CAAAACCTCAAAATGAAGATCTATTAAGTGAACGCGCTCCCCTCCGGTGGCGTGGTCAAACTCTACAGCC

AAAGAACAGATAATGGCATTTGTAAGATGTTGCACAATGGCTTCCAAAAGGCAAACGGCCCTCACGTCCA

AGTGGACGTAAAGGCTAAACCCTTCAGGGTGAATCTCCTCTATAAACATTCCAGCACCTTCAACCATGCC

CAAATAATTCTCATCTCGCCACCTTCTCAATATATCTCTAAGCAAATCCCGAATATTAAGTCCGGCCATT

GTAAAAATCTGCTCCAGAGCGCCCTCCACCTTCAGCCTCAAGCAGCGAATCATGATTGCAAAAATTCAGG

TTCCTCACAGACCTGTATAAGATTCAAAAGCGGAACATTAACAAAAATACCGCGATCCCGTAGGTCCCTT

CGCAGGGCCAGCTGAACATAATCGTGCAGGTCTGCACGGACCAGCGCGGCCACTTCCCCGCCAGGAACCA

TGACAAAAGAACCCACACTGATTATGACACGCATACTCGGAGCTATGCTAACCAGCGTAGCCCCGATGTA

AGCTTGTTGCATGGGCGGCGATATAAAATGCAAGGTGCTGCTCAAAAAATCAGGCAAAGCCTCGCGCAAA

AAAGAAAGCACATCGTAGTCATGCTCATGCAGATAAAGGCAGGTAAGCTCCGGAACCACCACAGAAAAAG

ACACCATTTTCTCTCAAACATGTCTGCGGGTTTCTGCATAAACACAAAATAAAATAACAAAAAAACATT

TAAACATTAGAAGCCTGTCTTACAACAGGAAAAACAACCCTTATAAGCATAAGACGGACTACGGCCATGC

CGGCGTGACCGTAAAAAAACTGGTCACCGTGATTAAAAAGCACCACCGACAGCTCCTCGGTCATGTCCGG

AGTCATAATGTAAGACTCGGTAAACACATCAGGTTGATTCACATCGGTCAGTGCTAAAAAGCGACCGAAA

TAGCCCGGGGAATACATACCCGCAGGCGTAGAGACAACATTACAGCCCCCATAGGAGGTATAACAAAAT

TAATAGGAGAGAAAAACACATAAACACCTGAAAAACCCTCCTGCCTAGGCAAAATAGCACCCTCCCGCTC

CAGAACAACATACAGCGCTTCCACAGCGGCAGCCATAACAGTCAGCCTTACCAGTAAAAAAGAAAACCTA

TTAAAAAAACACCACTCGACACGGCACCAGCTCAATCAGTCACAGTGTAAAAAAGGGCCAAGTGCAGAGC

GAGTATATATAGGACTAAAAAATGACGTAACGGTTAAAGTCCACAAAAAACACCCAGAAAACCGCACGCG

AACCTACGCCCAGAAACGAAAGCCAAAAAACCCACACTTCCTCAAATCGTCACTTCCGTTTTCCCACGT

TACGTAACTTCCCATTTTAAGAAAACTACAATTCCCAACACATACAAGTTACTCCGCCCTAAAACCTACG

TCACCCGCCCCGTTCCCACGCCCCGCGCCACGTCACAAACTCCACCCCCTCATTATCATATTGGCTTCAA

TCCAAAATAAGGTATATTATTGATGATG

Human adenovirus 35, complete genome
NCBI Reference Sequence: AC_000019.1
                                                            (SEQ ID NO: 41)
CATCATCAATAATATACCTTATAGATGGAATGGTGCCAATATGTAAATGAGGTGATTTTA

AAAAGTGTGGGCCGTGTGGTGATTGGCTGTGGGGTTAACGGTTAAAAGGGGCGGCGCGGC

CGTGGGAAAATGACGTTTTATGGGGGTGGAGTTTTTTTGCAAGTTGTCGCGGGAAATGTT

ACGCATAAAAAGGCTTCTTTTCTCACGGAACTACTTAGTTTTCCCACGGTATTTAACAGG

AAATGAGGTAGTTTTGACCGGATGCAAGTGAAAATTGCTGATTTTCGCGCGAAAACTGAA

TGAGGAAGTGTTTTTCTGAATAATGTGGTATTTATGGCAGGGTGGAGTATTTGTTCAGGG

CCAGGTAGACTTTGACCCATTACGTGGAGGTTTCGATTACCGTGTTTTTTACCTGAATTT

CCGCGTACCGTGTCAAAGTCTTCTGTTTTTACGTAGGTGTCAGCTGATCGCTAGGGTATT

TATACCTCAGGGTTTGTGTCAAGAGGCCACTCTTGAGTGCCAGCGAGAAGAGTTTTCTCC
```

-continued

```
TCTGCGCCGGCAGTTTAATAATAAAAAAATGAGAGATTTGCGATTTCTGCCTCAGGAAAT
AATCTCTGCTGAGACTGGAAATGAAATATTGGAGCTTGTGGTGCACGCCCTGATGGGAGA
CGATCCGGAGCCACCTGTGCAGCTTTTTGAGCCTCCTACGCTTCAGGAACTGTATGATTT
AGAGGTAGAGGGATCGGAGGATTCTAATGAGGAAGCTGTGAATGGCTTTTTTACCGATTC
TATGCTTTTAGCTGCTAATGAAGGATTAGAATTAGATCCGCCTTTGGACACTTTCAATAC
TCCAGGGGTGATTGTGGAAAGCGGTACAGGTGTAAGAAAATTACCTGATTTGAGTTCCGT
GGACTGTGATTTGCACTGCTATGAAGACGGGTTTCCTCCGAGTGATGAGGAGGACCATGA
AAAGGAGCAGTCCATGCAGACTGCAGCGGGTGAGGGAGTGAAGGCTGCCAATGTTGGTTT
TCAGTTGGATTGCCCGGAGCTTCCTGGACATGGCTGTAAGTCTTGTGAATTTCACAGGAA
AAATACTGGAGTAAAGGAACTGTTATGTTCGCTTTGTTATATGAGAACGCACTGCCACTT
TATTTACAGTAAGTGTGTTTAAGTTAAAATTTAAAGGAATATGCTGTTTTTCACATGTAT
ATTGAGTGTGAGTTTTGTGCTTCTTATTATAGGTCCTGTGTCTGATGCTGATGAATCACC
ATCTCCTGATTCTACTACCTCACCTCCTGATATTCAAGCACCTGTTCCTGTGGACGTGCG
CAAGCCCATTCCTGTGAAGCTTAAGCCTGGGAAACGTCCAGCAGTGGAGAAACTTGAGGA
CTTGTTACAGGGTGGGGACGGACCTTTGGACTTGAGTACACGGAAACGTCCAAGACAATA
AGTGTTCCATATCCGTGTTTACTTAAGGTGACGTCAATATTTGTGTGAGAGTGCAATGTA
ATAAAAATATGTTAACTGTTCACTGGTTTTTATTGCTTTTTGGGCGGGGACTCAGGTATA
TAAGTAGAAGCAGACCTGTGTGGTTAGCTCATAGGAGCTGGCTTTCATCCATGGAGGTTT
GGGCCATTTTGGAAGACCTTAGGAAGACTAGGCAACTGTTAGAGAGCGCTTCGGACGGAG
TCTCCGGTTTTTGGAGATTCTGGTTCGCTAGTGAATTAGCTAGGGTAGTTTTTAGGATAA
AACAGGACTATAAACAAGAATTTGAAAAGTTGTTGGTAGATTGCCCAGGACTTTTTGAAG
CTCTTAATTTGGGCCATCAGGTTCACTTTAAAGAAAAAGTTTTATCAGTTTTAGACTTTT
CAACCCCAGGTAGAACTGCTGCTGCTGTGGCTTTTCTTACTTTTATATTAGATAAATGGA
TCCCGCAGACTCATTTCAGCAGGGGATACGTTTTGGATTTCATAGCCACAGCATTGTGGA
GAACATGGAAGGTTCGCAAGATGAGGACAATCTTAGGTTACTGGCCAGTGCAGCCTTTGG
GTGTAGCGGGAATCCTGAGGCATCCACCGGTCATGCCAGCGGTTCTGGAGGAGGAACAGC
AAGAGGACAACCCGAGAGCCGGCCTGGACCCTCCAGTGGAGGAGGCGGAGTAGCTGACTT
GTCTCCTGAACTGCAACGGGTGCTTACTGGATCTACGTCCACTGGACGGGATAGGGCGT
TAAGAGGGAGAGGGCATCCAGTGGTACTGATGCTAGATCTGAGTTGGCTTTAAGTTTAAT
GAGTCGCAGACGTCCTGAAACCATTTGGTGGCATGAGGTTCAGAAAGAGGGAAGGGATGA
AGTTTCTGTATTGCAGGAGAAATATTCACTGGAACAGGTGAAAACATGTTGGTTGGAGCC
AGAGGATGATTGGGCGGTGGCCATTAAAAATTATGCCAAGATAGCTTTGAGGCCTGATAA
ACAGTATAAGATCAGTAGACGGATTAATATCCGGAATGCTTGTTACATATCTGGAAATGG
GGCTGAGGTGGTAATAGATACTCAAGACAAGACAGTTATTAGATGCTGCATGATGGATAT
GTGGCCTGGAGTAGTCGGTATGGAAGCAGTCACTTTTGTAAATGTTAAGTTTAGGGGAGA
TGGTTATAATGGAATAGTGTTTATGGCCAATACCAAACTTATATTGCATGGTTGTAGCTT
TTTTGGTTTCAACAATACCTGTGTAGATGCCTGGGGACAGGTTAGTGTACGGGGGTGTAG
TTTCTATGCGTGTTGGATTGCCACAGCTGGCAGAACCAAGAGTCAATTGTCTCTGAAGAA
ATGCATATTCCAAAGATGTAACCTGGGCATTCTGAATGAAGGCGAAGCAAGGGTCCGTCA
CTGCGCTTCTACAGATACTGGATGTTTTATTTTAATTAAGGGAAATGCCAGCGTAAAGCA
```

-continued

```
TAACATGATTTGTGGTGCTTCCGATGAGAGGCCTTATCAAATGCTCACTTGTGCTGGTGG
GCATTGTAATATGCTGGCTACTGTGCATATTGTTTCCCATCAACGCAAAAAATGGCCTGT
TTTTGATCACAATGTGTTGACCAAGTGCACCATGCATGCAGGTGGGCGTAGAGGAATGTT
TATGCCTTACCAGTGTAACATGAATCATGTGAAAGTGTTGTTGGAACCAGATGCCTTTTC
CAGAATGAGCCTAACAGGAATCTTTGACATGAACACGCAAATCTGGAAGATCCTGAGGTA
TGATGATACGAGATCGAGGGTGCGCGCATGCGAATGCGGAGGCAAGCATGCCAGGTTCCA
GCCGGTGTGTGTAGATGTGACCGAAGATCTCAGACCGGATCATTTGGTTATTGCCCGCAC
TGGAGCAGAGTTCGGATCCAGTGGAGAAGAAACTGACTAAGGTGAGTATTGGGAAAACTT
TGGGGTGGGATTTTCAGATGGACAGATTGAGTAAAAATTTGTTTTTTCTGTCTTGCAGCT
GACATGAGTGGAAATGCTTCTTTTAAGGGGGGAGTCTTCAGCCCTTATCTGACAGGGCGT
CTCCCATCCTGGGCAGGAGTTCGTCAGAATGTTATGGGATCTACTGTGGATGGAAGACCC
GTTCAACCCGCCAATTCTTCAACGCTGACCTATGCTACTTTAAGTTCTTCACCTTTGGAC
GCAGCTGCAGCCGCTGCCGCCGCCTCTGTCGCCGCTAACACTGTGCTTGGAATGGGTTAC
TATGGAAGCATCGTGGCTAATTCCACTTCCTCTAATAACCCTTCTACACTGACTCAGGAC
AAGTTACTTGTCCTTTTGGCCCAGCTGGAGGCTTTGACCCAACGTCTGGGTGAACTTTCT
CAGCAGGTGGCCGAGTTGCGAGTACAAACTGAGTCTGCTGTCGGCACGGCAAAGTCTAAA
TAAAAAAATTCCAGAATCAATGAATAAATAAACGAGCTTGTTGTTGATTTAAAATCAAG
TGTTTTTATTTCATTTTTCGCGCACGGTATGCCCTGGACCACCGATCTCGATCATTGAGA
ACTCGGTGGATTTTTTCCAGAATCCTATAGAGGTGGGATTGAATGTTTAGATACATGGGC
ATTAGGCCGTCTTTGGGGTGGAGATAGCTCCATTGAAGGGATTCATGCTCCGGGGTAGTG
TTGTAAATCACCCAGTCATAACAAGGTCGCAGTGCATGGTGTTGCACAATATCTTTTAGA
AGTAGGCTGATTGCCACAGATAAGCCCTTGGTGTAGGTGTTTACAAACCGGTTGAGCTGG
GAGGGGTGCATTCGAGGTGAAATTATGTGCATTTTGGATTGGATTTTTAAGTTGGCAATA
TTGCCGCCAAGATCCCGTCTTGGGTTCATGTTATGAAGGACTACCAAGACGGTGTATCCG
GTACATTTAGGAAATTTATCGTGCAGCTTGGATGGAAAAGCGTGAAAAATTTGGAGACA
CCCTTGTGTCCTCCGAGATTTTCCATGCACTCATCCATGATAATAGCAATGGGGCCGTGG
GCAGCGGCGCGGGCAAACACGTTCCGTGGGTCTGACACATCATAGTTATGTTCCTGAGTT
AAATCATCATAAGCCATTTTAATGAATTTGGGGCGGAGCGTACCAGATTGGGGTATGAAT
GTTCCTTCGGGCCCCGGAGCATAGTTCCCCTCACAGATTTGCATTTCCCAAGCTTTCAGT
TCTGAGGGTGGAATCATGTCCACCTGGGGGCTATGAAGAACACCGTTTCGGGGCGGGG
GTGATTAGTTGGGATGATAGCAAGTTTCTGAGCAATTGAGATTTGCCACATCCGGTGGGG
CCATAAATAATTCCGATTACAGGTTGCAGGTGGTAGTTTAGGGAACGGCAACTGCCGTCT
TCTCGAAGCAAGGGGGCCACCTCGTTCATCATTTCCCTTACATGCATATTTTCCCGCACC
AAATCCATTAGGAGGCGCTCTCCTCCTAGTGATAGAAGTTCTTGTAGTGAGGAAAAGTTT
TTCAGCGGTTTTAGACCGTCAGCCATGGGCATTTTGGAAAGAGTTTGCTGCAAAAGTTCT
AGTCTGTTCCACAGTTCAGTGATGTGTTCTATGGCATCTCGATCCAGCAGACCTCCTCGT
TTCGCGGGTTTGGACGGCTCCTGGAGTAGGGTATGAGACGATGGGCGTCCAGCGCTGCCA
GGGTTCGGTCCTTCCAGGGTCTCAGTGTTCGAGTCAGGGTTGTTTCCGTCACAGTGAAGG
GGTGTGCGCCTGCTTGGGCGCTTGCCAGGGTGCGCTTCAGACTCATTCTGCTGGTGGAGA
ACTTCTGTCGCTTGGCGCCCTGTATGTCGGCCAAGTAGCAGTTTACCATGAGTTCGTAGT
TGAGCGCCTCGGCTGCGTGGCCTTTGGCGCGGAGCTTACCTTTGGAAGTTTTCTTGCATA
```

-continued

```
CCGGGCAGTATAGGCATTTCAGCGCATACAGCTTGGGCGCAAGGAAAATGGATTCTGGGG

AGTATGCATCCGCGCCGCAGGAGGCGCAAACAGTTTCACATTCCACCAGCCAGGTTAAAT

CCGGTTCATTGGGGTCAAAAACAAGTTTTCCGCCATATTTTTTGATGCGTTTCTTACCTT

TGGTCTCCATAAGTTCGTGTCCTCGTTGAGTGACAAACAGGCTGTCCGTATCTCCGTAGA

CTGATTTTACAGGCCTCTTCTCCAGTGGAGTGCCTCGGTCTTCTTCGTACAGGAACTCTG

ACCACTCTGATACAAAGGCGCGCGTCCAGGCCAGCACAAAGGAGGCTATGTGGGAGGGGT

AGCGATCGTTGTCAACCAGGGGGTCCACCTTTTCCAAAGTATGCAAACACATGTCACCCT

CTTCAACATCCAGGAATGTGATTGGCTTGTAGGTGTATTTCACGTGACCTGGGGTCCCCG

CTGGGGGGGTATAAAAGGGGGCGGTTCTTTGCTCTTCCTCACTGTCTTCCGGATCGCTGT

CCAGGAACGTCAGCTGTTGGGGTAGGTATTCCCTCTCGAAGGCGGGCATGACCTCTGCAC

TCAGGTTGTCAGTTTCTAAGAACGAGGAGGATTTGATATTGACAGTGCCGGTTGAGATGC

CTTTCATGAGGTTTTCGTCCATTTGGTCAGAAAACACAATTTTTTTATTGTCAAGTTTGG

TGGCAAATGATCCATACAGGGCGTTGGATAAAAGTTTGGCAATGGATCGCATGGTTTGGT

TCTTTTCCTTGTCCGCGCGCTCTTTGGCGGCGATGTTGAGTTGGACATACTCGCGTGCCA

GGCACTTCCATTCGGGGAAGATAGTTGTTAATTCATCTGGCACGATTCTCACTTGCCACC

CTCGATTATGCAAGGTAATTAAATCCACACTGGTGGCCACCTCGCCTCGAAGGGGTTCAT

TGGTCCAACAGAGCCTACCTCCTTTCCTAGAACAGAAAGGGGGAAGTGGGTCTAGCATAA

GTTCATCGGGAGGGTCTGCATCCATGGTAAAGATTCCCGGAAGTAAATCCTTATCAAAAT

AGCTGATGGGAGTGGGGTCATCTAAGGCCATTTGCCATTCTCGAGCTGCCAGTGCGCGCT

CATATGGGTTAAGGGGACTGCCCCAGGGCATGGGATGGGTGAGAGCAGAGGCATACATGC

CACAGATGTCATAGACGTAGATGGGATCCTCAAAGATGCCTATGTAGGTTGGATAGCATC

GCCCCCCTCTGATACTTGCTCGCACATAGTCATATAGTTCATGTGATGGCGCTAGCAGCC

CCGGACCCAAGTTGGTGCGATTGGGTTTTTCTGTTCTGTAGACGATCTGGCGAAAGATGG

CGTGAGAATTGGAAGAGATGGTGGGTCTTTGAAAAATGTTGAAATGGGCATGAGGTAGAC

CTACAGAGTCTCTGACAAAGTGGGCATAAGATTCTTGAAGCTTGGTTACCAGTTCGGCGG

TGACAAGTACGTCTAGGGCGCAGTAGTCAAGTGTTTCTTGAATGATGTCATAACCTGGTT

GGTTTTTCTTTTCCCACAGTTCGCGGTTGAGAAGGTATTCTTCGCGATCCTTCCAGTACT

CTTCTAGCGGAAACCCGTCTTTGTCTGCACGGTAAGATCCTAGCATGTAGAACTGATTAA

CTGCCTTGTAAGGGCAGCAGCCCTTCTCTACGGGTAGAGAGTATGCTTGAGCAGCTTTTC

GTAGCGAAGCGTGAGTAAGGGCAAAGGTGTCTCTGACCATGACTTTGAGAAATTGGTATT

TGAAGTCCATGTCGTCACAGGCTCCCTGTTCCCAGAGTTGGAAGTCTACCCGTTTCTTGT

AGGCGGGGTTGGGCAAAGCGAAAGTAACATCATTGAAGAGAATCTTACCGGCTCTGGGCA

TAAAATTGCGAGTGATGCGGAAAGGCTGTGGTACTTCCGCTCGATTGTTGATCACCTGGG

CAGCTAGGACGATTTCGTCGAAACCGTTGATGTTGTGTCCTACGATGTATAATTCTATGA

AACGCGGCGTGCCTCTGACGTGAGGTAGCTTACTGAGCTCATCAAAGGTTAGGTCTGTGG

GGTCAGATAAGGCGTAGTGTTCGAGAGCCCATTCGTGCAGGTGAGGATTTGCATGTAGGA

ATGATGACCAAAGATCTACCGCCAGTGCTGTTTGTAACTGGTCCCGATACTGACGAAAAT

GCCGGCCAATTGCCATTTTTTCTGGAGTGACACAGTAGAAGGTTCTGGGGTCTTGTTGCC

ATCGATCCCACTTGAGTTTAATGGCTAGATCGTGGGCCATGTTGACGAGACGCTCTTCTC

CTGAGAGTTTCATGACCAGCATGAAAGGAACTAGTTGTTTGCCAAAGGATCCCATCCAGG
```

-continued

```
TGTAAGTTTCCACATCGTAGGTCAGGAAGAGTCTTTCTGTGCGAGGATGAGAGCCGATCG
GGAAGAACTGGATTTCCTGCCACCAGTTGGAGGATTGGCTGTTGATGTGATGGAAGTAGA
AGTTTCTGCGGCGCGCCGAGCATTCGTGTTTGTGCTTGTACAGACGGCCGCAGTAGTCGC
AGCGTTGCACGGGTTGTATCTCGTGAATGAGCTGTACCTGGCTTCCCTTGACGAGAAATT
TCAGTGGGAAGCCGAGGCCTGGCGATTGTATCTCGTGCTCTTCTATATTCGCTGTATCGG
CCTGTTCATCTTCTGTTTCGATGGTGGTCATGCTGACGAGCCCCGCGGGAGGCAAGTCC
AGACCTCGGCGCGGGAGGGGCGGAGCTGAAGGACGAGAGCGCGCAGGCTGGAGCTGTCCA
GAGTCCTGAGACGCTGCGGACTCAGGTTAGTAGGTAGGGACAGAAGATTAACTTGCATGA
TCTTTTCCAGGGCGTGCGGGAGGTTCAGATGGTACTTGATTTCCACAGGTTCGTTTGTAG
AGACGTCAATGGCTTGCAGGGTTCCGTGTCCTTTGGGCGCCACTACCGTACCTTTGTTTT
TTCTTTTGATCGGTGGTGGCTCTCTTGCTTCTTGCATGCTCAGAAGCGGTGACGGGGACG
CGCGCCGGGCGGCAGCGGTTGTTCCGGACCCGGGGGCATGGCTGGTAGTGGCACGTCGGC
GCCGCGCACGGGCAGGTTCTGGTATTGCGCTCTGAGAAGACTTGCGTGCGCCACCACGCG
TCGATTGACGTCTTGTATCTGACGTCTCTGGGTGAAAGCTACCGGCCCCGTGAGCTTGAA
CCTGAAAGAGAGTTCAACAGAATCAATTTCGGTATCGTTAACGGCAGCTTGTCTCAGTAT
TTCTTGTACGTCACCAGAGTTGTCCTGGTAGGCGATCTCCGCCATGAACTGCTCGATTTC
TTCCTCCTGAAGATCTCCGCGACCCGCTCTTTCGACGGTGGCCGCGAGGTCATTGGAGAT
ACGGCCCATGAGTTGGGAGAATGCATTCATGCCCGCCTCGTTCCAGACGCGGCTGTAAAC
CACGGCCCCTCGGAGTCTCTTGCGCGCATCACCACCTGAGCGAGGTTAAGCTCCACGTG
TCTGGTGAAGACCGCATAGTTGCATAGGCGCTGAAAAAGGTAGTTGAGTGTGGTGGCAAT
GTGTTCGGCGACGAAGAAATACATGATCCATCGTCTCAGCGGCATTTCGCTAACATCGCC
CAGAGCTTCCAAGCGCTCCATGGCCTCGTAGAAGTCCACGGCAAAATTAAAAAACTGGGA
GTTTCGCGCGGACACGGTCAATTCCTCCTCGAGAAGACGGATGAGTTCGGCTATGGTGGC
CCGTACTTCGCGTTCGAAGGCTCCCGGGATCTCTTCTTCCTCTTCTATCTCTTCTTCCAC
TAACATCTCTTCTTCGTCTTCAGGCGGGGCGGAGGGGGCACGCGGCGACGTCGACGGCG
CACGGGCAAACGGTCGATGAATCGTTCAATGACCTCTCCGCGGCGGCGGCGCATGGTTTC
AGTGACGGCGCGGCCGTTCTCGCGCGGTCGCAGAGTAAAAACACCGCCGCGCATCTCCTT
AAAGTGGTGACTGGGAGGTTCTCCGTTTGGGAGGGAGAGGGCGCTGATTATACATTTTAT
TAATTGGCCCGTAGGGACTGCGCGCAGAGATCTGATCGTGTCAAGATCCACGGGATCTGA
AAACCTTTCGACGAAAGCGTCTAACCAGTCACAGTCACAAGGTAGGCTGAGTACGGCTTC
TTGTGGGCGGGGTGGTTATGTGTTCGGTCTGGGTCTTCTGTTTCTTCTTCATCTCGGGA
AGGTGAGACGATGCTGCTGGTGATGAAATTAAAGTAGGCAGTTCTAAGACGGCGGATGGT
GGCGAGGAGCACCAGGTCTTTGGGTCCGGCTTGCTGGATACGCAGGCGATTGGCCATTCC
CCAAGCATTATCCTGACATCTAGCAAGATCTTTGTAGTAGTCTTGCATGAGCCGTTCTAC
GGGCACTTCTTCCTCACCCGTTCTGCCATGCATACGTGTGAGTCCAAATCCGCGCATTGG
TTGTACCAGTGCCAAGTCAGCTACGACTCTTTCGGCGAGGATGGCTTGCTGTACTTGGGT
AAGGGTGGCTTGAAAGTCATCAAAATCCACAAAGCGGTGGTAAGCCCCTGTATTAATGGT
GTAAGCACAGTTGGCCATGACTGACCAGTTAACTGTCTGGTGACCAGGGCGCACGAGCTC
GGTGTATTTAAGGCGCGAATAGGCGCGGGTGTCAAAGATGTAATCGTTGCAGGTGCGCAC
CAGATACTGGTACCCTATAAGAAAATGCGGCGGTGGTTGGCGGTAGAGAGGCCATCGTTC
TGTAGCTGGAGCGCCAGGGGCGAGGTCTTCCAACATAAGGCGGTGATAGCCGTAGATGTA
```

-continued

```
CCTGGACATCCAGGTGATTCCTGCGGCGGTAGTAGAAGCCCGAGGAAACTCGCGTACGCG

GTTCCAAATGTTGCGTAGCGGCATGAAGTAGTTCATTGTAGGCACGGTTTGACCAGTGAG

GCGCGCGCAGTCATTGATGCTCTATAGACACGGAGAAAATGAAAGCGTTCAGCGACTCGA

CTCCGTAGCCTGGAGGAACGTGAACGGGTTGGGTCGCGGTGTACCCCGGTTCGAGACTTG

TACTCGAGCCGGCCGGAGCCGCGGCTAACGTGGTATTGGCACTCCCGTCTCGACCCAGCC

TACAAAAATCCAGGATACGGAATCGAGTCGTTTTGCTGGTTTCCGAATGGCAGGGAAGTG

AGTCCTATTTTTTTTTTTTTTTGCCGCTCAGATGCATCCCGTGCTGCGACAGATGCGCC

CCCAACAACAGCCCCCTCGCAGCAGCAGCAGCAGCAACCACAAAAGGCTGTCCCTGCAA

CTACTGCAACTGCCGCCGTGAGCGGTGCGGGACAGCCCGCCTATGATCTGGACTTGGAAG

AGGGCGAAGGACTGGCACGTCTAGGTGCGCCTTCGCCCGAGCGGCATCCGCGAGTTCAAC

TGAAAAAGATTCTCGCGAGGCGTATGTGCCCCAACAGAACCTATTTAGAGACAGAAGCG

GCGAGGAGCCGGAGGAGATGCGAGCTTCCCGCTTTAACGCGGGTCGTGAGCTGCGTCACG

GTTTGGACCGAAGACGAGTGTTGCGAGACGAGGATTTCGAAGTTGATGAAGTGACAGGGA

TCAGTCCTGCCAGGGCACACGTGGCTGCAGCCAACCTTGTATCGGCTTACGAGCAGACAG

TAAAGGAAGAGCGTAACTTCCAAAAGTCTTTTAATAATCATGTGCGAACCCTGATTGCCC

GCGAAGAAGTTACCCTTGGTTTGATGCATTTGTGGGATTTGATGGAAGCTATCATTCAGA

ACCCTACTAGCAAACCTCTGACCGCCCAGCTGTTTCTGGTGGTGCAACACAGCAGAGACA

ATGAGGCTTTCAGAGAGGCGCTGCTGAACATCACCGAACCCGAGGGGAGATGGTTGTATG

ATCTTATCAACATTCTACAGAGTATCATAGTGCAGGAGCGGAGCCTGGGCCTGGCCGAGA

AGGTAGCTGCCATCAATTACTCGGTTTTGAGCTTGGGAAAATATTACGCTCGCAAAATCT

ACAAGACTCCATACGTTCCCATAGACAAGGAGGTGAAGATAGATGGGTTCTACATGCGCA

TGACGCTCAAGGTCTTGACCCTGAGCGATGATCTTGGGGTGTATCGCAATGACAGAATGC

ATCGCGCGGTTAGCGCCAGCAGGAGGCGCGAGTTAAGCGACAGGGAACTGATGCACAGTT

TGCAAAGAGCTCTGACTGGAGCTGGAACCGAGGGTGAGAATTACTTCGACATGGGAGCTG

ACTTGCAGTGGCAGCCTAGTCGCAGGGCTCTGAGCGCCGCGACGGCAGGATGTGAGCTTC

CTTACATAGAAGAGGCGGATGAAGGCGAGGAGGAAGAGGGCGAGTACTTGGAAGACTGAT

GGCACAACCCGTGTTTTTGCTAGATGGAACAGCAAGCACCGGATCCCGCAATGCGGGCG

GCGCTGCAGAGCCAGCCGTCCGGCATTAACTCCTCGGACGATTGGACCCAGGCCATGCAA

CGTATCATGGCGTTGACGACTCGCAACCCCGAAGCCTTTAGACAGCAACCCCAGGCCAAC

CGTCTATCGGCCATCATGGAAGCTGTAGTGCCTTCCCGATCTAATCCCACTCATGAGAAG

GTCCTGGCCATCGTGAACGCGTTGGTGGAGAACAAAGCTATTCGTCCAGATGAGGCCGGA

CTGGTATACAACGCTCTCTTAGAACGCGTGGCTCGCTACAACAGTAGCAATGTGCAAACC

AATTTGGACCGTATGATAACAGATGTACGCGAAGCCGTGTCTCAGCGCGAAAGGTTCCAG

CGTGATGCCAACCTGGGTTCGCTGGTGGCGTTAAATGCTTTCTTGAGTACTCAGCCTGCT

AATGTGCCGCGTGGTCAACAGGATTATACTAACTTTTTAAGTGCTTTGAGACTGATGGTA

TCAGAAGTACCTCAGAGCGAAGTGTATCAGTCCGGTCCTGATTACTTCTTTCAGACTAGC

AGACAGGGCTTGCAGACGGTAAATCTGAGCCAAGCTTTTAAAAACCTTAAAGGTTTGTGG

GGAGTGCATGCCCCGGTAGGAGAAAGAGCAACCGTGTCTAGCTTGTTAACTCCGAACTCC

CGCCTGTTATTACTGTTGGTAGCTCCTTTCACCGACAGCGGTAGCATCGACCGTAATTCC

TATTTGGGTTACCTACTAAACCTGTATCGCGAAGCCATAGGGCAAAGTCAGGTGGACGAG
```

```
CAGACCTATCAAGAAATTACCCAAGTCAGTCGCGCTTTGGGACAGGAAGACACTGGCAGT

TTGGAAGCCACTCTGAACTTCTTGCTTACCAATCGGTCTCAAAAGATCCCTCCTCAATAT

GCTCTTACTGCGGAGGAGGAGAGGATCCTTAGATATGTGCAGCAGAGCGTGGGATTGTTT

CTGATGCAAGAGGGGGCAACTCCGACTGCAGCACTGGACATGACAGCGCGAAATATGGAG

CCCAGCATGTATGCCAGTAACCGACCTTTCATTAACAAACTGCTGGACTACTTGCACAGA

GCTGCCGCTATGAACTCTGATTATTTCACCAATGCCATCTTAAACCCGCACTGGCTGCCC

CCACCTGGTTTCTACACGGGCGAATATGACATGCCCGACCCTAATGACGGATTTCTGTGG

GACGACGTGGACAGCGATGTTTTTTCACCTCTTTCTGATCATCGCACGTGGAAAAAGGAA

GGCGGTGATAGAATGCATTCTTCTGCATCGCTGTCCGGGGTCATGGGTGCTACCGCGGCT

GAGCCCGAGTCTGCAAGTCCTTTTCCTAGTCTACCCTTTTCTCTACACAGTGTACGTAGC

AGCGAAGTGGGTAGAATAAGTCGCCCGAGTTTAATGGGCGAAGAGGAGTACCTAAACGAT

TCCTTGCTCAGACCGGCAAGAGAAAAAATTTCCCAAACAATGGAATAGAAAGTTTGGTG

GATAAAATGAGTAGATGGAAGACTTATGCTCAGGATCACAGAGACGAGCCTGGGATCATG

GGGACTACAAGTAGAGCGAGCCGTAGACGCCAGCGCCATGACAGACAGAGGGGTCTTGTG

TGGGACGATGAGGATTCGGCCGATGATAGCAGCGTGTTGGACTTGGGTGGGAGAGGAAGG

GGCAACCCGTTTGCTCATTTGCGCCCTCGCTTGGGTGGTATGTTGTGAAAAAAAATAAAA

AAGAAAAACTCACCAAGGCCATGGCGACGAGCGTACGTTCGTTCTTCTTTATTATCTGTG

TCTAGTATAATGAGGCGAGTCGTGCTAGGCGGAGCGGTGGTGTATCCGGAGGGTCCTCCT

CCTTCGTACGAGAGCGTGATGCAGCAGCAGCAGGCGACGGCGGTGATGCAATCCCCACTG

GAGGCTCCCTTTGTGCCTCCGCGATACCTGGCACCTACGGAGGGCAGAAACAGCATTCGT

TACTCGGAACTGGCACCTCAGTACGATACCACCAGGTTGTATCTGGTGGACAACAAGTCG

GCGGACATTGCTTCTCTGAACTATCAGAATGACCACAGCAACTTCTTGACCACGGTGGTG

CAGAACAATGACTTTACCCCTACGGAAGCCAGCACCCAGACCATTTACTTTGATGAACGA

TCGCGGTGGGCGGTCAGCTAAAGACCATCATGCATACTAACATGCCAAACGTGAACGAG

TATATGTTTAGTAACAAGTTCAAAGCGCGTGTGATGGTGTCCAGAAAACCTCCCGACGGT

GCTGCAGTTGGGGATACTTATGATCACAAGCAGGATATTTTGGAATATGAGTGGTTCGAG

TTTACTTTGCCAGAAGGCAACTTTTCAGTTACTATGACTATTGATTTGATGAACAATGCC

ATCATAGATAATTACTTGAAAGTGGGTAGACAGAATGGAGTGCTTGAAAGTGACATTGGT

GTTAAGTTCGACACCAGGAACTTCAAGCTGGGATGGGATCCCGAAACCAAGTTGATCATG

CCTGGAGTGTATACGTATGAAGCCTTCCATCCTGACATTGTCTTACTGCCTGGCTGCGGA

GTGGATTTTACCGAGAGTCGTTTGAGCAACCTTCTTGGTATCAGAAAAAAACAGCCATTT

CAAGAGGGTTTTAAGATTTGTATGAAGATTTAGAAGGTGGTAATATTCCGGCCCTCTTG

GATGTAGATGCCTATGAGAACAGTAAGAAAGAACAAAAAGCCAAAATAGAAGCTGCTACA

GCTGCTGCAGAAGCTAAGGCAAACATAGTTGCCAGCGACTCTACAAGGGTTGCTAACGCT

GGAGAGGTCAGAGGAGACAATTTTGCGCCAACACCTGTTCCGACTGCAGAATCATTATTG

GCCGATGTGTCTGAAGGAACGGACGTGAAACTCACTATTCAACCTGTAGAAAAGATAGT

AAGAATAGAAGCTATAATGTGTTGGAAGACAAAATCAACACAGCCTATCGCAGTTGGTAT

CTTTCGTACAATTATGGCGATCCCGAAAAAGGAGTGCGTTCCTGGACATTGCTCACCACC

TCAGATGTCACCTGCGGAGCAGAGCAGGTTTACTGGTCGCTTCCAGACATGATGAAGGAT

CCTGTCACTTTCCGCTCCACTAGACAAGTCAGTAACTACCCTGTGGTGGGTGCAGAGCTT

ATGCCCGTCTTCTCAASGAGCTTCTACAACGTACAAGCTGTGTACTCCCAGCAGCTCCGC
```

-continued

```
CAGTCCACCTCGCTTACGCACGTCTTCAACCGCTTTCCTGAGAACCAGATTTTAATCCGT
CCGCCGGCGCCCACCATTACCACCGTCAGTGAAAACGTTCCTGCTCTCACAGATCACGGG
ACCCTGCCGTTGCGCAGCAGTATCCGGGGAGTCCAACGTGTGACCGTTACTGACGCCAGA
CGCCGCACCTGTCCCTACGTGTACAAGGCACTGGGCATAGTCGCACCGCGCGTCCTTTCA
AGCCGCACTTTCTAAAAAAAAAAAATGTCCATTCTTATCTCGCCCAGTAATAACACCGGT
TGGGGTCTGCGCGCTCCAAGCAAGATGTACGGAGGCGCACGCAAACGTTCTACCCAACAT
CCCGTGCGTGTTCGCGGACATTTTCGCGCTCCATGGGGTGCCCTCAAGGGCCGCACTCGC
GTTCGAACCACCGTCGATGATGTAATCGATCAGGTGGTTGCCGACGCCCGTAATTATACT
CCTACTGCGCCTACATCTACTGTGGATGCAGTTATTGACAGTGTAGTGGCTGACGCTCGC
AACTATGCTCGACGTAAGAGCCGGCGAAGGCGCATTGCCAGACGCCACCGAGCTACCACT
GCCATGCGAGCCGCAAGAGCTCTGCTACGAAGAGCTAGACGCGTGGGGCGAAGAGCCATG
CTTAGGGCGGCCAGACGTGCAGCTTCGGGCGCCAGCGCCGGCAGGTCCCGCAGGCAAGCA
GCCGCTGTCGCAGCGGCGACTATTGCCGACATGGCCCAATCGCGAAGAGGCAATGTATAC
TGGGTGCGTGACGCTGCCACCGGTCAACGTGTACCCGTGCGCACCCGTCCCCCTCGCACT
TAGAAGATACTGAGCAGTCTCCGATGTTGTGTCCCAGCGGCGAGGATGTCCAAGCGCAAA
TACAAGGAAGAAATGCTGCAGGTTATCGCACCTGAAGTCTACGGCCAACCGTTGAAGGAT
GAAAAAAACCCCGCAAAATCAAGCGGGTTAAAAAGGACAAAAAAGAAGAGGAAGATGGC
GATGATGGGCTGGCGGAGTTTGTGCGCGAGTTTGCCCCACGGCGACGCGTGCAATGGCGT
GGGCGCAAAGTTCGACATGTGTTGAGACCTGGAACTTCGGTGGTCTTTACACCCGGCGAG
CGTTCAAGCGCTACTTTTAAGCGTTCCTATGATGAGGTGTACGGGGATGATGATATTCTT
GAGCAGGCGGCTGACCGATTAGGCGAGTTTGCTTATGGCAAGCGTAGTAGAATAACTTCC
AAGGATGAGACAGTGTCAATACCCTTGGATCATGGAAATCCCACCCCTAGTCTTAAACCG
GTCACTTTGCAGCAAGTGTTACCCGTAACTCCGCGAACAGGTGTTAAACGCGAAGGTGAA
GATTTGTATCCCACTATGCAACTGATGGTACCCAAACGCCAGAAGTTGGAGGACGTTTTG
GAGAAAGTAAAAGTGGATCCAGATATTCAACCTGAGGTTAAAGTGAGACCCATTAAGCAG
GTAGCGCCTGGTCTGGGGGTACAAACTGTAGACATTAAGATTCCCACTGAAAGTATGGAA
GTGCAAACTGAACCCGCAAAGCCTACTGCCACCTCCACTGAAGTGCAAACGGATCCATGG
ATGCCCATGCCTATTACAACTGACGCCGCCGGTCCCACTCGAAGATCCCGACGAAAGTAC
GGTCCAGCAAGTCTGTTGATGCCCAATTATGTTGTACACCCATCTATTATTCCTACTCCT
GGTTACCGAGGCACTCGCTACTATCGCAGCCGAAACAGTACCTCCCGCCGTCGCCGCAAG
ACACCTGCAAATCGCAGTCGTCGCCGTAGACGCACAAGCAAACCGACTCCCGGCGCCCTG
GTGCGGCAAGTGTACCGCAATGGTAGTGCGGAACCTTTGACACTGCCGCGTGCGCGTTAC
CATCCGAGTATCATCACTTAATCAATGTTGCCGCTGCCTCCTTGCAGATATGGCCCTCAC
TTGTCGCCTTCGCGTTCCCATCACTGGTTACCGAGGAAGAAACTCGCGCCGTAGAAGAGG
GATGTTGGGACGCGGAATGCGACGCTACAGGCGACGGCGTGCTATCCGCAAGCAATTGCG
GGGTGGTTTTTTACCAGCCTTAATTCCAATTATCGCTGCTGCAATTGGCGCGATACCAGG
CATAGCTTCCGTGGCGGTTCAGGCCTCGCAACGACATTGACATTGGAAAAAAAACGTATA
AATAAAAAAAAATACAATGGACTCTGACACTCCTGGTCCTGTGACTATGTTTTCTTAGAG
ATGGAAGACATCAATTTTTCATCCTTGGCTCCGCGACACGGCACGAAGCCGTACATGGGC
ACCTGGAGCGACATCGGCACGAGCCAACTGAACGGGGGCGCCTTCAATTGGAGCAGTATC
```

-continued

```
TGGAGCGGGCTTAAAAATTTTGGCTCAACCATAAAAACATACGGGAACAAAGCTTGGAAC

AGCAGTACAGGACAGGCGCTTAGAAATAAACTTAAAGACCAGAACTTCCAACAAAAAGTA

GTCGATGGATAGCTTCCGGCATCAATGGAGTGGTAGATTTGGCTAACCAGGCTGTGCAG

AAAAAGATAAACAGTCGTTTGGACCCGCCGCCAGCAACCCCAGGTGAAATGCAAGTGGAG

GAAGAAATTCCTCCGCCAGAAAAACGAGGCGACAAGCGTCCGCGTCCCGATTTGGAAGAG

ACGCTGGTGACGCGCGTAGATGAACCGCCTTCTTATGAGGAAGCAACGAAGCTTGGAATG

CCCACCACTAGACCGATAGCCCCAATGGCCACCGGGGTGATGAAACCTTCTCAGTTGCAT

CGACCCGTCACCTTGGATTTGCCCCCTCCCCCTGCTGCTACTGCTGTACCCGCTTCTAAG

CCTGTCGCTGCCCCGAAACCAGTCGCCGTAGCCAGGTCACGTCCCGGGGGCGCTCCTCGT

CCAAATGCGCACTGGCAAAATACTCTGAACAGCATCGTGGGTCTAGGCGTGCAAAGTGTA

AAACGCCGTCGCTGCTTTTAATTAAATATGGAGTAGCGCTTAACTTGCCTATCTGTGTAT

ATGTGTCATTACACGCCGTCACAGCAGCAGAGGAAAAAAGGAAGAGGTCGTGCGTCGACG

CTGAGTTACTTTCAAGATGGCCACCCCATCGATGCTGCCCCAATGGGCATACATGCACAT

CGCCGGACAGGATGCTTCGGAGTACCTGAGTCCGGGTCTGGTGCAGTTCGCCCGCGCCAC

AGACACCTACTTCAATCTGGGAAATAAGTTTAGAAATCCCACCGTAGCGCCGACCCACGA

TGTGACCACCGACCGTAGCCAGCGGCTCATGTTGCGCTTCGTGCCCGTTGACCGGGAGGA

CAATACATACTCTTACAAAGTGCGGTACACCCTGGCCGTGGGCGACAACAGAGTGCTGGA

TATGGCCAGCACGTTCTTTGACATTAGGGGCGTGTTGGACAGAGGTCCCAGTTTCAAACC

CTATTCTGGTACGGCTTACAACTCTCTGGCTCCTAAAGGCGCTCCAAATGCATCTCAATG

GATTGCAAAAGGCGTACCAACTGCAGCAGCCGCAGGCAATGGTGAAGAAGAACATGAAAC

AGAGGAGAAAACTGCTACTTACACTTTTGCCAATGCTCCTGTAAAAGCCGAGGCTCAAAT

TACAAAAGAGGGCTTACCAATAGGTTTGGAGATTTCAGCTGAAAACGAATCTAAACCCAT

CTATGCAGATAAACTTTATCAGCCAGAACCTCAAGTGGGAGATGAAACTTGGACTGACCT

AGACGGAAAAACCGAAGAGTATGGAGGCAGGGCTCTAAAGCCTACTACTAACATGAAACC

CTGTTACGGGTCCTATGCGAAGCCTACTAATTTAAAAGGTGGTCAGGCAAAACCGAAAAA

CTCGGAACCGTCGAGTGAAAAAATTGAATATGATATTGACATGGAATTTTTTGATAACTC

ATCGCAAAGAACAAACTTCAGTCCTAAAATTGTCATGTATGCAGAAAATGTAGGTTTGGA

AACGCCAGACACTCATGTAGTGTACAAACCTGGAACAGAAGACACAAGTTCCGAAGCTAA

TTTGGGACAACAGTCTATGCCCAACAGACCCAACTACATTGGCTTCAGAGATAACTTTAT

TGGACTCATGTACTATAACAGTACTGGTAACATGGGGGTGCTGGCTGGTCAAGCGTCTCA

GTTAAATGCAGTGGTTGACTTGCAGGACAGAAACACAGAACTTTCTTACCAACTCTTGCT

TGACTCTCTGGGCGACAGAACCAGATACTTTAGCATGTGGAATCAGGCTGTGGACAGTTA

TGATCCTGATGTACGTGTTATTGAAAATCATGGTGTGGAAGATGAACTTCCCAACTATTG

TTTTCCACTGGACGGCATAGGTGTTCCAACAACCAGTTACAAATCAATAGTTCCAAATGG

AGAAGATAATAATAATTGGAAAGAACCTGAAGTAAATGGAACAAGTGAGATCGGACAGGG

TAATTTGTTTGCCATGGAAATTAACCTTCAAGCCAATCTATGGCGAAGTTTCCTTTATTC

CAATGTGGCTCTGTATCTCCCAGACTCGTACAAATACACCCCGTCCAATGTCACTCTTCC

AGAAAACAAAAACACCTACGACTACATGAACGGGCGGGTGGTGCCGCCATCTCTAGTAGA

CACCTATGTGAACATTGGTGCCAGGTGGTCTCTGGATGCCATGGACAATGTCAACCCATT

CAACCACCACCGTAACGCTGGCTTGCGTTACCGATCTATGCTTCTGGGTAACGGACGTTA

TGTGCCTTTCCACATACAAGTGCCTCAAAAATTCTTCGCTGTTAAAAACCTGCTGCTTCT
```

-continued

```
CCCAGGCTCCTACACTTATGAGTGGAACTTTAGGAAGGATGTGAACATGGTTCTACAGAG

TTCCCTCGGTAACGACCTGCGGGTAGATGGCGCCAGCATCAGTTTCACGAGCATCAACCT

CTATGCTACTTTTTTCCCCATGGCTCACAACACCGCTTCCACCCTTGAAGCCATGCTGCG

GAATGACACCAATGATCAGTCATTCAACGACTACCTATCTGCAGCTAACATGCTCTACCC

CATTCCTGCCAATGCAACCAATATTCCCATTTCCATTCCTTCTCGCAACTGGGCGGCTTT

CAGAGGCTGGTCATTTACCAGACTGAAAACCAAAGAAACTCCCTCTTTGGGGTCTGGATT

TGACCCCTACTTTGTCTATTCTGGTTCTATTCCCTACCTGGATGGTACCTTCTACCTGAA

CCACACTTTTAAGAAGGTTTCCATCATGTTTGACTCTTCAGTGAGCTGGCCTGGAAATGA

CAGGTTACTATCTCCTAACGAATTTGAAATAAAGCGCACTGTGGATGGCGAAGGCTACAA

CGTAGCCCAATGCAACATGACCAAAGACTGGTTCTTGGTACAGATGCTCGCCAACTACAA

CATCGGCTATCAGGGCTTCTACATTCCAGAAGGATACAAAGATCGCATGTATTCATTTTT

CAGAAACTTCCAGCCCATGAGCAGGCAGGTGGTTGATGAGGTCAATTACAAAGACTTCAA

GGCCGTCGCCATACCCTACCAACACAACAACTCTGGCTTTGTGGGTTACATGGCTCCGAC

CATGCGCCAAGGTCAACCCTATCCCGCTAACTATCCCTATCCACTCATTGGAACAACTGC

CGTAAATAGTGTTACGCAGAAAAAGTTCTTGTGTGACAGAACCATGTGGCGCATACCGTT

CTCGAGCAACTTCATGTCTATGGGGGCCCTTACAGACTTGGGACAGAATATGCTCTATGC

CAACTCAGCTCATGCTCTGGACATGACCTTTGAGGTGGATCCCATGGATGAGCCCACCCT

GCTTTATCTTCTCTTCGAAGTTTTCGACGTGGTCAGAGTGCATCAGCCACACCGCGGCAT

CATCGAGGCAGTCTACCTGCGTACACCGTTCTCGGCCGGTAACGCTACCACGTAAGAAGC

TTCTTGCTTCTTGCAAATAGCAGCTGCAACCATGGCCTGCGGATCCCAAAACGGCTCCAG

CGAGCAAGAGCTCAGAGCCATTGTCCAAGACCTGGGTTGCGGACCCTATTTTTTGGGAAC

CTACGATAAGCGCTTCCCGGGGTTCATGGCCCCCGATAAGCTCGCCTGTGCCATTGTAAA

TACGGCCGGACGTGAGACGGGGGGAGAGCACTGGTTGGCTTTCGGTTGGAACCCACGTTC

TAACACCTGCTACCTTTTTGATCCTTTTGGATTCTCGGATGATCGTCTCAAACAGATTTA

CCAGTTTGAATATGAGGGTCTCCTGCGCCGCAGCGCTCTTGCTACCAAGGACCGCTGTAT

TACGCTGGAAAAATCTACCCAGACCGTGCAGGGCCCCCGTTCTGCCGCCTGCGGACTTTT

CTGCTGCATGTTCCTTCACGCCTTTGTGCACTGGCCTGACCGTCCCATGGACGGAAACCC

CACCATGAAATTGCTAACTGGAGTGCCAAACAACATGCTTCATTCTCCTAAAGTCCAGCC

CACCCTGTGTGACAATCAAAAAGCACTCTACCATTTTCTTAATACCCATTCGCCTTATTT

TCGCTCTCATCGTACACACATCGAAAGGGCCACTGCGTTCGACCGTATGGATGTTCAATA

ATGACTCATGTAAACAACGTGTTCAATAAACATCACTTTATTTTTTTACATGTATCAAGG

CTCTGGATTACTTATTTATTTACAAGTCGAATGGGTTCTGACGAGAATCAGAATGACCCG

CAGGCAGTGATACGTTGCGGAACTGATACTTGGGTTGCCACTTGAATTCGGGAATCACCA

ACTTGGGAACCGGTATATCGGGCAGGATGTCACTCCACAGCTTTCTGGTCAGCTGCAAAG

CTCCAAGCAGGTCAGGAGCCGAAATCTTGAAATCACAATTAGGACCAGTGCTCTGAGCGC

GAGAGTTGCGGTACACCGGATTGCAGCACTGAAACACCATCAGCGACGGATGTCTCACGC

TTGCCAGCACGGTGGGATCTGCAATCATGCCCACATCCAGATCTTCAGCATTGGCAATGC

TGAACGGGGTCATCTTGCAGGTCTGCCTACCCATGGCGGGCACCCAATTAGGCTTGTGGT

TGCAATCGCAGTGCAGGGGATCAGTATCATCTTGGCCTGATCCTGTCTGATTCCTGGAT

ACACGGCTCTCATGAAAGCATCATATTGCTTGAAAGCCTGCTGGGCTTTACTACCCTCGG
```

-continued

```
TATAAAACATCCCGCAGGACCTGCTCGAAAACTGGTTAGCTGCACAGCCGGCATCATTCA

CACAGCAGCGGGCGTCATTGTTGGCTATTTGCACCACACTTCTGCCCCAGCGGTTTTGGG

TGATTTTGGTTCGCTCGGGATTCTCCTTTAAGGCTCGTTGTCCGTTCTCGCTGGCCACAT

CCATCTCGATAATCTGCTCCTTCTGAATCATAATATTGCCATGCAGGCACTTCAGCTTGC

CCTCATAATCATTGCAGCCATGAGGCCACAACGCACAGCCTGTACATTCCCAATTATGGT

GGGCGATCTGAGAAAAGAATGTATCATTCCCTGCAGAAATCTTCCCATCATCGTGCTCA

GTGTCTTGTGACTAGTGAAAGTTAACTGGATGCCTCGGTGCTCTTCGTTTACGTACTGGT

GACAGATGCGCTTGTATTGTTCGTGTTGCTCAGGCATTAGTTTAAAACAGGTTCTAAGTT

CGTTATCCAGCCTGTACTTCTCCATCAGCAGACACATCACTTCCATGCCTTTCTCCCAAG

CAGACACCAGGGGCAAGCTAATCGGATTCTTAACAGTGCAGGCAGCAGCTCCTTTAGCCA

GAGGGTCATCTTTAGCGATCTTCTCAATGCTTCTTTTGCCATCCTTCTCAACGATGCGCA

CGGGCGGGTAGCTGAAACCCACTGCTACAAGTTGCGCCTCTTCTCTTTCTTCTTCGCTGT

CTTGACTGATGTCTTGCATGGGATATGTTTGGTCTTCCTTGGCTTCTTTTTGGGGGGTA

TCGGAGGAGGAGGACTGTCGCTCCGTTCCGGAGACAGGGAGGATTGTGACGTTTCGCTCA

CCATTACCAACTGACTGTCGGTAGAAGAACCTGACCCCACACGGCGACAGGTGTTTTTCT

TCGGGGCAGAGGTGGAGGCGATTGCGAAGGGCTGCGGTCCGACCTGGAAGGCGGATGAC

TGGCAGAACCCCTTCCGCGTTCGGGGTGTGCTCCCTGTGGCGGTCGCTTAACTGATTTC

CTTCGCGGCTGGCCATTGTGTTCTCCTAGGCAGAGAAACAACAGACATGGAAACTCAGCC

ATTGCTGTCAACATCGCCACGAGTGCCATCACATCTCGTCCTCAGCGACGAGGAAAAGGA

GCAGAGCTTAAGCATTCCACCGCCCAGTCCTGCCACCACCTCTACCCTAGAAGATAAGGA

GGTCGACGCATCTCATGACATGCAGAATAAAAAAGCGAAAGAGTCTGAGACAGACATCGA

GCAAGACCCGGGCTATGTGACACCGGTGGAACACGAGGAAGAGTTGAAACGCTTTCTAGA

GAGAGAGGATGAAAACTGCCCAAAACAGCGAGCAGATAACTATCACCAAGATGCTGGAAA

TAGGGATCAGAACACCGACTACCTCATAGGGCTTGACGGGGAAGACGCGCTCCTTAAACA

TCTAGCAAGACAGTCGCTCATAGTCAAGGATGCATTATTGGACAGAACTGAAGTGCCCAT

CAGTGTGGAAGAGCTCAGCTGCGCCTACGAGCTTAACCTTTTTTCACCTCGTACTCCCCC

CAAACGTCAGCCAAACGGCACCTGCGAGCCAAATCCTCGCTTAAACTTTTATCCAGCTTT

TGCTGTGCCAGAAGTACTGGCTACCTATCACATCTTTTTTAAAAATCAAAAAATTCCAGT

CTCCTGCCGCGCTAATCGCACCCGCGCCGATGCCCTACTCAATCGGGACCTGGTTCACG

CTTACCTGATATAGCTTCCTTGGAAGAGGTTCCAAAGATCTTCGAGGGTCTGGGCAATAA

TGAGACTCGGGCCGCAAATGCTCTGCAAAAGGGAGAAAATGGCATGGATGAGCATCACAG

CGTTCTGGTGGAATTGGAAGGCGATAATGCCAGACTCGCAGTACTCAAGCGAAGCGTCGA

GGTCACACACTTCGCATATCCCGCTGTCAACCTGCCCCCTAAAGTCATGACGGCGGTCAT

GGACCAGTTACTCATTAAGCGCGCAAGTCCCCTTTCAGAAGACATGCATGACCCAGATGC

CTGTGATGAGGGTAAACCAGTGGTCAGTGATGAGCAGCTAACCCGATGGCTGGGCACCGA

CTCTCCCCGGGATTTGGAAGAGCGTCGCAAGCTTATGATGGCCGTGGTGCTGGTTACCGT

AGAACTAGAGTGTCTCCGACGTTTCTTTACCGATTCAGAAACCTTGCGCAAACTCGAAGA

GAATCTGCACTACACTTTTAGACACGGCTTTGTGCGGCAGGCATGCAAGATATCTAACGT

GGAACTCACCAACCTGGTTTCCTACATGGGTATTCTGCATGAGAATCGCCTAGGACAAAG

CGTGCTGCACAGCACCCTTAAGGGGGAAGCCCGCCGTGATTACATCCGCGATTGTGTCTA

TCTCTACCTGTGCCACACGTGGCAAACCGGCATGGGTGTATGGCAGCAATGTTTAGAAGA
```

-continued

```
ACAGAACTTGAAAGAGCTTGACAAGCTCTTACAGAAATCTCTTAAGGTTCTGTGGACAGG
GTTCGACGAGCGCACCGTCGCTTCCGACCTGGCAGACCTCATCTTCCCAGAGCGTCTCAG
GGTTACTTTGCGAAACGGATTGCCTGACTTTATGAGCCAGAGCATGCTTAACAATTTTCG
CTCTTTCATCCTGGAACGCTCCGGTATCCTGCCCGCCACCTGCTGCGCACTGCCCTCCGA
CTTTGTGCCTCTCACCTACCGCGAGTGCCCCCCGCCGCTATGGAGTCACTGCTACCTGTT
CCGTCTGGCCAACTATCTCTCCTACCACTCGGATGTGATCGAGGATGTGAGCGGAGACGG
CTTGCTGGAGTGCCACTGCCGCTGCAATCTGTGCACGCCCCACCGGTCCCTAGCTTGCAA
CCCCCAGTTGATGAGCGAAACCCAGATAATAGGCACCTTTGAATTGCAAGGCCCCAGCAG
CCAAGGCGATGGGTCTTCTCCTGGGCAAAGTTTAAAACTGACCCCGGGACTGTGGACCTC
CGCCTACTTGCGCAAGTTTGCTCCGGAAGATTACCACCCCTATGAAATCAAGTTCTATGA
GGACCAATCACAGCCTCCAAAGGCCGAACTTTCGGCTTGCGTCATCACCCAGGGGCAAT
TCTGGCCCAATTGCAAGCCATCCAAAAATCCCGCCAAGAATTTCTACTGAAAAAGGGTAA
GGGGGTCTACCTTGACCCCAGACCGGCGAGGAACTCAACACAAGGTTCCCTCAGGATGT
CCCAACGACGAGAAAACAAGAAGTTGAAGGTGCAGCCGCCGCCCCCAGAAGATATGGAGG
AAGATTGGGACAGTCAGGCAGAGGAGGCGGAGGAGGACAGTCTGGAGGACAGTCTGGAGG
AAGACAGTTTGGAGGAGGAAAACGAGGAGGCAGAGGAGGTGGAAGAAGTAACCGCCGACA
AACAGTTATCCTCGGCTGCGGAGACAAGCAACAGCGCTACCATCTCCGCTCCGAGTCGAG
GAACCCGGCGGCGTCCCAGCAGTAGATGGGACGAGACCGGACGCTTCCCGAACCCAACCA
GCGCTTCCAAGACCGGTAAGAAGGATCGGCAGGGATACAAGTCCTGGCGGGGCATAAGA
ATGCCATCATCTCCTGCTTGCATGAGTGCGGGGGCAACATATCCTTCACGCGGCGCTACT
TGCTATTCCACCATGGGGTGAACTTTCCGCGCAATGTTTTGCATTACTACCGTCACCTCC
ACAGCCCCTACTATAGCCAGCAAATCCCGACAGTCTCGACAGATAAAGACAGCGGCGGCG
ACCTCCAACAGAAAACCAGCAGCGGCAGTTAGAAAATACACAACAAGTGCAGCAACAGGA
GGATTAAAGATTACAGCCAACGAGCCAGCGCAAACCCGAGAGTTAAGAAATCGGATCTTT
CCAACCCTGTATGCCATCTTCCAGCAGAGTCGGGGTCAAGAGCAGGAACTGAAAATAAAA
AACCGATCTCTGCGTTCGCTCACCAGAAGTTGTTTGTATCACAAGAGCGAAGATCAACTT
CAGCGCACTCTCGAGGACGCCGAGGCTCTCTTCAACAAGTACTGCGCGCTGACTCTTAAA
GAGTAGGCAGCGACCGCGCTTATTCAAAAAAGGCGGGAATTACATCATCCTCGACATGAG
TAAAGAAATTCCCACGCCTTACATGTGGAGTTATCAACCCCAAATGGGATTGGCAGCAGG
CGCCTCCCAGGACTACTCCACCCGCATGAATTGGCTCAGCGCCGGGCCTTCTATGATTTC
TCGAGTTAATGATATACGCGCCTACCGAAACCAAATACTTTTGGAACAGTCAGCTCTTAC
CACCACGCCCCGCCAACACCTTAATCCCAGAAATTGGCCCGCCGCCCTAGTGTACCAGGA
AAGTCCCGCTCCCACCACTGTATTACTTCCTCGAGACGCCCAGGCCGAAGTCCAAATGAC
TAATGCAGGTGCGCAGTTAGCTGGCGGCTCCACCCTATGTCGTCACAGGCCTCGGCATAA
TATAAAACGCCTGATGATCAGAGGCCGAGGTATCCAGCTCAACGACGAGTCGGTGAGCTC
TCCGCTTGGTCTACGACCAGACGGAATCTTTCAGATTGCCGGCTGCGGGAGATCTTCCTT
CACCCCTCGTCAGGCTGTTCTGACTTTGGAAAGTTCGTCTTCGCAACCCCGCTCGGGCGG
AATCGGGACCGTTCAATTTGTAGAGGAGTTTACTCCCTCTGTCTACTTCAACCCCTTCTC
CGGATCTCCTGGGCACTACCCGGACGAGTTCATACCGAACTTCGACGCGATTAGCGAGTC
AGTGGACGGCTACGATTGATGTCTGGTGACGCGGCTGAGCTATCTCGGCTGCGACATCTA
```

-continued

```
GACCACTGCCGCCGCTTTCGCTGCTTTGCCCGGGAACTTATTGAGTTCATCTACTTCGAA

CTCCCCAAGGATCACCCTCAAGGTCCGGCCCACGGAGTGCGGATTACTATCGAAGGCAAA

ATAGACTCTCGCCTGCAACGAATTTTCTCCCAGCGGCCCGTGCTGATCGAGCGAGACCAG

GGAAACACCACGGTTTCCATCTACTGCATTTGTAATCACCCCGGATTGCATGAAAGCCTT

TGCTGTCTTATGTGTACTGAGTTTAATAAAAACTGAATTAAGACTCTCCTACGGACTGCC

GCTTCTTCAACCCGGATTTTACAACCAGAAGAACAAAACTTTTCCTGTCGTCCAGGACTC

TGTTAACTTCACCTTTCCTACTCACAAACTAGAAGCTCAACGACTACACCGCTTTTCCAG

AAGCATTTTCCCTACTAATACTACTTTCAAAACCGGAGGTGAGCTCCACGGTCTCCCTAC

AGAAAACCCTTGGGTGGAAGCGGGCCTTGTAGTACTAGGAATTCTTGCGGGTGGGCTTGT

GATTATTCTTTGCTACCTATACACACCTTGCTTCACTTTCCTAGTGGTGTTGTGGTATTG

GTTTAAAAAATGGGGCCCATACTAGTCTTGCTTGTTTTACTTTCGCTTTTGGAACCGGGT

TCTGCCAATTACGATCCATGTCTAGACTTTGACCCAGAAAACTGCACACTTACTTTTGCA

CCCGACACAAGCCGCATCTGTGGAGTTCTTATTAAGTGCGGATGGGAATGCAGGTCCGTT

GAAATTACACACAATAACAAAACCTGGAACAATACCTTATCCACCACATGGGAGCCAGGA

GTTCCCGAGTGGTACACTGTCTCTGTCCGAGGTCCTGACGGTTCCATCCGCATTAGTAAC

AACACTTTCATTTTTTCTGAAATGTGCGATCTGGCCATGTTCATGAGCAAACAGTATTCT

CTATGGCCTCCTAGCAAGGACAACATCGTAACGTTCTCCATTGCTTATTGCTTGTGCGCT

TGCCTTCTTACTGCTTTACTGTGCGTATGCATACACCTGCTTGTAACCACTCGCATCAAA

AACGCCAATAACAAAGAAAAAATGCCTTAACCTCTTTCTGTTTACAGACATGGCTTCTCT

TACATCTCTCATATTTGTCAGCATTGTCACTGCCGCTCACGGACAAACAGTCGTCTCTAT

CCCACTAGGACATAATTACACTCTCATAGGACCCCCAATCACTTCAGAGGTCATCTGGAC

CAAACTGGGAAGCGTTGATTACTTTGATATAATCTGTAACAAAACAAAACCAATAATAGT

AACTTGCAACATACAAAATCTTACATTGATTAATGTTAGCAAAGTTTACAGCGGTTACTA

TTATGGTTATGACAGATACAGTAGTCAATATAGAAATTACTTGGTTCGTGTTACCCAGTT

GAAAACCACGAAAATGCCAAATATGGCAAAGATTCGATCCGATGACAATTCTCTAGAAAC

TTTTACATCTCCCACCACACCCGACGAAAAAAACATCCCAGATTCAATGATTGCAATTGT

TGCAGCGGTGGCAGTGGTGATGGCACTAATAATAATATGCATGCTTTTATATGCTTGTCG

CTACAAAAGTTTCATCCTAAAAAACAAGATCTCCTACTAAGGCTTAACATTTAATTTCT

TTTTATACAGCCATGGTTTCCACTACCACATTCCTTATGCTTACTAGTCTCGCAACTCTG

ACTTCTGCTCGCTCACACCTCACTGTAACTATAGGCTCAAACTGCACACTAAAAGGACCT

CAAGGTGGTCATGTCTTTTGGTGGAGAATATATGACAATGGATGGTTTACAAAACCATGT

GACCAACCTGGTAGATTTTCTGCAACGGCAGAGACCTAACCATTATCAACGTGACAGCA

AATGACAAAGGCTTCTATTATGGAACCGACTATAAAAGTAGTTTAGATTATAACATTATT

GTACTGCCATCTACCACTCCAGCACCCCGCACAACTACTTTCTCTAGCAGCAGTGTCGCT

AACAATACAATTTCCAATCCAACCTTTGCCGCGCTTTTAAAACGCACTGTGAATAATTCT

ACAACTTCACATACAACAATTTCCACTTCAACAATCAGCATCATCGCTGCAGTGACAATT

GGAATATCTATTCTTGTTTTTACCATAACCTACTACGCCTGCTGCTATAGAAAAGACAAA

CATAAAGGTGATCCATTACTTAGATTTGATATTTAATTTGTTCTTTTTTTTATTTACAG

TATGGTGAACACCAATCATGGTACCTAGAAATTTCTTCTTCACCATACTCATCTGTGCTT

TTAATGTTTGCGCTACTTTCACAGCAGTAGCCACAGCAACCCCAGACTGTATAGGAGCAT

TTGCTTCCTATGCACTTTTTGCTTTTGTTACTTGCATCTGCGTATGTAGCATAGTCTGCC
```

```
TGGTTATTAATTTTTTCCAACTTCTAGACTGGATCCTTGTGCGAATTGCCTACCTGCGCC

ACCATCCCGAATACCGCAACCAAAATATCGCGGCACTTCTTAGACTCATCTAAAACCATG

CAGGCTATACTACCAATATTTTTGCTTCTATTGCTTCCCTACGCTGTCTCAACCCCAGCT

GCCTATAGTACTCCACCAGAACACCTTAGAAAATGCAAATTCCAACAACCGTGGTCATTT

CTTGCTTGCTATCGAGAAAAATCAGAAATCCCCCCAAATTTAATAATGATTGCTGGAATA

ATTAATATAATCTGTTGCACCATAATTTCATTTTTGATATACCCCCTATTTGATTTTGGC

TGGAATGCTCCCAATGCACATGATCATCCACAAGACCCAGAGGAACACATTCCCCCACAA

AACATGCAACATCCAATAGCGCTAATAGATTACGAAAGTGAACCACAACCCCCACTACTC

CCTGCTATTAGTTACTTCAACCTAACCGGCGGAGATGACTGAAACACTCACCACCTCCAA

TTCCGCCGAGGATCTGCTCGATATGGACGGCCGCGTCTCAGAACAACGACTTGCCCAACT

ACGCATCCGCCAGCAGCAGGAACGCGTGGCCAAAGAGCTCAGAGATGTCATCCAAATTCA

CCAATGCAAAAAAGGCATATTCTGTTTGGTAAAACAAGCCAAGATATCCTACGAGATCAC

CGCTACTGACCATCGCCTCTCTTACGAACTTGGCCCCCAACGACAAAAATTTACCTGCAT

GGTGGGAATCAACCCCATAGTTATCACCCAACAAAGTGGAGATACTAAGGGTTGCATTCA

CTGCTCCTGCGATTCCATCGAGTGCACCTACACCCTGCTGAAGACCCTATGCGGCCTAAG

AGACCTGCTACCAATGAATTAAAAAAAAATGATTAATAAAAAATCACTTACTTGAAATCA

GCAATAAGGTCTCTGTTGAAATTTTCTCCCAGCAGCACCTCACTTCCCTCTTCCCAACTC

TGGTATTCTAAACCCCGTTCAGCGGCATACTTTCTCCATACTTTAAAGGGGATGTCAAAT

TTTAGCTCCTCTCCTGTACCCACAATCTTCATGTCTTTCTTCCCAGATGACCAAGAGAGT

CCGGCTCAGTGACTCCTTCAACCCTGTCTACCCCTATGAAGATGAAAGCACCTCCCAACA

CCCCTTTATAAACCCAGGGTTTATTTCCCCAAATGGCTTCACACAAAGCCCAGACGGAGT

TCTTACTTTAAAATGTTTAACCCCACTAACAACCACAGGCGGATCTCTACAGCTAAAAGT

GGGAGGGGGACTTACAGTGGATGACACTGATGGTACCTTACAAGAAAACATACGTGCTAC

AGCACCCATTACTAAAAATAATCACTCTGTAGAACTATCCATTGGAAATGGATTAGAAAC

TCAAAACAATAAACTATGTGCCAAATTGGGAAATGGGTTAAAATTTAACAACGGTGACAT

TTGTATAAAGGATAGTATTAACACCTTATGGACTGGAATAAACCCTCCACCTAACTGTCA

AATTGTGGAAAACACTAATACAAATGATGGCAAACTTACTTTAGTATTAGTAAAAAATGG

AGGGCTTGTTAATGGCTACGTGTCTCTAGTTGGTGTATCAGACACTGTGAACCAAATGTT

CACACAAAAGACAGCAAACATCCAATTAAGATTATATTTTGACTCTTCTGGAAATCTATT

AACTGAGGAATCAGACTTAAAAATTCCACTTAAAAATAAATCTTCTACAGCGACCAGTGA

AACTGTAGCCAGCAGCAAAGCCTTTATGCCAAGTACTACAGCTTATCCCTTCAACACCAC

TACTAGGGATAGTGAAAACTACATTCATGGAATATGTTACTACATGACTAGTTATGATAG

AAGTCTATTTCCCTTGAACATTTCTATAATGCTAAACAGCCGTATGATTTCTTCCAATGT

TGCCTATGCCATACAATTTGAATGGAATCTAAATGCAAGTGAATCTCCAGAAAGCAACAT

AGCTACGCTGACCACATCCCCCTTTTTCTTTTCTTACATTACAGAAGACGACAACTAAAA

TAAAGTTTAAGTGTTTTTATTTAAAATCACAAAATTCGAGTAGTTATTTTGCCTCCACCT

TCCCATTTGACAGAATACACCAATCTCTCCCCACGCACAGCTTTAAACATTTGGATACCA

TTAGAGATAGACATTGTTTTAGATTCCACATTCCAAACAGTTTCAGAGCGAGCCAATCTG

GGGTCAGTGATAGATAAAAATCCATCGCGATAGTCTTTTAAAGCGCTTTCACAGTCCAAC

TGCTGCGGATGCGACTCCGGAGTTTGGATCACGGTCATCTGGAAGAAGAACGATGGGAAT
```

-continued
```
CATAATCCGAAAACGGTATCGGACGATTGTGTCTCATCAAACCCACAAGCAGCCGCTGTC
TGCGTCGCTCCGTGCGACTGCTGTTTATGGGATCAGGGTCCACAGTTTCCTGAAGCATGA
TTTTAATAGCCCTTAACATCAACTTTCTGGTGCGATGCGCGCAGCAACGCATTCTGATTT
CACTCAAATCTTTGCAGTAGGTACAACACATTATTACAATATTGTTTAATAAACCATAAT
TAAAAGCGCTCCAGCCAAAACTCATATCTGATATAATCGCCCCTGCATGACCATCATACC
AAAGTTTAATATAAATTAAATGACGTTCCCTCAAAAACACACTACCCACATACATGATCT
CTTTTGGCATGTGCATATTAACAATCTGTCTGTACCATGGACAACGTTGGTTAATCATGC
AACCCAATATAACCTTCCGGAACCACACTGCCAACACCGCTCCCCCAGCCATGCATTGAA
GTGAACCCTGCTGATTACAATGACAATGAAGAACCCAATTCTCTCGACCGTGAATCACTT
GAGAATGAAAAATATCTATAGTGGCACAACATAGACATAAATGCATGCATCTTCTCATAA
TTTTTAACTCCTCAGGATTTAGAAACATATCCCAGGGAATAGGAAGCTCTTGCAGAACAG
TAAAGCTGGCAGAACAAGGAAGACCACGAACACAACTTACACTATGCATAGTCATAGTAT
CACAATCTGGCAACAGCGGGTGGTCTTCAGTCATAGAAGCTCGGGTTTCATTTTCCTCAC
AACGTGGTAACTGGGCTCTGGTGTAAGGGTGATGTCTGGCGCATGATGTCGAGCGTGCGC
GCAACCTTGTCATAATGGAGTTGCTTCCTGACATTCTCGTATTTGTATAGCAAACGCG
GCCCTGGCAGAACACACTCTTCTTCGCCTTCTATCCTGCCGCTTAGCGTGTTCCGTGTGA
TAGTTCAAGTACAGCCACACTCTTAAGTTGGTCAAAAGAATGCTGGCTTCAGTTGTAATC
AAAACTCCATCGCATCTAATTGTTCTGAGGAAATCATCCACGGTAGCATATGCAAATCCC
AACCAAGCAATGCAACTGGATTGCGTTTCAAGCAGGAGAGGAGAGGGAAGAGACGGAAGA
ACCATGTTAATTTTTATTCCAAACGATCTCGCAGTACTTCAAATTGTAGATCGCGCAGAT
GGCATCTCTCGCCCCCACTGTGTTGGTGAAAAAGCACAGCTAAATCAAAAGAAATGCGAT
TTTCAAGGTGCTCAACGGTGGCTTCCAACAAAGCCTCCACGCGCACATCCAAGAACAAA
GAATACCAAAAGAAGGAGCATTTTCTAACTCCTCAATCATCATATTACATTCCTGCACCA
TTCCCAGATAATTTTCAGCTTTCCAGCCTTGAATTATTCGTGTCAGTTCTTGTGGTAAAT
CCAATCCACACATTACAAACAGGTCCCGGAGGGCGCCCTCCACCACCATTCTTAAACACA
CCCTCATAATGACAAAATATCTTGCTCCTGTGTCACCTGTAGCGAATTGAGAATGGCAAC
ATCAATTGACATGCCCTTGGCTCTAAGTTCTTCTTTAAGTTCTAGTTGTAAAAACTCTCT
CATATTATCACCAAACTGCTTAGCCAGAAGCCCCCCGGGAACAAGAGCAGGGGACGCTAC
AGTGCAGTACAAGCGCAGACCTCCCCAATTGGCTCCAGCAAAAACAAGATTGGAATAAGC
ATATTGGGAACCACCAGTAATATCATCGAAGTTGCTGGAAATATAATCAGGCAGAGTTTC
TTGTAGAAATTGAATAAAAGAAAAATTTGCCAAAAAAACATTCAAAACCTCTGGGATGCA
AATGCAATAGGTTACCGCGCTGCGCTCCAACATTGTTAGTTTTGAATTAGTCTGCAAAAA
TAAAAAAAAAACAAGCGTCATATCATAGTAGCCTGACGAACAGGTGGATAAATCAGTCTT
TCCATCACAAGACAAGCCACAGGGTCTCCAGCTCGACCCTCGTAAAACCTGTCATCGTGA
TTAAACAACAGCACCGAAAGTTCCTCGCGGTGACCAGCATGAATAAGTCTTGATGAAGCA
TACAATCCAGACATGTTAGCATCAGTTAAGGAGAAAAAACAGCCAACATAGCCTTTGGGT
ATAATTATGCTTAATCGTAAGTATAGCAAAGCCACCCCTCGCGGATACAAAGTAAAAGGC
ACAGGAGAATAAAAAATATAATTATTTCTCTGCTGCTGTTTAGGCAACGTCGCCCCCGGT
CCCTCTAAATACACATACAAAGCCTCATCAGCCATGGCTTACCAGAGAAAGTACAGCGGG
CACACAAACCACAAGCTCTAAAGTCACTCTCCAACCTCTCCACAATATATATACACAAGC
CCTAAACTGACGTAATGGGACTAAAGTGTAAAAAATCCCGCCAAACCCAACACACACCCC
```

```
GAAACTGCGTCACCAGGGAAAAGTACAGTTTCACTTCCGCAATCCCAACAAGCGTCACTT

CCTCTTTCTCACGGTACGTCACATCCCATTAACTTACAACGTCATTTTCCCACGGCCGCG

CCGCCCCTTTTAACCGTTAACCCCACAGCCAATCACCACACGGCCCACACTTTTTAAAAT

CACCTCATTTACATATTGGCACCATTCCATCTATAAGGTATATTATTGATGATG
```

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

The invention claimed is:

1. A recombinant adenovirus comprising a nucleotide sequence inserted in an IX-E2 insertion site, wherein the IX-E2 insertion site is located between the stop codon of adenovirus IX gene and the stop codon of adenovirus IVa2 gene, wherein the nucleotide sequence comprises a promoter, a transgene, and a second polyadenylation signal and the recombinant adenovirus comprises in a 5' to 3' orientation:
 (i) a first polyadenylation signal;
 (ii) the promoter;
 (iii) the transgene;
 (iv) the second polyadenylation signal; and
 (v) a third polyadenylation signal;
 wherein the transgene is operably linked to the promoter, and wherein the first polyadenylation signal is the polyadenylation signal of the IX gene, the second polyadenylation signal is the polyadenylation signal of the transgene, and the third polyadenylation signal is the polyadenylation signal of the adenovirus IVa2 gene, and a fourth polyadenylation signal is between the first polyadenylation signal and the promoter;
 wherein the fourth polyadenylation signal is in the opposite transcriptional direction of the first polyadenylation signal, and
 wherein the recombinant adenovirus is a type 5 adenovirus (Ad5) or a type 35 adenovirus (Ad35);
 wherein the nucleotide sequence is inserted between nucleotides 4029 and 4093 of the Ad5 genome (SEQ ID NO: 1) or between nucleotides 3899 and 3970 of the Ad35 genome (SEQ ID NO: 41).

2. The recombinant adenovirus of claim 1, wherein the recombinant adenovirus further comprises a nucleotide sequence inserted in an E1b-19K insertion site, an E3 insertion site, or an E4 insertion site.

3. The recombinant adenovirus of claim 1, wherein the recombinant adenovirus further comprises a nucleotide sequence inserted in an L5-E4 insertion site, wherein the L5-E4 insertion site is located between the stop codon of adenovirus fiber gene and the stop codon of ORF6 or ORF6/7 of adenovirus E4 gene.

4. The recombinant adenovirus of claim 1, wherein the recombinant adenovirus selectively replicates in a hyperproliferative cell.

5. The recombinant adenovirus of claim 1, wherein the recombinant adenovirus selectively expresses the transgene in a hyperproliferative cell.

6. A method of inhibiting tumor growth in a subject in need thereof, wherein the method comprises administering to the subject an effective amount of the recombinant adenovirus of claim 1 to inhibit growth of the tumor.

7. A recombinant adenovirus comprising a nucleotide sequence inserted in an L5-E4 insertion site, wherein the L5-E4 insertion site is located between the stop codon of adenovirus fiber gene (fiber L5 gene) and the stop codon of ORF6 or ORF6/7 of adenovirus E4 gene, wherein the nucleotide sequence comprises a promoter, a transgene, and a second polyadenylation signal and the recombinant adenovirus comprises in a 5' to 3' orientation:
 (i) a first polyadenylation signal;
 (ii) the promoter;
 (iii) the transgene;
 (iv) the second polyadenylation signal; and
 (v) a third polyadenylation signal;
 wherein the transgene is operably linked to the promoter, and wherein the first polyadenylation signal is the polyadenylation signal of the fiber (L5) gene, the second polyadenylation signal is the polyadenylation signal of the transgene, the third polyadenylation signal is the polyadenylation signal of the ORF6 or ORF6/7 of the adenovirus E4 gene, and a fourth polyadenylation signal is between the first polyadenylation signal and the promoter;
 wherein the fourth polyadenylation signal is in the opposite transcriptional direction of the first polyadenylation signal, and
 wherein the recombinant adenovirus is a type 5 adenovirus (Ad5) or a type 35 adenovirus (Ad35);
 wherein the nucleotide sequence is inserted between nucleotides 32785 to 32916 of the Ad5 genome (SEQ ID NO: 1) or between nucleotides 31799 and 31821 of the Ad35 genome (SEQ ID NO: 41)..

8. The recombinant adenovirus of claim 7, wherein the recombinant adenovirus further comprises a nucleotide sequence inserted in an E1b-19K insertion site, an E3 insertion site, or an E4 insertion site.

9. The recombinant adenovirus of claim 7, wherein the recombinant adenovirus further comprises a nucleotide sequence inserted in an IX-E2 insertion site, wherein the IX-E2 insertion site is located between the stop codon of an adenovirus IX gene and the stop codon of an adenovirus IVa2 gene.

10. The recombinant adenovirus of claim 7, wherein the recombinant adenovirus selectively replicates in a hyperproliferative cell.

11. The recombinant adenovirus of claim 7, wherein the recombinant adenovirus selectively expresses the transgene in a hyperproliferative cell.

12. A method of inhibiting tumor growth in a subject in need thereof, wherein the method comprises administering to the subject to an effective amount of the recombinant adenovirus of claim 7 to inhibit growth of the tumor.

13. A recombinant adenovirus comprising a first nucleotide sequence inserted in an IX-E2 insertion site and a second nucleotide sequence inserted in an L5-E4 insertion site, wherein the IX-E2 insertion site is located between the stop codon of adenovirus IX gene and the stop codon of adenovirus IVa2 gene, and wherein the L5-E4 insertion site is located between the stop codon of adenovirus fiber gene (L5) and the stop codon of ORF6 or ORF6/7 of adenovirus E4 gene, wherein the first nucleotide sequence comprises a first promoter, a first transgene, and a second polyadenylation signal and the recombinant adenovirus comprises in a 5' to 3' orientation:
 (i) a first polyadenylation signal;
 (ii) the first promoter;
 (iii) the first transgene;
 (iv) the second polyadenylation signal; and
 (v) a third polyadenylation signal;
 wherein the first transgene is operably linked to the first promoter, and wherein the first polyadenylation signal is the polyadenylation signal of the IX gene, the second polyadenylation signal is the polyadenylation signal of the first transgene, and the third polyadenylation signal is the polyadenylation signal of the adenovirus IVa2 gene, and
 a fourth polyadenylation signal is between the first polyadenylation signal and the first promoter;
 wherein the fourth polyadenylation signal is in the opposite transcriptional direction of the first polyadenylation signal, and
 wherein the recombinant adenovirus is a type 5 adenovirus (Ad5) or a type 35 adenovirus (Ad35);
 wherein the first nucleotide sequence is inserted between nucleotides 4029 and 4093 of the Ad5 genome (SEQ ID NO: 1) or between nucleotides 3899 and 3970 of the Ad35 genome (SEQ ID NO: 41).

14. The recombinant adenovirus of claim 13, wherein the second nucleotide sequence is inserted between nucleotides 32785 to 32916 of the Ad5 genome (SEQ ID NO: 1) or between nucleotides 31799 and 31821 of the Ad5 genome (SEQ ID NO: 41).

15. The recombinant adenovirus of claim 13, wherein the second nucleotide sequence comprises a second transgene.

16. The recombinant adenovirus of claim 15, wherein the second nucleotide sequence further comprises a second promoter, wherein the second transgene is operably linked to the second promoter.

17. The recombinant adenovirus of claim 13, wherein the second nucleotide sequence comprises a second promoter, a second transgene, and a sixth polyadenylation signal and the recombinant adenovirus comprises, in a 5' to 3' orientation:
 (i) a fifth polyadenylation signal;
 (ii) the second promoter;
 (iii) the second transgene;
 (iv) the sixth polyadenylation signal; and
 (v) a seventh polyadenylation signal;
 wherein the second transgene is operably linked to the second promoter, and wherein the fifth polyadenylation signal is the polyadenylation signal of the fiber (L5) gene, the sixth polyadenylation signal is the polyadenylation signal of the transgene, and the seventh polyadenylation signal is the polyadenylation signal of the ORF6 or ORF6/7 of the adenovirus E4 gene.

18. The recombinant adenovirus of claim 17, further comprising
 an eighth polyadenylation signal between the fifth polyadenylation signal and the second promoter;
 wherein the eighth polyadenylation signal is in the opposite transcriptional direction of the fifth polyadenylation signal.

19. The recombinant adenovirus of claim 13, wherein the recombinant adenovirus further comprises a third nucleotide sequence inserted in an E1b-19K insertion site, an E3 insertion site, or an E4 insertion site.

20. The recombinant adenovirus of claim 13, wherein the recombinant adenovirus selectively replicates in a hyperproliferative cell.

21. The recombinant adenovirus of claim 15, wherein the recombinant adenovirus selectively expresses the first transgene and the second transgene in a hyperproliferative cell.

22. A method of inhibiting tumor growth in a subject in need thereof, wherein the method comprises administering to the subject to an effective amount of the recombinant adenovirus of claim 13 to inhibit growth of the tumor.

23. The recombinant adenovirus of claim 1, wherein the nucleotide sequence is inserted between nucleotides 4029 and 4093 of the Ad5 genome (SEQ ID NO: 1).

24. The recombinant adenovirus of claim 1, wherein the nucleotide sequence is inserted between nucleotides 3899 and 3970 of the Ad35 genome (SEQ ID NO: 41).

* * * * *

SEQUENCE LISTING

```
<160> NUMBER OF SEQ ID NOS: 46

<210> SEQ ID NO 1
<211> LENGTH: 35938
<212> TYPE: DNA
<213> ORGANISM: Human adenovirus 5

<400> SEQUENCE: 1
catcatcaat aatataccct atttggatt gaagccaata tgataatgag ggggtggagt      60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttttg   180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtctttttgg accagctgat cgaagaggta ctggctgata atcttccacc    660
tcctagccat tttgaaccac ctaccccttca cgaactgtat gatttagacg tgacggcccc    720
cgaagatccc aacgaggagg cggtttcgca gattttttccc gactctgtaa tgttggcggt    780
gcaggaaggg attgacttac tcacttttccc gccggcgccc ggttctccgg agccgcctca    840
ccttttccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg   1020
caggtcttgt cattatcacc ggaggaatac ggggaccccca gatattatgt gttcgctttg   1080
ctatatgagg acctgtggca tgtttgtcta cagtaagtga aaattatggg cagtgggtga   1140
tagagtggtg ggtttggtgt ggtaatttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
```

```
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttgaagat    1740 ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgcttttt gagttttata aaggataaat ggagcgaaga aacccatctg    2040 agcgggggc acctgctgga ttttctggcc atgcatctgt ggagagcggt tgtgagacac    2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaaccttA tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag ggggtgttc ctaccttacc    3240 aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
```

```
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tccctcccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtgcggata tgagatgcat cttggactgt attttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacggggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaaggggggt ggggcgcgt tcgtcctcac tctcttccgc   6060
atcgctgtct gcgagggcca gctgttgggg tgagtactcc ctctgaaaag cgggcatgac   6120
```

```
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtaggggtc    6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atgggtggg tgagcgcgga    6720
ggcgtacatg ccgcaaatgt cgtaaacgta gaggggctct ctgagtattc aagatatgt    6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtcccttt ttttccacag ctcgcggttg aggacaaact cttcgcggtc    7140
tttccagtac tcttggatcg gaaacccgtc ggcctccgaa cggtaagagc ctagcatgta   7200
gaactggttg acggcctggt aggcgcagca tcccttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgcttttg gaacgcggat ttggcagggc gaaggtgaca tcgttgaaga gtatctttcc    7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat ttttaagtt cctcgtaggt    7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca agtccagat gtccgcgcgc ggcggtcgga gcttgatgac    8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
```

```
cctaatttcc agggctggt tggtggcggc gtcgatggct tgcaagaggc cgcatccccg   8520
cggcgcgact acgtaccgc gcggcgggcg gtgggccgcg ggggtgtcct tggatgatgc   8580
atctaaaagc ggtgacgcgg gcgagccccc ggaggtaggg ggggctccgg acccgccggg   8640
agaggggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcggcgcg catgaccacc    9060
tgcgcgagat tgagctccac gtgccgggcg aagacgcgcg agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatgccctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggaggggggga cacggcggcg acgacggcgc accgggaggc ggtcgacaaa gcgctcgatc   9480
atctccccgc ggcgacggcg catggtctcg gtgacggcgc ggccgttctc gcggggggcgc    9540
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagccttct    9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg accggctgc    10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccggggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcgt taccgccgc gtgtcgaacc    10740
caggtgtgcg acgtcagaca acgggggagt gctccttttg gcttccttcc aggcgcggcg  10800
gctgctgcgc tagcttttttt ggccactggc cgcgcgcagc gtaagcggtt aggctggaaa  10860
```

```
gcgaaagcat taagtggctc gctccctgta gccggagggt tatttccaa gggttgagtc   10920
gcgggacccc cggttcgagt ctcggaccgg ccggactgcg gcgaacgggg gtttgcctcc   10980
ccgtcatgca agaccccgct tgcaaattcc tccggaaaca gggacgagcc ccttttttgc   11040
ttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgg ttgacgcggc agcagatggt gattacgaac cccgcgcg ccgggcccgg    11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccataccct tacgttccca tagacaagga ggtaaagatc   11940
gaggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt gggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt caaaaacctt gcaggggctg tgggggtgc    12960
gggctcccac aggcgaccgc gcgaccgtgt ctagcttgct gacgcccaac tcgcgcctgt   13020
tgctgctgct aatagcgccc ttcacggaca gtggcagcgt gtcccgggac atacctag     13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
```

```
caacccctaaa ctacctgctg accaaccggc ggcagaagat cccctcgttg cacagtttaa   13260
acagcgagga ggagcgcatt ttgcgctacg tgcagcagag cgtgagcctt aacctgatgc   13320 gcgacgggt aacgcccagc gtggcgctgg acatgaccgc gcgcaacatg aaccgggca   13380 tgtatgcctc aaaccggccg tttatcaacc gcctaatgga ctacttgcat cgcgcggccg   13440
ccgtgaaccc cgagtatttc accaatgcca tcttgaaccc gcactggcta ccgcccctg   13500 gtttctacac cggggattc gaggtgcccg agggtaacga tggattcctc tgggacgaca   13560
tagacgacag cgtgttttcc ccgcaaccgc agaccctgct agagttgcaa cagcgcgagc   13620
aggcagaggc ggcgctgcga aaggaaagct ccgcaggcc aagcagcttg tccgatctag   13680
gcgctgcggc cccgcggtca gatgctagta gcccatttcc aagcttgata gggtctctta   13740
ccagcactcg caccacccgc ccgcgcctgc tgggcgagga ggagtaccta aacaactcgc   13800
tgctgcagcc gcagcgcgaa aaaaacctgc ctccggcatt tcccaacaac gggatagaga   13860
gcctagtgga caagatgagt agatggaaga cgtacgcgca ggagcacagg gacgtgccag   13920
gcccgcgccc gcccaccccgt cgtcaaaggc acgaccgtca gcggggtctg gtgtgggagg   13980
acgatgactc ggcagacgac agcagcgtcc tggatttggg agggagtggc aacccgtttg   14040
cgcaccttcg ccccaggctg gggagaatgt tttaaaaaaa aaaagcatg atgcaaaata   14100 aaaaactcac caaggccatg gcaccgagcg ttggttttct tgtattcccc ttagtatgcg   14160
gcgcgcggcg atgtatgagg aaggtcctcc tccctcctac gagagtgtgg tgagcgcggc   14220
gccagtggcg gcggcgctgg gttctcccctt cgatgctccc ctggacccgc cgtttgtgcc   14280
tccgcggtac ctgcggccta ccgggggggag aaacagcatc cgttactctg agttggcacc   14340
cctattcgac accacccgtg tgtacctggt ggacaacaag tcaacggatg tggcatccct   14400
gaactaccag aacgaccaca gcaactttct gaccacggtc attcaaaaca atgactacag   14460
cccgggggag gcaagcacac agaccatcaa tcttgacgac cggtcgcact ggggcggcga   14520
cctgaaaacc atcctgcata ccaacatgcc aaatgtgaac gagttcatgt ttaccaataa   14580
gtttaaggcg cgggtgatgg tgtcgcgctt gcctactaag gacaatcagg tggagctgaa   14640
atacgagtgg gtggagttca cgctgcccga gggcaactac tccgagacca tgaccataga   14700
ccttatgaac aacgcgatcg tggagcacta cttgaaagtg ggcagacaga acggggttct   14760
ggaaagcgac atcggggtaa agtttgacac ccgcaacttc agactggggt ttgacccccgt   14820 cactggtctt gtcatgcctg ggtatatac aaacgaagcc ttccatccag acatcatttt   14880
gctgccagga tgcggggtgg acttcacccca cagccgcctg agcaacttgt tgggcatccg   14940
caagcggcaa cccttccagg agggctttag gatcacctac gatgatctgg agggtggtaa   15000
cattcccgca ctgttggatg tggacgccta ccaggcgagc ttgaaagatg acaccgaaca   15060
gggcgggggt ggcgcaggcg gcagcaacag cagtggcagc ggcgcggaag agaactccaa   15120
cgcggcagcc gcggcaatgc agccggtgga ggacatgaac gatcatgcca ttcgcggcga   15180
cacctttgcc acacgggctg aggagaagcg cgctgaggcc gaagcagcgg ccgaagctgc   15240
cgcccccgct gcgcaacccg aggtcgagaa gcctcagaag aaaccggtga tcaaacccct   15300
gacagaggac agcaagaaac gcagttacaa cctaataagc aatgacagca ccttcaccca   15360
gtaccgcagc tggtaccttg catacaacta cggcgaccct cagaccggaa tccgctcatg   15420 gacccctgctt tgcactcctg acgtaacctg cggctcggag caggtctact ggtcgttgcc   15480
agacatgatg caagacccccg tgaccttccg ctccacgcgc cagatcagca ctttccggt   15540 ggtgggcgcc gagctgttgc ccgtgcactc caagagcttc tacaacgacc aggccgtcta   15600
```

| | |
|---|---|
| ctcccaactc atccgccagt ttacctctct gacccacgtg ttcaatcgct ttcccgagaa | 15660 |
| ccagattttg gcgcgcccgc cagccccac catcaccacc gtcagtgaaa acgttcctgc | 15720 |
| tctcacagat cacgggacgc taccgctgcg caacagcatc ggaggagtcc agcgagtgac | 15780 |
| cattactgac gccagacgcc gcacctgccc ctacgtttac aaggccctgg gcatagtctc | 15840 |
| gccgcgcgtc ctatcgagcc gcacttttg agcaagcatg tccatcctta tatcgcccag | 15900 |
| caataacaca ggctggggcc tgcgcttccc aagcaagatg tttggcgggg ccaagaagcg | 15960 |
| ctccgaccaa cacccagtgc gcgtgcgcgg gcactaccgc gcgccctggg gcgcgcacaa | 16020 |
| acgcggccgc actgggcgca ccaccgtcga tgacgccatc gacgcggtgg tggaggaggc | 16080 |
| gcgcaactac acgcccacgc cgccaccagt gtccacagtg gacgcggcca ttcagaccgt | 16140 |
| ggtgcgcgga gcccggcgct atgctaaaat gaagagacgg cggaggcgcg tagcacgtcg | 16200 |
| ccaccgccgc cgacccggca ctgccgccca acgcgcggcg gcggccctgc ttaaccgcgc | 16260 |
| acgtcgcacc ggccgacggg cggccatgcg ggccgctcga aggctggccg cgggtattgt | 16320 |
| cactgtgccc cccaggtcca ggcgacgagc ggccgccgca gcagccgcgg ccattagtgc | 16380 |
| tatgactcag ggtcgcaggg gcaacgtgta ttgggtgcgc gactcggtta gcggcctgcg | 16440 |
| cgtgcccgtg cgcacccgcc ccccgcgcaa ctagattgca agaaaaaact acttagactc | 16500 |
| gtactgttgt atgtatccag cggcggcggc gcgcaacgaa gctatgtcca agcgcaaaat | 16560 |
| caaagaagag atgctccagg tcatcgcgcc ggagatctat ggccccccga agaaggaaga | 16620 |
| gcaggattac aagccccgaa agctaaagcg ggtcaaaaag aaaaagaaag atgatgatga | 16680 |
| tgaacttgac gacgaggtgg aactgctgca cgctaccgcg cccaggcgac gggtacagtg | 16740 |
| gaaaggtcga cgcgtaaaac gtgttttgcg accggcacc accgtagtct ttacgcccgg | 16800 |
| tgagcgctcc acccgcacct acaagcgcgt gtatgatgag gtgtacggcg acgaggacct | 16860 |
| gcttgagcag gccaacgagc gcctcgggga gtttgcctac ggaaagcggc ataaggacat | 16920 |
| gctggcgttg ccgctggacg agggcaaccc aacacctagc ctaaagcccg taacactgca | 16980 |
| gcaggtgctg cccgcgcttg caccgtccga agaaaagcgc ggcctaaagc gcagtctgg | 17040 |
| tgacttggca cccaccgtgc agctgatggt acccaagcgc cagcgactgg aagatgtctt | 17100 |
| ggaaaaaatg accgtggaac ctgggctgga gcccgaggtc cgcgtgcggc caatcaagca | 17160 |
| ggtggcgccg gactgggcg tgcagaccgt ggacgttcag atacccacta ccagtagcac | 17220 |
| cagtattgcc accgccacag agggcatgga gacacaaacg tccccggttg cctcagcggt | 17280 |
| ggcggatgcc gcggtgcagg cggtcgctgc ggccgcgtcc aagacctcta cggaggtgca | 17340 |
| aacggacccg tggatgtttc gcgtttcagc cccccggcgc ccgcgcggtt cgaggaagta | 17400 |
| cggcgccgc agcgcgctac tgcccgaata tgccctacat ccttccattg cgcctacccc | 17460 |
| cggctatcgt ggctacacct accgcccag aagacgagca actacccgac gccgaaccac | 17520 |
| cactggaacc cgccgccgcc gtcgccgtcg ccagcccgtg ctggcccga tttccgtgcg | 17580 |
| cagggtggct cgcgaaggag gcaggaccct ggtgctgcca acagcgcgct accaccccag | 17640 |
| catcgtttaa aagccggtct ttgtggttct tgcagatatg gccctcacct gccgcctccg | 17700 |
| tttcccggtg ccgggattcc gaggaagaat gcaccgtagg aggggcatgg ccggcacgg | 17760 |
| cctgacgggc ggcatgcgtc gtgcgcacca ccggcggcgg cgcgcgtcgc accgtcgcat | 17820 |
| gcgcggcggt atcctgcccc tccttattcc actgatcgcc gcggcgattg gcgccgtgcc | 17880 |
| cggaattgca tccgtggcct tgcaggcgca gagacactga ttaaaaacaa gttgcatgtg | 17940 |

```
gaaaaatcaa ataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc aacaaaagg    18240 tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctccct cgtacgagga ggcactaaag caaggcctgc    18480
ccaccacccg tcccatcgcg cccatggcta ccggagtgct gggccagcac acacccgtaa    18540
cgctggacct gcctcccccc gccgacaccc agcagaaacc tgtgctgcca ggcccgaccg    18600
ccgttgttgt aacccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgcttttcaa    18840
gatggctacc ccttcgatga tgccgcagtg gtcttacatg cacatctcgg gccaggacgc    18900
ctcggagtac ctgagccccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcaccctag ctgtgggtga taaccgtgtg ctggacatgg cttccacgta    19140
ctttgacatc cgcggcgtgc tggacagggg ccctactttt aagccctact ctggcactgc    19200
ctacaacgcc ctggctccca agggtgcccc aaatccttgc gaatgggatg aagctgctac    19260
tgctcttgaa ataaacctag aagaagagga cgatgacaac gaagacgaag tagacgagca    19320
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc    19500
tgggagagtc cttaaaaaga ctaccccaat gaaaccatgt acggttcat atgcaaaacc    19560 cacaaatgaa aatggagggc aaggcattct tgtaaagcaa caaatggaa agctagaaag    19620 tcaagtggaa atgcaatttt ctcaactac tgaggcgacc gcaggcaatg gtgataactt    19680
gactcctaaa gtggtattgt acagtgaaga tgtagatata gaaaccccag acactcatat    19740
ttcttacatg cccactatta aggaaggtaa ctcacgagaa ctaatgggcc aacaatctat    19800
gcccaacagg cctaattaca ttgcttttag ggacaatttt attggtctaa tgtattacaa    19860
cagcacgggt aatatgggtg ttctggcggg ccaagcatcg cagttgaatg ctgttgtaga    19920
tttgcaagac agaaacacag agctttcata ccagcttttg cttgattcca ttggtgatag    19980
aaccaggtac ttttctatgt ggaatcaggc tgttgacagc tatgatccag atgttagaat    20040
tattgaaaat catggaactg aagatgaact tccaaattac tgctttccac tgggaggtgt    20100
gattaataca gagactctta ccaaggtaaa acctaaaaca ggtcaggaaa atggatggga    20160
aaaagatgct acagaatttt cagataaaaa tgaaataaga gttggaaata attttgccat    20220
ggaaatcaat ctaaatgcca acctgtggag aaatttcctg tactccaaca tagcgctgta    20280
tttgcccgac aagctaaagt acagtccttc caacgtaaaa atttctgata acccaaacac    20340
```

```
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct tgccattaa aaacctcctt ctcctgccgg gctcatacac    20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tcccctcccg caactgggcg ctttccgcg gctgggcctt    20880
cacgcgcctt aagactaagg aaaccccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatccat ggacgagccc accttctttt atgttttgtt    21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat atttttgg cacctatgac aagcgctttc caggctttgt ttctccacac     21840
aagctcgcct gcgccatagt caatacggcc ggtcgcgaga ctgggggcgt acactggatg   21900
gcctttgcct ggaacccgca ctcaaaaaca tgctacctct ttgagccctt ggcttttct    21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccccacc atgaaccta ttaccggggt acccaactcc    22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320
tcttttttgtc acttgaaaaa catgtaaaaa taatgtacta gagacacttt caataaaggc   22380
aaatgctttt atttgtacac tctcgggtga ttatttaccc ccaccttgc cgtctgcgcc    22440
gtttaaaaat caagggggtt ctgccgcgca tcgctatgcg ccactggcag ggacacgttg   22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
```

```
cagcactgga acactatcag cgccgggtgg tgcacgctgg ccagcacgct cttgtcggag    22740
atcagatccg cgtccaggtc ctccgcgttg ctcagggcga acggagtcaa ctttggtagc    22800
tgccttccca aaaagggcgc gtgcccaggc tttgagttgc actcgcaccg tagtggcatc    22860
aaaaggtgac cgtgcccggt ctgggcgtta ggatacagcg cctgcataaa agccttgatc    22920
tgcttaaaag ccacctgagc ctttgcgcct tcagagaaga acatgccgca agacttgccg    22980
gaaaactgat tggccggaca ggccgcgtcg tgcacgcagc accttgcgtc ggtgttggag    23040
atctgcacca catttcggcc ccaccggttc ttcacgatct tggccttgct agactgctcc    23100
ttcagcgcgc gctgcccgtt ttcgctcgtc atccatttt caatcacgtg ctccttattt     23160
atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
tacgcctgca ggaatcgccc catcatcgtc acaaaggtct tgttgctggt gaaggtcagc    23340
tgcaacccgc ggtgctcctc gttcagccag gtcttgcata cggccgccag agcttccact    23400
tggtcaggca gtagtttgaa gttcgccttt agatcgttat ccacgtggta cttgtccatc    23460
agcgcgcgcg cagcctccat gcccttctcc cacgcagaca cgatcggcac actcagcggg    23520
ttcatcaccg taatttcact ttccgcttcg ctgggctctt cctcttcctc ttgcgtccgc    23580
ataccacgcg ccactgggtc gtcttcattc agccgccgca ctgtgcgctt acctcctttg    23640
ccatgcttga ttagcaccgg tgggttgctg aaacccacca tttgtagcgc cacatcttct    23700
ctttcttcct cgctgtccac gattacctct ggtgatggcg ggcgctcggg cttgggagaa    23760
gggcgcttct ttttcttctt gggcgcaatg gccaaatccg ccgccgaggt cgatggccgc    23820
gggctgggtg tgcgcggcac cagcgcgtct tgtgatgagt cttcctcgtc ctcggactcg    23880
atacgccgcc tcatccgctt ttttggggc gcccggggag gcggcggcga cggggacggg    23940
gacgacacgt cctccatggt tggggacgt cgcgccgcac cgcgtccgcg ctcggggtg      24000 gtttcgcgct gctcctcttc ccgactggcc atttccttct cctataggca gaaaaagatc    24060
atggagtcag tcgagaagaa ggacagccta accgccccct ctgagttcgc caccaccgcc    24120
tccaccgatg ccgccaacgc gcctaccacc ttccccgtcg aggcacccc gcttgaggag      24180 gaggaagtga ttatcgagca ggacccaggt tttgtaagcg aagacgacga ggaccgctca    24240
gtaccaacag aggataaaaa gcaagaccag gacaacgcag aggcaaacga ggaacaagtc    24300
gggcgggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagataccc    24600
ctatcctgcc gtgccaaccg cagccgagcg acaagcagc tggccttgcg gcagggcgct     24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc actttgccta cccggcactt aacctacccc ccaaggtcat gagcacagtc    24900
atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
```

```
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcattttccc cgaacgcctg    25500
cttaaaaccc tgcaacaggg tctgccagac ttcaccagtc aaagcatgtt gcagaacttt    25560
aggaacttta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct ttgagctgca gggtccctcg    25860
cctgacgaaa agtccgcggc tccgggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
gtttacttgg accccagtc cggcgaggag ctcaacccaa tcccccgcc gccgcagccc    26160 tatcagcagc agccgcgggc ccttgcttcc aggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
gaaatcggca accggttcca gcatggctac aacctccgct cctcaggcgc cgccggcact    26460
gcccgttcgc cgacccaacc gtagatggga caccactgga accagggccg gtaagtccaa    26520
gcagccgccg ccgttagccc aagagcaaca acagcgccaa ggctaccgct catggcgcgg    26580
gcacaagaac gccatagttg cttgcttgca agactgtggg ggcaacatct ccttcgcccg    26640
ccgctttctt ctctaccatc acggcgtggc cttcccccgt aacatcctgc attactaccg    26700
tcatctctac agcccatact gcaccggcgg cagcggcagc ggcagcaaca gcagcggcca    26760
cacagaagca aaggcgaccg gatagcaaga ctctgacaaa gcccaagaaa tccacagcgg    26820
cggcagcagc aggaggagga gcgctgcgtc tggcgcccaa cgaacccgta tcgacccgcg    26880
agcttagaaa caggattttt cccactctgt atgctatatt tcaacagagc aggggccaag    26940
aacaagagct gaaaataaaa aacaggtctc tgcgatccct cacccgcagc tgcctgtatc    27000
acaaaagcga agatcagctt cggcgcacgc tggaagacgc ggaggctctc ttcagtaaat    27060
actgcgcgct gactcttaag gactagtttc gcgcccttte tcaaatttaa gcgcgaaaac    27120
tacgtcatct ccagcggcca cacccggcgc cagcacctgt cgtcagcgcc attatgagca    27180
aggaaattcc cacgccctac atgtggagtt accagccaca aatgggactt gcggctggag    27240
ctgcccaaga ctactcaacc cgaataaact acatgagcgc gggaccccac atgatatccc    27300
gggtcaacgg aatccgcgcc caccgaaacc gaattctctt ggaacaggcg gctattacca    27360
ccacacctcg taataacctt aatccccgta gttggcccgc tgccctggtg taccaggaaa    27420
```

```
gtcccgctcc caccactgtg gtacttccca gagacgccca ggccgaagtt cagatgacta    27480
actcaggggc gcagcttgcg ggcggctttc gtcacagggt gcggtcgccc gggcagggta    27540
taactcacct gacaatcaga gggcgaggta ttcagctcaa cgacgagtcg gtgagctcct    27600
cgcttggtct ccgtccggac gggacatttc agatcggcgg cgccggccgt ccttcattca    27660
cgcctcgtca ggcaatccta actctgcaga cctcgtcctc tgagccgcgc tctggaggca    27720
ttggaactct gcaatttatt gaggagtttg tgccatcggt ctactttaac cccttctcgg    27780
gacctcccgg ccactatccg gatcaattta ttcctaactt tgacgcggta aaggactcgg    27840
cggacggcta cgactgaatg ttaagtggag aggcagagca actgcgcctg aaacacctgg    27900
tccactgtcg ccgccacaag tgctttgccc gcgactccgg tgagttttgc tactttgaat    27960
tgcccgagga tcatatcgag ggccggcgc acggcgtccg gcttaccgcc cagggagagc    28020
ttgcccgtag cctgattcgg gagtttaccc agcgcccccct gctagttgag cgggacaggg    28080
gaccctgtgt tctcactgtg atttgcaact gtcctaacct tggattacat caagatcttt    28140
gttgccatct ctgtgctgag tataataaat acagaaatta aaatatactg gggctcctat    28200
cgccatcctg taaacgccac cgtcttcacc cgcccaagca aaccaaggcg aaccttacct    28260 ggtacttttta acatctctcc ctctgtgatt tacaacagtt tcaacccaga cggagtgagt    28320
ctacgagaga acctctccga gctcagctac tccatcagaa aaaacaccac cctccttacc    28380
tgccgggaac gtacgagtgc gtcaccggcc gctgcaccac acctaccgcc tgaccgtaaa    28440 ccagacttttt tccggacaga cctcaataac tctgtttacc agaacaggag gtgagcttag    28500 aaaacccttta gggtattagg ccaaaggcgc agctactgtg gggtttatga acaattcaag    28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcaccctt gcgtcagccc acggtaccac ccaaaaggtg    28800 gatttttaagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc cattttatga aatgtgcgac    29040
attaccatgt acatgagcaa acagtataag ttgtggcccc cacaaaattg tgtggaaaac    29100
actggcactt tctgctgcac tgctatgcta attacagtgc tcgctttggt ctgtaccccta    29160 ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg acccttgttg    29820
```

```
cgcttttttg tgcgtgctcc acattggctg cggtttctca catcgaagta gactgcattc   29880
cagccttcac agtctatttg ctttacggat ttgtcaccct cacgctcatc tgcagcctca   29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atctttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
agttgttgcc ggcggctttg tcccagccaa tcagcctcgc cccacttctc ccaccccccac  30420 tgaaatcagc tactttaatc taacaggagg agatgactga cacctagat ctagaaatgg    30480 acggaattat tacagagcag cgcctgctag aaagacgcag ggcagcggcc gagcaacagc   30540
gcatgaatca agagctccaa gacatggtta acttgcacca gtgcaaaagg ggtatctttt   30600
gtctggtaaa gcaggccaaa gtcacctacg acagtaatac caccggacac cgccttagct   30660
acaagttgcc aaccaagcgt cagaaattgg tggtcatggt gggagaaaag cccattacca   30720
taactcagca ctcggtagaa accgaaggct gcattcactc accttgtcaa ggacctgagg   30780
atctctgcac ccttattaag accctgtgcg gtctcaaaga tcttattccc tttaactaat   30840
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc cttttcttac tcctcccttt   31140
gtatccccca atgggtttca agagagtccc cctggggtac tctctttgcg cctatccgaa   31200
cctctagtta cctccaatgg catgcttgcg ctcaaaatgg gcaacggcct ctctctggac   31260
gaggccggca accttacctc ccaaaatgta accactgtga gcccacctct caaaaaaacc   31320
aagtcaaaca taaacctgga aatatctgca cccctcacag ttacctcaga agccctaact   31380
gtggctgccg ccgcacctct aatggtcgcg ggcaacacac tcaccatgca atcacaggcc   31440
ccgctaaccg tgcacgactc caaacttagc attgccaccc aaggacccct cacagtgtca   31500
gaaggaaagc tagccctgca aacatcaggc ccctcacca ccaccgatag cagtaccctt    31560
actatcactg cctcaccccc tctaactact gccactggta gcttgggcat tgacttgaaa   31620
gagcccattt atacacaaaa tggaaaacta ggactaaagt acggggctcc tttgcatgta   31680
acagacgacc taaacacttt gaccgtagca actggtccag gtgtgactat taataatact   31740
tccttgcaaa ctaaagttac tggagccttg ggttttgatt cacaaggcaa tatgcaactt   31800
aatgtagcag gaggactaag gattgattct caaaacagac gccttatact tgatgttagt   31860
tatccgtttg atgctcaaaa ccaactaaat ctaagactag acagggcccc tcttttttata  31920 aactcagccc acaacttgga tattaactac aacaaaggcc tttacttgtt tacagcttca   31980
aacaattcca aaaagcttga ggttaaccta agcactgcca aggggttgat gtttgacgct   32040
acagccatag ccattaatgc aggagatggg cttgaatttg gttcacctaa tgcaccaaac   32100
acaaatcccc tcaaaacaaa aattggccat ggcctagaat ttgattcaaa caaggctatg   32160
```

```
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700
ttttcatggg actggtctgg ccacaactac attaatgaaa tatttgccac atcctcttac    32760 acttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatcaaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctcttttgg catgttgtaa ttcaccacct cccggtacca    33600
tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgttttttt ttttattcca aaagattatc caaaacctca    34380
aaatgaagat ctattaagtg aacgcgctcc cctccggtgg cgtggtcaaa ctctacagcg    34440
aaagaacaga taatggcatt tgtaagatgt tgcacaatgg cttccaaaag gcaaacggcc    34500
ctcacgtcca agtggacgta aaggctaaac ccttcagggt gaatctcctc tataaacatt    34560
```

```
ccagcaccTt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttccccg ccaggaacca    34860
tgacaaaaga acccacactg attatgacac gcatactcgg agctatgcta accagcgtag    34920
ccccgatgta agcttgttgc atgggcggcg atataaaatg caaggtgctg ctcaaaaaat    34980
caggcaaagc ctcgcgcaaa aagaaagca catcgtagtc atgctcatgc agataaaggc     35040
aggtaagctc cggaaccacc acagaaaaag acaccatttt tctctcaaac atgtctgcgg    35100
gtttctgcat aaacacaaaa taaataaca aaaaaacatt taaacattag aagcctgtct      35160
tacaacagga aaacaaccc ttataagcat aagacggact acggccatgc cggcgtgacc      35220
gtaaaaaaac tggtcaccgt gattaaaaag caccaccgac agctcctcgg tcatgtccgg    35280
agtcataatg taagactcgg taaacacatc aggttgattc acatcggtca gtgctaaaaa    35340
gcgaccgaaa tagcccgggg gaatacatac ccgcaggcgt agagacaaca ttacagcccc    35400
cataggaggt ataacaaaat taataggaga gaaaaacaca taaacacctg aaaaaccctc    35460
ctgcctaggc aaaatagcac cctcccgctc cagaacaaca tacagcgctt ccacagcggc    35520
agccataaca gtcagcctta ccagtaaaaa agaaaaccta ttaaaaaaac accactcgac    35580
acggcaccag ctcaatcagt cacagtgtaa aaaagggcca agtgcagagc gagtatatat    35640
aggactaaaa aatgacgtaa cggttaaagt ccacaaaaaa cacccagaaa accgcacgcg    35700
aacctacgcc cagaaacgaa agccaaaaaa cccacaactt cctcaaatcg tcacttccgt    35760
tttcccacgt tacgtaactt cccatttaa gaaaactaca attcccaaca catacaagtt      35820
actccgccct aaaacctacg tcacccgccc cgttcccacg ccccgcgcca cgtcacaaac    35880 tccacccct cattatcata ttggcttcaa tccaaaataa ggtatattat tgatgatg        35938
```

<210> SEQ ID NO 2
<211> LENGTH: 8
<212> TYPE: DNA
<213> ORGANISM: Human adenovirus 5

<400> SEQUENCE: 2 tcaccagg                                                                    8

<210> SEQ ID NO 3
<211> LENGTH: 8
<212> TYPE: DNA
<213> ORGANISM: Human adenovirus 5

<400> SEQUENCE: 3 ctgacctc                                                                    8

<210> SEQ ID NO 4
<211> LENGTH: 10
<212> TYPE: DNA
<213> ORGANISM: Artificial Sequence
<220> FEATURE:
<223> OTHER INFORMATION: Modified E1a promoter

<400> SEQUENCE: 4
ggtgttttgg                                                                 10

<210> SEQ ID NO 5
<211> LENGTH: 9
<212> TYPE: DNA
<213> ORGANISM: Artificial Sequence
<220> FEATURE:
<223> OTHER INFORMATION: Modified E1a promoter

<400> SEQUENCE: 5 ctaggactg                                                                9

<210> SEQ ID NO 6
<211> LENGTH: 65
<212> TYPE: DNA
<213> ORGANISM: Human adenovirus 5

<400> SEQUENCE: 6
taaaacataa ataaaaaacc agactctgtt tggatttgga tcaagcaagt gtcttgctgt        60
cttta                                                                   65

<210> SEQ ID NO 7
<211> LENGTH: 132
<212> TYPE: DNA
<213> ORGANISM: Human adenovirus 5

<400> SEQUENCE: 7
taaagaatcg tttgtgttat gtttcaacgt gtttattttt caattgcaga aaatttcaag        60 tcattttca ttcagtagta tagccccacc accacatagc ttatacagat caccgtacct       120
taatcaaact ca                                                          132

<210> SEQ ID NO 8
<211> LENGTH: 3
<212> TYPE: DNA
<213> ORGANISM: Human adenovirus 5

<400> SEQUENCE: 8 taa                                                                      3

<210> SEQ ID NO 9
<211> LENGTH: 3
<212> TYPE: DNA
<213> ORGANISM: Human adenovirus 5

<400> SEQUENCE: 9 tta                                                                      3

<210> SEQ ID NO 10
<211> LENGTH: 3
<212> TYPE: DNA
<213> ORGANISM: Human adenovirus 5

<400> SEQUENCE: 10 tca                                                                      3

<210> SEQ ID NO 11
<211> LENGTH: 8
<212> TYPE: DNA
<213> ORGANISM: Unknown
<220> FEATURE:
<223> OTHER INFORMATION: SwaI restriction site

<400> SEQUENCE: 11 atttaaat                                                                 8

<210> SEQ ID NO 12
<211> LENGTH: 6
<212> TYPE: DNA
<213> ORGANISM: Human adenovirus 5

<400> SEQUENCE: 12 aataaa                                                                    6

<210> SEQ ID NO 13
<211> LENGTH: 6
<212> TYPE: DNA
<213> ORGANISM: Human adenovirus 5

<400> SEQUENCE: 13 tttatt                                                                    6

<210> SEQ ID NO 14
<211> LENGTH: 530
<212> TYPE: DNA
<213> ORGANISM: Artificial Sequence
<220> FEATURE:
<223> OTHER INFORMATION: L5 initial Empty

<400> SEQUENCE: 14
aataaagaat cgtttgtgtt atgtttcaac ctgtggaatg tgtgtcagtt agggtgtgga          60
aagtccccag gctccccagc aggcagaagt atgcaaagca tgcatctcaa ttagtcagca         120
accaggtgtg gaaagtcccc aggctcccca gcaggcagaa gtatgcaaag catgcatctc         180
aattagtcag caaccatagt cccgccccta actccgccca tcccgcccct aactccgccc         240
agttccgccc attctccgcc ccatggctga ctaattttt tatttatgc agaggccgag           300 gccgcctctg cctctgagct attccagaag tagtgaggag gcttttttgg aggcctaggc         360
ttttgcaaaa agctttgcaa agatttaaat aacttgttta ttgcagctta taatggttac         420
aaataaagca atagcatcac aaatttcaca aataaagcat ttttttcact gcattctagt         480
tgtggtttgt ccaaactcat caatgtatct tatcatgtct ggtgtttatt                    530

<210> SEQ ID NO 15
<211> LENGTH: 956
<212> TYPE: DNA
<213> ORGANISM: Artificial Sequence
<220> FEATURE:
<223> OTHER INFORMATION: L5 initial mGMCSF

<400> SEQUENCE: 15
aataaagaat cgtttgtgtt atgtttcaac ctgtggaatg tgtgtcagtt agggtgtgga          60
aagtccccag gctccccagc aggcagaagt atgcaaagca tgcatctcaa ttagtcagca         120
accaggtgtg gaaagtcccc aggctcccca gcaggcagaa gtatgcaaag catgcatctc         180
aattagtcag caaccatagt cccgccccta actccgccca tcccgcccct aactccgccc         240
agttccgccc attctccgcc ccatggctga ctaattttt tatttatgc agaggccgag           300 gccgcctctg cctctgagct attccagaag tagtgaggag gcttttttgg aggcctaggc         360
ttttgcaaaa agctttgcaa agatttatgt ggctgcagaa cctgctgttc ctgggcatcg         420
tggtgtacag cctgagcgcc cccaccagat cccccatcac cgtgaccaga ccctggaagc         480
acgtggaagc catcaaagag gccctgaacc tgctggacga catgcccgtg accctgaacg         540
aagaggtgga agtggtgtcc aacgagttca gcttcaagaa actgacctgc gtgcagacca         600

```
gactgaagat cttcgagcag ggcctgagag gcaacttcac caagctgaag ggcgctctga    660
acatgaccgc cagctactac cagacctact gccctcccac acccgagaca gactgcgaga    720
cacaggtcac aacctacgcc gacttcatcg acagcctgaa aaccttcctg accgacatcc    780
ccttcgagtg caagaaaccc ggccagaagt gaaaataact tgtttattgc agcttataat    840
ggttacaaat aaagcaatag catcacaaat ttcacaaata aagcattttt ttcactgcat    900
tctagttgtg gtttgtccaa actcatcaat gtatcttatc atgtctggtg tttatt        956
```

<210> SEQ ID NO 16
<211> LENGTH: 8
<212> TYPE: DNA
<213> ORGANISM: Unknown
<220> FEATURE:
<223> OTHER INFORMATION: NotI restriction site

<400> SEQUENCE: 16

```
gcggccgc                                                              8
```

<210> SEQ ID NO 17
<211> LENGTH: 858
<212> TYPE: DNA
<213> ORGANISM: Artificial Sequence
<220> FEATURE:
<223> OTHER INFORMATION: IX initial Empty

<400> SEQUENCE: 17

```
aataaaaaac cagactctgt ttggatttgg atcaagcaag tgtcttgctg tcttacggta     60
aatggcccgc ctggctgacc gcccaacgac ccccgcccat tgacgtcaat aatgacgtat    120
gttcccatag taacgccaat agggactttc cattgacgtc aatgggtgga gtatttacgg    180
taaactgccc acttggcagt acatcaagtg tatcatatgc caagtacgcc ccctattgac    240
gtcaatgacg gtaaatggcc cgcctggcat tatgcccagt acatgacctt atgggacttt    300
cctacttggc agtacatcta cgtattagtc atcgctatta ccatggtgat gcggttttgg    360
cagtacatca atgggcgtgg atagcggttt gactcacggg gatttccaag tctccacccc    420
attgacgtca atgggagttt gttttggcac caaaatcaac gggactttcc aaaatgtcgt    480
aacaactccg ccccattgac gcaaatgggc ggtaggcgtg tacggtggga ggtctatata    540
agcagagctc tctggctaac tagagaaccc actgcttact ggcttatcga attaatacg     600 actcactata gggagacccg cggccgcctg tgccttctag ttgccagcca tctgttgttt    660
gccccctccc cgtgccttcc ttgacccctgg aaggtgccac tcccactgtc ctttcctaat    720
aaaatgagga aattgcatcg cattgtctga gtaggtgtca ttctattctg gggggtgggg    780
tggggcagga cagcaagggg gaggattggg aagacaatag caggcatgct ggggatgcgg    840
tgggctctat ggtttatt                                                  858
```

<210> SEQ ID NO 18
<211> LENGTH: 500
<212> TYPE: DNA
<213> ORGANISM: Artificial Sequence
<220> FEATURE:
<223> OTHER INFORMATION: L5 mIL7

<400> SEQUENCE: 18

```
gctttgcaaa gatttatgtt ccatgttttct tttagatata tctttggaat tcctccactg     60
atccttgttc tgctgcctgt cacatcatct gagtgccaca ttaaagacaa agaaggtaaa    120
gcatatgaga gtgtactgat gatcagcatc gatgaattgg acaaaatgac aggaactgat    180
```

```
agtaattgcc cgaataatga accaaacttt tttagaaaac atgtatgtga tgatacaaag    240
gaagctgctt ttctaaatcg tgctgctcgc aagttgaagc aatttcttaa aatgaatatc    300
agtgaagaat tcaatgtcca cttactaaca gtatcacaag gcacacaaac actggtgaac    360
tgcacaagta aggaagaaaa aaacgtaaag gaacagaaaa agaatgatgc atgtttccta    420
aagagactac tgagagaaat aaaaacttgt tggaataaaa ttttgaaggg cagtatataa    480
aaataacttg tttattgcag                                                500

<210> SEQ ID NO 19
<211> LENGTH: 461
<212> TYPE: DNA
<213> ORGANISM: Artificial Sequence
<220> FEATURE:
<223> OTHER INFORMATION: L5 wt mGMCSF

<400> SEQUENCE: 19
gctttgcaaa gatttatgtg gctgcagaat ttacttttcc tgggcattgt ggtctacagc     60
ctctcagcac ccacccgctc acccatcact gtcacccggc cttggaagca tgtagaggcc    120
atcaaagaag ccctgaacct cctggatgac atgcctgtca cgttgaatga agaggtagaa    180
gtcgtctcta acgagttctc cttcaagaag ctaacatgtg tgcagacccg cctgaagata    240
ttcgagcagg gtctacgggg caatttcacc aaactcaagg gcgccttgaa catgacagcc    300
agctactacc agacatactg cccccccaact ccggaaacgg actgtgaaac acaagttacc    360
acctatgcgg atttcataga cagccttaaa acctttctga ctgatatccc ctttgaatgc    420
aaaaaaccag gccaaaaatg aaataacttg tttattgca g                         461

<210> SEQ ID NO 20
<211> LENGTH: 463
<212> TYPE: DNA
<213> ORGANISM: Artificial Sequence
<220> FEATURE:
<223> OTHER INFORMATION: IX wt mGMCSF

<400> SEQUENCE: 20
atagggagac ccgcggccat gtggctgcag aatttacttt tcctgggcat tgtggtctac     60
agcctctcag cacccacccg ctcacccatc actgtcaccc ggccttggaa gcatgtagag    120
gccatcaaag aagccctgaa cctcctggat gacatgcctg tcacgttgaa tgaagaggta    180
gaagtcgtct ctaacgagtt ctccttcaag aagctaacat gtgtgcagac ccgcctgaag    240
atattcgagc agggtctacg gggcaatttc accaaactca agggcgcctt gaacatgaca    300
gccagctact accagacata ctgcccccca actccggaaa cggactgtga aacacaagtt    360
accacctatg cggatttcat agacagcctt aaaaccttc tgactgatat ccccttgaa    420 tgcaaaaaac aggccaaaaa tgaggccgc tgtgccttct agt                       463

<210> SEQ ID NO 21
<211> LENGTH: 760
<212> TYPE: DNA
<213> ORGANISM: Artificial Sequence
<220> FEATURE:
<223> OTHER INFORMATION: IX revised Empty

<400> SEQUENCE: 21
aataaaatac accttttttc gattgtacgt atttttattt acggtaaatg gcccgcctgg     60
ctgaccgccc aacgaccccc gcccattgac gtcaataatg acgtatgttc ccatagtaac    120
```

```
gccaataggg actttccatt gacgtcaatg ggtggagtat ttacggtaaa ctgcccactt      180
ggcagtacat caagtgtatc atatgccaag tacgccccct attgacgtca atgacggtaa      240
atggcccgcc tggcattatg cccagtacat gaccttatgg gactttccta cttggcagta      300
catctacgta ttagtcatcg ctattaccat ggtgatgcgg ttttggcagt acatcaatgg      360
gcgtggatag cggtttgact cacggggatt tccaagtctc caccccattg acgtcaatgg      420
gagtttgttt tggcaccaaa atcaacggga ctttccaaaa tgtcgtaaca actccgcccc      480
attgacgcaa atgggcggta ggcgtgtacg gtgggaggtc tatataagca gagctctctg      540
gctaactaga acccactg cttactggct tatcgaaatt aatacgactc actatagggga      600 gacccgcggc cgctgtgcct tctagttgcc agccatctgt tgtttgcccc tccccgtgc      660 cttccttgac cctggaaggt gccactccca ctgtcctttc ctaataaaaa accagactct      720
gtttggattt ggatcaagca agtgtcttgc tgtctttatt                            760

<210> SEQ ID NO 22
<211> LENGTH: 1526
<212> TYPE: DNA
<213> ORGANISM: Artificial Sequence
<220> FEATURE:
<223> OTHER INFORMATION: IX revised hIL12A

<400> SEQUENCE: 22
aataaaatac cctttttttc gattgtacgt attttttattt acggtaaatg gcccgcctgg     60
ctgaccgccc aacgaccccc gcccattgac gtcaataatg acgtatgttc ccatagtaac    120
gccaataggg actttccatt gacgtcaatg ggtggagtat ttacggtaaa ctgcccactt    180
ggcagtacat caagtgtatc atatgccaag tacgccccct attgacgtca atgacggtaa    240
atggcccgcc tggcattatg cccagtacat gaccttatgg gactttccta cttggcagta    300
catctacgta ttagtcatcg ctattaccat ggtgatgcgg ttttggcagt acatcaatgg    360
gcgtggatag cggtttgact cacggggatt tccaagtctc caccccattg acgtcaatgg    420
gagtttgttt tggcaccaaa atcaacggga ctttccaaaa tgtcgtaaca actccgcccc    480
attgacgcaa atgggcggta ggcgtgtacg gtgggaggtc tatataagca gagctctctg    540
gctaactaga acccactg cttactggct tatcgaaatt aatacgactc actatagggga    600 gacccgcggc catgtggccc cctgggtcag cctcccagcc accgccctca cctgccgcgg    660
ccacaggtct gcatccagcg gctcgccctg tgtccctgca gtgccggctc agcatgtgtc    720
cagcgcgcag cctcctcctt gtggctaccc tggtcctcct ggaccacctc agtttggcca    780
gaaacctccc cgtggccact ccagacccag gaatgttccc atgccttcac cactcccaaa    840
acctgctgag gccgtcagc aacatgctcc agaaggccag acaaactcta gaattttacc    900
cttgcacttc tgaagagatt gatcatgaag atatcacaaa agataaaacc agcacagtgg    960
aggcctgttt accattggaa ttaaccaaga tgagagttg cctaaattcc agagagacct   1020
ctttcataac taatgggagt tgcctggcct ccagaaagac ctctttatg atggccctgt   1080 gccttagtag tatttatgaa gacttgaaga tgtaccaggt ggagttcaag accatgaatg   1140
caaagcttct gatggatcct aagaggcaga tctttctaga tcaaaacatg ctggcagtta   1200
ttgatgagct gatgcaggcc ctgaatttca acagtgagac tgtgccacaa aaatcctccc   1260
ttgaagaacc ggattttat aaaactaaaa tcaagctctg catacttctt catgctttca   1320
gaattcgggc agtgactatt gatagagtga tgagctatct gaatgcttcc taaggccgct   1380
gtgccttcta gttgccagcc atctgttgtt tgcccctccc ccgtgccttc cttgaccctg   1440
```

```
gaaggtgcca ctcccactgt cctttcctaa taaaaaacca gactctgttt ggatttggat    1500
caagcaagtg tcttgctgtc tttatt                                         1526

<210> SEQ ID NO 23
<211> LENGTH: 1517
<212> TYPE: DNA
<213> ORGANISM: Artificial Sequence
<220> FEATURE:
<223> OTHER INFORMATION: L5 initial hIL12B

<400> SEQUENCE: 23
aataaagaat cgtttgtgtt atgtttcaac ctgtggaatg tgtgtcagtt agggtgtgga      60
aagtccccag gctccccagc aggcagaagt atgcaaagca tgcatctcaa ttagtcagca    120
accaggtgtg gaaagtcccc aggctcccca gcaggcagaa gtatgcaaag catgcatctc    180
aattagtcag caaccatagt cccgccccta actccgccca tcccgcccct aactccgccc    240
agttccgccc attctccgcc ccatggctga ctaatttttt ttatttatgc agaggccgag    300
gccgcctctg cctctgagct attccagaag tagtgaggag cttttttgg aggcctaggc     360 ttttgcaaaa agctttgcaa agatttatgt gtcaccagca gttggtcatc tcttggtttt    420
ccctggtttt tctggcatct cccctcgtgg ccatatggga actgaagaaa gatgtttatg    480
tcgtagaatt ggattggtat ccggatgccc ctggagaaat ggtggtcctc acctgtgaca    540
cccctgaaga agatggtatc acctggacct tggaccagag cagtgaggtc ttaggctctg    600
gcaaaaccct gaccatccaa gtcaaagagt tggagatgc tggccagtac acctgtcaca    660
aaggaggcga ggttctaagc cattcgctcc tgctgcttca caaaaggaa gatggaattt     720 ggtccactga tattttaaag gaccagaaag aacccaaaaa taagaccttt ctaagatgcg    780
aggccaagaa ttattctgga cgtttcacct gctggtggct gacgacaatc agtactgatt    840
tgacattcag tgtcaaaagc agcagaggct cttctgaccc ccaaggggtg acgtgcggag    900
ctgctacact ctctgcagag agagtcagag gggacaacaa ggagtatgag tactcagtgg    960
agtgccagga ggacagtgcc tgcccagctg ctgaggagag tctgcccatt gaggtcatgg   1020
tggatgccgt tcacaagctc aagtatgaaa actacaccag cagcttcttc atcagggaca   1080
tcatcaaacc tgacccaccc aagaacttgc agctgaagcc attaaagaat tctcggcagg   1140
tggaggtcag ctgggagtac cctgacacct ggagtactcc acattcctac ttctcccctga  1200 cattctgcgt tcaggtccag ggcaagagca agagagaaaa gaaagatag gtcttcacgg     1260 acaagacctc agccacggtc atctgccgca aaaatgccag cattagcgtg cgggcccagg   1320
accgctacta tagctcatct tggagcgaat gggcatctgt gccctgcagt tagaaataac   1380
ttgtttattg cagcttataa tggttacaaa taaagcaata gcatcacaaa tttcacaaat   1440
aaagcatttt tttcactgca ttctagttgt ggtttgtcca aactcatcaa tgtatcttat   1500
catgtctggt gtttatt                                                  1517

<210> SEQ ID NO 24
<211> LENGTH: 4
<212> TYPE: PRT
<213> ORGANISM: Unknown
<220> FEATURE:
<223> OTHER INFORMATION: furin cleavage site

<400> SEQUENCE: 24

Arg Ala Lys Arg
1
```

<210> SEQ ID NO 25
<211> LENGTH: 1625
<212> TYPE: DNA
<213> ORGANISM: Artificial Sequence
<220> FEATURE:
<223> OTHER INFORMATION: hIL12 furin

<400> SEQUENCE: 25

| | |
|---|---|
| atctgacctc gtcgacatgt gtcaccagca gttggtcatc tcttggtttt ccctggtttt | 60 |
| tctggcatct cccctcgtgg ccatatggga actgaagaaa gatgtttatg tcgtagaatt | 120 |
| ggattggtat ccggatgccc tggagaaat ggtggtcctc acctgtgaca cccctgaaga | 180 |
| agatggtatc acctggacct tggaccagag cagtgaggtc ttaggctctg caaaaccct | 240 |
| gaccatccaa gtcaaagagt ttggagatgc tggccagtac acctgtcaca aggaggcga | 300 |
| ggttctaagc cattcgctcc tgctgcttca caaaaggaa gatggaattt ggtccactga | 360 |
| tattttaaag gaccagaaag aacccaaaaa taagaccttt ctaagatgcg aggccaagaa | 420 |
| ttattctgga cgtttcacct gctggtggct gacgacaatc agtactgatt tgacattcag | 480 |
| tgtcaaaagc agcagaggct cttctgaccc ccaaggggtg acgtgcggag ctgctacact | 540 |
| ctctgcagag agagtcagag gggacaacaa ggagtatgag tactcagtgg agtgccagga | 600 |
| ggacagtgcc tgcccagctg ctgaggagag tctgcccatt gaggtcatgg tggatgccgt | 660 |
| tcacaagctc aagtatgaaa actacaccag cagcttcttc atcagggaca tcatcaaacc | 720 |
| tgacccaccc aagaacttgc agctgaagcc attaaagaat ctcggcagg tggaggtcag | 780 |
| ctgggagtac cctgacacct ggagtactcc acattcctac ttctccctga cattctgcgt | 840 |
| tcaggtccag ggcaagagca gagagaaaa gaaagataga gtcttcacgg acaagacctc | 900 |
| agccacggtc atctgccgca aaaatgccag cattagcgtg cgggcccagg accgctacta | 960 |
| tagctcatct tggagcgaat ggcatctgt gccctgcagt cgtgctaagc gaagaaacct | 1020 |
| ccccgtggcc actccagacc caggaatgtt cccatgcctt caccactccc aaaacctgct | 1080 |
| gagggccgtc agcaacatgc tccagaaggc cagacaaact ctagaatttt acccttgcac | 1140 |
| ttctgaagag attgatcatg aagatatcac aaaagataaa accagcacag tggaggcctg | 1200 |
| tttaccattg gaattaacca agaatgagag ttgcctaaat tccagagaga cctctttcat | 1260 |
| aactaatggg agttgcctgg cctccagaaa gacctctttt atgatggccc tgtgccttag | 1320 |
| tagtatttat gaagacttga gatgtacca ggtggagttc aagaccatga atgcaaagct | 1380 |
| tctgatggat cctaagaggc agatctttct agatcaaaac atgctggcag ttattgatga | 1440 |
| gctgatgcag gccctgaatt tcaacagtga gactgtgcca caaaatcct cccttgaaga | 1500 |
| accggatttt tataaaacta aaatcaagct ctgcatactt cttcatgctt tcagaattcg | 1560 |
| ggcagtgact attgatagag tgatgagcta tctgaatgct tcctaataac tcgagtcacc | 1620 |
| aggcg | 1625 |

<210> SEQ ID NO 26
<211> LENGTH: 445
<212> TYPE: DNA
<213> ORGANISM: Artificial Sequence
<220> FEATURE:
<223> OTHER INFORMATION: L5 revised SV40

<400> SEQUENCE: 26

| | |
|---|---|
| aataaaaggt ttattctgtg gaatgtgtgt cagttagggt gtggaaagtc cccaggctcc | 60 |

```
ccagcaggca gaagtatgca aagcatgcat ctcaattagt cagcaaccag gtgtggaaag      120
tccccaggct ccccagcagg cagaagtatg caaagcatgc atctcaatta gtcagcaacc      180
atagtcccgc ccctaactcc gcccatcccg ccctaactc cgcccagttc cgcccattct      240
ccgccccatg gctgactaat ttttttatt tatgcagagg ccgaggccgc ctctgcctct      300
gagctattcc agaagtagtg aggaggcttt tttggaggcc taggcttttg caaaaagctt      360
tgcaaagatt taaataactt gtttattgca gcttataatg gttacaaata aagaatcgtt      420
tgtgttatgt ttcaacgtgt ttatt                                          445

<210> SEQ ID NO 27
<211> LENGTH: 502
<212> TYPE: DNA
<213> ORGANISM: Artificial Sequence
<220> FEATURE:
<223> OTHER INFORMATION: IX mIL7

<400> SEQUENCE: 27
atagggagac ccgcggccat gttccatgtt tcttttagat atatctttgg aattcctcca      60
ctgatccttg ttctgctgcc tgtcacatca tctgagtgcc acattaaaga caaagaaggt     120
aaagcatatg agagtgtact gatgatcagc atcgatgaat ggacaaaat gacaggaact      180 gatagtaatt gcccgaataa tgaaccaaac ttttttagaa aacatgtatg tgatgataca      240
aaggaagctg cttttctaaa tcgtgctgct cgcaagttga agcaatttct taaatgaat      300 atcagtgaag aattcaatgt ccacttacta acagtatcac aaggcacaca aacactggtg      360
aactgcacaa gtaaggaaga aaaaaacgta aggaacaga aaaagaatga tgcatgtttc      420
ctaaagagac tactgagaga aataaaaact tgttggaata aattttgaa gggcagtata      480 taaggccgct gtgccttcta gt                                             502

<210> SEQ ID NO 28
<211> LENGTH: 445
<212> TYPE: DNA
<213> ORGANISM: Artificial Sequence
<220> FEATURE:
<223> OTHER INFORMATION: L5 revised SV40 wt Empty

<400> SEQUENCE: 28
aataaaaggt ttattctgtg gaatgtgtgt cagttagggt gtggaaagtc cccaggctcc      60
ccagcaggca gaagtatgca aagcatgcat ctcaattagt cagcaaccag gtgtggaaag     120
tccccaggct ccccagcagg cagaagtatg caaagcatgc atctcaatta gtcagcaacc     180
atagtcccgc ccctaactcc gcccatcccg ccctaactc cgcccagttc cgcccattct      240
ccgccccatg gctgactaat ttttttatt tatgcagagg ccgaggccgc ctcggcctct      300
gagctattcc agaagtagtg aggaggcttt tttggaggcc taggcttttg caaaaagctt      360
tgcaaagatt taaataactt gtttattgca gcttataatg gttacaaata aagaatcgtt      420
tgtgttatgt ttcaacgtgt ttatt                                          445

<210> SEQ ID NO 29
<211> LENGTH: 525
<212> TYPE: DNA
<213> ORGANISM: Artificial Sequence
<220> FEATURE:
<223> OTHER INFORMATION: L5 revised EF1A Empty

<400> SEQUENCE: 29
aataaaaggt ttattaggcg gcctccccgt caccaccccc cccaacccgc cccgaccgga      60
```

```
gctgagagta attcatacaa aaggactcgc ccctgccttg gggaatccca gggaccgtcg      120
ttaaactccc actaacgtag aacccagaga tcgctgcgtt cccgcccct cacccgcccg      180 ctctcgtcat cactgaggtg gagaagagca tgcgtgaggc tccggtgccc gtcagtgggc      240
agagcgcaca tcgcccacag tccccgaaa gttgggggga ggggtcggca attgaaccgg      300
tgcctagaga aggtggcgcg gggtaaactg ggaaagtgat gtcgtgtact ggctccgcct      360
ttttcccgag ggtgggggag aaccgtatat aagtgcagta gtcgccgtga acgttctttt      420
tcgcaacggg tttgccgcca gaacacaatt taaataactt gtttattgca gcttataatg      480
gttacaaata aagaatcgtt tgtgttatgt ttcaacgtgt ttatt                     525

<210> SEQ ID NO 30
<211> LENGTH: 502
<212> TYPE: DNA
<213> ORGANISM: Artificial Sequence
<220> FEATURE:
<223> OTHER INFORMATION: mIL7 no poly-A

<400> SEQUENCE: 30
atagggagac ccgcggccat gttccatgtt tcttttagat atatctttgg aattcctcca      60
ctgatccttg ttctgctgcc tgtcacatca tctgagtgcc acattaaaga caaagaaggt     120
aaagcatatg agagtgtact gatgatcagc atcgatgaat tggacaaaat gacaggaact     180
gatagtaatt gcccgaataa tgaaccaaac ttttttagaa aacatgtatg tgatgataca     240
aaggaagctg cttttctaaa tcgtgctgct cgcaagttga agcaatttct taaaatgaat     300
atcagtgaag aattcaatgt ccacttacta acagtatcac aaggcacaca aacactggtg     360
aactgcacaa gtaaggaaga aaaaaacgta aaggaacaga aaagaatga tgcatgtttc     420 ctaaagagac tactgagaga aatcaaaact tgttggaaca aaattttgaa gggcagtata     480
taaggccgct gtgccttcta gt                                               502

<210> SEQ ID NO 31
<211> LENGTH: 456
<212> TYPE: DNA
<213> ORGANISM: Artificial Sequence
<220> FEATURE:
<223> OTHER INFORMATION: mGMCSF Kozak

<400> SEQUENCE: 31
atttgccacc atgtggctgc agaatttact tttcctgggc attgtggtct acagcctctc      60
agcacccacc cgctcaccca tcactgtcac ccggccttgg aagcatgtag aggccatcaa     120
agaagccctg aacctcctgg atgacatgcc tgtcacgttg aatgaagagg tagaagtcgt     180
ctctaacgag ttctccttca gaagctaac atgtgtgcag accgcctga agatattcga      240 gcagggtcta cggggcaatt tcaccaaaact caagggcgcc ttgaacatga cagccagcta     300
ctaccagaca tactgccccc caactccgga acggactgt gaaacacaag ttaccaccta     360
tgcggatttc atagacagcc ttaaaacctt tctgactgat atcccctttg aatgcaaaaa     420
accaggccaa aaatgaaaat aacttgttta ttgcag                                456

<210> SEQ ID NO 32
<211> LENGTH: 591
<212> TYPE: DNA
<213> ORGANISM: Unknown
<220> FEATURE:
<223> OTHER INFORMATION: adenoviral death protein
```

<400> SEQUENCE: 32

```
gaaaatgcct taatttacta agttacaaag ctaatgtcac cactaactgc tttactcgct      60
gcttgcaaaa caaattcaaa aagttagcat tataattaga ataggattta aaccccccgg     120
tcatttcctg ctcaatacca ttccctgaa caattgactc tatgtgggat atgctccagc      180
gctacaacct tgaagtcagg cttcctggat gtcagcatct gactttggcc agcacctgtc    240
ccgcggattt gttccagtcc aactacagcg acccaccta acagagatga ccaacacaac     300
caacgcggcc gccgctaccg gacttacatc taccacaaat acaccccaag tttctgcctt    360
tgtcaataac tgggataact tgggcatgtg gtggttctcc atagcgctta tgtttgtatg    420
ccttattatt atgtggctca tctgctgcct aaagcgcaaa cgcgcccgac cacccatcta    480
tagtcccatc attgtgctac acccaaacaa tgatggaatc catagattgg acggactgaa    540
acacatgttc ttttctctta cagtatgata taaaaaaaa ataataaagc a              591
```

<210> SEQ ID NO 33
<211> LENGTH: 4509
<212> TYPE: DNA
<213> ORGANISM: Artificial Sequence
<220> FEATURE:
<223> OTHER INFORMATION: Costim IRES

<400> SEQUENCE: 33

```
atctgacctc gtcgacatgg cttgcaattg tcagttgatg caggatacac cactcctcaa     60
gtttccatgt ccaaggctca ttcttctctt tgtgctgctg attcgtcttt cacaagtgtc    120
ttcagatgtt gatgaacaac tgtccaagtc agtgaaagat aaggtattgc tgccttgccg    180
ttacaactct cctcatgaag atgagtctga agaccgaatc tactggcaaa acatgacaa     240
agtggtgctg tctgtcattg ctgggaaact aaaagtgtgg cccgagtata agaaccggac    300
tttatatgac aacactacct actctcttat catcctgggc ctggtccttt cagaccgggg    360
cacatacagc tgtgtcgttc aaaagaagga agaggaacg tatgaagtta aacacttggc     420
tttagtaaag ttgtccatca agctgacttt ctctaccccc aacataactg agtctggaaa    480
cccatctgca gacactaaaa ggattacctg ctttgcttcc gggggtttcc caaagcctcg    540
cttctcttgg ttggaaaatg gaagagaatt acctggcatc aatacgacaa tttcccagga    600
tcctgaatct gaattgtaca ccattagtag ccaactagat ttcaatacga ctcgcaacca    660
caccattaag tgtctcatta aatatggaga tgctcacgtg tcagaggact tcacctggga    720
aaaaccccca gaagaccctc ctgatagcaa gaacacactt gtgctctttg ggcaggatt    780
cggcgcagta ataacagtcg tcgtcatcgt tgtcatcatc aaatgcttct gtaagcacag    840
aagctgtttc agaagaaatg aggcaagcag agaaacaaac aacagcctta ccttcgggcc    900
tgaagaagca ttagctgaac agaccgtctt cctttagtaa cgttactggc cgaagccgct    960
tggaataagg ccggtgtgcg tttgtctata tgttattttc caccatattg ccgtcttttg   1020
gcaatgtgag ggcccggaaa cctggccctg tcttcttgac gagcattcct aggggtcttt   1080
cccctctcgc caaggaatg caaggtctgt tgaatgtcgt gaaggaagca gttcctctgg    1140
aagcttcttg aagacaaaca acgtctgtag cgacccttgt caggcagcgg aaccccccac   1200
ctggcgacag gtgcctctgc ggccaaaagc cacgtgtata agatacacct gcaaaggcgg    1260
cacaacccca gtgccacgtt gtgagttgga tagttgtgga aagagtcaaa tggctctcct    1320
caagcgtatt caacaggggg ctgaaggatg cccagaaggt accccattgt atgggatctg    1380
atctggggcc tcggtgcaca tgctttacat gtgtttagtc gaggttaaaa aacgtctagg    1440
```

```
cccccccgaac cacggggacg tggttttcct ttgaaaaaca cgatgataat atggaccagc   1500
acacacttga tgtggaggat accgcggatg ccagacatcc agcaggtact tcgtgcccct   1560
cggatgcggc gctcctcaga gataccgggc tcctcgcgga cgctgcgctc ctctcagata   1620
ctgtgcgccc cacaaatgcc gcgctcccca cggatgctgc ctaccctgcg gttaatgttc   1680
gggatcgcga ggccgcgtgg ccgcctgcac tgaacttctg ttcccgccac ccaaagctct   1740
atggcctagt cgctttggtt ttgctgcttc tgatcgccgc ctgtgttcct atcttcaccc   1800
gcaccgagcc tcggccagcg ctcacaatca ccacctcgcc caacctgggt acccgagaga   1860
ataatgcaga ccaggtcacc cctgtttccc acattggctg ccccaacact acacaacagg   1920
gctctcctgt gttcgccaag ctactggcta aaaccaagc atcgttgtgc aatacaactc   1980
tgaactggca cagccaagat ggagctggga gctcatacct atctcaaggt ctgaggtacg   2040
aagaagacaa aaaggagttg gtggtagaca gtcccgggct ctactacgta ttttggaac   2100 tgaagctcag tccaacattc acaaacacag gccacaaggt gcagggctgg gtctctcttg   2160
ttttgcaagc aaagcctcag gtagatgact ttgacaactt ggccctgaca gtggaactgt   2220
tcccttgctc catggagaac aagttagtgg accgttcctg gagtcaactg ttgctcctga   2280
aggctggcca ccgcctcagt gtgggtctga ggcttatct gcatggagcc caggatgcat   2340
acagagactg ggagctgtct tatcccaaca ccaccagctt tggactcttt cttgtgaaac   2400
ccgacaaccc atgggaatga ggtttccaca actgataaaa ctcgtgcaac ttgaaactcc   2460
gcctggtctt tccaggtcta gaggggttac actttgtact gtgctcgact ccacgcccgg   2520
tccactggcg ggtgttagta gcagcactgt tgtttcgtag cggagcatgg tggccgtggg   2580
aactcctcct tggtgacaag ggcccacggg gccgaaagcc acgtccagac ggacccacca   2640
tgtgtgcaac cccagcacgg caacttttac tgcgaacacc accttaaggt gacactggta   2700
ctggtactcg gtcactggtg acaggctaag gatgccctc aggtacccg aggtaacacg   2760 ggacactcgg gatctgagaa ggggattggg acttctttaa aagtgcccag tttaaaaagc   2820
ttctacgcct gaataggcga ccggaggccg gcgcctttcc attcccact actaaatcca   2880 tggcttcaac ccgtgccaag cccacgctac ctctgctcct ggccctggtc accgttgtga   2940
tccctgggcc tggtgatgct caggtatcca tccatcccag agaagccttc ctgccccagg   3000
gtgggtccgt gcaggtgaac tgttcttcct catgcaagga ggacctcagc ctgggcttgg   3060
agactcagtg gctgaaagat gagctcgaga gtggacccaa ctggaagctg tttgagctga   3120
gcgagatcgg ggaggacagc agtccgctgt gctttgaaga ctgtggcacc gtgcagtcgt   3180
ccgcttccgc taccatcacc gtgtattcgt ttccggagag tgtggagctg agacctctgc   3240
cagcctggca gcaagtaggc aaggacctca ccctgcgctg ccacgtggat ggtggagcac   3300
cgcggaccca gctctcagca gtgctgctcc gtggggagga gatactgagc cgccagccag   3360
tgggtgggca cccaaggac cccaaggaga tcacattcac ggtgctggct agcagagggg   3420
accacggagc caatttctca tgccgcacag aactggatct caggccgcaa gggctggcat   3480
tgttctctaa tgtctccgag gccaggagcc tccggacttt cgatcttcca gctaccatcc   3540
caaagctcga caccctgac ctcctggagg tgggcaccca gcagaagttg ttttgctccc   3600
tggaaggcct gtttcctgcc tctgaagctc ggatatacct ggagctggga ggccagatgc   3660
cgacccagga gagcacaaac agcagtgact ctgtgtcagc cactgccttg gtagaggtga   3720
ctgaggagtt cgacagaacc ctgccgctgc gctgcgtttt ggagctagcg gaccagatcc   3780
```

-continued

| | |
|---|---|
| tggagacgca gaggacctta acagtctaca acttttcagc tccggtcctg accctgagcc | 3840 |
| agctggaggt ctcggaaggg agccaagtaa ctgtgaagtg tgaagcccac agtgggtcga | 3900 |
| aggtggttct tctgagcggc gtcgagccta ggccacccac cccgcaggtc caattcacac | 3960 |
| tgaatgccag ctcggaggat cacaaacgaa gcttcttttg ctctgccgct ctggaggtgg | 4020 |
| cgggaaagtt cctgtttaaa aaccagaccc tggaactgca cgtgctgtat ggtcctcggc | 4080 |
| tggacgagac ggactgcttg gggaactgga cctggcaaga ggggtctcag cagactctga | 4140 |
| aatgccaggc ctgggggaac ccatctccta agatgacctg cagacggaag cagatggtg | 4200 |
| ccctgctgcc catcggggtg gtgaagtctg tcaaacagga gatgaatggt acatacgtgt | 4260 |
| gccatgcctt tagctcccat gggaatgtca ccaggaatgt gtacctgaca gtactgtacc | 4320 |
| actctcaaaa taactggact ataatcattc tggtgccagt actgctggtc attgtgggcc | 4380 |
| tcgtgatggc agcctcttat gtttataacc gccagagaaa gatcaggata tacaagttac | 4440 |
| agaaggctca ggaggaggcc ataaaactca agggacaagc cccacctccc tgactcgagt | 4500 |
| caccaggcg | 4509 |

<210> SEQ ID NO 34
<211> LENGTH: 951
<212> TYPE: DNA
<213> ORGANISM: Artificial Sequence
<220> FEATURE:
<223> OTHER INFORMATION: 19k mCD80

<400> SEQUENCE: 34

| | |
|---|---|
| atctgacctc atggcttgca attgtcagtt gatgcaggat acaccactcc tcaagtttcc | 60 |
| atgtccaagg ctcattcttc tctttgtgct gctgattcgt ctttcacaag tgtcttcaga | 120 |
| tgttgatgaa caactgtcca agtcagtgaa agataaggta ttgctgcctt gccgttacaa | 180 |
| ctctcctcat gaagatgagt ctgaagaccg aatctactgg caaaaacatg acaaagtggt | 240 |
| gctgtctgtc attgctggga aactaaaagt gtggcccgag tataagaacc ggactttata | 300 |
| tgacaacact acctactctc ttatcatcct gggcctggtc ctttcagacc ggggcacata | 360 |
| cagctgtgtc gttcaaaaga aggaaagagg aacgtatgaa gttaaacact ggctttagt | 420 |
| aaagttgtcc atcaaagctg acttctctac ccccaacata actgagtctg aaacccatc | 480 |
| tgcagacact aaaaggatta cctgctttgc ttccgggggt ttcccaaagc ctcgcttctc | 540 |
| ttggttggaa aatggaagag aattacctgg catcaatacg acaatttccc aggatcctga | 600 |
| atctgaattg tacaccatta gtagccaact agatttcaat acgactcgca accacaccat | 660 |
| taagtgtctc attaaatatg gagatgctca cgtgtcagag gacttcacct gggaaaaacc | 720 |
| cccagaagac cctcctgata gcaagaacac acttgtgctc tttggggcag gattcggcgc | 780 |
| agtaataaca gtcgtcgtca tcgttgtcat catcaaatgc ttctgtaagc acagaagctg | 840 |
| tttcagaaga aatgaggcaa gcagagaaac aaacaacagc cttaccttcg ggcctgaaga | 900 |
| agcattagct gaacagaccg tcttcctttta gtcaggtgaa tctgggtcac c | 951 |

<210> SEQ ID NO 35
<211> LENGTH: 967
<212> TYPE: DNA
<213> ORGANISM: Artificial Sequence
<220> FEATURE:
<223> OTHER INFORMATION: IX mCD137L

<400> SEQUENCE: 35

| | |
|---|---|
| atagggagac ccgcggccat ggaccagcac acacttgatg tggaggatac cgcggatgcc | 60 |

```
agacatccag caggtacttc gtgcccctcg gatgcggcgc tcctcagaga taccgggctc    120
ctcgcggacg ctgcgctcct ctcagatact gtgcgcccca caaatgccgc gctcccacg    180 gatgctgcct accctgcggt taatgttcgg gatcgcgagg ccgcgtggcc gcctgcactg    240
aacttctgtt cccgccaccc aaagctctat ggcctagtcg ctttggtttt gctgcttctg    300
atcgccgcct gtgttcctat cttcacccgc accgagcctc ggccagcgct cacaatcacc    360
acctcgccca acctgggtac ccgagagaat aatgcagacc aggtcacccc tgtttcccac    420
attggctgcc ccaacactac acaacagggc tctcctgtgt tcgccaagct actggctaaa    480
aaccaagcat cgttgtgcaa tacaactctg aactggcaca gccaagatgg agctgggagc    540
tcatacctat ctcaaggtct gaggtacgaa gaagacaaaa aggagttggt ggtagacagt    600
cccgggctct actacgtatt tttggaactg aagctcagtc caacattcac aaacacaggc    660
cacaaggtgc agggctgggt ctctcttgtt ttgcaagcaa agcctcaggt agatgacttt    720
gacaacttgg ccctgacagt ggaactgttc ccttgctcca tggagaacaa gttagtggac    780
cgttcctgga gtcaactgtt gctcctgaag ctggccaccg cctcagtgt gggtctgagg    840 gcttatctgc atggagccca ggatgcatac agagactggg agctgtctta tcccaacacc    900
accagctttg gactctttct tgtgaaaccc gacaacccat gggaatgagg ccgctgtgcc    960
ttctagt                                                             967

<210> SEQ ID NO 36
<211> LENGTH: 1649
<212> TYPE: DNA
<213> ORGANISM: Artificial Sequence
<220> FEATURE:
<223> OTHER INFORMATION: L5 mICAM1

<400> SEQUENCE: 36
cgccagaaca catttatggc ttcaacccgt gccaagccca cgctacctct gctcctggcc     60
ctggtcaccg ttgtgatccc tgggcctggt gatgctcagg tatccatcca tcccagagaa    120
gccttcctgc ccagggtgg gtccgtgcag gtgaactgtt cttcctcatg caaggaggac    180
ctcagcctgg gcttggagac tcagtggctg aaagatgagc tcgagagtgg acccaactgg    240
aagctgtttg agctgagcga gatcggggag gacagcagtc cgctgtgctt tgagaactgt    300
ggcaccgtgc agtcgtccgc ttccgctacc atcaccgtgt attcgtttcc ggagagtgtg    360
gagctgagac tctgccagc ctggcagcaa gtaggcaagg acctcaccct gcgctgccac    420
gtggatggtg gagcaccgcg gacccagctc tcagcagtgc tgctccgtgg ggaggagata    480
ctgagccgcc agccagtggg tgggcacccc aaggacccca aggagatcac attcacggtg    540
ctggctagca gagggaccac cggagccaat ttctcatgcc gcacagaact ggatctcagg    600
ccgcaagggc tggcattgtt ctctaatgtc tccgaggcca ggagcctccg gactttcgat    660
cttccagcta ccatcccaaa gctcgacacc cctgacctcc tggaggtggg cacccagcag    720
aagttgtttt gctccctgga aggcctgttt cctgcctctg aagctcggat ataccctggag    780 ctggaggcc agatgccgac ccaggagagc acaaacagca gtgactctgt gtcagccact    840
gccttggtag aggtgactga ggagttcgac agaaccctgc cgctgcgctg cgttttggag    900
ctagcggacc agatcctgga gacgcagagg accttaacag tctacaactt ttcagctccg    960 gtcctgacc tgagccagct ggaggtctcg gaagggagcc aagtaactgt gaagtgtgaa    1020
gcccacagtg ggtcgaaggt ggttcttctg agcggcgtcg agcctaggcc acccaccccg    1080
```

```
caggtccaat tcacactgaa tgccagctcg gaggatcaca aacgaagctt cttttgctct    1140
gccgctctgg aggtggcggg aaagttcctg tttaaaaacc agaccctgga actgcacgtg    1200
ctgtatggtc ctcggctgga cgagacggac tgcttgggga actggacctg gcaagagggg    1260
tctcagcaga ctctgaaatg ccaggcctgg gggaacccat ctcctaagat gacctgcaga    1320
cggaaggcag atggtgccct gctgcccatc ggggtggtga agtctgtcaa acaggagatg    1380
aatggtacat acgtgtgcca tgcctttagc tcccatggga atgtcaccag gaatgtgtac    1440
ctgacagtac tgtaccactc tcaaaataac tggactataa tcattctggt gccagtactg    1500
ctggtcattg tgggcctcgt gatggcagcc tcttatgttt ataaccgcca gagaaagatc    1560
aggatataca agttacagaa ggctcaggag gaggccataa aactcaaggg acaagcccca    1620
cctccctgaa ataaacttgt ttattgcag                                      1649

<210> SEQ ID NO 37
<211> LENGTH: 72
<212> TYPE: DNA
<213> ORGANISM: Human adenovirus 35

<400> SEQUENCE: 37
aataaaaaaa attccagaat caatgaataa ataaacgagc ttgttgttga tttaaaatca     60
agtgttttta tt                                                         72

<210> SEQ ID NO 38
<211> LENGTH: 23
<212> TYPE: DNA
<213> ORGANISM: Human adenovirus 35

<400> SEQUENCE: 38
aataaagttt aagtgttttt att                                             23

<210> SEQ ID NO 39
<211> LENGTH: 789
<212> TYPE: DNA
<213> ORGANISM: Artificial Sequence
<220> FEATURE:
<223> OTHER INFORMATION: Ad35 IX-E2 cassette

<400> SEQUENCE: 39
tcgagatcgg tggtccaggg cataccgtgc gcgaaaaatg aaataaaata cacctttttt     60
cgattgtacg tatttttatt tacggtaaat ggcccgcctg gctgaccgcc caacgacccc    120
cgcccattga cgtcaataat gacgtatgtt cccatagtaa cgccaatagg gactttccat    180
tgacgtcaat gggtggagta tttacggtaa actgcccact ggcagtacat caagtgtat    240 catatgccaa gtacgccccc tattgacgtc aatgacggta atggcccgc ctggcattat    300 gcccagtaca tgaccttatg gactttcct acttggcagt acatctacgt attagtcatc    360
gctattacca tggtgatgcg gttttggcag tacatcaatg ggcgtggata gcggtttgac    420
tcacggggat ttccaagtct ccaccccatt gacgtcaatg ggagtttgtt ttggcaccaa    480
aatcaacggg actttccaaa atgtcgtaac aactccgccc cattgacgca aatgggcggt    540
aggcgtgtac ggtgggaggt ctatataagc agagctctct ggctaactag agaacccact    600
gcttactggc ttatcgaaat taatacgact cactataggg agacccgcgg ccgctgtgcc    660
ttctagttgc cagccatctg ttgtttgccc ctcccccgtg ccttccttga ccctggaagg    720
tgccactccc actgtccttt cctaataaaa acacttgatt taaatcaac aacaagctcg    780 tttatttat                                                           789
```

```
<210> SEQ ID NO 40
<211> LENGTH: 560
<212> TYPE: DNA
<213> ORGANISM: Artificial Sequence
<220> FEATURE:
<223> OTHER INFORMATION: Ad35 L5-E4 cassette

<400> SEQUENCE: 40
tttcttttct tacattacag aagacgacaa ctaaaataaa aggtttatta ggcggcctcc      60
ccgtcaccac cccccccaac ccgccccgac cggagctgag agtaattcat acaaaaggac     120
tcgcccctgc cttggggaat cccagggacc gtcgttaaac tcccactaac gtagaaccca     180
gagatcgctg cgttcccgcc ccctcacccg cccgctctcg tcatcactga ggtggagaag     240
agcatgcgtg aggctccggt gcccgtcagt gggcagagcg cacatcgccc acagtccccg     300
agaagttggg gggaggggtc ggcaattgaa ccggtgccta gagaaggtgg cgcggggtaa     360
actgggaaag tgatgtcgtg tactggctcc gccttttcc cgagggtggg ggagaaccgt     420
atataagtgc agtagtcgcc gtgaacgttc tttttcgcaa cgggtttgcc gccagaacac     480
aatttaaata acttgtttat tgcagcttat aatggttaca aataaagttt aagtgttttt     540
atttaaaatc acaaaattcg                                                 560

<210> SEQ ID NO 41
<211> LENGTH: 34794
<212> TYPE: DNA
<213> ORGANISM: Human adenovirus 35

<400> SEQUENCE: 41
catcatcaat aatataccct atagatggaa tggtgccaat atgtaaatga ggtgatttta      60
aaaagtgtgg gccgtgtggt gattggctgt ggggttaacg gttaaaaggg gcggcgcggc     120
cgtgggaaaa tgacgtttta tgggggtgga gtttttttgc aagttgtcgc gggaaatgtt     180
acgcataaaa aggcttcttt tctcacggaa ctacttagtt ttcccacggt atttaacagg     240
aaatgaggta gttttgaccg gatgcaagtg aaaattgctg attttcgcgc gaaaactgaa     300
tgaggaagtg ttttttctgaa taatgtggta tttatggcag ggtggagtat tgttcaggg     360 ccaggtagac tttgacccat tacgtggagg tttcgattac cgtgtttttt acctgaattt     420
ccgcgtaccg tgtcaaagtc ttctgttttt acgtaggtgt cagctgatcg ctagggtatt     480
tatacctcag ggttgtgtc aagaggccac tcttgagtgc cagcgagaag agttttctcc     540
tctgcgccgg cagtttaata ataaaaaaat gagagatttg cgattctgc ctcaggaaat     600 aatctctgct gagactggaa atgaaatatt ggagcttgtg gtgcacgccc tgatgggaga     660
cgatccggag ccacctgtgc agcttttga gcctcctacg cttcaggaac tgtatgattt     720
agaggtagag ggatcggagg attctaatga ggaagctgtg aatggctttt ttaccgattc     780
tatgctttta gctgctaatg aaggattaga attagatccg cctttggaca ctttcaatac     840
tccaggggtg attgtggaaa gcggtacagg tgtaagaaaa ttacctgatt tgagttccgt     900
ggactgtgat ttgcactgct atgaagacgg gtttcctccg agtgatgagg aggaccatga     960
aaaggagcag tccatgcaga ctgcagcggg tgagggagtg aaggctgcca atgttggttt    1020
tcagttggat tgcccggagc ttcctggaca tggctgtaag tcttgtgaat ttcacaggaa    1080
aaatactgga gtaaaggaac tgttatgttc gctttgttat atgagaacgc actgccactt    1140
tatttacagt aagtgtgttt aagttaaaat ttaaaggaat atgctgtttt tcacatgtat    1200
```

```
attgagtgtg agttttgtgc ttcttattat aggtcctgtg tctgatgctg atgaatcacc   1260
atctcctgat tctactacct cacctcctga tattcaagca cctgttcctg tggacgtgcg   1320
caagcccatt cctgtgaagc ttaagcctgg gaaacgtcca gcagtggaga aacttgagga   1380
cttgttacag ggtggggacg gacctttgga cttgagtaca cggaaacgtc caagacaata   1440
agtgttccat atccgtgttt acttaaggtg acgtcaatat ttgtgtgaga gtgcaatgta   1500
ataaaaatat gttaactgtt cactggtttt tattgctttt gggcgggga ctcaggtata    1560
taagtagaag cagacctgtg tggttagctc ataggagctg gctttcatcc atggaggttt   1620
gggccatttt ggaagacctt aggaagacta ggcaactgtt agagagcgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga cttttttgaag  1800
ctcttaattt gggccatcag gttcacttta agaaaaagt tttatcagtt ttagactttt    1860
caaccccagg tagaactgct gctgctgtgg ctttttcttac ttttatatta gataaatgga  1920
tcccgcagac tcatttcagc aggggatacg ttttggattt catagccaca gcattgtgga  1980
gaacatggaa ggttcgcaag atgaggacaa tcttaggtta ctggccagtg cagcctttgg  2040
gtgtagcggg aatcctgagg catccaccgg tcatgccagc ggttctggag gaggaacagc  2100
aagaggacaa cccgagagcc ggcctggacc ctccagtgga ggaggcggag tagctgactt  2160
gtctcctgaa ctgcaacggg tgcttactgg atctacgtcc actggacggg ataggggcgt  2220
taagagggag agggcatcca gtggtactga tgctagatct gagttggctt taagtttaat  2280
gagtcgcaga cgtcctgaaa ccatttggtg gcatgaggtt cagaaagagg aagggatga   2340
agtttctgta ttgcaggaga aatattcact ggaacaggtg aaaacatgtt ggttggagcc  2400
agaggatgat tgggcggtgg ccattaaaaa ttatgccaag atagctttga ggcctgataa  2460
acagtataag atcagtagac ggattaatat ccggaatgct tgttacatat ctggaaatgg  2520
ggctgaggtg gtaatagata ctcaagacaa gacagttatt agatgctgca tgatggatat  2580
gtggcctgga gtagtcggta tggaagcagt cacttttgta aatgttaagt ttaggggaga  2640
tggttataat ggaatagtgt ttatggccaa taccaaactt atattgcatg ttgtagctt   2700
ttttggtttc aacaataccct gtgtagatgc ctggggacag gttagtgtac ggggtgtag   2760
tttctatgcg tgttggattg ccacagctgg cagaaccaag agtcaattgt ctctgaagaa  2820
atgcatattc caaagatgta acctgggcat tctgaatgaa ggcgaagcaa gggtccgtca  2880
ctgcgcttct acagatactg gatgttttat tttaattaag ggaaatgcca gcgtaaagca  2940
taacatgatt tgtggtgctt ccgatgagag gccttatcaa atgctcactt gtgctggtgg  3000
gcattgtaat atgctggcta ctgtgcatat tgtttcccat caacgcaaaa aatggcctgt  3060
ttttgatcac aatgtgttga ccaagtgcac catgcatgca ggtgggcgta gaggaatgtt  3120
tatgccttac cagtgtaaca tgaatcatgt gaaagtgttg ttggaaccag atgccttttc  3180
cagaatgagc ctaacaggaa tctttgacat gaacacgcaa atctggaaga tcctgaggta  3240
tgatgatacg agatcgaggg tgcgcgcatg cgaatgcgga ggcaagcatg ccaggttcca  3300
gccggtgtgt gtagatgtga ccgaagatct cagaccggga catttggtta ttgcccgcac  3360
tggagcagag ttcggatcca gtggagaaga aactgactaa ggtgagtatt gggaaaactt  3420
tggggtggga ttttcagatg gacagattga gtaaaaattt gttttttctg tcttgcagct  3480
gacatgagtg gaaatgcttc ttttaagggg ggagtcttca gcccttatct gacagggcgt  3540
ctcccatcct gggcaggagt tcgtcagaat gttatgggat ctactgtgga tggaagaccc  3600
```

-continued

```
gttcaacccg ccaattcttc aacgctgacc tatgctactt taagttcttc acctttggac  3660
gcagctgcag ccgctgccgc cgcctctgtc gccgctaaca ctgtgcttgg aatgggttac  3720
tatggaagca tcgtggctaa ttccacttcc tctaataacc cttctacact gactcaggac  3780
aagttacttg tccttttggc ccagctggag gctttgaccc aacgtctggg tgaactttct  3840
cagcaggtgg ccgagttgcg agtacaaact gagtctgctg tcggcacggc aaagtctaaa  3900
taaaaaaaat tccagaatca atgaataaat aaacgagctt gttgttgatt taaaatcaag  3960
tgtttttatt tcattttttcg cgcacggtat gccctggacc accgatctcg atcattgaga  4020
actcggtgga tttttttccag aatcctatag aggtgggatt gaatgtttag atacatgggc  4080
attaggccgt ctttggggtg gagatagctc cattgaaggg attcatgctc cggggtagtg  4140
ttgtaaatca cccagtcata acaaggtcgc agtgcatggt gttgcacaat atcttttaga  4200
agtaggctga ttgccacaga taagcccttg tgtaggtgt ttacaaaccg gttgagctgg  4260
gaggggtgca ttcgaggtga aattatgtgc attttggatt ggattttttaa gttggcaata  4320 ttgccgccaa gatcccgtct tgggttcatg ttatgaagga ctaccaagac ggtgtatccg  4380
gtacatttag gaaatttatc gtgcagcttg atggaaaag cgtggaaaaa tttggagaca  4440
cccttgtgtc ctccgagatt ttccatgcac tcatccatga taatagcaat ggggccgtgg  4500
gcagcggcgc gggcaaacac gttccgtggg tctgacacat catagttatg ttcctgagtt  4560
aaatcatcat aagccatttt aatgaatttg gggcggagcg taccagattg gggtatgaat  4620
gttccttcgg gccccggagc atagttcccc tcacagattt gcatttccca agctttcagt  4680
tctgagggtg gaatcatgtc cacctggggg gctatgaaga acaccgtttc ggggggcgggg  4740 gtgattagtt gggatgatag caagtttctg agcaattgag atttgccaca tccggtgggg  4800
ccataaataa ttccgattac aggttgcagg tggtagttta gggaacggca actgccgtct  4860
tctcgaagca aggggggccac ctcgttcatc atttcccctta catgcatatt ttcccgcacc  4920
aaatccatta ggaggcgctc tcctcctagt gatagaagtt cttgtagtga ggaaaagttt  4980
ttcagcggtt ttagaccgtc agccatgggc attttggaaa gagtttgctg caaaagttct  5040
agtctgttcc acagttcagt gatgtgttct atggcatctc gatccagcag acctcctcgt  5100
ttcgcgggtt tggacggctc ctggagtagg gtatgagacg atgggcgtcc agcgctgcca  5160
gggttcggtc cttccagggt ctcagtgttc gagtcagggt tgtttccgtc acagtgaagg  5220
ggtgtgcgcc tgcttgggcg cttgccaggg tgcgcttcag actcattctg ctggtggaga  5280
acttctgtcg cttggcgccc tgtatgtcgg ccaagtagca gtttaccatg agttcgtagt  5340
tgagcgcctc ggctgcgtgg cctttggcgc ggagcttacc tttggaagtt ttcttgcata  5400
ccgggcagta taggcatttc agcgcataca gcttgggcgc aaggaaaatg gattctgggg  5460
agtatgcatc cgcgccgcag gaggcgcaaa cagtttcaca ttccaccagc caggttaaat  5520
ccggttcatt ggggtcaaaa acaagttttc cgccatattt tttgatgcgt ttcttaccttt  5580 tggtctccat aagttcgtgt cctcgttgag tgacaaacag gctgtccgta tctccgtaga  5640
ctgattttac aggcctcttc tccagtggag tgcctcggtc ttcttcgtac aggaactctg  5700
accactctga tacaaaggcg cgcgtccagg ccagcacaaa ggaggctatg tgggaggggt  5760
agcgatcgtt gtcaaccagg gggtccacct tttccaaagt atgcaaacac atgtcaccct  5820
cttcaacatc caggaatgtg attggcttgt aggtgtattt cacgtgacct ggggtccccg  5880 ctggggggggt ataaaagggg gcggttcttt gctcttcctc actgtcttcc ggatcgctgt  5940
```

```
ccaggaacgt cagctgttgg ggtaggtatt ccctctcgaa ggcgggcatg acctctgcac      6000
tcaggttgtc agtttctaag aacgaggagg atttgatatt gacagtgccg gttgagatgc      6060 cttcatgag gttttcgtcc atttggtcag aaaacacaat ttttttattg tcaagtttgg       6120
tggcaaatga tccatacagg gcgttggata aaagtttggc aatggatcgc atggtttggt      6180
tcttttcctt gtccgcgcgc tctttggcgg cgatgttgag ttggacatac tcgcgtgcca      6240
ggcacttcca ttcggggaag atagttgtta attcatctgg cacgattctc acttgccacc      6300
ctcgattatg caaggtaatt aaatccacac tggtggccac ctcgcctcga aggggttcat      6360
tggtccaaca gagcctacct cctttcctag aacagaaagg gggaagtggg tctagcataa      6420
gttcatcggg agggtctgca tccatggtaa agattcccgg aagtaaatcc ttatcaaaat      6480
agctgatggg agtggggtca tctaaggcca tttgccattc tcgagctgcc agtgcgcgct      6540
catatgggtt aaggggactg ccccagggca tgggatgggt gagagcagag gcatacatgc      6600
cacagatgtc atagacgtag atgggatcct caaagatgcc tatgtaggtt ggatagcatc      6660
gcccccctct gatacttgct cgcacatagt catatagttc atgtgatggc gctagcagcc      6720
ccggacccaa gttggtgcga ttgggttttt ctgttctgta gacgatctgg cgaaagatgg      6780
cgtgagaatt ggaagagatg gtgggtcttt gaaaaatgtt gaaatgggca tgaggtagac      6840
ctacagagtc tctgacaaag tgggcataag attcttgaag cttggttacc agttcggcgg      6900
tgacaagtac gtctagggcg cagtagtcaa gtgtttcttg aatgatgtca taacctggtt      6960
ggttttcttt ttcccacagt tcgcggttga gaaggtattc ttcgcgatcc ttccagtact      7020
cttctagcgg aaacccgtct ttgtctgcac ggtaagatcc tagcatgtag aactgattaa      7080
ctgccttgta agggcagcag cccttctcta cgggtagaga gtatgcttga gcagcttttc      7140
gtagcgaagc gtgagtaagg gcaaaggtgt ctctgaccat gactttgaga aattggtatt      7200
tgaagtccat gtcgtcacag gctccctgtt cccagagttg gaagtctacc cgtttcttgt      7260
aggcggggtt gggcaaagcg aaagtaacat cattgaagag aatcttaccg gctctgggca      7320
taaaattgcg agtgatgcgg aaaggctgtg gtacttccgc tcgattgttg atcacctggg      7380
cagctaggac gatttcgtcg aaaccgttga tgttgtgtcc tacgatgtat aattctatga      7440
aacgcggcgt gcctctgacg tgaggtagct tactgagctc atcaaaggtt aggtctgtgg      7500
ggtcagataa ggcgtagtgt tcgagagccc attcgtgcag gtgaggattt gcatgtagga      7560
atgatgacca aagatctacc gccagtgctg tttgtaactg gtcccgatac tgacgaaaat      7620
gccggccaat tgccattttt tctggagtga cacagtagaa ggttctgggg tcttgttgcc      7680
atcgatccca cttgagttta atggctagat cgtgggccat gttgacgaga cgctcttctc      7740
ctgagagttt catgaccagc atgaaaggaa ctagttgttt gccaaaggat cccatccagg      7800
tgtaagtttc cacatcgtag gtcaggaaga gtctttctgt gcgaggatga gagccgatcg      7860
ggaagaactg gatttcctgc caccagttgg aggattggct gttgatgtga tggaagtaga      7920
agtttctgcg gcgcgccgag cattcgtgtt tgtgcttgta cagacggccg cagtagtcgc      7980
agcgttgcac gggttgtatc tcgtgaatga gctgtacctg gcttcccttg acgagaaatt      8040
tcagtgggaa gccgaggcct ggcgattgta tctcgtgctc ttctatattc gctgtatcgc      8100
cctgttcatc ttctgtttcg atggtggtca tgctgacgag ccccgcgggg aggcaagtcc      8160
agacctcggc gcgggagggg cggagctgaa ggacgagagc gcgcaggctg gagctgtcca      8220
gagtcctgag acgctgcgga ctcaggttag taggtaggga cagaagatta acttgcatga      8280
tcttttccag ggcgtgcggg aggttcagat ggtacttgat ttccacaggt tcgtttgtag      8340
```

```
agacgtcaat ggcttgcagg gttccgtgtc ctttgggcgc cactaccgta cctttgtttt   8400
ttcttttgat cggtggtggc tctcttgctt cttgcatgct cagaagcggt gacgggacg    8460 cgcgccgggc ggcagcggtt gttccggacc cgggggcatg gctggtagtg gcacgtcggc   8520
gccgcgcacg ggcaggttct ggtattgcgc tctgagaaga cttgcgtgcg ccaccacgcg   8580
tcgattgacg tcttgtatct gacgtctctg ggtgaaagct accggccccg tgagcttgaa   8640
cctgaaagag agttcaacag aatcaatttc ggtatcgtta acggcagctt gtctcagtat   8700
ttcttgtacg tcaccagagt tgtcctggta ggcgatctcc gccatgaact gctcgatttc   8760
ttcctcctga agatctccgc gacccgctct ttcgacggtg gccgcgaggt cattggagat   8820
acggcccatg agttgggaga atgcattcat gcccgcctcg ttccagacgc ggctgtaaac   8880 cacgccccc tcggagtctc ttgcgcgcat caccacctga gcgaggttaa gctccacgtg    8940
tctggtgaag accgcatagt tgcataggcg ctgaaaaagg tagttgagtg tggtggcaat   9000
gtgttcggcg acgaagaaat acatgatcca tcgtctcagc ggcatttcgc taacatcgcc   9060
cagagcttcc aagcgctcca tggcctcgta gaagtccacg gcaaaattaa aaaactggga   9120
gtttcgcgcg gacacggtca attcctcctc gagaagacgg atgagttcgg ctatggtggc   9180
ccgtacttcg cgttcgaagg ctcccgggat ctcttcttcc tcttctatct cttcttccac   9240
taacatctct tcttcgtctt caggcggggg cggaggggc acgcggcgac gtcgacggcg    9300
cacgggcaaa cggtcgatga atcgttcaat gacctctccg cggcggcggc gcatggtttc   9360
agtgacggcg cggccgttct cgcgcggtcg cagagtaaaa acaccgccgc gcatctcctt   9420
aaagtggtga ctgggaggtt ctccgtttgg gagggagagg gcgctgatta tacattttat   9480 taattgccc gtagggactg cgcgcagaga tctgatcgtg tcaagatcca cgggatctga    9540
aaacctttcg acgaaagcgt ctaaccagtc acagtcacaa ggtaggctga gtacggcttc   9600
ttgtgggcgg gggtggttat gtgttcggtc tgggtcttct gtttcttctt catctcggga   9660
aggtgagacg atgctgctgg tgatgaaatt aaagtaggca gttctaagac ggcggatggt   9720
ggcgaggagc accaggtctt tgggtccggc ttgctggata cgcaggcgat tggccattcc   9780
ccaagcatta tcctgacatc tagcaagatc tttgtagtag tcttgcatga gccgttctac   9840
gggcacttct tcctcacccg ttctgccatg catacgtgtg agtccaaatc cgcgcattgg   9900
ttgtaccagt gccaagtcag ctacgactct ttcggcgagg atggcttgct gtacttgggt   9960
aagggtggct tgaaagtcat caaaatccac aaagcggtgg taagcccctg tattaatggt  10020
gtaagcacag ttggccatga ctgaccagtt aactgtctgg tgaccagggc gcacgagctc  10080
ggtgtattta aggcgcgaat aggcgcgggt gtcaaagatg taatcgttgc aggtgcgcac  10140
cagatactgg taccctataa gaaaatgcgg cggtggttgg cggtagagag gccatcgttc  10200
tgtagctgga gcgccagggg cgaggtcttc caacataagg cggtgatagc cgtagatgta  10260
cctggacatc caggtgattc ctgcggcggt agtagaagcc cgaggaaact cgcgtacgcg  10320
gttccaaatg ttgcgtagcg gcatgaagta gttcattgta ggcacggttt gaccagtgag  10380
gcgcgcgcag tcattgatgc tctatagaca cggagaaaat gaaagcgttc agcgactcga  10440
ctccgtagcc tggaggaacg tgaacgggtt gggtcgcggt gtaccccggt tcgagacttg  10500
tactcgagcc ggccggagcc gcggctaacg tggtattggc actcccgtct cgacccagcc  10560
tacaaaaatc caggatacgg aatcgagtcg ttttgctggt ttccgaatgg cagggaagtg  10620
agtcctattt ttttttttt tttgccgctc agatgcatcc cgtgctgcga cagatgcgcc  10680
```

```
cccaacaaca gcccccctcg cagcagcagc agcagcaacc acaaaaggct gtccctgcaa    10740
ctactgcaac tgccgccgtg agcggtgcgg gacagcccgc ctatgatctg gacttggaag    10800
agggcgaagg actggcacgt ctaggtgcgc cttcgcccga gcggcatccg cgagttcaac    10860
tgaaaaaaga ttctcgcgag gcgtatgtgc cccaacagaa cctatttaga dacagaagcg    10920
gcgaggagcc ggaggagatg cgagcttccc gctttaacgc gggtcgtgag ctgcgtcacg    10980
gtttggaccg aagacgagtg ttgcgagacg aggatttcga agttgatgaa gtgacaggga    11040
tcagtcctgc cagggcacac gtggctgcag ccaaccttgt atcggcttac gagcagacag    11100
taaaggaaga gcgtaacttc caaaagtctt ttaataatca tgtgcgaacc ctgattgccc    11160
gcgaagaagt taccctttggt ttgatgcatt tgtgggattt gatggaagct atcattcaga    11220
accctactag caaacctctg accgcccagc tgtttctggt ggtgcaacac agcagagaca    11280
atgaggcttt cagagaggcg ctgctgaaca tcaccgaacc cgaggggaga tggttgtatg    11340
atcttatcaa cattctacag agtatcatag tgcaggagcg gagcctgggc ctggccgaga    11400
aggtagctgc catcaattac tcggttttga gcttgggaaa atattacgct cgcaaaatct    11460
acaagactcc atacgttccc atagacaagg aggtgaagat agatgggttc tacatgcgca    11520
tgacgctcaa ggtcttgacc ctgagcgatg atcttggggt gtatcgcaat gacagaatgc    11580
atcgcgcggt tagcgccagc aggaggcgcg agttaagcga cagggaactg atgcacagtt    11640
tgcaaagagc tctgactgga gctggaaccg agggtgagaa ttacttcgac atgggagctg    11700
acttgcagtg gcagcctagt cgcagggctc tgagcgccgc gacggcagga tgtgagcttc    11760
cttacataga agaggcggat gaaggcgagg aggaagaggg cgagtacttg gaagactgat    11820
ggcacaaccc gtgttttttg ctagatggaa cagcaagcac cggatcccgc aatgcgggcg    11880
gcgctgcaga gccagccgtc cggcattaac tcctcggacg attggaccca ggccatgcaa    11940
cgtatcatgg cgttgacgac tcgcaaccc gaagccttta gacagcaacc ccaggccaac    12000
cgtctatcgg ccatcatgga agctgtagtg ccttcccgat ctaatcccac tcatgagaag    12060
gtcctggcca tcgtgaacgc gttggtggag aacaaagcta ttcgtccaga tgaggccgga    12120
ctggtataca acgctctctt agaacgcgtg gctcgctaca acagtagcaa tgtgcaaacc    12180
aatttggacc gtatgataac agatgtacgc gaagccgtgt ctcagcgcga aaggttccag    12240
cgtgatgcca acctgggttc gctggtggcg ttaaatgctt tcttgagtac tcagcctgct    12300
aatgtgccgc gtggtcaaca ggattatact aacttttaa gtgctttgag actgatggta    12360
tcagaagtac ctcagagcga agtgtatcag tccggtcctg attacttctt tcagactagc    12420
agacagggct tgcagacggt aaatctgagc caagctttta aaaaccttaa aggtttgtgg    12480
ggagtgcatg ccccggtagg agaaagagca accgtgtcta gcttgttaac tccgaactcc    12540
cgcctgttat tactgttggt agctcctttc accgacagcg gtagcatcga ccgtaattcc    12600
tatttggggtt acctactaaa cctgtatcgc gaagccatag gcaaagtca ggtgacgag    12660
cagacctatc aagaaattac ccaagtcagt cgcgctttgg dacaggaaga cactggcagt    12720
ttggaagcca ctctgaactt cttgcttacc aatcggtctc aaaagatccc tcctcaatat    12780
gctcttactg cggaggagga gaggatcctt agatatgtgc agcagagcgt gggattgttt    12840
ctgatgcaag aggggcaac tccgactgca gcactggaca tgacagcgcg aaatatggag    12900
cccagcatgt atgccagtaa ccgacctttc attaacaaac tgctggacta cttgcacaga    12960
gctgccgcta tgaactctga ttatttcacc aatgccatct aaaccccgca ctggctgccc    13020
ccacctggtt tctacacggg cgaatatgac atgcccgacc ctaatgacgg atttctgtgg    13080
```

```
gacgacgtgg acagcgatgt tttttcacct ctttctgatc atcgcacgtg gaaaaaggaa   13140
ggcggtgata gaatgcattc ttctgcatcg ctgtccgggg tcatgggtgc taccgcggct   13200
gagcccgagt ctgcaagtcc ttttcctagt ctacccttt ctctacacag tgtacgtagc    13260
agcgaagtgg gtagaataag tcgcccgagt ttaatgggcg aagaggagta cctaaacgat   13320
tccttgctca gaccggcaag agaaaaaaat ttcccaaaca atggaataga aagtttggtg   13380
gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg gagaggaagg   13560
ggcaacccgt ttgctcattt gcgccctcgc ttgggtggta tgttgtgaaa aaaaataaaa   13620
aagaaaaact caccaaggcc atggcgacga gcgtacgttc gttcttcttt attatctgtg   13680
tctagtataa tgaggcgagt cgtgctaggc ggagcggtgg tgtatccgga gggtcctcct   13740
ccttcgtacg agagcgtgat gcagcagcag caggcgacgg cggtgatgca atccccactg   13800
gaggctccct ttgtgcctcc gcgatacctg gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca acttcttgac cacggtggtg   13980
cagaacaatg actttacccc tacggaagcc agcacccaga ccattaactt tgatgaacga   14040
tcgcggtggg gcggtcagct aaagaccatc atgcatacta acatgccaaa cgtgaacgag   14100
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa cttttcagtt actatgacta ttgatttgat gaacaatgcc   14280
atcatagata attacttgaa agtgggtaga cagaatggag tgcttgaaag tgacattggt   14340
gttaagttcg acaccaggaa cttcaagctg ggatgggatc ccgaaaccaa gttgatcatg   14400
cctggagtgt atacgtatga agccttccat cctgacattg tcttactgcc tggctgcgga   14460
gtggatttta ccgagagtcg tttgagcaac cttcttggta tcagaaaaaa acagccattt   14520
caagagggtt ttaagatttt gtatgaagat ttagaaggtg gtaatattcc ggccctcttg   14580
gatgtagatg cctatgagaa cagtaagaaa gaacaaaaag ccaaaataga agctgctaca   14640
gctgctgcag aagctaaggc aaacatagtt gccagcgact ctacaagggt tgctaacgct   14700
ggagaggtca gaggagacaa ttttgcgcca acacctgttc cgactgcaga atcattattg   14760
gccgatgtgt ctgaaggaac ggacgtgaaa ctcactattc aacctgtaga aaagatagt    14820
aagaatagaa gctataatgt gttggaagac aaaatcaaca cagcctatcg cagttggtat   14880
ctttcgtaca attatggcga tcccgaaaaa ggagtgcgtt cctggacatt gctcaccacc   14940
tcagatgtca cctgcggagc agagcaggtt tactggtcgc ttccagacat gatgaaggat   15000
cctgtcactt tccgctccac tagacaagtc agtaactacc ctgtggtggg tgcagagctt   15060
atgcccgtct tctcaaagag cttctacaac gaacaagctg tgtactccca gcagctccgc   15120
cagtccacct cgcttacgca cgtcttcaac cgctttcctg agaaccagat tttaatccgt   15180
ccgccggcgc ccaccattac caccgtcagt gaaaacgttc ctgctctcac agatcacggg   15240
accctgccgt tgcgcagcag tatccgggga gtccaacgtg tgaccgttac tgacgccaga   15300
cgccgcacct gtcctacgt gtacaaggca ctgggcatag tcgcaccgcg cgtcctttca    15360
agccgcactt tctaaaaaaa aaaatgtcc attcttatct cgcccagtaa taacaccggt    15420
```

```
tggggtctgc gcgctccaag caagatgtac ggaggcgcac gcaaacgttc tacccaacat    15480
cccgtgcgtg ttcgcggaca ttttcgcgct ccatggggtg ccctcaaggg ccgcactcgc    15540
gttcgaacca ccgtcgatga tgtaatcgat caggtggttg ccgacgcccg taattatact    15600
cctactgcgc ctacatctac tgtggatgca gttattgaca gtgtagtggc tgacgctcgc    15660
aactatgctc gacgtaagag ccggcgaagg cgcattgcca gacgccaccg agctaccact    15720
gccatgcgag ccgcaagagc tctgctacga agagctagac gcgtggggcg aagagccatg    15780
cttagggcgg ccagacgtgc agcttcgggc gccagcgccg gcaggtcccg caggcaagca    15840
gccgctgtcg cagcggcgac tattgccgac atggcccaat cgcgaagagg caatgtatac    15900
tgggtgcgtg acgctgccac cggtcaacgt gtacccgtgc gcacccgtcc ccctcgcact    15960
tagaagatac tgagcagtct ccgatgttgt gtcccagcgg cgaggatgtc caagcgcaaa    16020
tacaaggaag aaatgctgca ggttatcgca cctgaagtct acggccaacc gttgaaggat    16080
gaaaaaaaac cccgcaaaat caagcgggtt aaaaaggaca aaaaagaaga ggaagatggc    16140
gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acggggatga tgatattctt    16320
gagcaggcgg ctgaccgatt aggcgagttt gcttatggca agcgtagtag aataacttcc    16380
aaggatgaga cagtgtcaat acccttggat catggaaatc ccacccctag tcttaaaccg    16440
gtcactttgc agcaagtgtt acccgtaact ccgcgaacag gtgttaaacg cgaaggtgaa    16500
gatttgtatc ccactatgca actgatggta cccaaacgcc agaagttgga ggacgttttg    16560
gagaaagtaa aagtggatcc agatattcaa cctgaggtta agtgagacc cattaagcag    16620 gtagcgcctg gtctgggggt acaaactgta gacattaaga ttcccactga agtatggaa    16680 gtgcaaactg aacccgcaaa gcctactgcc acctccactg aagtgcaaac ggatccatgg    16740
atgcccatgc ctattacaac tgacgccgcc ggtcccactc gaagatcccg acgaaagtac    16800
ggtccagcaa gtctgttgat gcccaattat gttgtacacc catctattat tcctactcct    16860
ggttaccgag gcactcgcta ctatcgcagc cgaaacagta cctcccgccg tcgccgcaag    16920
acacctgcaa atcgcagtcg tcgccgtaga cgcacaagca aaccgactcc cggcgccctg    16980
gtgcggcaag tgtaccgcaa tggtagtgcg gaacctttga cactgccgcg tgcgcgttac    17040
catccgagta tcatcactta atcaatgttg ccgctgcctc cttgcagata tggccctcac    17100
ttgtcgcctt cgcgttccca tcactggtta ccgaggaaga aactcgcgcc gtagaagagg    17160
gatgttggga cgcggaatgc gacgctacag gcgacggcgt gctatccgca agcaattgcg    17220
gggtggtttt ttaccagcct taattccaat tatcgctgct gcaattggcg cgataccagg    17280
catagcttcc gtggcggttc aggcctcgca acgacattga cattggaaaa aaaacgtata    17340
aataaaaaaa aatacaatgg actctgacac tcctggtcct gtgactatgt tttcttagag    17400
atggaagaca tcaattttc atccttggct ccgcgacacg gcacgaagcc gtacatgggc    17460
acctggagcg acatcggcac gagccaactg aacgggggcg ccttcaattg gagcagtatc    17520
tggagcgggc ttaaaaattt tggctcaacc ataaaaacat acgggaacaa gcttggaac    17580 agcagtacag gacaggcgct tagaaataaa cttaaagacc agaacttcca acaaaaagta    17640
gtcgatggga tagcttccgg catcaatgga gtggtagatt tggctaacca ggctgtgcag    17700
aaaaagataa acagtcgttt ggaccgcgcg ccagcaaccc caggtgaaat gcaagtggag    17760
gaagaaattc ctccgccaga aaaacgaggc gacaagcgtc cgcgtcccga tttggaagag    17820
```

```
acgctggtga cgcgcgtaga tgaaccgcct tcttatgagg aagcaacgaa gcttggaatg    17880
cccaccacta gaccgatagc cccaatggcc accggggtga tgaaaccttc tcagttgcat    17940
cgacccgtca ccttggattt gcccctccc cctgctgcta ctgctgtacc cgcttctaag    18000
cctgtcgctg ccccgaaacc agtcgccgta gccaggtcac gtcccggggg cgctcctcgt    18060
ccaaatgcgc actggcaaaa tactctgaac agcatcgtgg gtctaggcgt gcaaagtgta    18120
aaacgccgtc gctgctttta attaaatatg gagtagcgct taacttgcct atctgtgtat    18180
atgtgtcatt acacgccgtc acagcagcag aggaaaaaag gaagaggtcg tgcgtcgacg    18240
ctgagttact ttcaagatgg ccaccccatc gatgctgccc caatgggcat acatgcacat    18300
cgccggacag gatgcttcgg agtacctgag tccgggtctg gtgcagttcg cccgcgccac    18360
agacacctac ttcaatctgg gaataagtt tagaaatccc accgtagcgc cgacccacga    18420
tgtgaccacc gaccgtagcc agcggctcat gttgcgcttc gtgcccgttg accgggagga    18480
caatacatac tcttacaaag tgcggtacac cctggccgtg ggcgacaaca gagtgctgga    18540
tatgccagc acgttctttg acattagggg cgtgttggac agaggtccca gtttcaaacc    18600
ctattctggt acggcttaca actctctggc tcctaaaggc gctccaaatg catctcaatg    18660
gattgcaaaa ggcgtaccaa ctgcagcagc cgcaggcaat ggtgaagaag aacatgaaac    18720
agaggagaaa actgctactt acactttgc caatgctcct gtaaaagccg aggctcaaat    18780
tacaaaagag ggcttaccaa taggtttgga gatttcagct gaaaacgaat ctaaacccat    18840
ctatgcagat aaactttatc agccagaacc tcaagtggga gatgaaactt ggactgacct    18900
agacggaaaa accgaagagt atggaggcag ggctctaaag cctactacta acatgaaacc    18960
ctgttacggg tcctatgcga agcctactaa tttaaaaggt ggtcaggcaa aaccgaaaaa    19020
ctcggaaccg tcgagtgaaa aaattgaata tgatattgac atggaatttt tgataactc    19080
atcgcaaaga acaaacttca gtcctaaaat tgtcatgtat gcagaaaatg taggtttgga    19140
aacgccagac actcatgtag tgtacaaacc tggaacagaa gacacaagtt ccgaagctaa    19200
tttgggacaa cagtctatgc ccaacagacc caactacatt ggcttcagag ataactttat    19260
tggactcatg tactataaca gtactggtaa catgggggtg ctggctggtc aagcgtctca    19320
gttaaatgca gtggttgact tgcaggacag aaacacagaa ctttcttacc aactcttgct    19380
tgactctctg ggcgacagaa ccagatactt tagcatgtgg aatcaggctg tggacagtta    19440
tgatcctgat gtacgtgtta ttgaaaatca tggtgtggaa gatgaacttc ccaactattg    19500
ttttccactg gacggcatag gtgttccaac aaccagttac aaatcaatag ttccaaatgg    19560
agaagataat aataattgga aagaacctga agtaaatgga acaagtgaga tcggacaggg    19620
taatttgttt gccatggaaa ttaaccttca agccaatcta tggcgaagtt tcctttattc    19680
caatgtggct ctgtatctcc cagactcgta caaatacacc ccgtccaatg tcactcttcc    19740
agaaaacaaa aacacctacg actacatgaa cgggcgggtg gtgccgccat ctctagtaga    19800
cacctatgtg aacattggtg ccaggtggtc tctggatgcc atggacaatg tcaacccatt    19860
caaccaccac cgtaacgctg gcttgcgtta ccgatctatg cttctgggta acggacgtta    19920
tgtgcctttc cacatacaag tgcctcaaaa attcttcgct gttaaaaacc tgctgcttct    19980
cccaggctcc tacacttatg agtggaactt taggaaggat gtgaacatgg ttctacagag    20040
ttccctcggt aacgacctgc gggtagatgg cgccagcatc agtttcacga gcatcaacct    20100
ctatgctact tttttcccca tggctcacaa caccgcttcc acccttgaag ccatgctgcg    20160
```

```
gaatgacacc aatgatcagt cattcaacga ctacctatct gcagctaaca tgctctaccc    20220
cattcctgcc aatgcaacca atattcccat ttccattcct tctcgcaact gggcggcttt    20280
cagaggctgg tcatttacca gactgaaaac caaagaaact ccctctttgg ggtctggatt    20340
tgacccctac tttgtctatt ctggttctat tccctacctg gatggtacct tctacctgaa    20400
ccacactttt aagaaggttt ccatcatgtt tgactcttca gtgagctggc ctggaaatga    20460
caggttacta tctcctaacg aatttgaaat aaagcgcact gtggatggcg aaggctacaa    20520
cgtagcccaa tgcaacatga ccaaagactg gttcttggta cagatgctcg ccaactacaa    20580
catcggctat cagggcttct acattccaga aggatacaaa gatcgcatgt attcattttt    20640
cagaaacttc cagcccatga gcaggcaggt ggttgatgag gtcaattaca aagacttcaa    20700
ggccgtcgcc ataccctacc aacacaacaa ctctggcttt gtgggttaca tggctccgac    20760
catgcgccaa ggtcaaccct atcccgctaa ctatccctat ccactcattg gaacaactgc    20820
cgtaaatagt gttacgcaga aaagttctt gtgtgacaga accatgtggc gcataccgtt     20880
ctcgagcaac ttcatgtcta tggggccct tacagacttg ggacagaata tgctctatgc      20940
caactcagct catgctctgg acatgacctt tgaggtggat cccatggatg agcccaccct    21000
gctttatctt ctcttcgaag ttttcgacgt ggtcagagtg catcagccac accgcggcat    21060
catcgaggca gtctacctgc gtacaccgtt ctcggccggt aacgctacca cgtaagaagc    21120
ttcttgcttc ttgcaaatag cagctgcaac catggcctgc ggatcccaaa acggctccag    21180
cgagcaagag ctcagagcca ttgtccaaga cctgggttgc ggaccctatt ttttgggaac    21240
ctacgataag cgcttcccgg ggttcatggc ccccgataag ctcgcctgtg ccattgtaaa    21300
tacggccgga cgtgagacgg ggggagagca ctggttggct ttcggttgga acccacgttc    21360
taacacctgc taccttttg atcctttgg attctcggat gatcgtctca aacagattta      21420
ccagtttgaa tatgagggtc tcctgcgccg cagcgctctt gctaccaagg accgctgtat    21480
tacgctggaa aaatctaccc agaccgtgca gggcccccgt tctgccgcct gcggactttt    21540
ctgctgcatg ttccttcacg cctttgtgca ctggcctgac cgtcccatgg acggaaaccc    21600
caccatgaaa ttgctaactg gagtgccaaa caacatgctt cattctccta aagtccagcc    21660
caccctgtgt gacaatcaaa agcactcta ccatttctt aatacccatt cgccttattt       21720
tcgctctcat cgtacacaca tcgaaagggc cactgcgttc gaccgtatgg atgttcaata    21780
atgactcatg taaacaacgt gttcaataaa catcacttta ttttttttaca tgtatcaagg    21840 ctctggatta cttatttatt tacaagtcga atgggtctg acgagaatca gaatgacccg      21900
caggcagtga tacgttgcgg aactgatact tgggttgcca cttgaattcg ggaatcacca    21960
acttgggaac cggtatatcg ggcaggatgt cactccacag ctttctggtc agctgcaaag    22020
ctccaagcag gtcaggagcc gaaatcttga aatcacaatt aggaccagtg ctctgagcgc    22080
gagagttgcg gtacaccgga ttgcagcact gaaacaccat cagcgacgga tgtctcacgc    22140
ttgccagcac ggtgggatct gcaatcatgc ccacatccag atcttcagca ttggcaatgc    22200
tgaacggggt catcttgcag gtctgcctac ccatggcggg cacccaatta ggcttgtggt    22260
tgcaatcgca gtgcaggggg atcagtatca tcttggcctg atcctgtctg attcctggat    22320
acacggctct catgaaagca tcatattgct tgaaagcctg ctgggcttta ctaccctcgg    22380
tataaaacat cccgcaggac ctgctcgaaa actggttagc tgcacagccg gcatcattca    22440
cacagcagcg ggcgtcattg ttggctattt gcaccacact tctgccccag cggttttggg    22500
tgattttggt tcgctcggga ttctccttta aggctcgttg tccgttctcg ctggccacat    22560
```

```
ccatctcgat aatctgctcc ttctgaatca taatattgcc atgcaggcac ttcagcttgc  22620
cctcataatc attgcagcca tgaggccaca acgcacagcc tgtacattcc caattatggt  22680
gggcgatctg agaaaaagaa tgtatcattc cctgcagaaa tcttcccatc atcgtgctca  22740
gtgtcttgtg actagtgaaa gttaactgga tgcctcggtg ctcttcgttt acgtactggt  22800
gacagatgcg cttgtattgt tcgtgttgct caggcattag tttaaaacag gttctaagtt  22860
cgttatccag cctgtacttc tccatcagca gacacatcac ttccatgcct ttctcccaag  22920
cagacaccag gggcaagcta atcggattct taacagtgca ggcagcagct cctttagcca  22980
gagggtcatc tttagcgatc ttctcaatgc ttcttttgcc atccttctca acgatgcgca  23040
cgggcgggta gctgaaaccc actgctacaa gttgcgcctc ttctctttct tcttcgctgt  23100
cttgactgat gtcttgcatg gggatatgtt tggtcttcct tggcttcttt ttgggggta  23160 tcggaggagg aggactgtcg ctccgttccg agacaggga ggattgtgac gtttcgctca  23220
ccattaccaa ctgactgtcg gtagaagaac ctgaccccac acggcgacag gtgttttct  23280 tcggggcag aggtggaggc gattgcgaag ggctgcggtc cgacctggaa ggcggatgac  23340
tggcagaacc ccttccgcgt tcgggggtgt gctccctgtg gcggtcgctt aactgatttc  23400
cttcgcggct ggccattgtg ttctcctagg cagagaaaca acagacatgg aaactcagcc  23460
attgctgtca acatcgccac gagtgccatc acatctcgtc ctcagcgacg aggaaaagga  23520
gcagagctta agcattccac cgcccagtcc tgccaccacc tctaccctag aagataagga  23580
ggtcgacgca tctcatgaca tgcagaataa aaaagcgaaa gagtctgaga cagacatcga  23640
gcaagacccg ggctatgtga caccggtgga acacgaggaa gagttgaaac gctttctaga  23700
gagagaggat gaaaactgcc caaaacagcg agcagataac tatcaccaag atgctggaaa  23760
tagggatcag aacaccgact acctcatagg gcttgacggg gaagacgcgc tccttaaaca  23820
tctagcaaga cagtcgctca tagtcaagga tgcattattg gacagaactg aagtgcccat  23880
cagtgtggaa gagctcagct gcgcctacga gcttaacctt ttttcacctc gtactccccc  23940
caaacgtcag ccaaacggca cctgcgagcc aaatcctcgc ttaaacttt atccagcttt  24000 tgctgtgcca gaagtactgg ctacctatca catctttttt aaaaatcaaa aaattccagt  24060
ctcctgccgc gctaatcgca cccgcgccga tgccctactc aatctgggac ctggttcacg  24120
cttacctgat atagcttcct tggaagaggt tccaaagatc ttcgagggtc tgggcaataa  24180
tgagactcgg gccgcaaatg ctctgcaaaa gggagaaaat ggcatggatg agcatcacag  24240
cgttctggtg gaattggaag gcgataatgc cagactcgca gtactcaagc gaagcgtcga  24300
ggtcacacac ttcgcatatc ccgctgtcaa cctgccccct aaagtcatga cggcggtcat  24360
ggaccagtta ctcattaagc gcgcaagtcc ctttcagaa gacatgcatg acccagatgc  24420
ctgtgatgag ggtaaaccag tggtcagtga tgagcagcta acccgatggc tgggcaccga  24480
ctctccccgg gatttggaag agcgtcgcaa gcttatgatg gccgtggtgc tggttaccgt  24540
agaactagag tgtctccgac gtttctttac cgattcagaa accttgcgca aactcgaaga  24600
gaatctgcac tacactttta gacacggctt tgtgcggcag gcatgcaaga tatctaacgt  24660
ggaactcacc aacctggttt cctacatggg tattctgcat gagaatcgcc taggacaaag  24720
cgtgctgcac agcacccctta aggggaagc ccgccgtgat tacatccgcg attgtgtcta  24780
tctctacctg tgccacacgt ggcaaaccgg catgggtgta tggcagcaat gtttagaaga  24840
acagaacttg aaagagcttg acaagctctt acagaaatct cttaaggttc tgtggacagg  24900
```

```
gttcgacgag cgcaccgtcg cttccgacct ggcagacctc atcttcccag agcgtctcag   24960
ggttactttg cgaaacggat tgcctgactt tatgagccag agcatgctta acaattttcg   25020
ctctttcatc ctggaacgct ccggtatcct gcccgccacc tgctgcgcac tgccctccga   25080
ctttgtgcct ctcacctacc gcgagtgccc ccgccgcta tggagtcact gctacctgtt   25140
ccgtctggcc aactatctct cctaccactc ggatgtgatc gaggatgtga gcggagacgg   25200
cttgctggag tgccactgcc gctgcaatct gtgcacgccc caccggtccc tagcttgcaa   25260
cccccagttg atgagcgaaa cccagataat aggcaccttt gaattgcaag ccccagcag   25320 ccaaggcgat gggtcttctc ctgggcaaag tttaaaactg accccgggac tgtggacctc   25380
cgcctacttg cgcaagtttg ctccggaaga ttaccacccc tatgaaatca gttctatga   25440 ggaccaatca cagcctccaa aggccgaact ttcggcttgc gtcatcaccc aggggcaat   25500 tctggcccaa ttgcaagcca tccaaaaatc ccgccaagaa tttctactga aaagggtaa   25560 gggggtctac cttgaccccc agaccggcga ggaactcaac acaaggttcc ctcaggatgt   25620
cccaacgacg agaaaacaag aagttgaagg tgcagccgcc gccccagaa gatatggagg   25680 aagattggga cagtcaggca gaggaggcgg aggaggacag tctggaggac agtctggagg   25740
aagacagttt ggaggaggaa aacgaggagg cagaggaggt ggaagaagta accgccgaca   25800
aacagttatc ctcggctgcg gagacaagca acagcgctac catctccgct ccgagtcgag   25860
gaacccggcg gcgtcccagc agtagatggg acgagaccgg acgcttcccg aacccaacca   25920
gcgcttccaa gaccggtaag aaggatcggc agggatacaa gtcctggcgg gggcataaga   25980
atgccatcat ctcctgcttg catgagtgcg ggggcaacat atccttcacg cggcgctact   26040
tgctattcca ccatggggtg aactttccgc gcaatgtttt gcattactac cgtcacctcc   26100
acagccccta ctatagccag caaatcccga cagtctcgac agataaagac agcggcggcg   26160
acctccaaca gaaaccagc agcggcagtt agaaaataca caacaagtgc agcaacagga   26220
ggattaaaga ttcagccaa cgagccgcg caaacccgag agttaagaaa tcggatcttt   26280
ccaaccctgt atgccatctt ccagcagagt cggggtcaag agcaggaact gaaaataaaa   26340
aaccgatctc tgcgttcgct caccagaagt tgtttgtatc acaagagcga agatcaactt   26400
cagcgcactc tcgaggacgc cgaggctctc ttcaacaagt actgcgcgct gactcttaaa   26460
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagctcttac   26700
caccacgccc cgccaacacc ttaatcccag aaattggccc gccgccctag tgtaccagga   26760
aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000
cacccctcgt caggctgttc tgactttgga aagttcgtct tcgcaacccc gctcgggcgg   27060
aatcgggacc gttcaatttg tagaggagtt tactccctct gtctacttca accccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
```

```
ctccccaagg atcaccctca aggtccggcc cacggagtgc ggattactat cgaaggcaaa   27360
atagactctc gcctgcaacg aatttctcc cagcggcccg tgctgatcga gcagaccag    27420 ggaaacacca cggtttccat ctactgcatt tgtaatcacc ccggattgca tgaaagcctt   27480
tgctgtctta tgtgtactga gtttaataaa aactgaatta agactctcct acggactgcc   27540
gcttcttcaa cccggatttt acaaccagaa gaacaaaact tttcctgtcg tccaggactc   27600
tgttaacttc acctttccta ctcacaaact agaagctcaa cgactacacc gcttttccag   27660
aagcattttc cctactaata ctactttcaa aaccggaggt gagctccacg gtctccctac   27720
agaaaaccct tgggtggaag cgggccttgt agtactagga attcttgcgg gtgggcttgt   27780
gattattctt tgctacctat acacaccttg cttcactttc ctagtggtgt tgtggtattg   27840
gtttaaaaaa tggggcccat actagtcttg cttgttttac tttcgctttt ggaaccgggt   27900
tctgccaatt acgatccatg tctagacttt gacccagaaa actgcacact acttttgca   27960 cccgacacaa gccgcatctg tggagttctt attaagtgcg gatgggaatg caggtccgtt   28020
gaaattacac acaataacaa acctggaac  aataccttat ccaccacatg ggagccagga   28080
gttcccgagt ggtacactgt ctctgtccga ggtcctgacg gttccatccg cattagtaac   28140
aacactttca ttttttctga aatgtgcgat ctggccatgt tcatgagcaa acagtattct   28200
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata caaagaaaa  aatgccttaa cctctttctg tttacagaca tggcttctct   28380
tacatctctc atatttgtca gcattgtcac tgccgctcac ggacaaacag tcgtctctat   28440
cccactagga cataattaca ctctcatagg acccccaatc acttcagagg tcatctggac   28500
caaactggga agcgttgatt actttgatat aatctgtaac aaaacaaaac caataatagt   28560
aacttgcaac atacaaaatc ttacattgat taatgttagc aaagtttaca gcggttacta   28620
ttatggttat gacagataca gtagtcaata tagaaattac ttggttcgtg ttacccagtt   28680
gaaaaccacg aaaatgccaa atatggcaaa gattcgatcc gatgacaatt ctctagaaac   28740
ttttacatct cccaccacac ccgacgaaaa aaacatccca gattcaatga ttgcaattgt   28800
tgcagcggtg gcagtggtga tgcactaat  aataatatgc atgcttttat atgcttgtcg   28860
ctacaaaaag tttcatccta aaaacaaga  tctcctacta aggcttaaca tttaatttct   28920
ttttatacag ccatggtttc cactaccaca ttccttatgc ttactagtct cgcaactctg   28980
acttctgctc gctcacacct cactgtaact ataggctcaa actgcacact aaaaggacct   29040
caaggtggtc atgtcttttg gtggagaata tatgacaatg gatggtttac aaaaccatgt   29100
gaccaacctg gtagattttt ctgcaacggc agagacctaa ccattatcaa cgtgacagca   29160
aatgacaaag gcttctatta tggaaccgac tataaaagta gtttagatta taacattatt   29220
gtactgccat ctaccactcc agcacccgc  acaactactt tctctagcag cagtgtcgct   29280
aacaatacaa tttccaatcc aaccttttgcc gcgcttttaa aacgcactgt gaataattct   29340
acaacttcac atacaacaat ttccacttca caatcagca  tcatcgctgc agtgacaatt   29400
ggaatatcta ttcttgtttt taccataacc tactacgcct gctgctatag aaaagacaaa   29460
cataaaggtg atccattact tagatttgat atttaatttg ttctttttt  ttatttacag   29520 tatggtgaac accaatcatg gtacctagaa atttcttctt caccatactc atctgtgctt   29580
ttaatgtttg cgctactttc acagcagtag ccacagcaac cccagactgt ataggagcat   29640
```

```
ttgcttccta tgcactttt gcttttgtta cttgcatctg cgtatgtagc atagtctgcc   29700
tggttattaa ttttttccaa cttctagact ggatccttgt gcgaattgcc tacctgcgcc   29760
accatcccga ataccgcaac caaaatatcg cggcacttct tagactcatc taaaaccatg   29820
caggctatac taccaatatt tttgcttcta ttgcttccct acgctgtctc aaccccagct   29880
gcctatagta ctccaccaga acaccttaga aaatgcaaat tccaacaacc gtggtcattt   29940
cttgcttgct atcgagaaaa atcagaaatc cccccaaatt taataatgat tgctggaata   30000
attaatataa tctgttgcac cataatttca ttttttgatat accccctatt tgattttggc   30060
tggaatgctc ccaatgcaca tgatcatcca caagacccag aggaacacat tcccccacaa   30120
aacatgcaac atccaatagc gctaatagat tacgaaagtg aaccacaacc cccactactc   30180
cctgctatta gttacttcaa cctaaccggc ggagatgact gaaacactca ccacctccaa   30240
ttccgccgag gatctgctcg atatggacgg ccgcgtctca gaacaacgac ttgcccaact   30300
acgcatccgc cagcagcagg aacgcgtggc caaagagctc agagatgtca tccaaattca   30360
ccaatgcaaa aaaggcatat tctgtttggt aaaacaagcc aagatatcct acgagatcac   30420
cgctactgac catcgcctct cttacgaact tggcccccaa cgacaaaaat ttacctgcat   30480
ggtgggaatc aaccccatag ttatcaccca acaaagtgga gatactaagg gttgcattca   30540
ctgctcctgc gattccatcg agtgcaccta caccctgctg aagaccctat gcggcctaag   30600
agacctgcta ccaatgaatt aaaaaaaaat gattaataaa aaatcactta cttgaaatca   30660
gcaataaggt ctctgttgaa attttctccc agcagcacct cacttccctc ttcccaactc   30720
tggtattcta aaccccgttc agcggcatac tttctccata ctttaaaggg gatgtcaaat   30780
tttagctcct ctcctgtacc cacaatcttc atgtctttct tcccagatga ccaagagagt   30840
ccggctcagt gactccttca accctgtcta cccctatgaa gatgaaagca cctcccaaca   30900
cccctttata aacccagggt ttatttcccc aaatggcttc acacaaagcc cagacggagt   30960
tcttacttta aaatgtttaa ccccactaac aaccacaggc ggatctctac agctaaaagt   31020
gggaggggga cttacagtgg atgacactga tggtacctta caagaaaaca tacgtgctac   31080
agcacccatt actaaaaata atcactctgt agaactatcc attggaaatg gattagaaac   31140
tcaaaacaat aaactatgtg ccaaattggg aaatggggtta aaatttaaca acggtgacat   31200
ttgtataaag gatagtatta acaccttatg gactggaata aaccctccac ctaactgtca   31260
aattgtggaa aacactaata caaatgatgg caaacttact ttagtattag taaaaaatgg   31320
agggcttgtt aatggctacg tgtctctagt tggtgtatca gacactgtga accaaatgtt   31380
cacacaaaag acagcaaaca tccaattaag attatatttt gactcttctg gaaatctatt   31440
aactgaggaa tcagacttaa aaattccact taaaaataaa tcttctacag cgaccagtga   31500
aactgtagcc agcagcaaag cctttatgcc aagtactaca gcttatccct tcaacaccac   31560
tactagggat agtgaaaact acattcatgg aatatgttac tacatgacta gttatgatag   31620
aagtctattt cccttgaaca tttctataat gctaaacagc cgtatgattt cttccaatgt   31680
tgcctatgcc atacaatttg aatggaatct aaatgcaagt gaatctccag aaagcaacat   31740
agctacgctg accacatccc cctttttctt ttcttacatt acagaagacg acaactaaaa   31800
taaagtttaa gtgttttat ttaaaatcac aaaattcgag tagttatttt gcctccacct   31860 tcccattga cagaatacac caatctctcc ccacgcacag ctttaaacat ttggatacca   31920
ttagagatag acattgtttt agattccaca ttccaaacag tttcagagcg agccaatctg   31980
gggtcagtga tagataaaaa tccatcgcga tagtctttta aagcgctttc acagtccaac   32040
```

```
tgctgcggat gcgactccgg agtttggatc acggtcatct ggaagaagaa cgatgggaat   32100
cataatccga aaacggtatc ggacgattgt gtctcatcaa acccacaagc agccgctgtc   32160
tgcgtcgctc cgtgcgactg ctgtttatgg gatcagggtc cacagtttcc tgaagcatga   32220
ttttaatagc ccttaacatc aactttctgg tgcgatgcgc gcagcaacgc attctgattt   32280
cactcaaatc tttgcagtag gtacaacaca ttattacaat attgtttaat aaaccataat   32340
taaaagcgct ccagccaaaa ctcatatctg atataatcgc ccctgcatga ccatcatacc   32400
aaagtttaat ataaattaaa tgacgttccc tcaaaaacac actacccaca tacatgatct   32460
cttttggcat gtgcatatta acaatctgtc tgtaccatgg acaacgttgg ttaatcatgc   32520
aacccaatat aaccttccgg aaccacactg ccaacaccgc tcccccagcc atgcattgaa   32580
gtgaaccctg ctgattacaa tgacaatgaa gaacccaatt ctctcgaccg tgaatcactt   32640
gagaatgaaa aatatctata gtggcacaac atagacataa atgcatgcat cttctcataa   32700
tttttaactc ctcaggattt agaaacatat cccaggggaat aggaagctct tgcagaacag   32760
taaagctggc agaacaagga agaccacgaa cacaacttac actatgcata gtcatagtat   32820
cacaatctgg caacgcggg tggtcttcag tcatagaagc tcgggtttca ttttcctcac   32880
aacgtggtaa ctgggctctg gtgtaagggt gatgtctggc gcatgatgtc gagcgtgcgc   32940
gcaaccttgt cataatggag ttgcttcctg acattctcgt attttgtata gcaaaacgcg   33000
gccctggcag aacacactct tcttcgcctt ctatcctgcc gcttagcgtg ttccgtgtga   33060
tagttcaagt acagccacac tcttaagttg gtcaaaagaa tgctggcttc agttgtaatc   33120
aaaactccat cgcatctaat tgttctgagg aaatcatcca cggtagcata tgcaaatccc   33180
aaccaagcaa tgcaactgga ttgcgtttca agcaggagag gagagggaag agacggaaga   33240
accatgttaa ttttttattcc aaacgatctc gcagtacttc aaattgtaga tcgcgcagat   33300
ggcatctctc gcccccactg tgttggtgaa aaagcacagc taaatcaaaa gaaatgcgat   33360
tttcaaggtg ctcaacggtg gcttccaaca aagcctccac gcgcacatcc aagaacaaaa   33420
gaataccaaa agaaggagca ttttctaact cctcaatcat catattacat tcctgcacca   33480
ttcccagata attttcagct ttccagcctt gaattattcg tgtcagttct tgtggtaaat   33540
ccaatccaca cattacaaac aggtcccgga gggcgccctc caccaccatt cttaaacaca   33600
ccctcataat gacaaaatat cttgctcctg tgtcacctgt agcgaattga gaatggcaac   33660
atcaattgac atgcccttgg ctctaagttc ttctttaagt tctagttgta aaaactctct   33720
catattatca ccaaactgct tagccagaag ccccccggga acaagagcag gggacgctac   33780
agtgcagtac aagcgcagac ctccccaatt ggctccagca aaaacaagat tggaataagc   33840
atattgggaa ccaccagtaa tatcatcgaa gttgctggaa atataatcag gcagagtttc   33900
ttgtagaaat tgaataaaag aaaaatttgc caaaaaaaca ttcaaaacct ctgggatgca   33960
aatgcaatag gttaccgcgc tgcgctccaa cattgttagt tttgaattag tctgcaaaaa   34020
taaaaaaaaa acaagcgtca tatcatagta gcctgacgaa caggtggata aatcagtctt   34080
tccatcacaa gacaagccac agggtctcca gtcgacccct cgtaaaacct gtcatcgtga   34140
ttaaacaaca gcaccgaaag ttcctcgcgg tgaccagcat gaataagtct tgatgaagca   34200
tacaatccag acatgttagc atcagttaag gagaaaaaac agccaacata gcctttgggt   34260
ataattatgc ttaatcgtaa gtatagcaaa gccaccctc gcggatacaa agtaaaaggc   34320
acaggagaat aaaaaatata attatttctc tgctgctgtt taggcaacgt cgccccccggt   34380
```

```
cectctaaat acacatacaa agcctcatca gccatggctt accagagaaa gtacagcggg    34440
cacacaaacc acaagctcta aagtcactct ccaacctctc cacaatatat atacacaagc    34500
cctaaactga cgtaatggga ctaaagtgta aaaaatcccg ccaaacccaa cacacacccc    34560
gaaactgcgt caccagggaa aagtacagtt tcacttccgc aatcccaaca agcgtcactt    34620
cctctttctc acggtacgtc acatcccatt aacttacaac gtcatttcc cacggccgcg     34680 ccgcccettt taaccgttaa ccccacagcc aatcaccaca cggccacac  ttttaaaat     34740 cacctcattt acatattggc accattccat ctataaggta tattattgat gatg          34794
```

<210> SEQ ID NO 42
<211> LENGTH: 688
<212> TYPE: DNA
<213> ORGANISM: Artificial Sequence
<220> FEATURE:
<223> OTHER INFORMATION: mouse IL12A cloned into the NotI restriction
      site of the revised IX-E2 site with an expression cassette

<400> SEQUENCE: 42

```
ctataggag acccgcggcc atgtgtcaat cacgctacct cctcttttg gccaccttg       60 ccctcctaaa ccacctcagt ttggccaggg tcattccagt ctctggacct gccaggtgtc    120
ttagccagtc ccgaaacctg ctgaagacca cagatgacat ggtgaagacg ccagagaaa     180 aactgaaaca ttattcctgc actgctgaag acatcgatca tgaagacatc acacgggacc    240
aaaccagcac attgaagacc tgtttaccac tggaactaca caagaacgag agttgcctgg    300
ctactagaga gacttcttcc acaacaagag ggagctgcct gccccacag aagacgtctt     360 tgatgatgac cctgtgcctt ggtagcatct atgaggactt gaagatgtac cagacagagt    420
tccaggccat caacgcagca cttcagaatc acaaccatca gcagatcatt ctagacaagg    480
gcatgctggt ggccatcgat gagctgatgc agtctctgaa tcataatggc gagactctgc    540
gccagaaacc tcctgtggga gaagcagacc cttacagagt gaaatgaag ctctgcatcc     600 tgcttcacgc cttcagcacc cgcgtcgtga ccatcaacag ggtgatgggc tatctgagct    660
ccgcctgagg ccgctgtgcc ttctagtt                                      688
```

<210> SEQ ID NO 43
<211> LENGTH: 1048
<212> TYPE: DNA
<213> ORGANISM: Artificial Sequence
<220> FEATURE:
<223> OTHER INFORMATION: mouse IL12B cloned into the SwaI restriction
      site of the L5-E4 site with an expression cassette using the EF1A
      promoter

<400> SEQUENCE: 43

```
ttgccgccag aacacaattt atgtgtcctc agaagctaac catctcctgg tttgccatcg    60
ttttgctggt gtctccactc atggccatgt gggagctgga aaagacgtt tatgttgtag     120 aggtggactg gactcccgat gcccctggag aaacagtgaa cctcacctgt gacacgcctg    180
aagaagatga catcacctgg acctcagacc agagacatgg agtcataggc tctggaaaga    240
ccctgaccat cactgtcaaa gagttttcta gatgctggca gtacacctgc acaaaggag    300 gcgagactct gagccactca catctgctgc tccacaagaa ggaaaatgga atttggtcca    360
ctgaaatttt aaaaaatttc aaaacaaga cttttcctga agtgtgaagca ccaaattact    420 ccggacggtt cacgtgctca tggctggtgc aaagaaacat ggacttgaag ttcaacatca    480
agagcagtag cagttcccct gactctcggg cagtgacatg tggaatggcg tctctgtctg    540
```

-continued

```
cagagaaggt cacactggac caaagggact atgagaagta ttcagtgtcc tgccaggagg    600
atgtcacctg cccaactgcc gaggagaccc tgcccattga actggcgttg gaagcacggc    660
agcagaataa atatgagaac tacagcacca gcttcttcat cagggacatc atcaaaccag    720
acccgcccaa gaacttgcag atgaagcctt tgaagaactc acaggtggag gtcagctggg    780
agtaccctga ctcctggagc actccccatt cctacttctc cctcaagttc tttgttcgaa    840
tccagcgcaa gaaagaaaag atgaaggaga cagaggaggg gtgtaaccag aaaggtgcgt    900
tcctcgtaga gaagacatct accgaagtcc aatgcaaagg cgggaatgtc tgcgtgcaag    960
ctcaggatcg ctattacaat tcctcatgca gcaagtgggc atgtgttccc tgcagggtcc   1020
gatcctagaa ataacttgtt tattgcag                                      1048
```

<210> SEQ ID NO 44
<211> LENGTH: 8
<212> TYPE: DNA
<213> ORGANISM: Artificial Sequence
<220> FEATURE:
<223> OTHER INFORMATION: modified TATA box

<400> SEQUENCE: 44 agtgcccg                                                               8

<210> SEQ ID NO 45
<211> LENGTH: 8
<212> TYPE: DNA
<213> ORGANISM: Artificial Sequence
<220> FEATURE:
<223> OTHER INFORMATION: modified TATA box

<400> SEQUENCE: 45 tattcccg                                                               8

<210> SEQ ID NO 46
<211> LENGTH: 10
<212> TYPE: DNA
<213> ORGANISM: Artificial Sequence
<220> FEATURE:
<223> OTHER INFORMATION: modified CAAT box

<400> SEQUENCE: 46
ttccgtggcg                                                            10